United States Patent
Holyoake et al.

(10) Patent No.: US 11,904,097 B2
(45) Date of Patent: Feb. 20, 2024

(54) USER INTERFACE AND SYSTEM FOR SUPPLYING GASES TO AN AIRWAY

(71) Applicant: Fisher & Paykel Healthcare Limited, Auckland (NZ)

(72) Inventors: Bruce Gordon Holyoake, Auckland (NZ); Dexter Chi Lun Cheung, Auckland (NZ); Anil Patel, London (GB); Seyed Ahmad Reza Nouraei, London (GB); Milanjot Singh Assi, Sydney (AU); Thomas Heinrich Barnes, Surrey (GB); Alicia Jerram Hunter Evans, Galway (IE); Craig Karl White, Auckland (NZ); Matthew John Payton, Auckland (NZ); Laith Adeeb Hermez, Auckland (NZ); German Klink, Auckland (NZ); Samantha Dale Oldfield, Auckland (NZ); Taylor James Edwards, Auckland (NZ); Aidan Robert Burgess, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 541 days.

(21) Appl. No.: 16/897,759

(22) Filed: Jun. 10, 2020

(65) Prior Publication Data

US 2020/0368471 A1 Nov. 26, 2020

Related U.S. Application Data

(63) Continuation of application No. 15/563,085, filed as application No. PCT/IB2016/051819 on Mar. 31, 2016, now Pat. No. 10,716,912.

(Continued)

(51) Int. Cl.
*A61M 16/06* (2006.01)
*A61M 16/00* (2006.01)
(Continued)

(52) U.S. Cl.
CPC .......... *A61M 16/0666* (2013.01); *A61M 16/0051* (2013.01); *A61M 16/0066* (2013.01);
(Continued)

(58) Field of Classification Search
CPC .......... A61M 16/06; A61M 16/0611; A61M 16/0616; A61M 16/0666; A61M 16/0672;
(Continued)

(56) References Cited

U.S. PATENT DOCUMENTS

| | | |
|---|---|---|
| 27,846 A | 4/1860 | Underwood |
| 207,626 A | 9/1878 | Sargent |

(Continued)

FOREIGN PATENT DOCUMENTS

| | | |
|---|---|---|
| AU | 2528471 A | 8/1972 |
| AU | 479953 B | 5/1973 |

(Continued)

OTHER PUBLICATIONS

Australian Examination Report in Application No. 2016241572, dated Feb. 15, 2021, in 4 pages.
(Continued)

*Primary Examiner* — Joseph D. Boecker
(74) *Attorney, Agent, or Firm* — Knobbe Martens Olson & Bear LLP

(57) ABSTRACT

The invention relates to a respiratory system comprising a first patient interface for delivery of a first flow of gases to a patient, a second patient interface for delivery of a second flow of gases to the patient, and a device and/or sensing arrangement that is configure to facilitate a switching of the system between a first respiratory mode where the device (Continued)

allowing delivery of the first flow of gases to an outlet of the first patient interface when the second patient interface is absent from the patient, and a second respiratory mode where the device reducing or stopping delivery of the first flow of gases to the outlet of the first patient interface when the second patient interface is located together with the first patient interface upon the patient.

18 Claims, 61 Drawing Sheets

Related U.S. Application Data

(60) Provisional application No. 62/196,256, filed on Jul. 23, 2015, provisional application No. 62/196,248, filed on Jul. 23, 2015, provisional application No. 62/193,213, filed on Jul. 16, 2015, provisional application No. 62/140,650, filed on Mar. 31, 2015, provisional application No. 62/140,613, filed on Mar. 31, 2015, provisional application No. 62/140,593, filed on Mar. 31, 2015, provisional application No. 62/140,625, filed on Mar. 31, 2015.

(51) Int. Cl.
| | |
|---|---|
| A61M 16/08 | (2006.01) |
| A61M 16/16 | (2006.01) |
| A61M 39/26 | (2006.01) |
| A61M 16/20 | (2006.01) |
| A61M 16/01 | (2006.01) |
| A61M 16/10 | (2006.01) |
| A61M 16/12 | (2006.01) |

(52) U.S. Cl.
CPC ........ *A61M 16/0078* (2013.01); *A61M 16/01* (2013.01); *A61M 16/024* (2017.08); *A61M 16/06* (2013.01); *A61M 16/0616* (2014.02); *A61M 16/0672* (2014.02); *A61M 16/0858* (2014.02); *A61M 16/0875* (2013.01); *A61M 16/16* (2013.01); *A61M 16/201* (2014.02); *A61M 16/202* (2014.02); *A61M 16/209* (2014.02); *A61M 39/26* (2013.01); *A61M 16/0683* (2013.01); *A61M 16/0688* (2014.02); *A61M 16/0816* (2013.01); *A61M 16/105* (2013.01); *A61M 16/109* (2014.02); *A61M 16/1095* (2014.02); *A61M 16/12* (2013.01); *A61M 16/161* (2014.02); *A61M 16/208* (2013.01); *A61M 2016/0027* (2013.01); *A61M 2016/0033* (2013.01); *A61M 2016/103* (2013.01); *A61M 2016/1025* (2013.01); *A61M 2016/1035* (2013.01); *A61M 2202/0208* (2013.01); *A61M 2202/0241* (2013.01); *A61M 2205/0216* (2013.01); *A61M 2205/13* (2013.01); *A61M 2205/14* (2013.01); *A61M 2205/332* (2013.01); *A61M 2205/3303* (2013.01); *A61M 2205/3306* (2013.01); *A61M 2205/3317* (2013.01); *A61M 2205/3334* (2013.01); *A61M 2205/3365* (2013.01); *A61M 2205/3368* (2013.01); *A61M 2205/3375* (2013.01); *A61M 2205/3569* (2013.01); *A61M 2205/3592* (2013.01); *A61M 2205/505* (2013.01); *A61M 2205/507* (2013.01); *A61M 2205/581* (2013.01); *A61M 2205/582* (2013.01); *A61M 2205/583* (2013.01); *A61M 2230/04* (2013.01); *A61M 2230/06* (2013.01); *A61M 2230/10* (2013.01); *A61M 2230/201* (2013.01); *A61M 2230/202* (2013.01); *A61M 2230/205* (2013.01); *A61M 2230/60* (2013.01); *A61M 2230/63* (2013.01)

(58) Field of Classification Search
CPC .............. A61M 16/08; A61M 16/0816; A61M 16/0866; A61M 16/0875; A61M 16/20; A61M 16/204

See application file for complete search history.

(56) References Cited

U.S. PATENT DOCUMENTS

| | | | |
|---|---|---|---|
| 260,959 A | 7/1882 | Emery | |
| 286,561 A | 10/1883 | Smith et al. | |
| 396,528 A | 1/1889 | Blake | |
| 402,632 A | 5/1889 | Traves | |
| 495,439 A | 4/1893 | Thacher | |
| 509,409 A | 11/1893 | Totten | |
| 531,766 A | 1/1895 | Block | |
| 538,895 A | 5/1895 | Casgrain | |
| 540,255 A | 6/1895 | Hirsch | |
| 543,125 A | 7/1895 | Brown | |
| 553,000 A | 1/1896 | Hunt | |
| 584,501 A | 6/1897 | Gates | |
| 596,341 A | 12/1897 | Seymour | |
| 613,979 A | 11/1898 | Eaglesfield | |
| 614,676 A | 11/1898 | Tucker | |
| 639,193 A | 12/1899 | Alliger | |
| 642,549 A | 1/1900 | Kennedy | |
| 727,385 A | 5/1903 | Kops | |
| 733,852 A | 7/1903 | Lee | |
| 827,243 A | 7/1906 | Larson | |
| 829,677 A | 8/1906 | Sillamn | |
| 897,955 A | 9/1908 | Barrett et al. | |
| 899,670 A | 9/1908 | Hyde, Jr. | |
| 906,215 A | 12/1908 | Gammeter | |
| 939,726 A | 11/1909 | Magdiel | |
| 973,242 A | 10/1910 | Wayson, Jr. | |
| 1,125,542 A * | 1/1915 | Humphries ....... | A61M 16/0694 128/207.18 |
| 1,146,111 A | 7/1915 | Styll | |
| 1,156,385 A | 10/1915 | Willson, Jr. | |
| 1,364,513 A | 1/1921 | Ono | |
| 1,431,052 A | 10/1922 | Shukie | |
| 1,471,360 A | 10/1923 | Sangren | |
| 1,471,726 A | 10/1923 | Ginty | |
| 1,479,900 A | 1/1924 | Dorner et al. | |
| 1,560,889 A | 11/1925 | Wearham | |
| 1,705,115 A | 3/1929 | Hollestelle | |
| 1,706,314 A | 3/1929 | Norris | |
| 1,722,599 A | 7/1929 | Test et al. | |
| 1,805,442 A | 5/1931 | Wallfisch | |
| 1,806,586 A | 5/1931 | Christmas | |
| 1,824,759 A | 9/1931 | Bainbridge | |
| 1,894,467 A | 1/1933 | Heinrich | |
| 1,918,998 A | 7/1933 | Wells | |
| 1,945,617 A | 2/1934 | Nelson | |
| 1,970,137 A | 8/1934 | Harte | |
| 1,998,560 A | 4/1935 | Smith | |
| 2,013,242 A | 9/1935 | Stinson | |
| 2,073,471 A | 3/1937 | Franz | |
| 2,111,053 A | 3/1938 | Olsen | |
| 2,116,488 A | 5/1938 | Jackson | |
| 2,116,490 A | 5/1938 | Arthur | |
| 2,157,061 A | 5/1939 | Ernst | |
| 2,169,968 A | 8/1939 | Clifford | |
| 2,176,735 A | 10/1939 | Freedlander et al. | |
| 2,220,453 A | 11/1940 | Lowres | |
| 2,234,265 A | 3/1941 | Lowres | |
| 2,236,304 A | 3/1941 | Snavely | |
| 2,241,814 A | 5/1941 | Hansen | |
| 2,267,051 A | 12/1941 | Stevens | |
| 2,277,981 A | 3/1942 | Horton | |
| 2,284,848 A | 6/1942 | Ryan | |
| 2,287,409 A | 6/1942 | Samuel | |
| 2,310,622 A | 2/1943 | Ray | |
| 2,314,814 A | 3/1943 | Bruce | |
| 2,338,145 A | 1/1944 | Webb | |

(56) References Cited

U.S. PATENT DOCUMENTS

| | | |
|---|---|---|
| 2,348,277 A | 5/1944 | Boothyby et al. |
| 2,377,970 A | 6/1945 | Rives |
| 2,400,077 A | 5/1946 | Dauster |
| 2,514,432 A | 7/1950 | Whitford |
| 2,529,301 A | 11/1950 | Lykken |
| 2,533,271 A | 12/1950 | Livermon |
| 2,564,326 A | 8/1951 | Dray |
| 2,567,150 A | 9/1951 | Frazier et al. |
| 2,576,154 A | 11/1951 | Trautvetter |
| 2,589,439 A | 3/1952 | Seidel |
| 2,601,083 A | 6/1952 | Brouse |
| 2,609,699 A | 9/1952 | Rohn |
| 2,620,513 A | 12/1952 | Cryor et al. |
| 2,643,380 A | 6/1953 | David |
| 2,661,503 A | 12/1953 | Longstreet |
| 2,669,127 A | 2/1954 | Raser, Jr. |
| 2,687,333 A | 8/1954 | Kostolnik |
| 2,690,591 A | 10/1954 | Wallace |
| 2,831,487 A | 12/1954 | Tafilaw |
| 2,709,371 A | 5/1955 | Hale |
| 2,718,255 A | 9/1955 | Samuel |
| 2,735,432 A * | 2/1956 | Hudson .............. A61M 16/0666 128/207.18 |
| 2,738,688 A | 3/1956 | Eaton |
| 2,801,547 A | 8/1957 | Guibert |
| 2,811,967 A | 11/1957 | Stampe |
| 2,819,780 A | 1/1958 | Fallon et al. |
| 2,868,199 A * | 1/1959 | Hudson .............. A61M 16/0666 128/207.18 |
| 2,931,277 A | 4/1960 | La Bombard |
| 2,943,775 A | 7/1960 | Mack et al. |
| 2,969,081 A | 1/1961 | Pipes |
| 2,986,276 A | 5/1961 | Perine |
| 2,998,818 A | 9/1961 | Tabor et al. |
| 3,002,304 A | 10/1961 | Drese et al. |
| 3,004,535 A | 10/1961 | Nielson |
| 3,095,876 A | 7/1963 | Neal |
| 3,096,279 A | 7/1963 | Komline |
| 3,101,029 A | 8/1963 | Johnston et al. |
| 3,197,201 A | 7/1965 | Craig |
| 3,208,505 A | 9/1965 | Craemer |
| 3,234,806 A | 2/1966 | Albrecht et al. |
| 3,245,276 A | 4/1966 | Daon |
| 3,263,292 A | 8/1966 | Fekete |
| 3,362,403 A | 1/1968 | Fleming et al. |
| 3,365,966 A | 1/1968 | Heyer |
| 3,365,967 A | 1/1968 | Moogk |
| 3,377,712 A | 4/1968 | Farkas et al. |
| 3,429,761 A | 2/1969 | Bleher |
| 3,446,880 A | 5/1969 | Enicks |
| 3,513,844 A | 5/1970 | Smith |
| 3,542,116 A | 11/1970 | Machlin |
| 3,563,166 A | 2/1971 | Bajak et al. |
| 3,576,138 A | 4/1971 | Wildhagen |
| 3,585,639 A | 6/1971 | Enicks |
| 3,603,384 A | 9/1971 | Huggins et al. |
| 3,616,818 A | 11/1971 | Case et al. |
| 3,623,377 A | 11/1971 | Lewis et al. |
| 3,632,932 A | 1/1972 | Beaudoin et al. |
| 3,640,143 A | 2/1972 | Krohn-Holm |
| 3,654,640 A | 4/1972 | Katzman |
| 3,656,359 A | 4/1972 | Dorf et al. |
| 3,677,801 A | 7/1972 | Hardy |
| 3,679,214 A | 7/1972 | Boyte |
| 3,682,171 A | 8/1972 | Dali et al. |
| 3,695,264 A | 10/1972 | Laeral |
| 3,718,137 A | 2/1973 | Gaylord |
| 3,734,270 A | 5/1973 | Foody |
| 3,754,552 A | 8/1973 | King |
| 3,783,705 A | 1/1974 | Moogk |
| 3,802,824 A | 4/1974 | Amster et al. |
| 3,834,439 A | 9/1974 | Mirtain |
| 3,839,738 A | 10/1974 | Coslett |
| 3,857,295 A | 12/1974 | Hall et al. |
| 3,858,615 A | 1/1975 | Weigl |
| 3,869,933 A | 3/1975 | Dorf |
| 3,894,900 A | 7/1975 | Redmond, Jr. |
| 3,910,025 A | 10/1975 | Takai |
| 3,915,075 A | 10/1975 | Luke et al. |
| 3,941,637 A | 3/1976 | Masuda et al. |
| 3,944,432 A | 3/1976 | Brinkmann et al. |
| 3,957,282 A | 5/1976 | Finnigan |
| 3,964,328 A | 6/1976 | Redmond, Jr. |
| 3,968,701 A | 7/1976 | Maruyama |
| 4,007,644 A | 2/1977 | Weinberger |
| 4,019,399 A | 4/1977 | Waugh |
| 4,030,300 A | 6/1977 | Thompson |
| 4,033,360 A | 7/1977 | Nienow et al. |
| 4,049,300 A | 9/1977 | Schneider |
| 4,051,741 A | 10/1977 | Marczewski |
| 4,079,633 A | 3/1978 | Cheema et al. |
| 4,106,505 A | 8/1978 | Salter et al. |
| 4,108,011 A | 8/1978 | Gregg et al. |
| 4,120,324 A | 10/1978 | Pahl |
| 4,147,069 A | 4/1979 | Derner |
| 4,168,024 A | 9/1979 | D'Alo |
| 4,196,760 A | 4/1980 | McDaniel et al. |
| 4,198,167 A | 4/1980 | Deal et al. |
| 4,201,205 A | 5/1980 | Bartholomew |
| 4,202,344 A | 5/1980 | Mills et al. |
| 4,241,775 A | 12/1980 | Jackson |
| 4,262,406 A | 4/1981 | Fredrickson et al. |
| 4,263,908 A | 4/1981 | Mizerak |
| 4,266,912 A | 5/1981 | Roman |
| 4,270,888 A | 6/1981 | Kane et al. |
| 4,274,069 A | 6/1981 | Troebel et al. |
| 4,289,230 A | 9/1981 | McGee |
| 4,292,365 A | 9/1981 | Kane et al. |
| 4,330,287 A | 5/1982 | Fischer |
| 4,337,056 A | 6/1982 | Bruns |
| 4,355,741 A | 10/1982 | Kayss |
| 4,359,445 A | 11/1982 | Kane et al. |
| 4,367,067 A | 1/1983 | Chao |
| 4,377,162 A | 3/1983 | Staver |
| 4,409,995 A | 10/1983 | Nichols |
| 4,416,368 A | 11/1983 | Muramatsu et al. |
| 4,417,800 A | 11/1983 | Hirose et al. |
| 4,422,456 A | 12/1983 | Tiep |
| 4,427,226 A | 1/1984 | Shartzer |
| 4,449,959 A | 5/1984 | Matsumura |
| 4,475,248 A | 10/1984 | L'Abbe et al. |
| 4,498,480 A | 2/1985 | Mortensen |
| 4,515,577 A | 5/1985 | Cathey et al. |
| 4,569,468 A | 2/1986 | Neer |
| 4,575,042 A | 3/1986 | Grimland et al. |
| 4,586,915 A | 5/1986 | Cathey et al. |
| 4,599,074 A | 7/1986 | Beckly |
| 4,603,442 A | 8/1986 | Barfield |
| 4,643,701 A | 2/1987 | Meyer et al. |
| 4,655,381 A | 4/1987 | Fontana |
| 4,674,994 A | 6/1987 | Tomiyori et al. |
| 4,706,683 A | 11/1987 | Chilton |
| 4,753,233 A | 6/1988 | Grimes |
| 4,786,274 A | 11/1988 | Robecchi et al. |
| 4,793,342 A | 12/1988 | Haber et al. |
| 4,809,640 A | 3/1989 | Pilley et al. |
| 4,810,153 A | 3/1989 | Armelin |
| 4,810,237 A | 3/1989 | Mantovaara |
| 4,824,502 A | 4/1989 | Nagayoshi et al. |
| 4,866,816 A | 9/1989 | Caveney |
| 4,873,100 A | 10/1989 | Dirksing et al. |
| 4,878,491 A | 11/1989 | McGilvray, III |
| 4,879,117 A | 11/1989 | Rombi |
| 4,885,127 A | 12/1989 | Yokoyama |
| 4,893,999 A | 1/1990 | Chmelir et al. |
| 4,944,442 A | 7/1990 | Buchko |
| 4,960,121 A | 10/1990 | Nelson et al. |
| 4,960,476 A | 10/1990 | White, Jr. et al. |
| 4,981,462 A | 1/1991 | White, Jr. et al. |
| 4,983,184 A | 1/1991 | Steinemann |
| 4,989,599 A | 2/1991 | Carter |
| 4,993,998 A | 2/1991 | Tanaka et al. |
| 5,005,571 A | 4/1991 | Dietz |
| 5,007,462 A | 4/1991 | Kanao |

(56) References Cited

U.S. PATENT DOCUMENTS

| | | |
|---|---|---|
| 5,018,471 A | 5/1991 | Stevens |
| 5,023,023 A | 6/1991 | Elenewski |
| 5,030,174 A | 7/1991 | Eguchi |
| 5,046,993 A | 9/1991 | Macchiarulo et al. |
| 5,052,084 A | 10/1991 | Braun |
| 5,088,162 A | 2/1992 | Allan |
| 5,089,189 A | 2/1992 | Staneluis et al. |
| 5,121,916 A | 6/1992 | Sanchez |
| 5,138,666 A | 8/1992 | Bauer et al. |
| 5,145,188 A | 9/1992 | Bartelt et al. |
| 5,154,446 A | 10/1992 | Blake |
| 5,171,310 A | 12/1992 | Chisena |
| 5,176,249 A | 1/1993 | Esterson et al. |
| 5,192,178 A | 3/1993 | Silbernagel |
| 5,201,398 A | 4/1993 | Clugston |
| 5,214,986 A | 6/1993 | Roberts |
| 5,224,719 A | 7/1993 | Goodspeed |
| 5,237,986 A | 8/1993 | Seppala et al. |
| 5,254,049 A | 10/1993 | Gregg |
| 5,269,296 A | 12/1993 | Landis |
| 5,291,880 A | 3/1994 | Almovist et al. |
| 5,348,000 A | 9/1994 | Teves |
| 5,349,949 A | 9/1994 | Schegerin |
| 5,355,184 A | 10/1994 | Varveris et al. |
| 5,373,980 A | 12/1994 | Rowell et al. |
| 5,390,373 A | 2/1995 | Flory |
| 5,435,321 A | 7/1995 | McMillen et al. |
| 5,441,046 A | 8/1995 | Starr et al. |
| 5,444,750 A | 8/1995 | Stewart et al. |
| 5,457,891 A | 10/1995 | Taylor |
| 5,458,831 A | 10/1995 | Saeki et al. |
| 5,477,852 A | 12/1995 | Landis et al. |
| 5,485,850 A | 1/1996 | Dietz |
| 5,487,461 A | 1/1996 | Focke et al. |
| 5,488,948 A | 2/1996 | Dubruille et al. |
| 5,509,409 A | 4/1996 | Weatherholt |
| 5,510,721 A | 4/1996 | Walles et al. |
| 5,533,506 A | 7/1996 | Wood |
| 5,538,000 A | 7/1996 | Rudolph |
| 5,618,266 A | 4/1997 | Liprie |
| 5,618,267 A | 4/1997 | Palestrant |
| 5,632,837 A | 5/1997 | Carmien |
| 5,640,744 A | 6/1997 | Allan |
| 5,655,643 A | 8/1997 | Bonnet |
| 5,697,107 A | 12/1997 | Takimoto |
| 5,697,362 A | 12/1997 | Albrecht |
| 5,697,363 A | 12/1997 | Hart |
| 5,713,542 A | 2/1998 | Benoit |
| 5,722,218 A | 3/1998 | Lerner |
| 5,762,373 A | 6/1998 | Sugimoto |
| 5,771,886 A | 6/1998 | Maire et al. |
| 5,734,995 A | 7/1998 | Chiang |
| 5,792,018 A | 8/1998 | Winninger |
| 5,827,243 A | 10/1998 | Palestrant |
| 5,861,116 A | 1/1999 | Mandich |
| 5,868,639 A | 2/1999 | Hormann |
| 5,901,607 A | 5/1999 | Kimura |
| 5,911,369 A | 6/1999 | Yamazaki |
| 5,915,542 A | 6/1999 | Swiet |
| 5,924,546 A | 7/1999 | Funaya |
| 5,934,275 A | 8/1999 | Gazzara |
| 5,935,086 A | 8/1999 | Beacon et al. |
| 6,010,304 A | 1/2000 | Moniz et al. |
| 6,019,101 A | 2/2000 | Cotner et al. |
| 6,035,852 A | 3/2000 | Hoftman |
| 6,038,706 A | 3/2000 | Seiler |
| 6,044,844 A | 4/2000 | Kwok et al. |
| 6,050,916 A | 4/2000 | Hunkert |
| 6,065,756 A | 5/2000 | Eignor |
| 6,070,579 A | 6/2000 | Bryant et al. |
| 6,109,578 A | 8/2000 | Guthrie et al. |
| 6,116,637 A | 9/2000 | Takeuchi et al. |
| 6,123,071 A | 9/2000 | Berthon-Jones et al. |
| 6,148,817 A | 11/2000 | Bryant et al. |
| 6,170,249 B1 | 1/2001 | Blase et al. |
| 6,196,090 B1 | 3/2001 | Dumont |
| 6,202,957 B1 | 3/2001 | Bannert et al. |
| 6,209,705 B1 | 4/2001 | Drewitz |
| 6,216,853 B1 | 4/2001 | Fujita |
| 6,244,621 B1 | 6/2001 | Kameyoshi et al. |
| 6,270,595 B1 | 8/2001 | Takayama et al. |
| 6,332,465 B1 | 12/2001 | Xue et al. |
| 6,341,383 B1 | 1/2002 | Beltrani |
| 6,346,800 B1 | 2/2002 | Mano et al. |
| 6,364,086 B1 | 4/2002 | Blaurock et al. |
| 6,367,732 B1 | 4/2002 | Bobren et al. |
| 6,390,915 B2 | 5/2002 | Brantley et al. |
| 6,402,194 B1 | 6/2002 | Takeuchi |
| 6,422,240 B1 | 7/2002 | Levitsky et al. |
| 6,443,507 B1 | 9/2002 | Korvemaker |
| 6,443,552 B1 | 9/2002 | Inoue et al. |
| 6,454,899 B1 | 9/2002 | Campbell et al. |
| 6,478,025 B1 | 11/2002 | Yort et al. |
| 6,478,026 B1 | 11/2002 | Wood |
| 6,484,871 B2 | 11/2002 | van Leeuwen |
| 6,485,384 B1 | 11/2002 | Ochiai et al. |
| 6,488,026 B2 | 12/2002 | Lauer |
| 6,527,474 B2 | 3/2003 | Nabeshima |
| 6,536,435 B1 | 3/2003 | Fecteau et al. |
| 6,561,344 B1 | 5/2003 | Basse |
| 6,571,797 B1 | 6/2003 | Magidson et al. |
| 6,574,449 B2 | 6/2003 | Yoda et al. |
| 6,580,894 B1 | 6/2003 | Kobashigawa |
| 6,588,424 B2 | 7/2003 | Bardel |
| 6,595,215 B2 | 7/2003 | Wood |
| 6,597,888 B1 | 7/2003 | Abe et al. |
| 6,631,253 B2 | 10/2003 | Nakafuji et al. |
| 6,637,434 B2 | 10/2003 | Noble |
| 6,652,691 B1 | 11/2003 | Yu et al. |
| 6,669,712 B1 | 12/2003 | Cardoso |
| 6,684,882 B1 | 2/2004 | Morine |
| 6,688,843 B2 | 2/2004 | Saeki |
| 6,695,771 B2 | 2/2004 | Takada |
| 6,709,552 B2 | 3/2004 | Sakuma et al. |
| 6,776,162 B2 | 8/2004 | Wood |
| 6,783,186 B1 | 8/2004 | McGanty |
| 6,792,787 B1 | 9/2004 | Coalson |
| 6,877,792 B2 | 4/2005 | Kanie et al. |
| 6,886,564 B2 | 5/2005 | Sullivan et al. |
| 6,938,806 B2 | 9/2005 | James |
| 6,941,710 B2 | 9/2005 | Eden |
| 6,962,101 B2 | 11/2005 | Granger |
| 6,981,503 B1 | 1/2006 | Shapiro |
| 6,999,732 B2 | 2/2006 | Fukuda |
| 7,017,577 B2 | 3/2006 | Matich |
| 7,036,503 B2 | 5/2006 | Miyazawa et al. |
| 7,073,688 B2 | 7/2006 | Choi et al. |
| 7,128,070 B2 | 10/2006 | Wiener et al. |
| 7,132,120 B2 | 11/2006 | Okaizumi et al. |
| 7,134,433 B2 | 11/2006 | Sato |
| 7,146,898 B2 | 12/2006 | O'Dwyer |
| 7,185,653 B2 | 3/2007 | Lee |
| 7,190,915 B2 | 3/2007 | Akizuki et al. |
| 7,201,169 B2 | 4/2007 | Wilkie et al. |
| 7,225,811 B2 | 6/2007 | Ruiz et al. |
| 7,242,895 B2 | 7/2007 | Inada et al. |
| 7,243,649 B2 | 7/2007 | Moenning et al. |
| 7,254,353 B2 | 8/2007 | Koyama et al. |
| 7,255,107 B1 | 8/2007 | Gomez |
| 7,257,341 B2 | 8/2007 | Hanamoto et al. |
| 7,260,337 B2 | 8/2007 | Koyama et al. |
| 7,261,105 B2 | 8/2007 | Fukunaga et al. |
| 7,275,541 B2 | 10/2007 | Fukunaga et al. |
| 7,277,651 B2 | 10/2007 | Hanamoto et al. |
| 7,283,763 B2 | 10/2007 | Akizuki et al. |
| 7,305,988 B2 | 12/2007 | Acker et al. |
| 7,308,968 B2 | 12/2007 | Denison |
| 7,331,349 B2 | 2/2008 | Brady et al. |
| 7,391,983 B2 | 6/2008 | Tatematsu et al. |
| 7,406,966 B2 | 8/2008 | Wondka |
| 7,407,279 B2 | 8/2008 | Nakashima |
| 7,416,073 B1 | 8/2008 | Talken et al. |
| 7,426,950 B2 | 9/2008 | Takagi |
| 7,462,154 B2 | 12/2008 | Yamamori et al. |

(56) References Cited

U.S. PATENT DOCUMENTS

| | | |
|---|---|---|
| 7,472,707 B2 | 1/2009 | Wood et al. |
| 7,481,219 B2 | 1/2009 | Lewis et al. |
| 7,481,220 B2 | 1/2009 | Meyer et al. |
| 7,490,359 B2 | 2/2009 | Landis |
| 7,491,351 B2 | 2/2009 | Taylor et al. |
| 7,493,900 B1 | 2/2009 | Japuntich et al. |
| 7,493,902 B2 | 2/2009 | White et al. |
| 7,550,243 B2 | 6/2009 | Matsumoto et al. |
| D597,200 S | 7/2009 | Grimsley |
| 7,588,139 B1 | 9/2009 | Campbell, III |
| 7,597,190 B2 | 10/2009 | Lee |
| 7,618,431 B2 | 11/2009 | Roehm, III et al. |
| 7,635,323 B2 | 12/2009 | Halbridge |
| 7,661,309 B2 | 2/2010 | Lan et al. |
| 7,726,309 B2 | 6/2010 | Ho et al. |
| 7,726,314 B1 | 6/2010 | Ming |
| 7,753,051 B2 | 7/2010 | Burrow et al. |
| 7,768,473 B2 | 8/2010 | Kardohely |
| 7,814,911 B2 | 10/2010 | Bordewick et al. |
| 7,841,026 B2 | 11/2010 | Makris et al. |
| 7,845,352 B2 | 12/2010 | Sleeper et al. |
| 7,850,052 B2 | 12/2010 | Thatcher |
| 7,856,979 B2 | 12/2010 | Doshi et al. |
| 7,856,982 B2 | 12/2010 | Matula, Jr. et al. |
| 7,874,293 B2 | 1/2011 | Gunaratnam et al. |
| 7,878,200 B2 | 2/2011 | Zollinger et al. |
| 7,905,028 B2 | 3/2011 | Sieber |
| 7,907,882 B2 | 3/2011 | Hara |
| 7,971,590 B2 | 7/2011 | Frater et al. |
| 7,975,693 B2 | 7/2011 | Geiselhart et al. |
| 7,993,553 B2 | 8/2011 | Brown |
| 8,042,691 B2 | 10/2011 | Brosseuk et al. |
| 8,136,527 B2 | 3/2012 | Wondka |
| 8,171,934 B1 | 5/2012 | Ho |
| 8,171,935 B2 | 5/2012 | Cortez et al. |
| 8,211,152 B2 | 7/2012 | Snyder et al. |
| 8,224,219 B2 | 7/2012 | Ishino et al. |
| 8,256,421 B2 | 9/2012 | Ho et al. |
| 8,262,864 B2 | 9/2012 | Takamura |
| 8,290,387 B2 | 10/2012 | Hara |
| 8,297,285 B2 | 10/2012 | Henry et al. |
| 8,346,140 B2 | 1/2013 | Yasumoto |
| 8,353,294 B2 | 1/2013 | Frater et al. |
| 8,573,201 B2 | 1/2013 | Rummery et al. |
| 8,365,735 B2 | 2/2013 | Chang |
| 8,365,736 B2 | 2/2013 | Doshi et al. |
| 8,385,801 B2 | 2/2013 | Sugaya |
| 8,393,324 B1 | 3/2013 | Saad |
| 8,393,327 B2 | 3/2013 | Omura et al. |
| 8,402,966 B2 | 3/2013 | Morgan, III et al. |
| 8,434,249 B2 | 5/2013 | Wieneke |
| 8,434,485 B2 | 5/2013 | Osier et al. |
| 8,464,709 B2 | 6/2013 | Wedemeyer |
| 8,478,180 B2 | 7/2013 | Arimoto et al. |
| 8,483,603 B2 | 7/2013 | Nihonyanagi et al. |
| 8,509,668 B2 | 8/2013 | Takemura |
| 8,517,022 B2 | 8/2013 | Halling et al. |
| 8,573,219 B2 | 11/2013 | Wondka |
| 8,596,271 B2 | 12/2013 | Matula, Jr. et al. |
| 8,616,209 B2 | 12/2013 | Amarasinghe |
| 8,631,793 B2 | 1/2014 | Omura et al. |
| 8,631,799 B2 | 1/2014 | Davenport et al. |
| 8,632,455 B2 | 1/2014 | Woodruff et al. |
| 8,636,007 B2 | 1/2014 | Rummery et al. |
| 8,639,313 B2 | 1/2014 | Westbrook et al. |
| 8,640,710 B2 | 2/2014 | Matthews |
| 8,667,964 B2 | 3/2014 | Ho |
| 8,673,433 B2 | 3/2014 | Reif et al. |
| 8,728,280 B2 | 5/2014 | Eagles et al. |
| 8,746,743 B2 | 6/2014 | Kawai et al. |
| 8,752,551 B2 | 6/2014 | Chandran et al. |
| 8,764,927 B2 | 7/2014 | Bäck |
| 8,813,749 B2 | 8/2014 | Hernandez et al. |
| 8,820,377 B2 | 9/2014 | Ueda et al. |
| 8,826,909 B2 | 9/2014 | Nashed |
| 8,838,000 B2 | 9/2014 | Tamura |
| 8,851,078 B2 | 10/2014 | Newman et al. |
| 8,857,435 B2 | 10/2014 | Matula, Jr. et al. |
| 8,887,725 B2 | 11/2014 | Hernandez et al. |
| 8,910,626 B2 | 12/2014 | Matula, Jr. et al. |
| 8,950,404 B2 | 2/2015 | Formica et al. |
| 8,956,373 B2 | 2/2015 | Ford et al. |
| 8,958,735 B2 | 2/2015 | Arimoto |
| 8,978,648 B2 | 3/2015 | Formica et al. |
| 8,985,115 B2 | 3/2015 | Baecke et al. |
| 8,985,117 B2 | 3/2015 | Gunaratnam et al. |
| 8,997,747 B2 | 4/2015 | Hobson et al. |
| 9,010,330 B2 | 4/2015 | Barlow et al. |
| 9,044,562 B2 | 6/2015 | Dillingham et al. |
| 9,061,113 B2 | 6/2015 | Thomas et al. |
| 9,072,855 B2 | 7/2015 | McAuley et al. |
| 9,119,708 B2 | 9/2015 | Wanderer et al. |
| 9,119,975 B2 | 9/2015 | Hu et al. |
| 9,126,767 B2 | 9/2015 | Carter |
| 9,131,894 B2 | 9/2015 | Kato et al. |
| 9,138,554 B2 | 9/2015 | Colbaugh |
| 9,162,034 B2 | 10/2015 | Veliss et al. |
| 9,179,209 B2 | 11/2015 | Emilsson |
| 9,182,062 B2 | 11/2015 | Kwok et al. |
| 9,199,053 B1 | 12/2015 | Allum et al. |
| 9,199,512 B2 | 12/2015 | Ueyoko et al. |
| 9,215,998 B2 | 12/2015 | Reinhold, Jr. et al. |
| 9,216,264 B2 | 12/2015 | Ho |
| 9,247,775 B2 | 2/2016 | Suzuki et al. |
| 9,248,251 B2 | 2/2016 | Gunaratnam |
| 9,259,542 B2 | 2/2016 | Acker et al. |
| 9,273,738 B2 | 3/2016 | Rehfus et al. |
| 9,274,555 B2 | 3/2016 | Otsuka et al. |
| 9,302,064 B2 | 4/2016 | Hussain |
| 9,316,974 B2 | 4/2016 | Yamaguchi et al. |
| 9,320,923 B2 | 4/2016 | Koehler |
| 9,375,545 B2 | 6/2016 | Darkin et al. |
| 9,381,106 B2 | 7/2016 | Gilmer et al. |
| 9,387,300 B2 | 7/2016 | Javier et al. |
| 9,393,378 B2 | 7/2016 | Fearnot et al. |
| 9,415,182 B2 | 8/2016 | Schneider et al. |
| 9,480,958 B2 | 11/2016 | Hollmann et al. |
| 9,492,627 B2 | 11/2016 | Amarasinghe |
| 9,526,857 B2 | 12/2016 | Rummery et al. |
| 9,541,235 B2 | 1/2017 | Travis |
| 9,562,636 B2 | 2/2017 | Zivanovic et al. |
| 9,582,035 B2 | 2/2017 | Connor |
| 9,597,541 B2 | 3/2017 | Hinds et al. |
| 9,599,009 B2 | 3/2017 | Smemo et al. |
| 9,600,030 B2 | 3/2017 | Bailey et al. |
| 9,625,065 B2 | 4/2017 | Feldhahn et al. |
| 9,651,278 B2 | 5/2017 | Palmieri et al. |
| 9,655,783 B2 | 5/2017 | McNeal |
| 9,656,037 B2 | 5/2017 | Guyette |
| 9,668,694 B2 | 6/2017 | Badower |
| 9,685,265 B2 | 6/2017 | Stutz |
| 9,687,195 B2 | 6/2017 | Sims et al. |
| 9,687,619 B2 | 6/2017 | Stuebiger et al. |
| 9,694,930 B2 | 7/2017 | Lane et al. |
| 9,704,412 B2 | 7/2017 | Wells et al. |
| 9,707,366 B2 | 7/2017 | Metelits |
| 9,707,393 B2 | 7/2017 | Hsueh et al. |
| 9,724,546 B2 | 8/2017 | Huggins et al. |
| 9,731,090 B2 | 8/2017 | Ovinsky et al. |
| 9,737,678 B2 | 8/2017 | Formica et al. |
| 9,744,325 B2 | 8/2017 | Ho |
| 9,754,079 B2 | 9/2017 | Knight et al. |
| 9,763,580 B2 | 9/2017 | Sadleir et al. |
| 9,802,018 B2 | 10/2017 | Ging et al. |
| 9,808,589 B2 | 11/2017 | Gunaratnam et al. |
| 9,826,789 B2 | 11/2017 | Dey et al. |
| 9,826,935 B2 | 11/2017 | Martinez et al. |
| 9,827,391 B2 | 11/2017 | Kwok et al. |
| 9,833,591 B1 * | 12/2017 | Ormrod ............... A61M 16/20 |
| 9,833,938 B2 | 12/2017 | Lane et al. |
| 9,839,798 B2 | 12/2017 | Franke et al. |
| 9,867,571 B2 | 1/2018 | Aimone et al. |
| D811,581 S | 2/2018 | Danford |
| 9,889,267 B2 | 2/2018 | Wells et al. |

(56) References Cited

U.S. PATENT DOCUMENTS

| | | |
|---|---|---|
| 9,901,699 B2 | 2/2018 | Veliss et al. |
| 9,909,953 B2 | 3/2018 | Shen et al. |
| 9,925,348 B2 | 3/2018 | Payton et al. |
| 9,937,312 B2 | 4/2018 | Kwok et al. |
| 9,943,443 B2 | 4/2018 | Schwartz |
| 9,949,688 B2 | 4/2018 | Goldman et al. |
| 9,961,969 B2 | 5/2018 | Kawabata et al. |
| 9,981,102 B2 | 5/2018 | Veliss et al. |
| 9,993,605 B2 | 6/2018 | Barlow et al. |
| 9,999,392 B1 | 6/2018 | Wordham et al. |
| 9,999,738 B2 | 6/2018 | Chimenti et al. |
| 10,004,866 B2 | 6/2018 | Davis |
| 10,016,572 B2 | 7/2018 | Haibach |
| 10,022,073 B2 | 7/2018 | Baxi et al. |
| 10,029,062 B2 | 7/2018 | Kwok et al. |
| 10,039,893 B2 | 8/2018 | Frater et al. |
| 10,039,894 B2 | 8/2018 | Walls et al. |
| 10,046,132 B2 | 8/2018 | Eifler et al. |
| 10,046,251 B2 | 8/2018 | Grave et al. |
| 10,052,448 B2 | 8/2018 | Barlow et al. |
| 10,058,259 B1 | 8/2018 | Kryzpow et al. |
| 10,061,352 B1 | 8/2018 | Trail |
| D828,917 S | 9/2018 | Prentice et al. |
| 10,076,251 B2 | 9/2018 | Tu et al. |
| 10,076,624 B2 | 9/2018 | Ozolins et al. |
| 10,080,858 B2 | 9/2018 | Chodkowski et al. |
| 10,086,220 B2 | 10/2018 | Dolan et al. |
| 10,117,599 B2 | 11/2018 | Orr et al. |
| 10,130,785 B2 | 11/2018 | Dravitzki et al. |
| 10,137,271 B2 | 11/2018 | McAuley et al. |
| 10,155,096 B2 | 12/2018 | Amarasinghe |
| 10,159,779 B2 | 12/2018 | Olivarez |
| 10,166,358 B2 | 1/2019 | Swift et al. |
| 10,172,533 B2 | 1/2019 | Kulach et al. |
| D841,149 S | 2/2019 | Collazo et al. |
| D841,150 S | 2/2019 | Collazo et al. |
| 10,194,702 B2 | 2/2019 | Cobbett et al. |
| 10,195,385 B2 | 2/2019 | Lang et al. |
| 10,198,930 B2 | 2/2019 | Melton et al. |
| 10,207,071 B2 | 2/2019 | Hobson et al. |
| 10,226,208 B2 | 3/2019 | Emery et al. |
| 10,231,669 B2 | 3/2019 | Wordham et al. |
| 10,232,136 B2 | 3/2019 | Kapust et al. |
| D849,933 S | 5/2019 | Collazo et al. |
| 10,279,138 B2 | 5/2019 | Ovzinsky et al. |
| D851,750 S | 6/2019 | Collazo et al. |
| D863,544 S | 10/2019 | Collazo et al. |
| 10,500,424 B2 | 12/2019 | Rummery et al. |
| D885,559 S | 5/2020 | Gabriel |
| 10,716,912 B2 | 7/2020 | Holyoake et al. |
| 11,040,165 B2 | 6/2021 | Kooij et al. |
| D950,709 S | 5/2022 | Holyoake et al. |
| 11,324,908 B2 | 5/2022 | Holyoake et al. |
| 2001/0022180 A1 | 9/2001 | Serneia |
| 2002/0055685 A1 | 5/2002 | Levitsky et al. |
| 2002/0068654 A1 | 6/2002 | Luk et al. |
| 2002/0086752 A1 | 7/2002 | Friedrich et al. |
| 2002/0096173 A1 | 7/2002 | Berthon-Jones et al. |
| 2002/0115513 A1 | 8/2002 | Yuan |
| 2002/0155911 A1 | 10/2002 | Hummel et al. |
| 2003/0004025 A1 | 1/2003 | Okuno et al. |
| 2003/0006646 A1 | 1/2003 | Musselman et al. |
| 2003/0092522 A1 | 5/2003 | Sauter et al. |
| 2003/0154980 A1 | 8/2003 | Berthon-Jones et al. |
| 2004/0016432 A1 | 1/2004 | Genger et al. |
| 2004/0094149 A1 | 5/2004 | Natale |
| 2004/0106485 A1 | 6/2004 | Prinsen et al. |
| 2004/0129273 A1 | 7/2004 | Hickle |
| 2004/0134250 A1 | 7/2004 | Durney et al. |
| 2004/0164613 A1 | 8/2004 | Konickson et al. |
| 2004/0244799 A1 | 12/2004 | Landis |
| 2005/0000024 A1 | 1/2005 | Jakubowski |
| 2005/0009655 A1 | 1/2005 | Kubo et al. |
| 2005/0011522 A1 | 1/2005 | Ho et al. |
| 2005/0028822 A1 | 2/2005 | Sleeper et al. |
| 2005/0090618 A1 | 4/2005 | Okuno |
| 2005/0113200 A1 | 5/2005 | Okuno et al. |
| 2005/0199239 A1 | 9/2005 | Lang et al. |
| 2005/0205096 A1 | 9/2005 | Matula et al. |
| 2005/0215373 A1 | 9/2005 | Lodge |
| 2005/0265151 A1 | 12/2005 | Kimura et al. |
| 2006/0084542 A1 | 4/2006 | Kubo et al. |
| 2006/0112962 A1 | 6/2006 | Tebbutt et al. |
| 2006/0163039 A1 | 7/2006 | Marshall et al. |
| 2006/0213521 A1 | 9/2006 | Radney |
| 2006/0270504 A1 | 11/2006 | Krause |
| 2007/0045152 A1 | 3/2007 | Kwok et al. |
| 2007/0060429 A1 | 3/2007 | Ono et al. |
| 2007/0087878 A1 | 4/2007 | Ogawa et al. |
| 2007/0105674 A1 | 5/2007 | Hogn |
| 2007/0107732 A1 | 5/2007 | Dennis et al. |
| 2007/0235034 A1 | 10/2007 | Weaver |
| 2007/0246043 A1 | 10/2007 | Kwok et al. |
| 2007/0290248 A1 | 12/2007 | Weis |
| 2008/0000472 A1 | 1/2008 | Wall |
| 2008/0038101 A1 | 2/2008 | Klatt |
| 2008/0047560 A1 | 2/2008 | Veliss et al. |
| 2008/0060649 A1* | 3/2008 | Veliss ............... A62B 18/025 |
| | | 128/207.18 |
| 2008/0064548 A1 | 3/2008 | Abate et al. |
| 2008/0099022 A1 | 5/2008 | Gebrewold et al. |
| 2008/0142015 A1* | 6/2008 | Groll ............... A61M 16/0694 |
| | | 128/206.24 |
| 2008/0194997 A1 | 8/2008 | Zhang |
| 2009/0028617 A1 | 1/2009 | Katakabe et al. |
| 2009/0042683 A1 | 2/2009 | Tohara |
| 2009/0054189 A1 | 2/2009 | Tani et al. |
| 2009/0055999 A1 | 3/2009 | Garcia |
| 2009/0091432 A1 | 4/2009 | Koser et al. |
| 2009/0183739 A1 | 7/2009 | Wondka |
| 2009/0191998 A1 | 7/2009 | De Meco et al. |
| 2009/0199610 A1 | 8/2009 | Sato et al. |
| 2009/0223518 A1 | 9/2009 | Kwok et al. |
| 2009/0234201 A1 | 9/2009 | Huang et al. |
| 2009/0254012 A1 | 10/2009 | Gavriely et al. |
| 2009/0283096 A1 | 11/2009 | Cerbini |
| 2009/0291796 A1 | 11/2009 | Mitsutomi et al. |
| 2009/0321191 A1 | 12/2009 | Broyan |
| 2010/0012221 A1 | 1/2010 | Lien |
| 2010/0018534 A1 | 1/2010 | Veliss et al. |
| 2010/0122704 A1 | 5/2010 | Moenning, Jr. |
| 2010/0152564 A1 | 6/2010 | Nguyen et al. |
| 2010/0261019 A1 | 10/2010 | Sano et al. |
| 2011/0067704 A1 | 3/2011 | Kooij et al. |
| 2011/0108041 A1 | 5/2011 | Sather et al. |
| 2011/0120460 A1 | 5/2011 | Wallnewitz et al. |
| 2011/0185541 A1 | 8/2011 | Guptill |
| 2011/0197893 A1 | 8/2011 | Ziv et al. |
| 2011/0247619 A1 | 10/2011 | Formica et al. |
| 2011/0259331 A1* | 10/2011 | Witt .................... A61M 16/20 |
| | | 128/204.18 |
| 2011/0259335 A1 | 10/2011 | Sullivan |
| 2011/0272986 A1 | 11/2011 | Iacovoni et al. |
| 2011/0284347 A1 | 11/2011 | MacLachlan et al. |
| 2011/0308517 A1 | 12/2011 | Emilsson et al. |
| 2012/0017901 A1 | 1/2012 | Mainusch et al. |
| 2012/0029145 A1 | 2/2012 | Brown |
| 2012/0030912 A1 | 2/2012 | Turdjian et al. |
| 2012/0035435 A1 | 2/2012 | Choi et al. |
| 2012/0047614 A1 | 3/2012 | Choi |
| 2012/0049533 A1 | 3/2012 | Kelly |
| 2012/0065621 A1 | 3/2012 | Steegers et al. |
| 2012/0071285 A1 | 3/2012 | Tay |
| 2012/0094795 A1 | 4/2012 | Wang |
| 2012/0125338 A1 | 5/2012 | Yarahmadi |
| 2012/0150119 A1* | 6/2012 | Schaeffer ............ A61M 27/002 |
| | | 604/164.11 |
| 2012/0198952 A1 | 8/2012 | Mamba |
| 2012/0298104 A1 | 11/2012 | Müller et al. |
| 2012/0318270 A1* | 12/2012 | McAuley ............ A61M 16/161 |
| | | 128/205.25 |
| 2012/0318271 A1 | 12/2012 | Ho |
| 2012/0318274 A1 | 12/2012 | Ho |
| 2012/0325219 A1 | 12/2012 | Smith et al. |

(56) References Cited

U.S. PATENT DOCUMENTS

| | | |
|---|---|---|
| 2013/0008448 A1 | 1/2013 | Todd |
| 2013/0019870 A1 | 1/2013 | Collazo et al. |
| 2013/0052014 A1 | 2/2013 | Kelly |
| 2013/0133646 A1 | 5/2013 | Rose et al. |
| 2013/0199537 A1* | 8/2013 | Formica ............ A61M 16/0816 128/205.25 |
| 2013/0206139 A1 | 8/2013 | Krepel et al. |
| 2013/0211208 A1 | 8/2013 | Varadan et al. |
| 2013/0230674 A1 | 9/2013 | Curti et al. |
| 2013/0237355 A1 | 9/2013 | Lubojatzky |
| 2013/0237397 A1 | 9/2013 | Seiler |
| 2013/0276781 A1 | 10/2013 | Steelman et al. |
| 2014/0053844 A1 | 2/2014 | Rummery et al. |
| 2014/0102456 A1 | 4/2014 | Ovizinsky et al. |
| 2014/0116429 A1 | 5/2014 | Patil et al. |
| 2014/0186909 A1 | 7/2014 | Calzia et al. |
| 2014/0261440 A1 | 9/2014 | Chodkowski |
| 2014/0264975 A1 | 9/2014 | Bath et al. |
| 2014/0283841 A1 | 9/2014 | Chodkowski et al. |
| 2014/0299131 A1 | 10/2014 | Chodkowski et al. |
| 2014/0311492 A1 | 10/2014 | Stuebiger et al. |
| 2014/0345604 A1 | 11/2014 | Wang et al. |
| 2015/0059764 A1 | 3/2015 | Metelits |
| 2015/0065904 A1 | 3/2015 | Stenzler et al. |
| 2015/0075524 A1* | 3/2015 | Millar ................. A61M 16/04 128/203.27 |
| 2015/0139703 A1 | 5/2015 | Takazawa |
| 2015/0151070 A1 | 6/2015 | Capra et al. |
| 2015/0157220 A1 | 6/2015 | Fish et al. |
| 2015/0201867 A1 | 7/2015 | Peindl et al. |
| 2015/0231355 A1 | 8/2015 | Kuo |
| 2015/0246198 A1 | 9/2015 | Bearne et al. |
| 2015/0246200 A1 | 9/2015 | Neff et al. |
| 2015/0250237 A1 | 9/2015 | Shoham et al. |
| 2015/0258823 A1 | 9/2015 | Otsuka et al. |
| 2015/0352306 A1 | 12/2015 | Scheiner et al. |
| 2015/0355585 A1 | 12/2015 | Suzuki et al. |
| 2015/0360060 A1 | 12/2015 | Dehmke et al. |
| 2016/0022954 A1 | 1/2016 | Bath et al. |
| 2016/0030696 A1 | 2/2016 | Klenner et al. |
| 2016/0089261 A1 | 3/2016 | Quinn |
| 2016/0106367 A1 | 4/2016 | Jorov et al. |
| 2016/0114118 A1 | 4/2016 | Gunaratnam et al. |
| 2016/0144144 A1 | 5/2016 | Smith et al. |
| 2016/0150958 A1 | 6/2016 | Kranz |
| 2016/0153853 A1 | 6/2016 | Brenner et al. |
| 2016/0157779 A1 | 6/2016 | Baxi et al. |
| 2016/0199612 A1 | 7/2016 | Foote et al. |
| 2016/0228666 A1 | 8/2016 | Sullivan et al. |
| 2016/0256653 A1 | 9/2016 | McAuley et al. |
| 2016/0256655 A1 | 9/2016 | Mah et al. |
| 2016/0297505 A1 | 10/2016 | Caprice et al. |
| 2016/0317770 A1 | 11/2016 | Kushida et al. |
| 2016/0324487 A1 | 11/2016 | Guo et al. |
| 2016/0346530 A1 | 12/2016 | Jeffrey et al. |
| 2016/0361512 A1 | 12/2016 | Lawrenson et al. |
| 2016/0367189 A1 | 12/2016 | Aimone et al. |
| 2016/0375205 A1 | 12/2016 | Cressman |
| 2016/0377149 A1 | 12/2016 | Furusawa |
| 2017/0002905 A1 | 1/2017 | Sessions |
| 2017/0028150 A1 | 2/2017 | McNulty |
| 2017/0042478 A1 | 2/2017 | Zheng et al. |
| 2017/0043113 A1 | 2/2017 | Ng et al. |
| 2017/0065785 A1 | 3/2017 | Roberts |
| 2017/0065787 A1 | 3/2017 | Rummery et al. |
| 2017/0081124 A1 | 3/2017 | Steinhert |
| 2017/0151408 A1 | 6/2017 | Lun et al. |
| 2017/0157435 A1 | 6/2017 | Choi |
| 2017/0157436 A1 | 6/2017 | Hosmer |
| 2017/0173290 A1 | 6/2017 | Pedro et al. |
| 2017/0202514 A1 | 7/2017 | Nousiainen et al. |
| 2017/0203071 A1 | 7/2017 | Lawrenson et al. |
| 2017/0224065 A1 | 8/2017 | Nipke et al. |
| 2017/0224943 A1 | 8/2017 | Creusot et al. |
| 2017/0266403 A1 | 9/2017 | Prentice et al. |
| 2017/0274167 A1 | 9/2017 | Huddart et al. |
| 2017/0281394 A1 | 10/2017 | Viken |
| 2017/0304576 A1 | 10/2017 | Lawrenson et al. |
| 2017/0304577 A1 | 10/2017 | Bearne et al. |
| 2017/0312465 A1 | 11/2017 | Kwok et al. |
| 2017/0312468 A1 | 11/2017 | Formica et al. |
| 2017/0314641 A1 | 11/2017 | Kamba et al. |
| 2017/0333662 A1 | 11/2017 | Ovizinsky et al. |
| 2017/0347923 A1 | 12/2017 | Roh |
| 2017/0348500 A1 | 12/2017 | Johnson et al. |
| 2018/0001046 A1 | 1/2018 | Rummery et al. |
| 2018/0036503 A1 | 2/2018 | Mohamed |
| 2018/0036505 A1 | 2/2018 | Bornholdt et al. |
| 2018/0043121 A1 | 2/2018 | Goulitski et al. |
| 2018/0043123 A1 | 2/2018 | Lei |
| 2018/0064897 A1 | 3/2018 | Kwok et al. |
| 2018/0064968 A1 | 3/2018 | Taslagyan |
| 2018/0071476 A1 | 3/2018 | Neff |
| 2018/0077481 A1 | 3/2018 | Kim |
| 2018/0078727 A1 | 3/2018 | Johnson et al. |
| 2018/0085544 A1 | 3/2018 | Holyoake et al. |
| 2018/0099112 A1 | 4/2018 | Belenkiy |
| 2018/0160749 A1 | 6/2018 | Kim |
| 2018/0162697 A1 | 6/2018 | Schmidt et al. |
| 2018/0185598 A1 | 7/2018 | Olsen et al. |
| 2018/0192727 A1 | 7/2018 | Chen |
| 2018/0192954 A1 | 7/2018 | Lumme et al. |
| 2018/0193581 A1 | 7/2018 | Frater et al. |
| 2018/0207385 A1 | 7/2018 | Freestone et al. |
| 2018/0213918 A1 | 8/2018 | Graves |
| 2018/0214655 A1 | 8/2018 | Kooij et al. |
| 2018/0214656 A1 | 8/2018 | McLaren |
| 2018/0221191 A1 | 8/2018 | Scott et al. |
| 2018/0236198 A1 | 8/2018 | Veliss et al. |
| 2018/0236276 A1 | 8/2018 | Moon |
| 2018/0244499 A1 | 8/2018 | Zapf |
| 2018/0250482 A1 | 9/2018 | Barlow et al. |
| 2018/0256844 A1 | 9/2018 | Galgali et al. |
| 2018/0264220 A1 | 9/2018 | Hurt |
| 2018/0289914 A1 | 10/2018 | Kwok et al. |
| 2018/0301224 A1 | 10/2018 | Matichuk et al. |
| 2018/0318540 A1 | 11/2018 | Barlow et al. |
| 2018/0338704 A1 | 11/2018 | Laman et al. |
| 2018/0355682 A1 | 12/2018 | Pessin et al. |
| 2018/0361096 A1 | 12/2018 | Grashow et al. |
| 2018/0361099 A1 | 12/2018 | Wells |
| 2019/0009046 A1 | 1/2019 | Kooij et al. |
| 2019/0021668 A1 | 1/2019 | Fujita |
| 2019/0038226 A1 | 2/2019 | Davidson et al. |
| 2019/0053568 A1 | 2/2019 | Choukeir |
| 2019/0062118 A1 | 2/2019 | Valjus et al. |
| 2019/0076613 A1 | 3/2019 | Amarasinghe |
| 2019/0082968 A1 | 3/2019 | Karnik et al. |
| 2019/0083733 A1 | 3/2019 | Gulliver et al. |
| 2019/0090763 A1 | 3/2019 | Woerlee et al. |
| 2019/0091068 A1 | 3/2019 | Schwartz |
| 2019/0091430 A1 | 3/2019 | Barlow et al. |
| 2019/0091433 A1 | 3/2019 | Barlow et al. |
| 2019/0134332 A1 | 5/2019 | Kwok et al. |
| 2019/0151589 A1 | 5/2019 | Kwok et al. |
| 2019/0175861 A1 | 6/2019 | Holyoake et al. |
| 2019/0209799 A1 | 6/2019 | Ovzinsky et al. |
| 2019/0344036 A1 | 11/2019 | O'Donnell et al. |
| 2020/0360637 A1 | 11/2020 | Holyoake et al. |
| 2020/0368479 A1* | 11/2020 | Flynn ................... A61M 16/16 |

FOREIGN PATENT DOCUMENTS

| | | |
|---|---|---|
| AU | 505422 B2 | 11/1979 |
| AU | 198317585 A | 2/1984 |
| AU | 542540 B2 | 2/1985 |
| AU | 543022 B2 | 3/1985 |
| AU | 580417 B | 1/1989 |
| AU | 587397 B | 8/1989 |
| AU | 1999063955 A1 | 3/2001 |
| AU | 2002330895 A1 | 5/2003 |
| AU | 2004203100 A1 | 7/2004 |
| AU | 2004202274 | 12/2004 |
| AU | 20042666693 B2 | 3/2005 |

(56) References Cited

FOREIGN PATENT DOCUMENTS

| | | |
|---|---|---|
| AU | 2004303643 A1 | 7/2005 |
| AU | 784321 B2 | 3/2006 |
| AU | 2005287747 A1 | 3/2006 |
| AU | 2008203174 A1 | 8/2008 |
| AU | 2005206344 B2 | 9/2009 |
| AU | 2007245691 B2 | 12/2010 |
| AU | 2006299938 B2 | 5/2011 |
| AU | 2005253641 B2 | 12/2011 |
| AU | 2009326861 B2 | 12/2013 |
| AU | 2013200267 B2 | 4/2014 |
| AU | 2011308094 B2 | 5/2014 |
| AU | 2011308095 B2 | 10/2014 |
| AU | 2008/316306 B2 | 2/2015 |
| AU | 2014201200 B2 | 8/2015 |
| AU | 2014224136 B2 | 4/2016 |
| AU | 2016101634 A4 | 10/2016 |
| AU | 2017216448 A1 | 3/2018 |
| AU | 2018100107 A4 | 3/2018 |
| AU | 2018201087 | 4/2018 |
| CA | 1058914 A | 7/1979 |
| CA | 1137793 A1 | 12/1982 |
| CA | 1142234 A1 | 3/1983 |
| CA | 1158071 A1 | 12/1983 |
| CA | 1165593 A | 4/1984 |
| CA | 1178752 A | 12/1984 |
| CA | 1267257 A | 4/1990 |
| CA | 2004020 A1 | 5/1990 |
| CA | 1291349 C | 10/1991 |
| CA | 1307395 C | 9/1992 |
| CA | 2087812 C | 12/1995 |
| CA | 2269819 A1 | 6/1998 |
| CA | 2246823 A1 | 3/1999 |
| CA | 2263627 A1 | 9/1999 |
| CA | 2214732 C | 5/2002 |
| CA | 2310350 C | 12/2004 |
| CA | 2587526 A1 | 5/2006 |
| CA | 2798822 A1 | 11/2011 |
| CA | 2750638 A1 | 2/2013 |
| CA | 2602653 C | 1/2016 |
| CH | 701564 A2 | 1/2011 |
| CH | 701918 A2 | 3/2011 |
| CN | 2114727 U | 9/1992 |
| CN | 2116121 U | 9/1992 |
| CN | 2305523 Y | 1/1999 |
| CN | 2334953 Y | 8/1999 |
| CN | 1826151 A | 8/2006 |
| CN | 2903582 Y | 5/2007 |
| CN | 201043586 Y | 4/2008 |
| CN | 101204328 A | 6/2008 |
| CN | 101495170 | 7/2009 |
| CN | 101516427 | 8/2009 |
| CN | 101629612 A | 1/2010 |
| CN | 201496473 U | 6/2010 |
| CN | 202040271 U | 11/2011 |
| CN | 202251664 U | 5/2012 |
| CN | 102537208 A | 7/2012 |
| CN | 102762249 A | 10/2012 |
| CN | 103153379 A | 6/2013 |
| CN | 203033307 U | 7/2013 |
| CN | 203486450 U | 3/2014 |
| CN | 203614658 U | 5/2014 |
| CN | 203614659 U | 5/2014 |
| CN | 104114637 A | 10/2014 |
| CN | 104254709 A | 12/2014 |
| CN | 104295665 A | 1/2015 |
| CN | 104295710 A | 1/2015 |
| CN | 104302337 | 1/2015 |
| CN | 104315082 A | 1/2015 |
| CN | 104455310 A | 3/2015 |
| CN | 204200955 U | 3/2015 |
| CN | 104476789 A | 4/2015 |
| CN | 104524675 A | 4/2015 |
| CN | 204312619 U | 5/2015 |
| CN | 204327859 U | 5/2015 |
| CN | 204344806 U | 5/2015 |
| CN | 105102048 A | 11/2015 |
| CN | 204736990 U | 11/2015 |
| CN | 204805430 U | 11/2015 |
| CN | 105190089 A | 12/2015 |
| CN | 204985507 U | 1/2016 |
| CN | 205226231 U | 5/2016 |
| CN | 105752809 A | 7/2016 |
| CN | 205534007 U | 8/2016 |
| CN | 205555824 U | 9/2016 |
| CN | 106005898 A | 10/2016 |
| CN | 205639467 U | 10/2016 |
| CN | 106170641 A | 11/2016 |
| CN | 106352034 A | 1/2017 |
| CN | 205859041 U | 1/2017 |
| CN | 106438881 A | 2/2017 |
| CN | 106763488 A | 5/2017 |
| CN | 106969092 A | 7/2017 |
| CN | 107191539 A | 9/2017 |
| CN | 206592477 U | 10/2017 |
| CN | 206770516 U | 12/2017 |
| CN | 206988367 U | 2/2018 |
| CN | 108087494 A | 5/2018 |
| CN | 207406705 U | 5/2018 |
| CN | 108180254 A | 6/2018 |
| CN | 108506433 A | 9/2018 |
| CN | 108996374 A | 12/2018 |
| CN | 109073041 A | 12/2018 |
| CN | 208237006 U | 12/2018 |
| CN | 208381203 U | 1/2019 |
| CN | 208381207 U | 1/2019 |
| CN | 208417402 U | 1/2019 |
| CN | 208457110 U | 2/2019 |
| CN | 208519118 U | 2/2019 |
| DE | 2726319 A1 | 12/1978 |
| DE | 2836030 A1 | 3/1979 |
| DE | 3542990 A1 | 6/1987 |
| DE | 4101293 A1 | 10/1991 |
| DE | 10315636 A1 | 10/2004 |
| DE | 102011011500 A1 | 12/2011 |
| DK | 434583 A | 3/1985 |
| DK | 198304345 A | 3/1985 |
| EP | 0 001 518 A1 | 4/1979 |
| EP | 0 011 986 B1 | 12/1982 |
| EP | 0 087 969 A1 | 9/1983 |
| EP | 0125424 A1 | 11/1984 |
| EP | 0 050 174 B1 | 5/1985 |
| EP | 0151396 A2 | 8/1985 |
| EP | 0180143 A2 | 5/1986 |
| EP | 0201562 A1 | 11/1986 |
| EP | 0255333 A1 | 2/1988 |
| EP | 0278545 A1 | 8/1988 |
| EP | 0285406 A2 | 10/1988 |
| EP | 0316197 A1 | 5/1989 |
| EP | 0320698 A2 | 6/1989 |
| EP | 0327873 A1 | 8/1989 |
| EP | 0384049 A1 | 8/1990 |
| EP | 0 398 562 B1 | 11/1990 |
| EP | 0 412 453 B1 | 2/1991 |
| EP | 0 482 735 A2 | 4/1992 |
| EP | 0 506 490 A1 | 9/1992 |
| EP | 0571178 A1 | 11/1993 |
| EP | 0633408 A2 | 1/1995 |
| EP | 0677682 A1 | 10/1995 |
| EP | 0933094 A2 | 1/1998 |
| EP | 0 847 940 B1 | 5/1999 |
| EP | 0 529 053 B1 | 1/2000 |
| EP | 0697225 B1 | 5/2000 |
| EP | 0 928 757 B1 | 4/2002 |
| EP | 0 917 692 B1 | 9/2002 |
| EP | 1 239 184 A2 | 9/2002 |
| EP | 1190616 B1 | 12/2002 |
| EP | 1026038 B1 | 9/2004 |
| EP | 1660004 A2 | 5/2006 |
| EP | 1391222 B1 | 10/2006 |
| EP | 1749705 A2 | 2/2007 |
| EP | 1452770 B1 | 9/2007 |
| EP | 1837439 A2 | 9/2007 |
| EP | 0 965 670 B1 | 1/2008 |
| EP | 1929179 A1 | 6/2008 |

(56) References Cited

FOREIGN PATENT DOCUMENTS

| | | |
|---|---|---|
| EP | 2159448 A1 | 3/2010 |
| EP | 2163424 A1 | 3/2010 |
| EP | 2489899 A1 | 8/2012 |
| EP | 1481702 B1 | 9/2012 |
| EP | 1740247 B1 | 9/2012 |
| EP | 1787670 B1 | 10/2012 |
| EP | 2605993 A1 | 6/2013 |
| EP | 2101855 B1 | 8/2013 |
| EP | 2621572 A1 | 8/2013 |
| EP | 2670491 A2 | 12/2013 |
| EP | 2051760 B1 | 3/2014 |
| EP | 2717954 A1 | 4/2014 |
| EP | 2744554 A1 | 6/2014 |
| EP | 1623745 B1 | 7/2014 |
| EP | 2425868 B1 | 11/2014 |
| EP | 2844325 A1 | 3/2015 |
| EP | 2846064 A1 | 3/2015 |
| EP | 2894115 A1 | 7/2015 |
| EP | 2519295 B1 | 9/2015 |
| EP | 2717806 B1 | 9/2015 |
| EP | 2928532 A1 | 10/2015 |
| EP | 2428240 B1 | 2/2016 |
| EP | 2481435 B1 | 2/2016 |
| EP | 2022528 B1 | 3/2016 |
| EP | 2046430 B1 | 4/2016 |
| EP | 2481434 B1 | 4/2016 |
| EP | 2428241 B1 | 7/2016 |
| EP | 3053621 A1 | 8/2016 |
| EP | 3085405 A1 | 10/2016 |
| EP | 2621573 B1 | 12/2016 |
| EP | 3130371 A1 | 2/2017 |
| EP | 3157601 A1 | 4/2017 |
| EP | 2723430 B1 | 7/2017 |
| EP | 1773195 B1 | 8/2017 |
| EP | 3231470 A1 | 10/2017 |
| EP | 3266482 A1 | 1/2018 |
| EP | 3034286 B1 | 5/2018 |
| EP | 3323458 A1 | 5/2018 |
| EP | 3235544 B1 | 8/2018 |
| EP | 1765443 B1 | 1/2019 |
| EP | 2828183 B1 | 3/2019 |
| EP | 2114500 B1 | 6/2019 |
| EP | 2844325 B1 | 11/2019 |
| FR | 2394457 A1 | 1/1979 |
| FR | 2660039 A3 | 9/1991 |
| FR | 2861445 A1 | 4/2005 |
| GB | 190419761 A | 7/1905 |
| GB | 190826914 A | 7/1909 |
| GB | 191228764 A | 5/1913 |
| GB | 155079 A | 12/1920 |
| GB | 216224 A | 5/1924 |
| GB | 268133 A | 3/1927 |
| GB | 311747 A | 5/1929 |
| GB | 344485 A | 3/1931 |
| GB | 353777 A | 7/1931 |
| GB | 390005 A | 3/1933 |
| GB | 395932 A | 7/1933 |
| GB | 425152 A | 3/1935 |
| GB | 443649 A | 3/1936 |
| GB | 474843 A | 11/1937 |
| GB | 477368 A | 12/1937 |
| GB | 486401 A | 6/1938 |
| GB | 500525 A | 2/1939 |
| GB | 505229 A | 5/1939 |
| GB | 506795 A | 6/1939 |
| GB | 509048 A | 6/1939 |
| GB | 514910 A | 11/1939 |
| GB | 566171 A | 12/1944 |
| GB | 570861 A | 7/1945 |
| GB | 571283 A | 8/1945 |
| GB | 573704 A | 12/1945 |
| GB | 746711 A | 3/1956 |
| GB | 755865 A | 8/1956 |
| GB | 814268 A | 6/1959 |
| GB | 840638 A | 7/1960 |
| GB | 843810 A | 8/1960 |
| GB | 877472 A | 9/1961 |
| GB | 877473 A | 9/1961 |
| GB | 915886 A | 1/1963 |
| GB | 925067 A | 5/1963 |
| GB | 945622 A | 1/1964 |
| GB | 962714 A | 7/1964 |
| GB | 971939 A | 10/1964 |
| GB | 1095321 A | 12/1966 |
| GB | 1065362 A | 4/1967 |
| GB | 1073129 A | 6/1967 |
| GB | 1105267 A | 3/1968 |
| GB | 1197700 A | 7/1970 |
| GB | 1215682 A | 12/1970 |
| GB | 1229390 A | 4/1971 |
| GB | 1265008 A | 3/1972 |
| GB | 1294104 A | 10/1972 |
| GB | 1357935 A | 6/1974 |
| GB | 1364838 A | 8/1974 |
| GB | 1369198 A | 10/1974 |
| GB | 1369199 A | 10/1974 |
| GB | 1369348 A | 10/1974 |
| GB | 1380573 A | 1/1975 |
| GB | 1400431 A | 7/1975 |
| GB | 1427985 A | 3/1976 |
| GB | 1483216 A | 8/1977 |
| GB | 1492009 A | 11/1977 |
| GB | 1498893 A | 1/1978 |
| GB | 1499105 A | 1/1978 |
| GB | 2011577 A | 7/1979 |
| GB | 2024605 A | 1/1980 |
| GB | 1603557 A | 11/1981 |
| GB | 2092704 A | 8/1982 |
| GB | 2116287 A | 9/1983 |
| GB | 2155134 A | 9/1985 |
| GB | 2194207 A | 3/1988 |
| GB | 2218726 A | 11/1989 |
| GB | 2266614 A | 11/1993 |
| GB | 2266671 A | 11/1993 |
| GB | 2373777 A | 10/2002 |
| GB | 2439152 A | 12/2007 |
| GB | 2467122 A | 7/2010 |
| GB | 2475044 A | 5/2011 |
| GB | 2500860 A | 10/2013 |
| GB | 2529238 A | 2/2016 |
| GB | 2540153 B | 10/2018 |
| IT | 1117812 B | 2/1986 |
| JP | S51151844 U | 12/1976 |
| JP | S52160041 U | 12/1977 |
| JP | S55119441 U | 9/1980 |
| JP | S55152945 A | 11/1980 |
| JP | S55161948 U | 12/1980 |
| JP | S55175650 U | 12/1980 |
| JP | S564057 U | 1/1981 |
| JP | S5683635 A | 7/1981 |
| JP | S5684146 U | 7/1981 |
| JP | S5689057 U | 7/1981 |
| JP | S56109939 A | 8/1981 |
| JP | S56141245 U | 10/1981 |
| JP | S56167955 A | 12/1981 |
| JP | S5723451 U | 2/1982 |
| JP | S5794153 A | 6/1982 |
| JP | S58106642 U | 7/1983 |
| JP | S58134249 A | 8/1983 |
| JP | S58169244 U | 10/1983 |
| JP | S58184338 A | 10/1983 |
| JP | S58187637 A | 11/1983 |
| JP | S58220720 A | 12/1983 |
| JP | S5945346 U | 3/1984 |
| JP | S5977146 A | 5/1984 |
| JP | S6040846 U | 3/1985 |
| JP | S6095233 A | 5/1985 |
| JP | S60113843 A | 6/1985 |
| JP | S60234172 A | 11/1985 |
| JP | H0126928 Y2 | 2/1986 |
| JP | S61127942 A | 6/1986 |
| JP | S6280321 A | 4/1987 |
| JP | S62159857 A | 7/1987 |
| JP | S636246 A | 1/1988 |

(56) References Cited

FOREIGN PATENT DOCUMENTS

| | | |
|---|---|---|
| JP | H0159888 B2 | 12/1989 |
| JP | H01307544 A | 12/1989 |
| JP | H0221046 A | 1/1990 |
| JP | H0242230 A | 2/1990 |
| JP | H0269225 A | 3/1990 |
| JP | H0299236 A | 4/1990 |
| JP | H02122910 A | 5/1990 |
| JP | H02199339 A | 8/1990 |
| JP | H0248773 B2 | 10/1990 |
| JP | H02248740 A | 10/1990 |
| JP | H0362536 B2 | 9/1991 |
| JP | H0449076 A | 2/1992 |
| JP | H0513821 B2 | 2/1993 |
| JP | H0557457 B2 | 8/1993 |
| JP | H0562656 B2 | 9/1993 |
| JP | H0650398 A | 2/1994 |
| JP | H0627528 B2 | 4/1994 |
| JP | H0630548 U | 4/1994 |
| JP | H0694081 A | 4/1994 |
| JP | H0640503 U | 5/1994 |
| JP | H06123333 A | 5/1994 |
| JP | H0665650 U | 9/1994 |
| JP | H0640352 Y2 | 10/1994 |
| JP | H06328590 A | 11/1994 |
| JP | H074469 A | 1/1995 |
| JP | H07243483 A | 9/1995 |
| JP | 2500290 B2 | 5/1996 |
| JP | 2516855 B2 | 7/1996 |
| JP | 2534192 B2 | 9/1996 |
| JP | 2566319 B2 | 12/1996 |
| JP | H08326851 A | 12/1996 |
| JP | H0942381 A | 2/1997 |
| JP | H09257103 A | 9/1997 |
| JP | H09329205 A | 12/1997 |
| JP | H1078086 A | 3/1998 |
| JP | H10132031 A | 5/1998 |
| JP | H10132061 A | 5/1998 |
| JP | H10141446 A | 5/1998 |
| JP | H10153239 A | 6/1998 |
| JP | H10153243 A | 6/1998 |
| JP | H10205584 A | 8/1998 |
| JP | H10213183 A | 8/1998 |
| JP | 2802039 B2 | 9/1998 |
| JP | H10235742 A | 9/1998 |
| JP | H10311390 A | 11/1998 |
| JP | H10318336 A | 12/1998 |
| JP | H11132291 A | 5/1999 |
| JP | H11166596 A | 6/1999 |
| JP | 2002-098195 A | 4/2002 |
| JP | 2002-098196 A | 4/2002 |
| JP | 2002-098201 A | 4/2002 |
| JP | 2002-098202 A | 4/2002 |
| JP | 2004-225749 A | 8/2004 |
| JP | 3143503 U | 7/2008 |
| JP | 2013-514821 A | 5/2013 |
| JP | 2014-516601 | 7/2014 |
| JP | 2014-521471 | 8/2014 |
| JP | 2016-517765 A | 6/2016 |
| JP | 2016-124160 A | 7/2016 |
| JP | 2016-135213 A | 7/2016 |
| JP | 2016-183707 A | 10/2016 |
| JP | 2016-183779 A | 10/2016 |
| JP | 6159907 B1 | 7/2017 |
| JP | WO2016/047052 A1 | 7/2017 |
| JP | 2017-177545 A | 10/2017 |
| JP | 2018-025296 A | 2/2018 |
| JP | 2017-082377 A | 6/2018 |
| JP | 6371763 B2 | 8/2018 |
| JP | 2018-146048 A | 9/2018 |
| JP | 2018-170841 A | 11/2018 |
| JP | 2018-185040 A | 11/2018 |
| JP | 2018-193710 A | 12/2018 |
| JP | 2018-197496 A | 12/2018 |
| JP | 2019-011861 A | 1/2019 |
| KR | 10-0505555 | 11/2005 |
| KR | 10-0655193 | 12/2006 |
| KR | 10-0735214 | 7/2007 |
| KR | 10-2007-0104332 | 10/2007 |
| KR | 10-2013-0035156 | 4/2013 |
| KR | 10-1265565 | 5/2013 |
| KR | 10-2013-0138733 | 12/2013 |
| KR | 10-1399680 | 5/2014 |
| KR | 10-1454053 | 10/2014 |
| KR | 10-1476013 | 12/2014 |
| KR | 10-1495453 | 2/2015 |
| KR | 10-2017-0063917 A | 6/2017 |
| KR | 10-2018-0029646 | 3/2018 |
| KR | 10-2018-0137524 | 12/2018 |
| KR | 10-1927274 | 12/2018 |
| KR | 10-1933204 | 12/2018 |
| NZ | 552296 | 11/2010 |
| NZ | 550423 | 1/2011 |
| NZ | 551715 | 2/2011 |
| NZ | 567432 | 3/2012 |
| NZ | 587820 | 3/2012 |
| NZ | 583929 | 4/2012 |
| NZ | 580173 | 6/2012 |
| NZ | 575405 | 9/2012 |
| NZ | 595133 | 6/2013 |
| NZ | 597302 | 8/2013 |
| NZ | 599372 | 10/2013 |
| NZ | 596570 | 2/2014 |
| NZ | 596802 | 2/2014 |
| NZ | 607679 | 7/2014 |
| NZ | 608551 | 10/2014 |
| NZ | 607879 | 11/2014 |
| NZ | 612086 | 12/2014 |
| NZ | 610731 | 2/2015 |
| NZ | 610755 | 3/2015 |
| NZ | 615330 | 3/2015 |
| NZ | 618892 | 7/2015 |
| NZ | 701074 | 10/2015 |
| NZ | 701501 | 10/2015 |
| NZ | 625429 | 12/2015 |
| NZ | 630741 | 3/2016 |
| NZ | 702644 | 6/2016 |
| NZ | 701722 | 7/2016 |
| NZ | 700217 | 11/2016 |
| NZ | 709784 | 2/2017 |
| NZ | 713055 | 4/2017 |
| NZ | 713455 | 4/2017 |
| NZ | 714595 | 6/2017 |
| NZ | 720629 | 12/2017 |
| NZ | 721025 | 1/2018 |
| NZ | 727624 | 7/2018 |
| NZ | 728600 | 10/2018 |
| NZ | 730762 | 10/2018 |
| NZ | 732004 | 11/2018 |
| NZ | 736962 | 5/2019 |
| NZ | 738046 | 6/2019 |
| NZ | 739208 | 7/2019 |
| PL | 201840 B1 | 5/2009 |
| RU | 2141979 C1 | 11/1999 |
| RU | 2253773 C1 | 6/2005 |
| RU | 92605 U1 | 3/2010 |
| RU | 125225 U1 | 2/2013 |
| RU | 159556 U1 | 2/2016 |
| RU | 2015117275 A | 11/2016 |
| RU | 172161 U1 | 6/2017 |
| TW | 201007027 A | 2/2010 |
| TW | 201114647 A | 5/2011 |
| TW | 201328933 | 7/2013 |
| WO | WO 1985/004844 | 11/1985 |
| WO | WO 1988/003036 | 5/1988 |
| WO | WO 1993/018813 | 9/1993 |
| WO | WO 1995/016865 | 6/1995 |
| WO | WO 1996/000181 | 1/1996 |
| WO | WO 2000/053389 | 9/2000 |
| WO | WO 2000/074612 | 12/2000 |
| WO | WO 2001/075834 | 10/2001 |
| WO | WO 2003/026808 | 4/2003 |
| WO | WO 2003/066145 | 8/2003 |
| WO | WO 2004/028897 | 4/2004 |
| WO | WO 2004/030723 | 4/2004 |

(56) References Cited

FOREIGN PATENT DOCUMENTS

| | | |
|---|---|---|
| WO | WO 2005/065480 | 7/2005 |
| WO | WO 2005/075732 | 8/2005 |
| WO | WO 2005/075736 | 8/2005 |
| WO | WO 2005/076874 | 8/2005 |
| WO | WO 2005/079726 | 9/2005 |
| WO | WO 2005/099801 | 10/2005 |
| WO | WO 2006/111875 | 10/2006 |
| WO | WO 2006/114327 | 11/2006 |
| WO | WO 2007/019624 | 2/2007 |
| WO | WO 2007/036959 | 4/2007 |
| WO | WO 2007/041786 | 4/2007 |
| WO | WO 2007/124966 | 11/2007 |
| WO | WO 2007/139890 | 12/2007 |
| WO | WO 2007/142318 | 12/2007 |
| WO | WO 2008/011683 | 1/2008 |
| WO | WO 2008/040050 | 4/2008 |
| WO | WO 2008/078558 | 7/2008 |
| WO | WO 2008/100150 | 8/2008 |
| WO | WO 2008/102459 | 8/2008 |
| WO | WO 2008/106716 | 9/2008 |
| WO | WO 2008/117695 | 10/2008 |
| WO | WO 2008/142766 | 11/2008 |
| WO | WO 2009/003137 | 12/2008 |
| WO | WO 2009/011344 | 1/2009 |
| WO | WO 2009/109005 | 9/2009 |
| WO | WO 2010/021645 | 2/2010 |
| WO | WO 2010/035645 | 4/2010 |
| WO | WO 2010/047051 | 4/2010 |
| WO | WO 2010/061599 | 6/2010 |
| WO | WO 2010/131189 | 11/2010 |
| WO | WO 2010/139087 | 12/2010 |
| WO | WO 2011/019582 | 2/2011 |
| WO | WO 2011/077274 A1 | 6/2011 |
| WO | WO 2011/078703 | 6/2011 |
| WO | WO 2011/085427 | 7/2011 |
| WO | WO 2012/040791 | 4/2012 |
| WO | WO 2012/040792 | 4/2012 |
| WO | WO 2012/066984 | 5/2012 |
| WO | WO 2012/106373 A2 | 8/2012 |
| WO | WO 2012/132567 | 10/2012 |
| WO | WO 2012/133922 | 10/2012 |
| WO | WO 2012/174602 | 12/2012 |
| WO | WO 2013/022356 A1 | 2/2013 |
| WO | WO 2013/061538 | 5/2013 |
| WO | WO 2013/088439 A1 | 6/2013 |
| WO | WO 2013/163685 A1 | 11/2013 |
| WO | WO 2014/015382 | 1/2014 |
| WO | WO 2014/025591 | 2/2014 |
| WO | WO 2014/069588 | 5/2014 |
| WO | WO 2014/089506 A1 | 6/2014 |
| WO | WO 2014/138804 | 9/2014 |
| WO | WO 2014/142681 | 9/2014 |
| WO | WO 2014/169241 | 10/2014 |
| WO | WO 2014/208628 | 12/2014 |
| WO | WO 2015/005055 | 1/2015 |
| WO | WO 2015/025318 | 2/2015 |
| WO | WO 2015/029840 | 3/2015 |
| WO | WO 2015/031349 | 3/2015 |
| WO | WO 2015/034942 | 3/2015 |
| WO | WO 2015/043119 | 4/2015 |
| WO | WO 2015/043229 | 4/2015 |
| WO | WO 2015/106726 | 7/2015 |
| WO | WO 2015/122113 | 8/2015 |
| WO | WO 2015/178391 | 11/2015 |
| WO | WO 2015/178615 | 11/2015 |
| WO | WO 2015/192186 | 12/2015 |
| WO | WO 2016/024373 | 2/2016 |
| WO | WO 2016/044881 | 3/2016 |
| WO | WO 2016/046776 | 3/2016 |
| WO | WO 2016/051160 | 4/2016 |
| WO | WO 2016/114079 | 7/2016 |
| WO | WO 2016/157105 | 10/2016 |
| WO | WO 2016/203211 | 12/2016 |
| WO | WO 2017/073647 | 5/2017 |
| WO | WO 2017/110784 | 6/2017 |
| WO | WO 2017/110790 | 6/2017 |
| WO | WO 2017/121662 | 7/2017 |
| WO | WO 2017/150990 | 9/2017 |
| WO | WO 2017/158476 | 9/2017 |
| WO | WO 2017/168920 | 10/2017 |
| WO | WO 2017/182987 | 10/2017 |
| WO | WO 2017/185140 | 11/2017 |
| WO | WO 2017/204207 | 11/2017 |
| WO | WO 2017/204250 | 11/2017 |
| WO | WO 2017/206104 | 12/2017 |
| WO | WO 2017/213297 | 12/2017 |
| WO | WO 2018/008204 | 1/2018 |
| WO | WO 2018/017209 | 1/2018 |
| WO | WO 2018/021454 | 2/2018 |
| WO | WO 2018/025853 | 2/2018 |
| WO | WO 2018/029638 | 2/2018 |
| WO | WO 2018/029689 | 2/2018 |
| WO | WO 2018/042376 | 3/2018 |
| WO | WO 2018/085951 | 5/2018 |
| WO | WO 2018/124889 | 7/2018 |
| WO | WO 2018/134767 | 7/2018 |
| WO | WO 2018/155722 | 8/2018 |
| WO | WO 2018/159627 | 9/2018 |
| WO | WO 2018/179636 | 10/2018 |
| WO | WO 2018/198657 | 11/2018 |
| WO | WO 2018/202952 | 11/2018 |
| WO | WO 2018/204969 | 11/2018 |
| WO | WO 2019/042486 | 3/2019 |

OTHER PUBLICATIONS

U.S. Appl. No. 16/185,163, filed Nov. 9, 2018, Amarasinghe.
U.S. Appl. No. 60/808,034, filed May 23, 2006, Doshi et al.
European Supplemental Search Report for Application No. EP 16 77 1501, dated Oct. 9, 2018 in 7 pages.
Extended European Search Report for Application No. 17838905.2 dated Mar. 2, 2020 in 4 pages.
International Search Report, PCT/IB2017/054896; dated Dec. 18, 2017; 12 pages.
International Search Report for Application No. PCT/IB2016/051819, dated Jun. 29, 2016 in 7 pages.
Japanese Exam Report for Japanese Application No. 2017-551052 dated Jan. 27, 2020.
United Kingdom Examination Report in Application No. GB1715236.4, dated Mar. 26, 2020, in 3 pages.
European Search Report for Application No. 16771501.0 dated May 25, 2020, 4 pages.
Taiwanese Examination Report for Patent Application No. 108104857.
European Search Report for Application No. 22205879.4 dated Feb. 6, 2023.
Japanese Office Action for Application No. 2022-113710.
Optiflow™ + Nasal Cannula Interface, posted at fphcare.com, earliest date available on Jun. 24, 2018, [online], acquired on Nov. 18/u, 2021, Available on internet. url:https://www.fphcare.com/us/hospital/adult-respiratory/optiflow/optiflow-plus-nasal-cannula/ (Year:2018).

* cited by examiner

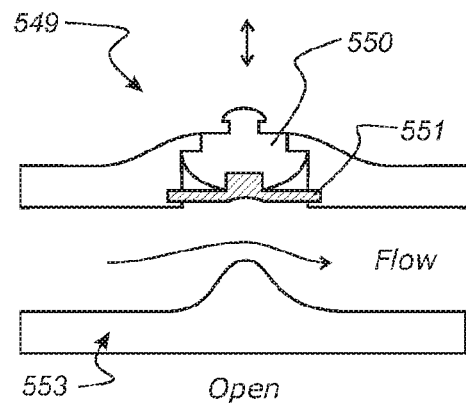
FIGURE 16B(i)
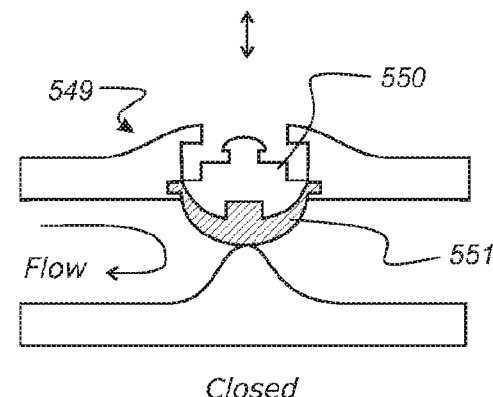
FIGURE 16B(ii)
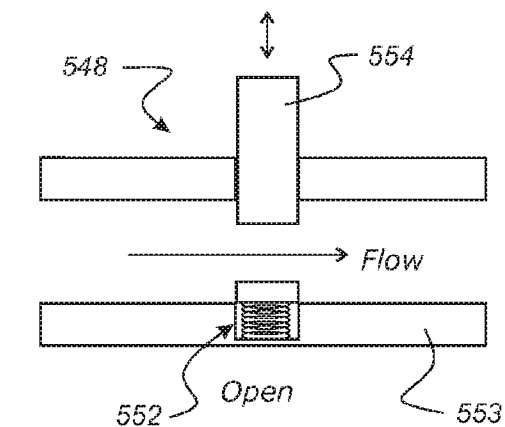
FIGURE 16C(i)
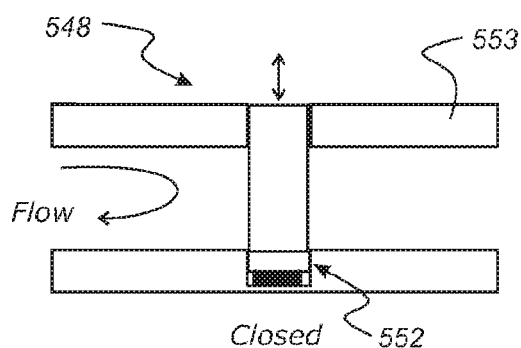
FIGURE 16C(ii)

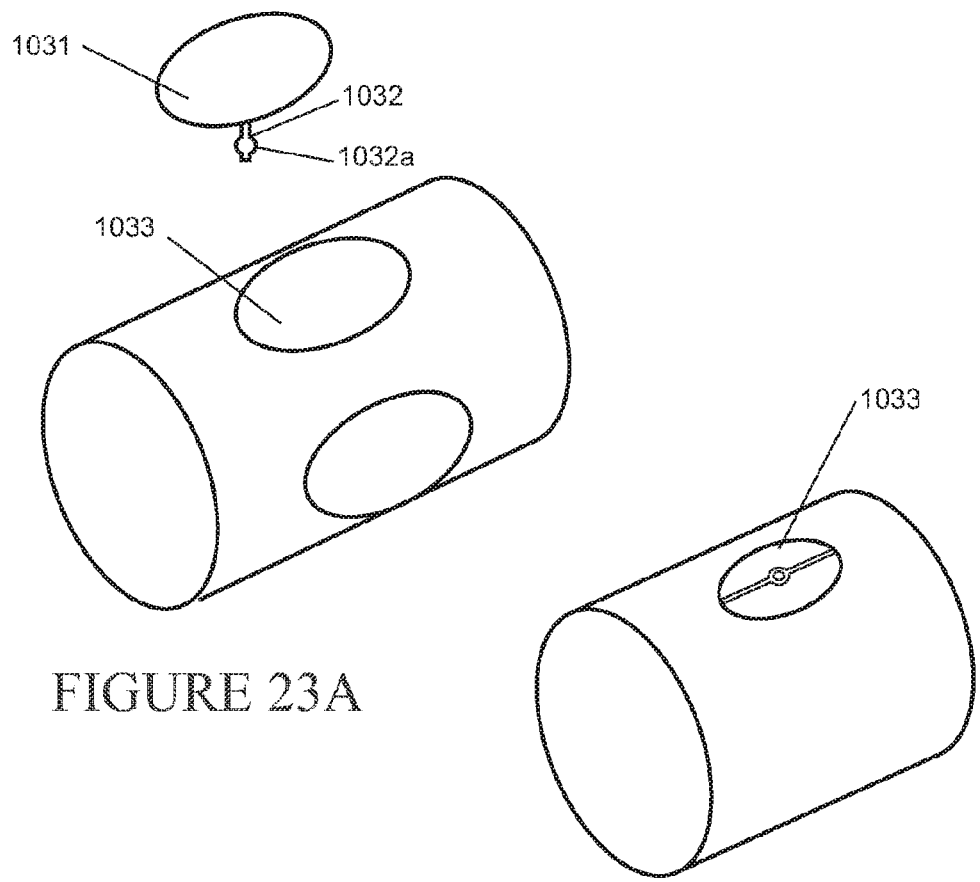
FIGURE 23A
FIGURE 23B
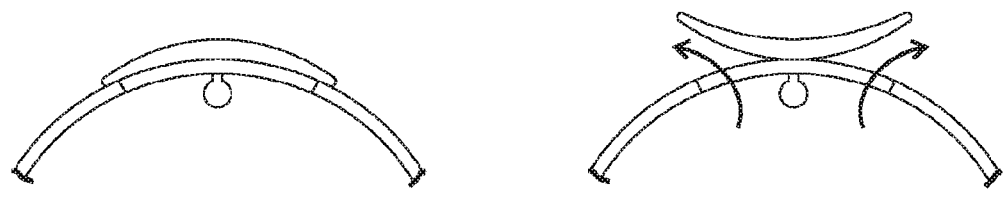
FIGURE 23C   FIGURE 23D

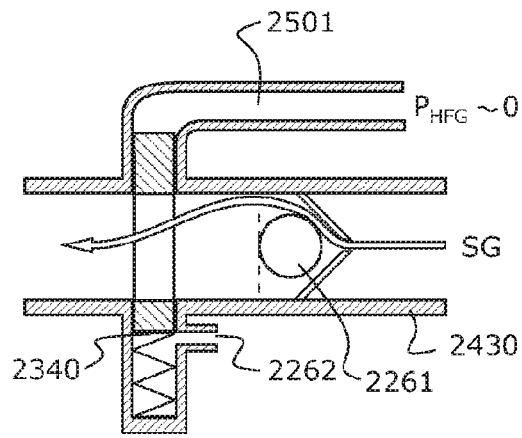
FIGURE 45B - i
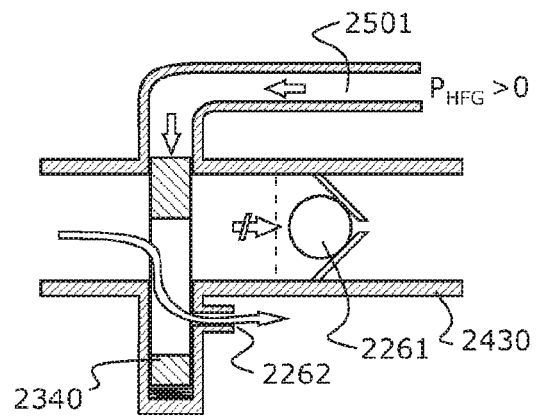
FIGURE 45B - ii
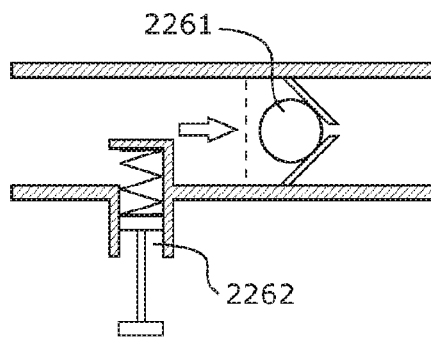
FIGURE 45B - iii
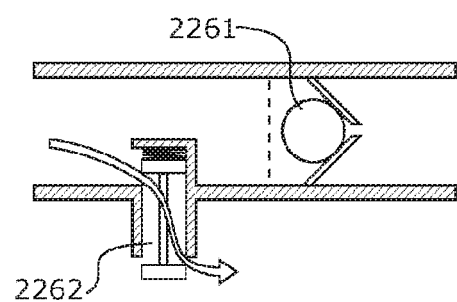
FIGURE 45B - iv

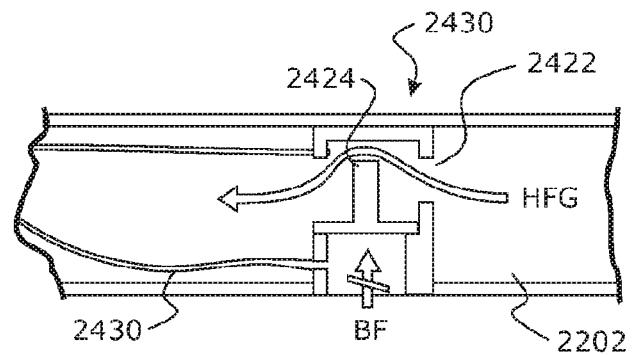
FIGURE 45C - i
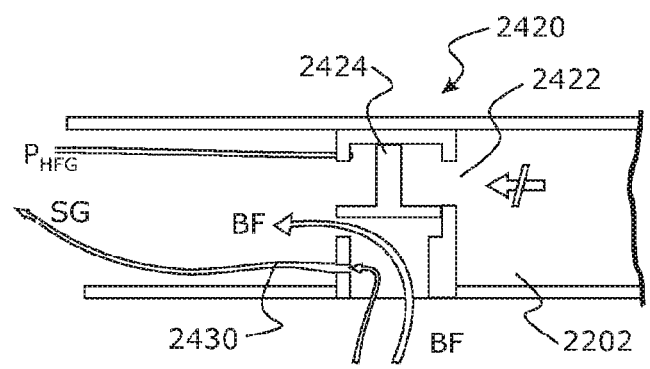
FIGURE 45C - ii

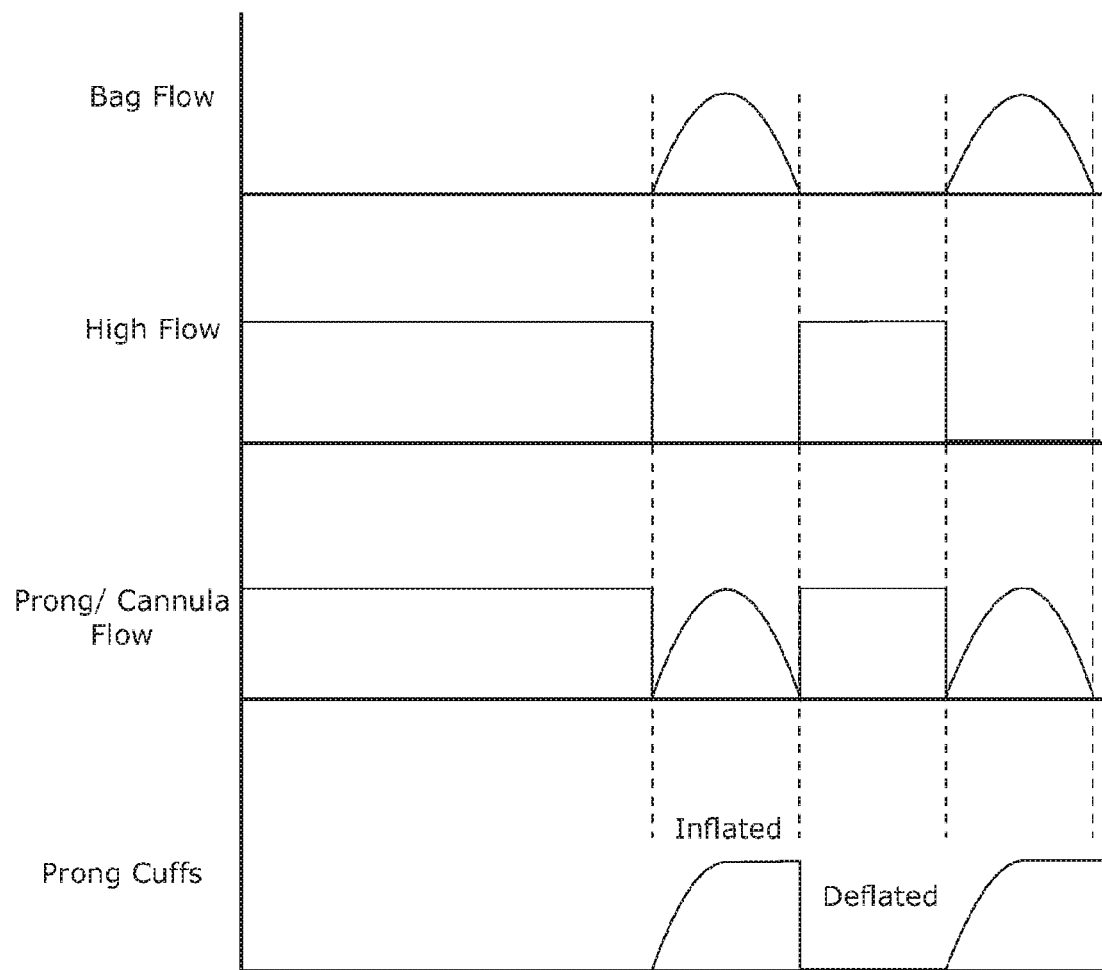
FIGURE 45D - i

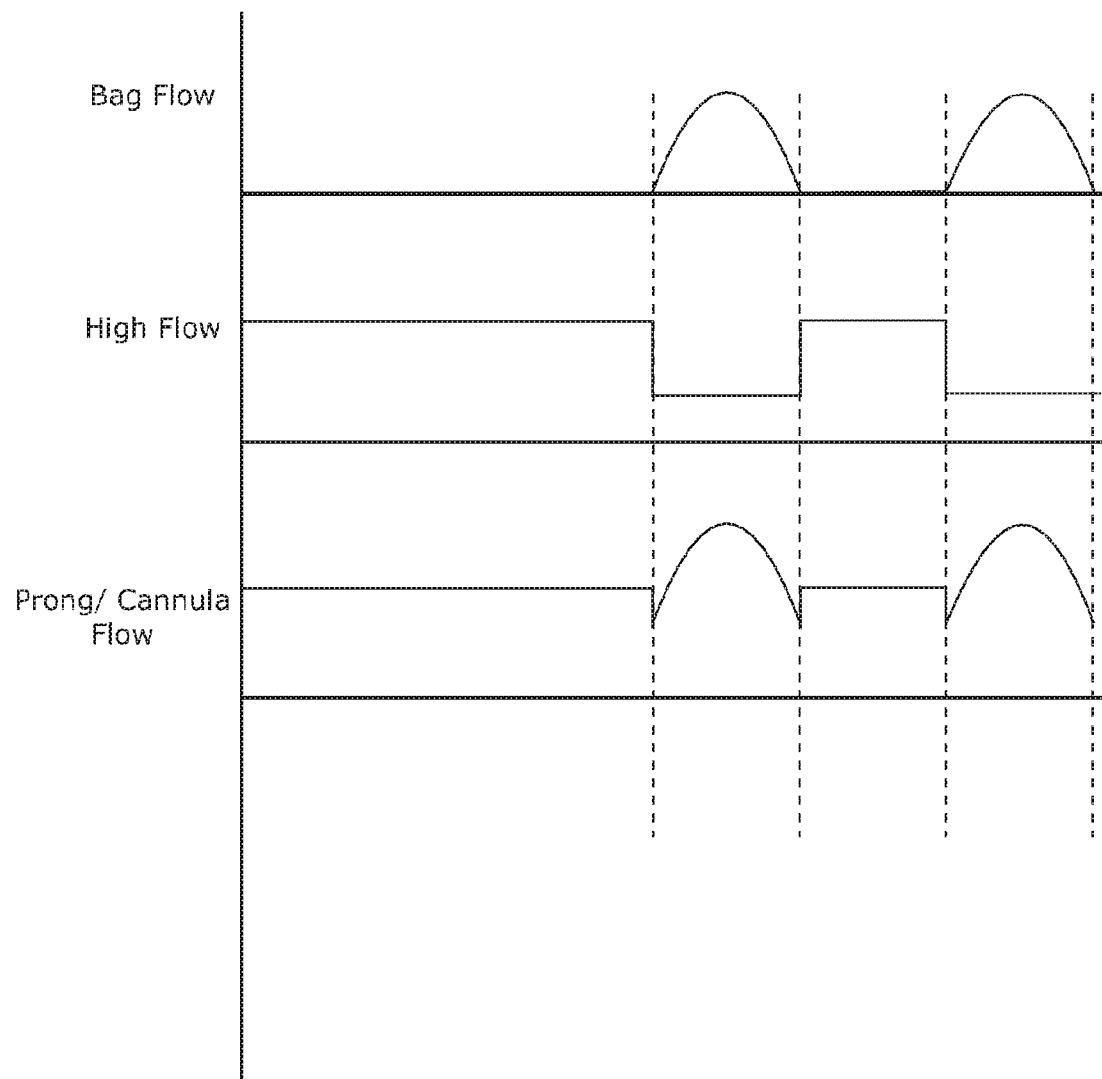
FIGURE 45D - ii

USER INTERFACE AND SYSTEM FOR SUPPLYING GASES TO AN AIRWAY

TECHNICAL FIELD

This disclosure relates to user interfaces and respiratory therapy systems comprising user interfaces, for conveying gases to and/or from a user, and in particular but not limited to, respiratory systems adapted to provide multiple types of respiratory therapy to a user, and patient interfaces and devices for such systems.

BACKGROUND ART

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

In procedures where multiple respiratory support systems are required, there may be a concern that the combination(s) of support systems could cause excessive pressure delivery (for example when a cannula is in place on a patient and an anaesthetist wishes to deliver support through a mask over top of the cannula).

Furthermore, switching between difference support systems may be time consuming or difficult. It may therefore be desirable to have a configuration that allows easy interchange between respiratory support, for example support via high flow and respiratory support via a face mask and bag. It would may also be desirable to allow gas flows to be quickly and easily turned off or reduced.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

SUMMARY

It is an object of this disclosure to provide for a respiratory therapy system, or devices or patient interfaces therefore, which go at least some way towards providing for an alternative or for providing the industry/public with a useful choice.

In one aspect, this disclosure relates to a respiratory apparatus for providing respiratory support to a patient, the apparatus comprising:
a nasal interface and a gas conduit for delivering a flow of gases to an outlet of the nasal interface, and a device and/or a sensing arrangement adapted to configure the apparatus between a first configuration for providing a first level of the flow of gases to the outlet and a second configuration for providing a second level of the flow of gases to the outlet, the second level less than the first level, wherein the device and/or the sensor arrangement is located at the nasal interface or at or near to a patient end of the conduit.

In a further aspect, this disclosure relates to a respiratory apparatus for providing respiratory support to a patient, the apparatus comprising:
a nasal interface and a gas conduit for delivering a flow of gases to an outlet of the nasal interface, and a device adapted to configure the gas conduit between a first configuration for providing a first level of the flow of gases to the outlet and a second configuration for providing a second level of the flow of gases to the outlet, the second level less than the first level,
a sensing arrangement comprising a first pressure sensor located downstream of the device, and a second pressure sensor located upstream of the device, such that the first or second configuration of the conduit can be determined based on a generated signal or output from the first and second sensors.

The first configuration may be an open configuration and the second configuration may be a partially or substantially closed configuration, the second level of the flow of gases being substantially less than the first level or is a substantially zero flow of the flow of gases.

The device may comprises a collapsible portion of the gas conduit configured to transition between the first configuration and the second configuration.

The gas conduit may comprise a bulkhead or pair of bulkheads within the collapsible portion,
in the first configuration the conduit comprising a gap between the bulkhead and a side wall of the conduit or between the pair of bulkheads to allow the first level of the flow of gases, and
in the second configuration the bulkhead moved towards the side wall of the conduit or the bulkheads moved towards each other to allow the second level of the flow of gases.

The collapsible portion may be adapted to transition from the first configuration to the second configuration when: (i) a second patient interface is located upon the collapsible portion, or (ii) a user presses the collapsible portion.

The device may comprise a valve configurable between the first and second configurations.

In the second configuration the valve may vent or divert at least a portion of the flow of gases from the apparatus.

The device may comprise a pressure relief device, and in the first configuration is in a closed or non-venting configuration, and in the second configuration is in an open or venting configuration to vent or divert at least a portion of the flow of gases from the apparatus.

The valve may vent or divert the portion of the flow of gases in a direction away from the patient.

The valve may be adapted to switch from the first configuration to the second configuration when: (i) a second patient interface is located upon at least a component of the valve, or (ii) a user presses at least a component of the valve.

The nasal interface may comprise the device, or the gas conduit may be connected or connectable to the nasal interface and comprises the device.

In a further aspect, this disclosure relates to a system for providing respiratory support to a patient comprising:
- a first respiratory support system comprising a first patient interface for providing a first flow of gases to the patient,
- the first patient interface being independently locatable upon the patient,
- wherein the system comprises a device and/or a sensing arrangement, such that with the first patient interface located upon the patient, the device and/or sensing arrangement is configured to facilitate a switching of the system between different respiratory modes:
  - in a first respiratory mode, the device allowing delivery of the first flow of gases to an outlet of the first patient interface when a second patient interface is absent or removed from the patient and/or when a second flow of gases is stopped from being delivered to the patient by the second patient interface,
  - in a second respiratory mode, the device reducing or stopping delivery of the first flow of gases to the outlet of the first patient interface when the second patient interface is located together with the first patient interface upon the patient and/or when the second flow of gases is delivered to the patient by the second patient interface.

The system may comprise:
- a second respiratory support system comprising the second patient interface for providing the second flow of gases to the patient,
- said first and second interfaces each being independently locatable upon the patient.

In a further aspect, this disclosure relates to a system for providing respiratory support to a patient comprising:
- a first respiratory support system comprising a first patient interface for providing a first flow of gases to the patient,
- a second respiratory support system comprising a second patient interface for providing a second flow of gases to the patient,
- said first and second interfaces each being independently locatable upon the patient,
- wherein the first respiratory support system comprises a device and/or a sensing arrangement, such that with the first patient interface located upon the patient, the device and/or a sensing arrangement is configured to facilitate a switching of the system between different respiratory modes:
  - in a first respiratory mode, the device allowing delivery of the first flow of gases to an outlet of the first patient interface when a second patient interface is absent or removed from the patient and/or when a second flow of gases is stopped from being delivered to the patient by the second patient interface,
  - in a second respiratory mode, the device reducing or stopping delivery of the first flow of gases to the outlet of the first patient interface when the second patient interface is located together with the first patient interface upon the patient and/or when the second flow of gases is delivered to the patient by a second patient interface.

The first patient interface may be a nasal interface, such as a nasal cannula, and the second patient interface may be a face mask or oral mask.

The device or sensing arrangement may be adapted to switch the system from the first mode to the second mode by the closure or partial closure of a gas conduit providing the first flow of gases to the outlet of the first patient interface.

The device or sensing arrangement may be adapted to switch the system from the second mode to the first mode by opening a gas conduit or allowing a gas conduit to provide the first flow of gases to the outlet of the first patient interface.

The first respiratory support system may comprise a first gas conduit and the device, the device comprising a collapsible portion of the first gas conduit configured to transition between a first configuration for providing a first level of the first flow of gases to the outlet and a second configuration for providing a second level of the first flow of gases to the outlet, the second level less than the first level, and one or both of:
- wherein the system switches from the first respiratory mode to the second respiratory mode by transitioning the collapsible portion from the first configuration to the second configuration,
- wherein the system switches from the second respiratory mode to the first respiratory mode by transitioning the collapsible portion from the second configuration to the first configuration.

The first configuration may be an open configuration and the second configuration may be a partially or substantially closed configuration, the second level of the first flow of gases being substantially less than the first level or is a substantially zero flow of the first flow of gases.

The collapsible portion may be adapted to transition from the first configuration to the second configuration when the second patient interface is located upon the collapsible portion.

The second patient interface may be a face mask and the collapsible portion is adapted to be collapsed to the second configuration by a mask seal of the face mask.

The collapsible portion may be adapted to form a seal with the mask seal when in the second configuration, and/or wherein the collapsible portion is adapted to collapse to allow the mask seal to form a seal with the patient's face.

The collapsible portion may comprise a cross section comprising a hinged or articulated or a concertina-type or bellows-type conduit wall arrangement allowing for the collapsible portion to be collapsed from the first condition to the second condition under application of a force or load acting on the collapsible portion.

The first patient interface may comprise the collapsible portion of the first conduit, or the first gas conduit may be connected or connectable to the first patient interface and comprises the collapsible portion of the first conduit.

The first respiratory support system may comprise the device, the device may comprise a valve for controlling the delivery of the first flow of respiratory gases to the outlet of the first patient interface, and wherein the system switches from the first respiratory mode to the second respiratory mode by switching the valve between a first configuration for providing a first level of the first flow of gases to the outlet and a second configuration for providing a second level of the first flow of gases to the outlet, the second level less than the first level.

The first patient interface may comprise the valve, or the first respiratory support system may comprise a first gas conduit for providing the first flow of gases to the first patient interface, the first gas conduit comprising said valve.

The first configuration may be an open configuration and the second configuration may be a partially or substantially closed configuration, the second level of the first flow of gases being substantially less than the first level or is a substantially zero flow of the first flow of gases.

In the second configuration the valve may vent or divert at least a portion of the first flow of gases from the first respiratory support system.

The valve may be a pressure relief device, and in the first configuration may be in a closed or non-venting configuration, and in the second configuration may be in an open or venting configuration to vent or divert at least a portion of the first flow of gases from the first respiratory support system.

The valve may vent or divert the portion of the first flow of gases in a direction away from the patient.

The valve may be adapted to switch between the first configuration and the second configuration by applying a portion of the second patient interface against at least a component of the valve.

The second patient interface may be a face mask and the portion is a mask seal of the face mask.

The system or apparatus may comprise the sensing arrangement, the sensing arrangement generating a signal or output to facilitate the switching of the device between the first and second configurations.

The system or apparatus may comprise the sensing arrangement, the sensing arrangement generating a signal or output to facilitate the switching of the system or apparatus between the first and second respiratory modes or configurations in response to a sensed condition.

A sensor or sensors of the sensing arrangement may be associated with one or more of:
  i. the first patient interface or the nasal interface,
  ii. the second patient interface,
  iii. both the first and second patient interfaces,
  iv. an item associated with the first patient interface,
  v. an item associated with the second patient interface,
  vi. an item associated both the first and second patient interfaces,
  vii. an item to be associated with the patient.

The sensor or sensors may generate the signal or output upon sensing a change in condition in the gas conduit, or the first respiratory support system comprises a first gas conduit and the sensor or sensors generate the signal or output upon sensing a change in condition in the first gas conduit.

The sensor may sense a change in pressure in the gas conduit or first gas conduit and/or an occlusion of the gas conduit or first gas conduit.

The first respiratory support system may comprise the device, and the sensor arrangement comprises a first pressure sensor located downstream of the device, a second pressure sensor located upstream of the device, and a controller configured to determine, based on a generated signal or output from the first and second sensors, when the system switches or is to switch between the first and second respiratory modes.

The sensor may sense an in-situ combination of the or a second patient interface with the first patient interface or the nasal interface.

The sensor may be arranged to sense a pressure external of the first patient interface or nasal interface and internal of the or a second patient interface, when the first patient interface or the nasal interface and the second interface are in an in-situ combination.

The system may comprise a controller adapted to receive said signal or output and in response activates or controls one or more of the following system outcomes:
  one or more of a visual, or audible, or haptic, or tactile alarm or warning:
    indicative of one or other of the first and second respiratory modes, or
    indicative of the switching between the first and second respiratory modes, or
    to alert a user to switch between the first and second respiratory modes, or
  a flow controller device, including a valve or flow generator or pressure relief device, for controlling the first flow of gas to the outlet of the first patient interface.

The system may comprise a spacer component as a block or mount, wherein the spacer component may comprise a channel or groove or pathway for receiving a portion of the gas conduit and a sealing surface over which a seal of the second patient interface forms a seal together with patient's face.

The spacer component may be the item associated with the first patient interface, the second patient interface, both the first and second patient interfaces, or the patient.

The second patient interface may comprise:
  a body, said body comprising an aperture or a port allowing for communication of gases to and/or from a gas supply or source to an interior volume of the second patient interface, the interior volume defined by an interior of the body and the face of the user,
  a seal provided for creating or forming of a seal between the body and the patient's face so that the interior volume is a sealed interior volume, and
  wherein the seal may be adapted or configured to accommodate the creating or forming of the seal between the body and the patient's face and facilitate a gas conduit or the first patient interface extending between the body and the patient's face into the sealed interior volume.

The first respiratory support system may comprise a pressure relief device located upstream of the device to vent or divert at least a portion of the first flow of gases from the first respiratory support system.

The first respiratory support system may comprise a one way valve to prevent or reduce a back flow in the first respiratory support system from the second respiratory support system.

The second patient interface may be a hand held patient interface.

In a further aspect, this disclosure relates to a patient interface comprising:
  a first gases lumen adapted to receive gases from a gases source,
  wherein a first portion of the first gases lumen is configured to transition from a first configuration in which a first level of gases is able to pass through the first portion of the first gases lumen to a second configuration in which a second level of gases is able to pass through the first portion of the first gases lumen.

The first portion of the first gases lumen may transition or progress between the first and second configurations based on a relative level of force applied to an external wall, or experienced by an internal wall, of the first portion of the first gases lumen.

The first portion of the first gases lumen may transition or progress between the first and second configurations based on a level of pressure of gases passing through the first portion of the gases lumen.

The first portion of the first gases lumen may be in the first configuration when gases having pressures above a first predetermined pressure level are passing through the first gases lumen and the first portion of the first gases lumen may be in the second configuration when gases having pressures below the first predetermined pressure level are passing through the first gases lumen.

The first configuration may be a substantially open configuration and the second configuration is a substantially closed configuration.

The first level of gases may be greater than the second level of gases.

The first portion of the first gases lumen may comprise a wall that is thinner than one or more walls of other portions of the first gases lumen.

The patient interface may further comprise a substantially smooth, or substantially linear, transition in thickness between the wall of the first portion of the first gases lumen and the one or more walls of other portions of the first gases lumen.

The first portion of the first gases lumen may comprise a wall that is more flexible than walls of other portions of the first gases lumen, preferably the (more flexible) wall is formed at least in part from a material that is more flexible than the wall or walls of other portions of the first gases lumen.

A wall of the first portion of the first gases lumen may be configured to substantially collapse or be collapsible or does not retain a gases or fluid pathway or is substantially not self-supporting when in the second configuration.

The cross-sectional area of the first portion of the first gases lumen when taken along the length of the first gases lumen may be substantially reduced (e.g. may be reduced to zero) when in the second configuration, optionally may assume a substantially flat or flattened shape when in the second configuration.

The first portion of the first gases lumen may comprise an element about, or within or under a wall of the first portion of the first gases lumen adapted to limit compression of the first portion of the first gases lumen.

The element may be configured to promote the passage of a minimum level of gases flow through the first portion of the first gases lumen regardless of the configuration of the first portion of the first gases lumen. Optionally, such an element may be a reinforcement element.

The first gases lumen may comprise an element at or near a wall of the first gases lumen adapted to limit compression of the first gases lumen, wherein the strength, thickness and/or width of the element is decreased at or near the first portion of the first gases lumen.

The patient interface may comprise a substantially smooth, or substantially linear, transition in strength, thickness and/or width of the element from a portion of the element at or near the first portion of the first gases lumen to one or more portions of the or another element distal from the first portion of the first gases lumen.

The patient interface may further comprise a second gases lumen extending along at least an inner region of the first gases lumen through, at or near the first portion of the first gases lumen.

The second gases lumen may be less compressible or may be more resistant to a compression than the first portion of the first gases lumen. In some such configurations, a wall of the second gases lumen is formed at least in part from a material that is more rigid or less flexible than a wall of the first portion of the first gases lumen. Optionally, the second gases lumen may be formed by the element or elements (such as a reinforcement element) when the element or a plurality of elements are brought together. For example, a reinforcement element may be shaped or configured or otherwise adapted to interact with a wall of the first gases lumen to provide for a second gases lumen, alternatively reinforcement elements may be brought together in a configuration for formation of the second gases lumen, and optionally the closure of the first gases lumen.

The first portion of the first gases lumen may be wider than, or is larger or presents a wider or larger cross-sectional surface area, or may be a bellowed or enlarged localized region relative to other portions of the first gases lumen.

The patient interface may further comprises a substantially smooth, or substantially linear, transition in width or cross-sectional area or side from the first portion of the first gases lumen to portions of the first gases lumen distal from the first portion of the first gases lumen.

The patient interface may further comprise a pressure relief arrangement adapted to reduce the pressure of gases in the first gases lumen when the first portion of the first gases lumen is in the second configuration.

In a further aspect, this disclosure relates to a nasal cannula. The nasal cannula may comprise a first tubular section; and at least one nasal delivery element (e.g. at least one nasal prong) in fluid (e.g. pneumatic) communication with the first tubular section, one or more of the at least one nasal delivery elements adapted to rest in one or more nares of a user; wherein the first tubular section comprises a first gases lumen adapted to receive gases from a gases source; and wherein a first portion of the first gases lumen comprises a greater propensity than other portions of the first gases lumen to progress from a first configuration in which a first level of gases is able to pass through the first portion of the first gases lumen to a second configuration in which a second level of gases is able to pass through the first portion of the first gases lumen.

The at least one nasal delivery element may be adapted to non-sealingly rest in or be located within one or more nares of the user.

A flow manifold may be interposed between the first tubular section and the at least one nasal delivery element.

The at least one nasal delivery element may extend from the flow manifold.

The first portion of the first gases lumen may progress between the first and second configurations based on a level of force applied to an external wall or an internal wall (e.g. as experienced by an internal wall) of the first portion of the first gases lumen.

The first portion of the first gases lumen may progress between the first and second configurations based, at least in part, on a level of pressure of gases passing through the first portion of the gases lumen.

The first portion of the first gases lumen may be in the first configuration when gases having pressures above a first predetermined pressure level are passing through the first gases lumen and the first portion of the first gases lumen may be in the second configuration when gases having pressures below the first predetermined pressure level are passing through the first gases lumen.

The first configuration may be a substantially open configuration and the second configuration is a substantially closed configuration.

The first level of gases may be greater than the second level of gases.

The first portion of the first gases lumen may comprise a wall that is thinner than one or more walls of other portions of the first gases lumen.

The nasal cannula may further comprise a substantially smooth transition in thickness between the wall of the first portion of the first gases lumen and the one or more walls of other portions of the first gases lumen.

The first portion of the first gases lumen may comprise a wall formed at least in part from a material that is more flexible than walls of other portions of the first gases lumen.

A wall of the first portion of the first gases lumen may be configured to substantially collapse or be non-self-supporting in the second configuration.

The cross-sectional area of the first portion of the first gases lumen when taken along the length of the first gases lumen may be substantially reduced (e.g. may be reduced to zero) when in the second configuration, optionally may assume a substantially flat or flattened shape or configuration when in the second configuration.

The first portion of the first gases lumen may comprise a reinforcement element about, within or under a wall of the first portion of the first gases lumen adapted to limit compression of the first portion of the first gases lumen.

The reinforcement element may be configured to promote the passage of a minimum level of gases flow through the first portion of the first gases lumen regardless of the configuration of the first portion of the first gases lumen.

The first gases lumen may comprise a reinforcement element at or near a wall of the first gases lumen adapted to limit compression of the first gases lumen, wherein the strength, thickness and/or width of the reinforcement element is decreased at or near the first portion of the first gases lumen.

The nasal cannula may comprise a substantially smooth, or substantially linear, transition in strength, thickness and/or width of the reinforcement element from a portion of the reinforcement element at or near the first portion of the first gases lumen to one or more portions of the reinforcement element distal from or adjacent to the first portion of the first gases lumen.

The first portion of the first gases lumen may have a greater propensity than other portions of the first gases lumen to transition from a first configuration in which a first level of gases is able to pass through the first portion of the first gases lumen to a second configuration in which a second level of gases is able to pass through the first portion of the first gases lumen.

The nasal cannula may further comprise a second gases lumen extending along at least an inner region of the first gases lumen at or near the first portion of the first gases lumen.

The second gases lumen may be less compressible than the first portion of the first gases lumen.

A wall of the second gases lumen may be formed at least in part from a material that is more rigid or less flexible than a wall of the first portion of the first gases lumen.

The first portion of the first gases lumen may be wider than or is larger or presents a wider or larger cross-sectional surface area, or may be a bellowed or enlarged localized region relative to other portions of the first gases lumen.

The nasal cannula may further comprise a substantially smooth, or substantially linear transition in width from the first portion of the first gases lumen to portions of the first gases lumen distal from the first portion of the first gases lumen.

The nasal cannula may further comprise a pressure relief valve, device or arrangement adapted to reduce or alleviate the pressure of gases in the first gases lumen when the first portion of the first gases lumen is in the second configuration.

The nasal cannula may further comprise one or more attachment structures secured or attached or connected to one or more user facing portions of the nasal cannula, the one or more attachment structures adapted to fasten or attach or connect the nasal cannula to the face of the user (optionally in a removable manner).

The one or more attachment structures may be adapted to interface with one or more fixation structures secured to the face to fasten the nasal cannula to the face, such as in a removable manner.

The at least one nasal delivery element may be shaped or angled such that it extends inwardly towards a septum of the user.

The at least one nasal delivery element may be shaped or angled such that a tip of the at least one nasal delivery element points, in use, towards a back of the user's head, or is angled to direct a flow of supplied gases toward the back or an inner-more region of a user's nare or nares.

A respiratory support system is disclosed, the respiratory system may comprise a first respiratory support subsystem and a second respiratory support subsystem, wherein the first respiratory support subsystem comprises the patient interface as described, and wherein the system is configured to switch delivery of respiratory support to a patient from the first subsystem to the second subsystem when said first portion of the first gases lumen of the patient interface transitions from said first configuration to said second configuration.

The first respiratory support subsystem may be a high flow system.

The first respiratory support subsystem may further comprise the nasal cannula described.

The second respiratory support subsystem may comprise a face mask.

The first portion of the first gases lumen may transition from the first configuration to the second configuration when compressed by a seal of the face mask.

A method of switching between two respiratory support modes is disclosed, wherein a first respiratory support mode delivers respiratory support to a patient using the patient interface described, and comprising a step of transitioning said first portion of the first gases lumen from said first configuration, in which the first respiratory support mode delivers respiratory support to the patient, to said second configuration in which a second respiratory support mode delivers respiratory support to the patient.

The first mode may be a high flow therapy mode.

In a further aspect, this disclosure relates to a conduit comprising a collapsible portion, wherein the collapsible portion comprises a cross section comprising a hinged or articulated or a concertina-type or bellows-type conduit wall arrangement allowing for the collapsible portion to be collapsed from the first condition to the second condition under application of a force or load acting on the collapsible portion.

The cross section may comprise a single folding portion on a side of the collapsible portion extending between an outer side of the conduit and an inner side of the conduit, in use the inner side of the conduit in contact with a patient's face, and wherein
the folding portion comprises a pair of side portions, the side portions diverging from a folding point to present an externally facing acute or obtuse angle when in the first condition, and in the second position the cross section deforming at the folding point so that the pair of side portions come together to collapse the collapsible portion to the second condition.

The cross section may comprise a first said single folding portion on a first side of the collapsible portion, and a second said single folding portion on a second side of the collapsible portion, the second side opposite to the first side, the first and second folding portions extending between the outer side of the conduit and the inner side of the conduit.

The cross section may comprise the single folding portion on a first side of the collapsible portion and a second folding point at a second side of the collapsible portion, the second side opposite to the first side, the outer side of the conduit and an inner side of the conduit diverging from the second folding point.

The inner and outer sides of the conduit may fold together at the second folding point when transitioning from the first configuration to the second configuration.

The angle may be an acute angle.

The angle may be less than 60 degrees, or 55 degrees, or 50 degrees, or 45 degrees, or 40 degrees, or 35 degrees.

In the second condition, the collapsible portion may collapse so that external surfaces of the side portions are in contact.

In the second condition, internal surfaces of the side portions contact internal surfaces of the inner side and the outer side of the conduit.

In another aspect, according to this disclosure, there is provided a conduit, or at least a part length of a conduit, for use as a part of a respiratory therapy delivery system, the conduit or part length of the conduit comprising:
at least one form or an array of forms is/are supportive, or form a part, of a conduit wall, an internal surface of said conduit wall forming a lumen or gas flow path of the conduit,
the at least one form or the array of forms is/are biased so as to preferentially maintain the lumen or gas flow path in a first condition, the first condition being a substantially open or a substantially non-collapsed conduit wall condition,
and wherein the conduit or part length of the conduit comprising the at least one form or the array of forms is/are configured to be distortable or buckle from the first condition to a second condition in response to a force or load applied to an outside surface of the conduit wall comprising the at least one form or the array of forms,
the second condition being a substantially closed or substantially collapsed conduit wall condition or where the lumen or gas flow path are substantially occluded or obstructed as to a gas flow therethrough.

The at least one form or array of forms may be substantially unrestrictively distortable or buckling in response to application of the force or load.

The distortion or buckling of the at least one form or array of forms from the first condition to the second condition may be to a pre-determined distorted or buckled orientation or arrangement or configuration of the least one form or the array of forms.

The force or load applied to the outside surface of the conduit, in use, may be sufficient to overcome the bias.

The force or load applied to the outside surface of the conduit may be, in use, sufficient to induce distortion or buckling of the at least one form or array of forms.

The second condition may be a preferentially pre-determined re-configuration (or re-arrangement or re-orientation) of the at least one form or the array of forms.

In the second condition, internal surfaces of the conduit wall may be brought together upon themselves, or at least are partially brought together upon themselves, whether into contact with, or to be substantially adjacent with, each other, to provide for the substantially closed or substantially collapsed conduit wall condition or where the lumen or gas flow path are substantially occluded or obstructed as to a gas flow therethrough.

The form or the array of forms may be biased toward the first condition.

The form of the array of forms may be capable of being distorted or buckled from the first condition toward the second condition upon application of the force or load, yet reduction or removal of the force or load allows the form or array of forms to return or recover the conduit to the first condition.

The form or array of forms may be independent of the conduit wall or an internal wall surface. That is, the form or forms are not attached or connected to the conduit wall or an internal surface thereof.

The form may be a spiraled or helically wound or coiled member being of a pitch angle of about 20° to about 70°, or about 25° to about 65°, or about 35° to about 55°, or about 45° from a horizontal longitudinal axis extending along the conduit or the at least part of the conduit comprising the form or array of forms, or being an angle relative to the conduit wall, the pitch angle being the angle between each wind or coil of the member.

The form may be of a spiraled or helically wound or coiled member having a pitch of greater than about ¼ the internal diameter of the conduit to about 10 times the internal diameter of the conduit, or about ½ to about 8 times the internal diameter of the conduit, or about ⅔ to about 6 times the internal diameter of the conduit, or about 1 times to about 4 times the internal diameter of the conduit, or the pitch being substantially the length as the internal diameter of the conduit, pitch being the distance from a centre to a centre of adjacent spirals or helical windings or coils of the member.

The form may be a spiraled or helically wound or coiled member being of a pitch angle or a pitch (or both), such that application of the load or force to an outside surface of the conduit allows the form to fold over upon itself or to be re-oriented so that the form lies in a substantially flat orientation when in the second condition.

The form may be a series of rings, each ring of the series including a hinged inter-connection to at least one other ring.

The hinged inter-connection may facilitate the distortion or buckling of the form.

The form may be a series of hingedly connected components, arranged so as to provide for at least a substantially continuous support of the conduit wall at least in the part length of the conduit comprising the form.

The conduit wall may comprise at least one form or an array of forms extending substantially longitudinally along a conduit wall, or at least substantially longitudinally along the part length of the conduit wall comprising the form.

The at least one form or the array of forms may be a flap or hinge formed as a part of or provided at or within a conduit wall.

The flap or hinge may allow for the conduit wall to fold over upon itself.

The form or array of forms may be a concertina-type arrangement or a bellows-type arrangement, said arrangement allowing for the conduit to be distorted or buckled from the first condition to the second condition under application of the force or load.

The form may be a hinge formed or integrated as a part of or provided at or within a conduit wall.

A plurality of hinges may be formed as part of a conduit wall.

The hinges may extend substantially longitudinally along a conduit wall, or at least substantially longitudinally along the part length of the conduit wall comprising the hinges.

In a further aspect, this disclosure relates to a conduit provided as part of a breathing circuit or for use in a respiratory therapy delivery system, wherein the conduit is devoid of supporting structure that otherwise maintains the conduit in gas flow capable condition, the wall of the conduit defining a lumen therethrough, the wall being sufficiently flexible as to be non-self supporting.

The conduit may be maintained in a gas flow configuration by a positive pressure of gas provided to the lumen of the conduit.

In a further aspect, this disclosure relates to a conduit for supplying or delivering a gas to a patient interface, the conduit comprising:
 a one-way valve, and
 relative to the flow of gas being delivered to the interface, and upstream of the one-way valve, is a vent or pressure relief valve for venting or relieving of pressure build-up within the lumen of the conduit above a pre-set or pre-determined pressure level (e.g. the vent or pressure relief valve can be configured to "open" or release pressure once a pre-set pressure or pre-determined pressure within the conduit is reached)
 and wherein the one-way valve prevents the flow of gas upstream from the patient interface.

The build-up of pressure may be experienced upon application of a subsequent respiratory therapy being administered to the patient, not limited to, but including, application of a full face mask delivering a respiratory therapy to the patient of a pressure P2, while the pressure within the conduit comprising the vent or pressure relief device and one-way valve is of a pressure P1, where P1 is less than P2.

The one-way valve may be operational to substantially prevent back flow of gases otherwise supplied to the patient either from the patient interface or the subsequent patient interface.

In a further aspect, the disclosure relates to a pressure relief device for use with a conduit that delivers pressurised gas from a gas source to a patient, the pressure relief device comprising:
 a first wall and a generally opposing second wall wherein during normal use the first wall is substantially flush with an adjacent wall of the conduit such that substantially all of the gases from said gas source pass through said conduit and when a force is applied to the first wall, the first wall moves towards or away from the second wall to provide a passage through which gas may flow from within the conduit to exit to atmosphere.

The first wall may be relatively rigid and the second wall is relatively flexible.

The pressure relief device may further comprises a tongue extending from the first wall such that the tongue overlaps the adjacent wall of the conduit.

The first wall may be relatively flexible and the second wall is relatively rigid.

The force may be due to an item being pressed against the first wall.

The force may be a pressure of the gas within the conduit reaching a threshold pressure.

In a further aspect, the disclosure relates to a pressure relief device for use with a component of a respiratory support system that delivers pressurised gas from a gas source to a patient, the component of the respiratory support system having an aperture, the pressure relief device comprising: a biased component engageable with the aperture, wherein during normal use the biased component is biased towards the aperture in the component of the respiratory support system to substantially seal the aperture such that substantially all of the gases from a gas source pass through a conduit and when the pressure of the gas within the conduit reaches a threshold pressure the biased member moves away from the aperture in the component of the respiratory support system to provide a passage through which gas may flow from within the component of the respiratory support system to exit to atmosphere.

The component of the respiratory support system may comprise a filter.

The component of the respiratory support system may comprise the conduit.

The component of the respiratory support system may comprise a chamber.

In a further aspect, the disclosure relates to a pressure relief device for use with a conduit that delivers pressurised gas from a gas source to a patient, the conduit having an aperture, the pressure relief device comprising:
 a lever mounted within the conduit, the lever including a pivot, an operating portion, and a sealing portion that substantially seals the aperture in the conduit such that substantially all of the gases from said gas source pass through said conduit
 wherein when the operating portion is moved, the lever is caused to pivot about the pivot and the sealing portion moves away from the aperture to provide a passage through which gas may flow from within the conduit to exit to atmosphere.

The operating portion may be on one side of the pivot and the sealing portion is on the other side of the pivot.

The operating portion may be on one side of the pivot and the sealing portion is on the same side of the pivot.

In a further aspect, the disclosure relates to a flow restricting device for use with a conduit that delivers pressurised gas from a gas source to a patient the flow restricting device comprising a gate that is movable in a transverse direction across the conduit from a first position in which substantially a first level of gases from said gas source pass through said conduit to a second position in which a second level of gases pass.

The first position may be a substantially open configuration and the second position is a substantially closed configuration. In some configurations, the first level of gases is greater than the second level of gases.

The second position may be a completely closed or occluded or blocked gas flow path, or may be a partially closed or occluded or blocked gas flow path, including but not limited to being a restricted or constricted gas flow path.

The flow restricting device may comprise two gates having complementary engageable features.

In a further aspect, the disclosure relates to a pressure relief device for use with a component of a respiratory support system that delivers pressurised gas from a gas source to a patient, the component of the respiratory support system having an aperture, the pressure relief device comprising: a movable component engageable with the aperture, wherein during normal use the movable component is biased towards sealing the aperture in the component of the respiratory support system such that substantially all of the gases from a gas source pass through a conduit and when the pressure of the gas within the conduit reaches a threshold pressure the movable member clears the aperture in the component of the respiratory support system to provide a passage through which gas may flow from within the component of the respiratory support system to exit to atmosphere.

In a further aspect, the disclosure relates to a combination of a pressure relief device as disclosed herein together with a conduit.

The pressure relief device may be integrally formed with the conduit.

In a further aspect, the disclosure relates to a patient interface comprising: one or two sides arms extending from a manifold, and one or two outlets (such as nasal prongs) at or extending from the manifold, wherein one or both side arms comprises: a lumen for supply of a flow of gases from a respiratory tube to the manifold, and a venting arrangement to vent gases from the lumen to determine a maximum pressure at a user's airway or the patient interface.

The side arm may comprise a sealing portion over which a seal of a face mask can seal together with sealing against a user's face, and wherein the vent is positioned on the side arm outside of a sealing area of the face mask.

The sealing portion may comprise a profile allowing the seal of the face mask to seal against the portion together with the face of the user.

The side arm may be configured to resist an external force such that it does not compress or collapse in use.

The side arm may be formed from a relatively rigid material.

In a further aspect, the disclosure relates to an item such as a block or mount for use with a patient interface, the item in contact with, or to be placed in contact with, a patient's face, the item comprising: at least one lumen there through for allowing a gas supply conduit to pass, or for a connection of the gas supply conduit to be made at each end of the lumen, wherein the supplied gas is fluidly connected to the patient interface, and a venting arrangement to vent gases from the lumen to determine a maximum pressure at a user's airway or the patient interface.

The item may comprise a sealing portion over which a seal of a face mask can seal together with sealing against a user's face, and wherein the vent is positioned on the item outside of a sealing area of the face mask.

The sealing portion may comprise a profile allowing the seal of the face mask to seal against the portion together with the face of the user.

The item may be configured to resist an external force such that it does not compress or collapse in use.

The item may be formed from a relatively rigid material.

The item may be integrally formed with a side arm of a patient interface such as a cannula.

The patient interface or item may comprise a filter device to prevent contamination of a breathing circuit providing a flow of gases to the item or interface, and the filter device comprises the venting arrangement.

In a further aspect, the disclosure relates to a respiratory tube for use with a patient interface comprising a window in a wall of the tube, and a perimeter portion of the window configured to seal against the face of the user.

The tube may comprise a seal around the perimeter of the window to seal against the user's face.

The tube may have a relatively flat cross section compared to a conventional circular cross section.

The tube may be formed from a resilient material in a portion of the tube in which the window is formed.

The patient interface may be a nasal cannula.

The tube may comprise a membrane over the window.

In a further aspect, the disclosure relates to a respiratory system adapted to provide a flow of respiratory gases to a user, comprising a bladder in fluid communication with a lumen of a respiratory gases tube, the bladder configured to reduce pressure fluctuations in the lumen of the tube and/or reduce a pressure increase of the gases provided to the user.

The bladder may form or provide a portion of the lumen of the tube.

The bladder may be a section of the tube that has a reduced wall thickness and/or may be formed of a more resilient material than a remainder of the tube.

The bladder may be integrally formed with portions of the tube extending from each end of the bladder, or may be releasably attachable to a respiratory tube.

The bladder may be releasably attachable to a respiratory tube, each end of the bladder configured to be attached to a tube to form a respiratory tube assembly comprising a first length of tube attached to one end of the bladder, the bladder, and a second length of tube attached to the other end of the bladder.

The bladder may provide an indication of an increased pressure in the lumen of the tube.

The system may comprise a venting arrangement, such that once an increased pressure is reached the venting arrangement operates to vent respiratory gases from the lumen of the tube into the bladder.

The bladder may be configured to accommodate a predetermined volume and pressure of gases amounting to a predetermined flow rate and pressure.

The bladder may be configured to store a volume of gases equivalent to a flow rate of 70 L/min for 3 to 5 minutes at a typical operating pressure for a desired therapy to be delivered.

The system may comprise a relief valve or vent to vent the bladder to atmosphere once the bladder reaches a predetermined vent pressure.

In a further aspect, the disclosure relates to a respiratory tube configured to provide a flow of respiratory gases to a user, comprising a bladder configured to reduce pressure fluctuations in the lumen of the tube and/or reduce a pressure increase of the gases provided to the user.

The bladder may form or provide a portion of the lumen of the tube.

The bladder may be a section of the tube that has a reduced wall thickness and/or is formed of a more resilient material than a remainder of the tube.

The bladder may be integrally formed with portions of the tube extending from each end of the bladder, or may be releasably attachable to a respiratory tube.

A respiratory tube may be a respiratory tube assembly, each end of the bladder may be configured to be attached to a tube to form the respiratory tube assembly comprising a first length of tube attached to one end of the bladder, the bladder, and a second length of tube attached to the other end of the bladder.

The bladder may provide an indication of an increased pressure in the lumen of the tube.

The respiratory tube may comprise a venting arrangement, such that once an increased pressure is reached the venting arrangement operates to vent respiratory gases from the lumen of the tube into the bladder.

The bladder may be configured to accommodate a predetermined volume and pressure of gases amounting to a predetermined flow rate and pressure.

The bladder may be configured to store a volume of gases equivalent to a flow rate of 70 L/min for 3 to 5 minutes at a typical operating pressure for a desired therapy to be delivered.

A system may comprise a patient interface, a valve, and a vent.

In a further aspect, the disclosure relates to a patient interface comprising: a device for blocking flow between an inlet for receiving a flow of gases and an outlet for delivering the flow of gases to a patient, and/or a sensing arrangement. The device may be a collapsible portion of a conduit between the inlet and outlet, or a valve between the between the inlet and outlet. The sensing arrangement may comprise a first sensor upstream of the device and a sensor downstream of the device. The patient interface may comprise a pressure relief valve, upstream of the device. The device may be a pressure relieve device.

The interface may be a nasal cannula.

The respiratory tube may comprise a relief valve or vent to vent the bladder to atmosphere once the bladder reaches a predetermined vent pressure.

The valve may be a switch, a collapsible portion of a conduit, or a one way valve.

The vent may be a pressure relief valve.

A respiratory therapy delivery system may comprise any one or more of the above.

A patient interface may be provided in fluid communication with a gas supply conduit or tube, said conduit or tube comprising any one or more of the above.

A conduit or tube may be provided as a part of a respiratory therapy delivery system for supplying gas to a patient interface, said conduit or tube comprising any one or more of the above.

A system may comprise any one or more of the above, wherein said system is provided as a part of respiratory delivery therapy system for a patient undergoing a medical procedure.

In one embodiment, there is provided a system for providing respiratory support to a patient comprising:
  a nasal cannula having a body portion locatable upon a face of a patient in an operational position, at least one nasal prong extending from the body portion, the nasal prong being adapted to direct a flow of gas into a nare of the patient's nose when the body portion is in the operational position, and
  a flow controller for selectively controlling the flow of gas into the nare of the patient's nose from the nasal prong, the flow controller adapted to operate when a pressure in the system is above a predetermined value to restrict or prevent the flow of gas into the nare of the patient from the nasal prong.

A system may comprise:
  a pressure sensor or pressure sensing or sampling conduit for measuring or sampling a pressure within the system, and
  the flow controller adapted to operate in response to the measured or sampled pressure when the measured or sampled pressure is above the predetermined value.

The pressure sensor may be located at or near the nasal cannula, or at or near the nasal prong, or on a conduit adapted to deliver gas to the nasal cannula, or at a humidifier adapted to humidify the flow of gas, or at the flow controller, or the pressure sampling line samples a pressure at any one of these locations.

The pressure sensor may be located at or near the at least one nasal prong.

The pressure sensor may be located on a conduit adapted to deliver gas to the nasal cannula.

The flow controller may comprise a mechanical valve.

The mechanical valve may be a pressure relief device.

The system may comprise at least one processor to control the flow controller based on a pressure sensed by the pressure sensor.

The pressure relief device may comprise a valve member, the pressure acting on the valve member to operate the pressure relief device to restrict or prevent the flow of gas into the nare of the patient from the nasal prong.

The pressure relief device may comprise a cap or housing, to house the valve member on an outer side of a gas lumen of the system.

The valve member may be biased to a closed position to provide the flow of gas into the nare of the patient from the nasal prong.

The valve member may be or may comprise a piston or shuttle, the pressure acting on the piston or shuttle to operate the pressure relieve device to restrict or prevent the flow of gas into the nare of the patient from the nasal prong.

The predetermined value may be a maximum pressure.

The predetermined value may be an adjustable value.

The flow controller may be operated to deliver a maximum flow while maintaining the pressure below the predetermined value.

The set flow may be delivered at all times, unless a set pressure is exceeded at which point, the system maximises the flow possible to stay below that pressure.

The flow controller may be located remote from the nasal cannula.

A system may further comprise a mask to be in-situ with the nasal cannula in use.

The nasal cannula may be an unsealed patient interface.

The mechanical valve may comprise a valve member, a spring biasing the valve member into an open position allowing the flow of gas to be delivered to the patient.

The valve member may be adapted such that when the pressure in or near the nare of the patient's nose is greater than the force of the spring the valve member is urged to a closed position by the flow pressure, and the flow of gas is not delivered to patient.

The mechanical valve may have an excess flow outlet.

The tension of the spring may be a fixed spring tension. In other embodiments, the tension of the spring may be an adjustable spring tension.

The flow controller may comprise at least one processor and a user interface.

The predetermined value may be a fixed value.

The predetermined value may be an adjustable value.

The system further may comprise an anaesthetic mask.

The nasal cannula may be an unsealed patient interface.

The system further may comprise a second respiratory support system for directing a flow of gas into a patient's airway. The flow of gas may be a respiratory gas or another gas. The secondary respiratory support system may comprise a mask.

The flow controller may control the flow of gas from one or more gas sources.

In one embodiment, there is provided a method of providing respiratory support to a patient comprising:
  placing a nasal cannula upon a face of a patient in an operational position, the nasal cannula having a body portion and at least one nasal prong extending from the body portion,
  directing a flow of gas into a nare of the patient's nose via the nasal prong,
  measuring or sampling a pressure in the system, restricting or preventing the flow of gas into the nare of the patient's nose from the nasal prong when the measured or sampled pressure is above a predetermined value, and allowing the flow of gas into the nare of the patient's nose from the nasal prong when the pressure in or near the nare of the patient's nose is below the predetermined value.

In some embodiments, step iv) comprises preventing the flow of gas into the nare of the patient's nose from the nasal prong.

Flow may be prevented from entering the system when the measured pressure is above a limit.

The method may further comprise directing a flow of gas into a patient's airway using a second respiratory support system. The flow of gas may be a respiratory gas or another gas. The gas may be delivered to the patient via a mask.

The system may comprise an overall pressure relief system that can account for overall pressure and control one or more flow generator or one or more gas sources (this is because sometimes there might not be a flow generator and only a gas source might be present).

The pressure sensor may be located at or near the nasal cannula, or at or near the nasal prong, or on a conduit adapted to deliver gas to the nasal cannula, or at a humidifier adapted to humidify the flow of gas, or at the flow controller, or the pressure sampling line samples a pressure at any one of these locations.

The pressure sensor may be located on the humidifier

The pressure sensor may be located at the flow control valve

The mechanical valve may be a pressure relief device.

The system may comprise flow controller controlled by at least one processor to control the flow controller based on a pressure sensed by the pressure sensor and a user interface.

The pressure relief device may comprises a valve member, the pressure acting on the valve member to operate the pressure relief device to restrict or prevent the flow of gas into the nare of the patient from the nasal prong.

The pressure relief device may comprise a cap or housing, to house the valve member on an outer side of a gas lumen of the system.

The valve member may be biased to a closed position to provide the flow of gas into the nare of the patient from the nasal prong.

The valve member may be or may comprise a piston or shuttle, the pressure acting on the piston or shuttle to operate the pressure relieve device to restrict or prevent the flow of gas into the nare of the patient from the nasal prong.

The flow controller may be operated to deliver a maximum flow while maintaining the pressure below the predetermined value delivered flow is maximized to maintain the set pressure.

The set flow may be delivered at all times, unless a set pressure is exceeded at which point, the system maximizes the flow possible to stay below that pressure.

The flow controller may be located remote from the nasal cannula.

In a further aspect, this disclosure relates to, a user interface device to enable a user to control gas flow in a respiratory therapy system for delivering high flow gas to a patient is disclosed, the user interface device comprising: at least one user actuable controller for controlling the flow rate and/or concentration of two gases through a patient interface, and for substantially blocking or reducing the flow rate of at least one of the gases through the patient interface.

The gases is a high flow gas. In some configurations, another of said gases is an anaesthetic gas.

In some configurations, said patient interface is a nasal cannula, and wherein a user actuated controller comprises a switch positioned on the cannula.

In a further aspect, this disclosure relates to a respiratory therapy system comprising: a cannula for delivering a high flow gas to a patient; a mask for delivering a gas to the patient; and a pressure sensor associated with the cannula; wherein the system is configured to adjust flow of the high flow gas through the cannula in response to at least one type of pressure change sensed by the sensor.

The pressure sensor may be provided on an external surface of the cannula or on an external surface of a tube in fluid communication with the cannula.

The system may be configured to reduce or substantially stop flow of the high flow gas when the pressure sensor detects a pressure increase.

The pressure sensor may be configured to detect a pressure increase in response to the mask being placed on the patient, the patient exhaling, or actuation of an anaesthetic bag.

The system may further comprise a valve to partially or substantially block flow of the high flow rate gas through the cannula in response to the detected pressure increase.

In a further aspect, this disclosure relates to a respiratory therapy system comprising: a cannula circuit for delivering a high flow gas to a patient through a cannula; a bag circuit to enable a user to manually deliver gas to a patient by actuating a bag; and a connector that connects the bag circuit to the cannula circuit, the connector comprising a separation to substantially prevent high flow gas from travelling into the bag circuit.

The connector may be configured to enable both high flow gas and gas from the bag circuit to be delivered to a patient through the cannula.

The connector may be configured to substantially prevent delivery of high flow gas to the cannula when the bag circuit is connected to the cannula circuit.

The separation may comprise one or more walls in the connector.

The cannula may be a nasal cannula with at least one prong for receipt in a patient's naris, the cannula comprising inflatable cuff(s) associated with the prong(s) to assist with creating a seal in the patient's naris or nares.

The system may be configured to inflate the cuff(s) in response to actuation of the bag.

In a further aspect, this disclosure relates to, a cannula circuit for delivering a high flow gas to a patient through a cannula; a bag circuit to enable a user to manually deliver gas to a patient by actuating a bag, the bag circuit in fluid communication with the cannula circuit; and a valve arranged to allow the delivery of high flow gas to the cannula when the bag is not actuated, and to allow the delivery of gas from the bag circuit to the cannula when the bag is actuated.

The valve may be arranged such that flow of high flow gas to the cannula is substantially blocked or reduced in response to actuation of the bag.

The cannula may be a nasal cannula with at least one prong for receipt in a patient's nares, the cannula comprising inflatable cuff(s) associated with the prong(s) to assist with creating a seal in the patient's naris or nares.

The system may be configured to inflate the cuff(s) in response to actuation of the bag.

In a further aspect, this disclosure relates to a cannula comprising at least one prong for receipt in a patient's nares, the cannula comprising inflatable cuff(s) associated with the prong(s) to assist with creating a seal in the patient's naris or nares.

In a further aspect, this disclosure relates to a respiratory therapy system comprising: a patient interface for delivering gas to a patient; and a processor configured to control flow of gas through the patient interface to deliver gas to a patient at a first flow rate and/or pressure when the patient is spontaneously breathing, and configured to deliver gas to a patient at a second flow rate and/or pressure when the patient is not spontaneously breathing.

The system may be configured to detect the presence of apnoea and configured to deliver gas at the second flow rate and/or pressure in response to the detection of apnoea.

The system may be configured to detect the presence of apnoea based on the cessation of activation of brain signals, diaphragm signal, airway pressure, or $CO_2$ measurements.

The first flow rate and/or pressure may comprise a relatively low flow rate and/or pressure, and the second flow rate and/or pressure may comprise a relatively high flow rate and/or pressure.

The processor may be a remote processor.

In a further aspect, this disclosure relates to a respiratory therapy system comprising: a patient interface for delivering gas to a patient; a sensor arranged to sense fluctuations in pressure in the patient interface or in a conduit in fluid communication with the patient interface; and a processor configured to adjust flow of gas to the patient interface to deliver gas at an increased flow rate to the patient interface if a reduction in airway pressure is sensed.

The processor may be configured to adjust flow of gas to the patient interface to deliver gas at an increased flow rate to the patient interface if the reduction in airway pressure is determined to be occurring during and/or after apnoea.

In a further aspect, this disclosure relates to a patient interface comprising: a cannula for delivering gas to a patient; a connector portion in fluid communication with the cannula and configured for removably connecting the cannula to a complementary connector portion on a main gas conduit for delivering high flow gas to the cannula; and a secondary conduit in fluid communication with the cannula, the secondary conduit configured to provide fluid communication between the cannula and an alternative gas source.

The connector portion in fluid communication with the cannula may be configured to seal when the connector portion is disconnected from the complementary connector portion on the main gas conduit.

In another aspect, there is provided a patient interface comprising a mechanically activated switch or valve to control the flow of gas to the outlet or outlets from the patient interface.

The mechanically activated switch may be activated by a user, or alternatively may be activated by placement of a component of a respiratory therapy delivery system being brought into contact with the switch, such as a subsequent patient interface being brought into contact with the patient interface comprising the switch.

The patient interface comprising the switch may include a vent or pressure relief device to relieve pressure build-up due to activation of the switch and the flow of gas to the outlet or outlets being partially or completely stopped or prevented.

When activated, the switch may be partially blocking of the gas flow path through the patient interface or may be completely blocking of the flow path.

In another aspect, there is provided a conduit for use with a patient interface or as part of a respiratory therapy delivery system, the conduit comprising a mechanically activated switch or valve to control the flow of gas through the conduit and from being supplied to an outlet from the conduit (e.g. to a patient interface which may be connected to the conduit).

The mechanically activated switch may be activated by a user, or alternatively may be activated by placement of a component of a respiratory delivery system being brought into contact with the switch, such as a subsequent patient interface being brought into contact with the conduit comprising the switch.

The conduit comprising the switch may include a vent or pressure relief device to relieve pressure build-up due to activation of the switch and the flow of gas to the outlet from the conduit being partially or completely stopped or prevented.

When activated, the switch may be partially blocking of the gas flow path through the conduit or may be completely blocking of the flow path.

The conduit may be a self-supporting conduit (i.e. the conduit is not a collapsible conduit).

In a further aspect, this disclosure relates to a respiratory therapy system comprising:
 a first patient interface for delivery of a flow of gas to a patient, and
 a second patient interface for delivery of a flow of gas to the patient,
 wherein a sensor is associated with one or more of:
 the first patient interface,
 the second patient interface,
 both the first and second patient interfaces,
 an item associated with the first patient interface,
 an item associated with the second patient interface,
 an item associated both the first and second patient interfaces,
 an item to be associated with the patient, The first patient interface may comprise one or a pair of first patient interface outlets for directing the flow of gas to the patient's nose.

The first patient interface may be of a non-sealing interface type.

The first patient interface may be substantially non-sealing with a nare or nares of the patient's nose.

The first patient interface may be of a sealing type interface.

The first patient interface may be substantially sealing with a nare or nares of the patient's nose.

The first patient interface may deliver a first flow of gas to the patient.

The first flow of gas may be of a first flow-rate and/or pressure.

The percentage of oxygen in the first flow of gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

The first patient interface may be configured to deliver said flow of gas to a nare or nares of a patient's nose.

The first patient interface may comprise one or a pair of nasal prongs.

The prong or prongs may deliver and/or direct a flow of supplied gas to a nare or nares of the patient's nose.

The first patient interface may comprise a face mount part and at least one (preferably a pair of) side arm(s) extending from the face mount part.

The side arm(s) may be configured to assist in positioning of the face mount part or of the first patient interface upon a patient.

The side arms may comprise a connection system for connecting with a headgear or a face mounted connection system.

The connection system may be of a releasable type or re-usable type connection system.

The headgear may comprise at least one head-strap.

The at least one headstrap may be splittable or bifurcatable or at least a portion of said headstrap is separable along a line of weakness or a preferential zone of split or separation.

The at least one headstrap may comprises single connection point to the, or each of the, at least one side arm(s).

The first patient interface may comprises removable manifold portion.

In further embodiments, when in attachment with the face mount portion, the removable manifold portion provides for a fluid connection of the one or pair of first patient interface outlets with a source of gas.

The manifold portion may be configured so as to be attachable to the face mount portion from either of a left-side or a right-side of the first patient interface.

The removable manifold portion may be a downstream-end connector to the first patient interface of a gas supply conduit for supplying the flow of gas to the first patient interface.

The manifold portion may be of a push-fit type connection with the face mount part.

The manifold part may be removably attached to the face mount part, configured to be removably attached from connection with the face mount part and to swivel or rotate relative to the face mount part from a first operatively connected orientation and to at least one other (preferably a second) operatively connected orientation.

The first operatively connected orientation may provide for the removable manifold portion and an associated gas supply conduit to extend from a patient's left-side or a right-side in use, or vice versa; and wherein the second operatively connected operation may provide for the removable manifold portion and an associated gas supply conduit to extend from the patient's right-side or left-side in use, or vice-versa.

The first patient interface may be a nasal cannula.

The second patient interface may comprise at least one second patient interface outlet for directing the flow of gas to the patient's respiratory airways.

The second patient interface may direct the flow of gas to the patient's: nose, or mouth, or nose and mouth.

The second patient interface may be of a non-sealing interface type. In further embodiments, the second patient interface may be of a sealing type interface.

The second patient interface may be a substantially sealing interface in which a seal is created with a patient's face when the second patient interface is in-situ.

The second patient interface may deliver a second flow of gas to the patient.

The second flow of gas may be of a second pressure.

The percentage of oxygen in the gases delivered in the second flow of gas may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

The second patient interface may comprise a body with a seal portion, the seal portion to be substantially engaging or sealing with the patient when in-situ.

The seal portion may be over-moulded to the body or is otherwise attached to the body.

The second patient interface may comprise a frame to which a body is attachable.

The patient interface may comprise an inlet for connection thereto by a gas supply conduit for supplying the flow of gas to the second patient interface.

The second patient interface may be a hand held patient interface.

The inlet may be a joint.

The joint may be a ball-type joint, or a swivel or pivoting type joint, or an articulated joint, or a joint capable of movement relative to the body.

The second patient interface may be a hand-held interface

The second patient interface may comprise a connection system for connecting of a headgear, the headgear for supporting or positioning of the second patient interface upon the patient.

The connection system may be a releasable connection system, such that in-use, the headgear is removable or disconnectable from the second patient interface.

The second patient interface may be a mask.

The mask may be one of: a nasal mask, an oral mask, an oro-nasal mask, a full face mask, a nasal pillows mask, an endotracheal tube, or a combination of these or some other gas conveying system providing for a second flow of gas to the patient.

The item may be a block or mount in contact with, or to be placed in contact with, the patient's face, the block or mount comprising at least one lumen therethrough for allowing a gas supply conduit to pass, or for a connection of the gas supply conduit to be made at each end of the lumen, wherein the supplied gas is fluidly connected to the first patient interface.

The item may co-locate at least one gas supply conduit for supply of gas to the first patient interface.

The at least one gas supply conduit may extend or pass through the body of said item.

The at least one gas supply conduit may be a component extending through said item and which is sealingly engaged by said item.

The lumen through the item may be receivable of a gas supply conduit.

The lumen through the item may form a part of a fluid passageway for delivery of gas to the first patient interface.

The item may comprise a compressible portion or a portion that is capable of being squashed or deformed under an exerted force or pressure.

One or more of the at least one lumen may be located within the compressible portion or portion that is capable of being squashed or deformed. The compressible portion may be made of any suitable material, such as a polymer or silicone.

A lumen and/or conduit located within the compressible portion or portion may be capable of being squashed or deformed and may be compressed or deformed so as to block or obstruct (or prevent), or partially obstruct, the flow of gas from being supplied to the first patient interface.

The item may be an integral part of a side arm of the first patient interface.

The item may be removeably attachable to a supply conduit to the first patient interface.

The item may be removeably attachable to a side arm of the first patient interface.

The item may be a discreet component separately positionable or locatable upon a patient, more particularly upon a patient's face.

The item may be a gas conduit in fluid connection with the first patient interface, or the second patient interface, of gas conduits in fluid connection with connection with each of the first and second patient interfaces.

The item may be a patch or pad or wearable device that is attachable or locatable upon the patient for sensing the in-situ combination of the first patient interface and the second patient interface upon the patient during delivery of gas to the patient, wherein such a sensed combination generates a signal or output.

The signal or output may be fed to, or may activate or control (or activates and controls) one or more of the following system outcomes:
- a visual alarm or warning
- an audible alarm or warning, including but not limited to a whistle,
- a haptic or tactile feedback fed or directed to a wearable electronic device, including but not limited to: watches, phones, head mounted displays or other articles of clothing incorporating such an electronic device,
- a flow controller, including a flow valve or flow generator, preferably for controlling the flow of gas being directed to the first patient interface; optionally in addition or separately, including controlling the flow of gas being directed to the second patient interface,
- a pressure regulator or pressure throttling device, preferably for controlling the pressure of gas being directed to the first patient interface; optionally in addition or separately, including controlling the pressure of gas being directed to the second patient interface,
- a diverter to divert the flow of gas otherwise to be controlled to a vent,
- a micro-processor associated with the flow controller or the pressure regulator (or both),
- a graphical user interface (GUI).

The signal or output of the sensed in-situ combination may provide for control of the flow (or pressure) of the gas being directed to the first patient interface.

The sensor may uses one or a combination of any one of the following in sensing the in-situ combination:
- optical sensors (including infra-red, IR)
- acoustic (including audible or ultrasonic) sensors
- pressure or flow sensors of the pressure or flow, or both pressure and flow, of gas in a supply conduit supplying a gas to the first patient interface, or the second patient interface, or both the first and second patient interfaces, or of the pressure or flow (or both) of the gas delivered to the patient's respiratory system or a part of the patient respiratory system,
- electrical conductivity or resistance electrodes embedded within, or placed on a part of, one or more of:
  the first patient interface,
  or the second patient interface,
  or both the first and second interfaces,
  or an item associated with the first or the second or both the first and second patient interfaces,
  or an item to be associated with the patient,
- radio-frequency or proximity sensing sensors to sense the in-situ combination,
- mechanically activated or triggered sensors, comprising but not limited to: a mechanical switch activated or triggered by being depressed or being placed into contact with another surface, pressure relief valves or pressure sensitive valves, solenoid valves, mechanical valves with a pre-determined spring constant (optionally but not limited to such a spring constant being relatively higher when the valve is closed and relatively lower when the valve is open), optionally a pressure relief valve comprising of a whistle activated by the release of gas from the valve when moving to the open position from the closed position.

The sensor may be located on or within the first patient interface or the second patient interface, or both of the first and second patient interfaces, the sensor sensing:
- the presence or placement of the second patient interface upon or in combination with the first patient interface upon the patient,
- the presence or placement of the first patient interface on a patient's face and the subsequent placement or presence of the second patient interface in combination upon the patient.

A sensor may be located on or within the first patient interface.

A sensor may be located on or within the second patient interface.

The sensor may senses when the second patient interface is in-situ or "in place" on a patient, and generates the signal or output.

The sensor may detect the placement of the second patient interface upon a patient.

The sensor used may be one or more of: an optical sensor (including IR), an acoustic sensor (audible or ultrasonic), a mechanically activated or triggered sensor (e.g. a mechanical switch activated when in contact with another object).

The acoustic sensing system may comprise a transmitter and a receiver, the transmitter transmitting a pre-determined code (e.g. a modulated acoustic signal) and the receiver receiving and detecting the code. The acoustic signal may be sent by a transmitter and if the second patient interface is present the signal is reflected back to a receiver located proximal to the transmitter. For example, the transmitter and receiver may be on or within the first patient interface and the signal may be reflected by the second patient interface. Alternatively, the transmitter and receiver may be on or within the second patient interface and the signal may be reflected by the patient's face or the first patient interface.

The optical sensing system may comprise a transmitter and a receiver, the transmitter transmitting a pre-determined code (e.g. a specific binary code) and the receiver receiving and detecting the code. For example, the transmitter and receiver may be on or within the first patient interface and the signal may be reflected by the second patient interface. Alternatively, the transmitter and receiver may be on or within the second patient interface and the signal may be reflected by the patient's face or the second patient interface.

In The sensor may sense the in-situ combination, the gas flow to the first patient interface is controlled. Wherein control of the gas flow to the first patient interface is a discontinuation or ceasing of the gas supply.

The sensor may sense the patient's face, or the first patient interface, or both of the patient's face and the first patient interface, the gas flow to the first patient interface is controlled or a signal or output is generated by the sensor to control or regulate the flow of gas to the first patient interface or to generate an alarm or warning.

The sensor may be chosen or tuned so as to sense a component located on or embedded with the first or the second patient interface or that is located on or embedded within each of the first and second patient interfaces.

The sensor may be is chosen or tuned so as to avoid an accidental false positive sensing.

The sensor may be located on or embedded within an item, the item being a block or mount in contact with, or to be placed in contact with, (or optionally being attachable to or mountable upon) the patient's face, the block or mount may comprise at least one lumen therethrough for allowing a gas supply conduit to pass, or for a connection of the gas supply conduit to be made at each end of the lumen, wherein the supplied gas is fluidly connected to the first patient interface.

The second patient interface may be placed in contact with the item, the sensor located or embedded within the item sensing the presence of the second patient interface and generating the signal or output.

The sensor may be at least one pair of electrodes that generate a signal or output based on the change in dielectric constant or change in capacitance between the electrodes, the signal or output being used to feed, or activate or control (or activate and control) any one or more of the system outcomes as defined above.

The sensor may be a mechanical switch activated by the second patient interface being placed into contact with said sensor, and generating the signal or output.

The mechanical switch may comprise an actuatable projection or prong extending from the item, the projection or prong extending from the item at a point which is to come into contact with the second patient interface when the second patient interface is provided in an operational configuration with the patient.

The actuatable projection or prong may be a depressible button, which once depressed is actuated and generated the signal or output.

The mechanical switch may comprise a strain gauge, said strain gauge generating a signal or output once a pre-determined quantity of strain is sensed, the pre-determined quantity of strain being indicative of a second patient interface being placed in contact with the item when the second patient interface is in an operational configuration with the patient.

The item may comprise an optically transmissive portion (such as, but not limited to an optically clear window section), wherein an optical sensor is located within the transmissive portion, the optical sensor optically sensing the presence of the second patient interface when placed substantially in contact with at least a part of the portion.

Prior to the presence or placement of the second patient interface substantially upon the optically transmissive portion, the sensing system may sense a total internal reflection; and when the second patient interface is present or placed upon the optically transmissive portion, the sensing system may sense a frustrated internal reflection.

The sensor may be a pressure sensitive switch or sensing system, sensing or detecting of an increase in pressure when the second patient interface is placed in contact with the item.

The pressure sensitive switch or sensing system may comprise a pressure sensor within a gas filled chamber within the item, and a flexible or pressure sensitive membrane provided as a barrier or external surface upon the second patient interface is to be placed when provided for use with the patient, the placement of the second patient interface upon the barrier or external surface generating a change of pressure within the chamber.

The change in pressure within the chamber may be sensed by the sensor and a signal or output generated indicative of the presence of the second patient interface in combination with the item.

The pressure sensitive switch or sensing system may comprise a pressure sensor within the seal of the second patient interface, and the placement of the second patient interface upon the patient induces a change in pressure within the seal which is sensed by the sensor and a signal or output generated indicative of the presence of the second patient interface on the patient.

The sensor may be located on or embedded within the first patient interface.

The sensor may uses one or more of: an acoustic (audible or ultrasonic) sensing system, an optical beam sensing system (including IR), a temperature sensing system.

The sensor may be a temperature sensing system that senses a change in temperature, in particular, a pre-determined temperature or range of temperatures associated with that of a patient or their skin to sense when the first patient interface is in place or operational position on the patient.

A temperature sensing system may be activated to allow other sensors to become operational. This would prevent other sensors from operating when the first patient interface is not in place or operational position on the patient.

The item associated with the first patient interface, or the second patient interface, or both of the first and second patient interfaces, may be a gas supply conduit.

The sensor may be associated with the item.

The sensor associated with the item may be an acoustic type sensing system.

The sensor may sense a change in a parameter or characteristic of the item, indicative of an increase in pressure or a decrease in gas flow in or through the item.

The parameter or characteristic may be a change in shape of a gas supply conduit resultant from one or more of: an increased pressure within the conduit, a decrease in gas flow through the conduit, a change in shape of the conduit due to application of an external force or pressure, such as from a force or pressure exerted upon the conduit from a second patient interface (whether the force or pressure is applied directly or indirectly).

The sensor may comprise an acoustic signal transmitter and an acoustic signal receiver, such that a transmitted acoustic signal is altered or modified by a change in a shape of the gas supply conduit indicative of an increase in pressure or decrease in gas flow in or through the conduit.

The sensor may sense a reflected signal (e.g. due to a closure of the conduit or a change or deviation in the shape of the conduit outside of a pre-determined operating range), or may sense a change in resonance (e.g. due to a standing wave form being formed within the conduit when the conduit is closed or a change or deviation in the shape of the conduit outside of a pre-determined operating range).

In a further aspect, this disclosure relates to a respiratory system comprising:
 a controller,
 a flow generator,
 a sensor system, such as a pressure sensor system, a flow sensor system and/or a motor speed sensor system,
 a first patient interface, and
 a second patient interface.

The controller may be adapted to detect a change in pressure, a change in flow, or a change in motor speed of a mechanical blower, and in response to the detection of a change the controller activates or controls (or activate and control) any one or more of the 'system outcomes' as defined above.

The respiratory system may comprise a humidifier and a chamber with a chamber inlet and a chamber outlet and the pressure sensor system is positioned at the chamber outlet.

The system may comprise a flow sensor at the chamber inlet and/or chamber outlet. The flow sensor may be a heated bead sensor. Alternatively, the flow sensor may be an ultrasonic flow sensor integrated with the controller.

In a further aspect, this disclosure relates to a respiratory therapy system comprising:
- a nasal cannula for delivery of a flow of gas to a patient, and
- a mask for delivery of a flow of gas to the patient.

A sensor may be associated with one or more of:
- the nasal cannula,
- the mask,
- both the cannula and the mask,
- an item associated with the nasal cannula,
- an item associated with the mask,
- an item associated both the nasal cannula and the mask,
- an item to be associated with the patient.

The sensor may sense an in-situ combination of the nasal cannula and the mask upon the patient during delivery of gas to the patient, and the sensed combination generates a signal.

In a further aspect, this disclosure relates to a patient interface comprising a sensor associated with said interface, said sensor for determining the dual operational application of a pair of patient interfaces to a patient's airways.

The patient interface may be a nasal cannula.

The patient interface may be a mask.

The mask may be one of: a nasal mask, an oral mask, an oro-nasal mask, a full face mask, a nasal pillows mask, an endotracheal tube, or a combination of these or some other gas conveying system providing for a second flow of gas to the patient.

A first patient interface of the pair of interfaces may be a nasal cannula.

A second patient interface of the pair of interfaces may be a mask.

The sensor may be associated with either the first or second patient interfaces, or both of the first and second patient interfaces.

The sensor may be associated with an item to be provided in operational combination with either the first or second patient interfaces, or both of the first and second patient interfaces.

In a further aspect, this disclosure relates to a user interface for supplying gases to an airway of a user, comprising:
- a body, said body comprising an aperture or a port allowing for communication of gases to and/or from a gas supply or source to an interior volume of the interface, the interior volume defined by an interior of the body and the face of the user when in-use,
- a face seal provided for creating or forming of a seal between the user interface and the user's face and/or a spacer component provided on the user's face so that the interior volume is a sealed interior volume, and wherein the face seal and/or the spacer component so provided on the user's face is adapted or configured to accommodate the creating or forming of the seal between the user interface and the user's face and/or the spacer component so provided on said face and facilitate intrusion of a gas conduit extending between the body and the user's face into the sealed interior volume.

The face seal comprises one or more accommodation sites or portions adapted to facilitate intrusion of the gas conduit into the sealed interior volume while maintaining the seal between the user interface and the user's face.

The seal may be substantially located or provided at, or about, or adjacent to, a rim or a perimeter of the body.

The one or more accommodation sites or portions comprise a cut-out or suitably shaped portion in the face seal or the face seal and the body.

The cut-out or suitably shaped portion may be adapted to accommodate a profile of the gas conduit or the spacer component.

The spacer component may comprise a channel or groove or pathway for receiving a portion of the gas conduit and a sealing surface over which the face seal forms a seal together with user's face.

The spacer component may be a sleeve enveloping or at least partly surrounding a portion of the gas conduit.

The spacer component may comprise a first portion and a second portion adapted to receive or clamp, house or retain the gas conduit between the two portions.

The first and the second portions may be hingedly or pivotably joined at one side and openable from another side to receive or clamp, house or retain the gas conduit between the two portions.

The first and/or the second portion comprises a groove, a channel or a pathway to accommodate or assist in locating the conduit between the first and the second portions.

The interface may also comprise a coupling arrangement for coupling the spacer component to the interface.

The coupling arrangement may comprise a protrusion and a complimentary groove, the protrusion may be being provided on one of the face seal and the spacer component and the groove being provided on the other one of the face seal and the spacer component.

The spacer component may allow partial collapse of the gas conduit when the interface is worn by the user, the spacer component adapted to collapse under a force provided by the face seal on the user's face.

In a further aspect, this disclosure relates to a spacer component for use in a gases supply system which conveys breathable gases to and/or from a user via the user interface of any one of the above statements, and a gas conduit for delivering breathable gases to and/or from the user via a separate gas supply system or source, wherein the spacer component is configured and adapted to be positioned on the user's face and accommodate the creating or forming of the seal between the user interface and the user's face and facilitate intrusion of the gas conduit extending between the face seal and the user's face into the sealed interior volume.

The spacer component may be provided along a portion of the length of the conduit, preferably the length of the conduit which engages or contacts the face seal of the user interface.

The sleeve may comprise a first portion and a second portion adapted to receive or clamp, house or retain the gas conduit between the two portions.

The two portions may be pivotably or hingedly joined along one side and openable along another side to receive the conduit between the two portions.

The spacer component may be removably snapped or clipped or otherwise removably fitted onto the conduit.

The spacer component may comprise a channel or groove or pathway for receiving the conduit.

The spacer component may allow partial collapse of the gas conduit when the interface is worn by the user, the spacer component may be adapted to collapse under a force provided by the face seal on the user's face.

In accordance with at least one of the embodiments disclosed herein is a system for providing respiratory support to a patient, said system comprising:
  a nasal cannula for delivering gases to the nares of the patient via the gas conduit, and
  a user interface according to any one of the above aspects.

The system may be configured to deliver general anaesthetics to the user via the user interface, while separately or in addition, also to deliver a high flow of oxygen to the nares of the user via the nasal cannula.

In a further aspect, this disclosure relates to a system for providing respiratory support to a patient comprising a combination of an oro-nasal mask and a nasal cannula assembly, each of said mask and nasal cannula assembly provided with separate gas flow supply from one or more sources, said nasal cannula being independently locatable upon a user from said mask.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The disclosure consists in the foregoing and also envisages constructions of which the following gives examples only.

BRIEF DESCRIPTION OF THE FIGURES

Specific embodiments and modifications thereof will become apparent to those skilled in the art from the detailed description herein having reference to the figures that follow, of which:
FIG. 12A shows a cross section of a portion of a collapsible conduit, while
FIG. 14A shows the conduit having such a collapsible capability in a first "open" lumen or gas flow path condition, while
FIG. 15A shows the conduit having such a collapsible capability in a first "open" lumen or gas flow path condition, while
FIG. 16B(i) to 16C(ii) show cross sections of valve arrangements for stopping flow for example to a patient interface.
FIG. 23A to 23D show an embodiment of a pressure relief device.

FIG. 45B-i shows a pressure relief valve and check valve arrangement for selectively deflating a cuff of the connection-actuated changeover configuration of FIG. 45A. FIG. 45B-ii shows the pressure relief valve and check valve arrangement of FIG. 45B-i with the relief valve in an open configuration and the check valve in a closed position.

FIG. 45B-iii shows an alternative pressure relief valve and check valve arrangement for the connection-actuated changeover configuration of FIG. 45A.

FIG. 45B-iv shows the pressure relief valve and check valve arrangement in a venting configuration.

FIG. 45C-i shows a connector of the connection-actuated changeover configuration, the connector in a condition allowing high flow gas. FIG. 45C-ii shows the connector in a condition blocking high flow gas and allowing bag flow gas.

FIG. 45D-i shows an exemplary plot of cannula flow, bag flow, high gas flow and prong cuff status versus time during use of the connection-actuated changeover configuration.

FIG. 45D-ii shows an exemplary plot of cannula flow, bag flow, high gas flow and prong cuff status versus time during use of the connection-actuated changeover configuration for when at least a low level of a high flow gas is maintained at all times.

FIG. 45E shows an alternative connector of the connection-actuated changeover configuration.

FIG. 45F shows an exemplary plot of high flow, bag flow, and cannula flow versus time during use of the connection-actuated changeover configuration with the connector of FIG. 8e.

FIG. 54A shows a first patient interface in the form of a nasal cannula in operational position with a patient, including a gas supply conduit providing a flow of gas to the interface, and where a gas source provides the flow, and a sensor, such as an acoustic sensor, is used to sense a parameter or characteristic of the conduit.

FIG. 54B then shows a second patient interface, such as full face mask, in operational position on the patient, in combination with the first patient interface, with a part of the second patient interface (e.g. a seal) coming into contact with the item and applying a contacting force or pressure which in turn closes, or at least partially closes the conduit supply gas to the first patient interface, a resultant change in shape (such as the bulge) occurs and is sensed by the sensing system associated with the conduit.

FIG. 54C shows a further iteration of FIG. 54B, but where the conduit is still further changed in shape or bulged, for example resultant from a complete closure of the conduit and/or due to a build-up in the pressure within the conduit.

DETAILED DESCRIPTION

The foregoing description of the various embodiments and disclosure herein includes preferred forms thereof. Modifications may be made thereto without departing from the scope of the disclosure.

Figure 1:
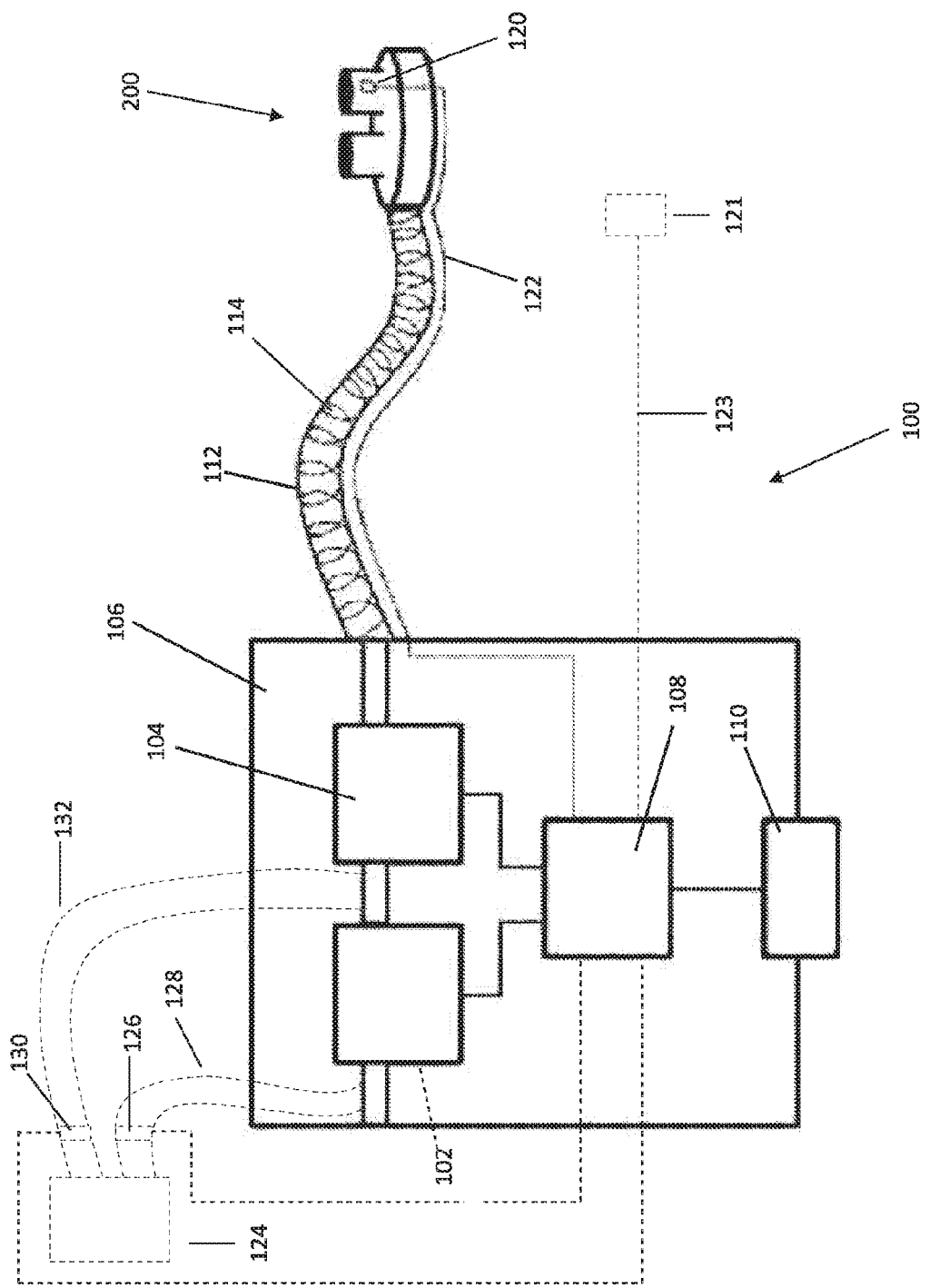
FIG. 1 shows a respiratory therapy system.

FIG. 1 shows a respiratory therapy system 100. The respiratory therapy system 100 comprises a flow generator 102. The flow generator 102 is configured to generate gas flows that are passed through the respiratory therapy system 100. The flow generator 102 passes the air to a humidifier 104. The humidifier 104 is configured to heat and humidify gas flows generated by the flow generator 102. In some configurations, the flow generator 102 comprises a blower adapted to receive gases from the environment outside of the respiratory therapy system 100 and propel them through the respiratory therapy system 100. In some configurations, the flow generator 102 may comprise some other gas generation means. For example, in some configurations, the flow generator 102 may comprise a source available from a hospital gas outlet (e.g. oxygen or air), or one or more containers of compressed air and/or another gas and one or more valve arrangements adapted to control the rate at which gases leave the one or more containers. As another example, in some configurations, the flow generator 102 may comprise an oxygen concentrator. In some configurations, the flow generator 102 may be adapted to deliver a high flow therapy.

According to various configurations and embodiments described herein, a flowrate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min). Flowrates above about 15 L/min in some embodiments may be used in such configurations or embodiments, in particular but not limited to flowrates of about 60-70 L/min. 'High flow' or 'high flow therapy' may refer to the delivery of gases to a patient at a flow rate of between about 5 or 10 L/min and about 100 L/min, or between about 15 L/min and about 95 L/min, or between about 20 L/min and about 90 L/min, or between about 25 L/min and about 85 L/min, or between about 30 L/min and about 80 L/min, or between about 35 L/min and about 75 L/min, or between about 40 L/min and about 70 L/min, or between about 45 L/min and about 65 L/min, or between about 50 L/min and about 60 L/min.

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal peak inspiratory demand, to increase oxygenation of the patient and/or reduce the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

As relatively high gas delivery flow rates may be used with the embodiments or configurations described herein, the gases being supplied or delivered to the user or patient may be delivered to different parts of the user's or a patient's airway.

Such relatively high flow rates of gases may assist in providing the supplied gases into a user's airway, or to different parts of a user's airway, for example such flow rates may allow for a delivery of such gases to the upper or lower airway regions. Upper airway region typically includes the nasal cavity, pharynx and larynx, while the lower airway region typically includes the trachea, primary bronchi and lungs.

Figure 11:
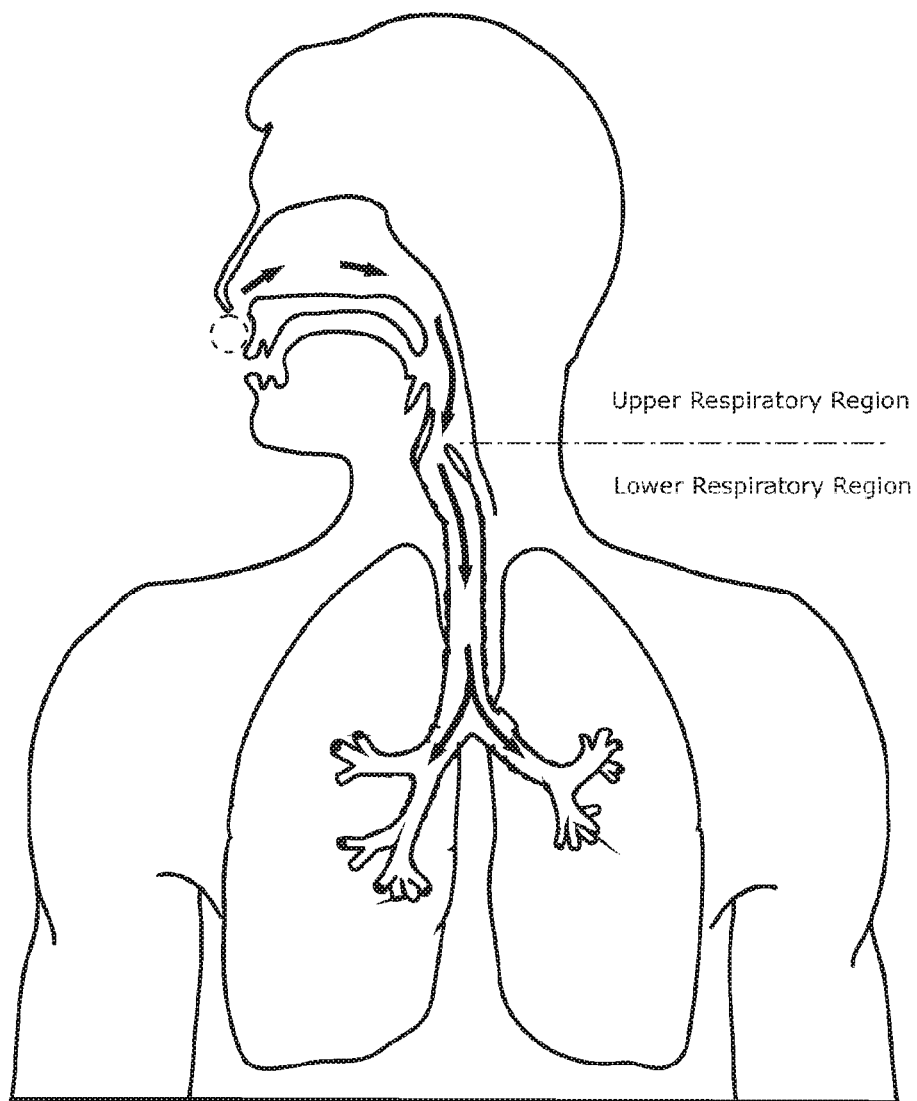
FIG. 11 shows a typical airway of a patient.
Figure 12A:
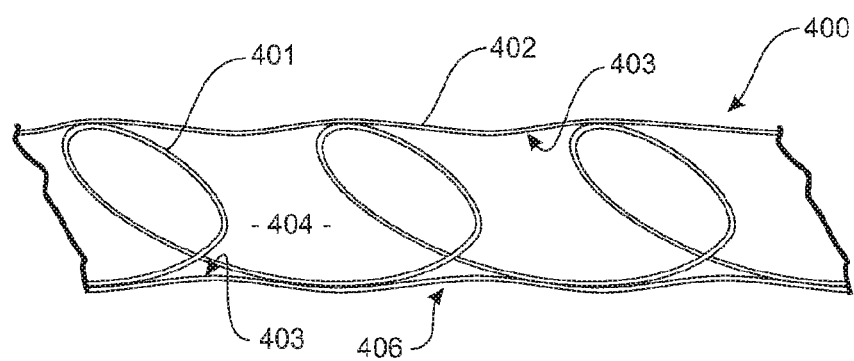
Figure 12B:
FIG. 12B shows the same conduit in a more "closed" or second condition.

FIG. 11 shows a typical airway of a person, and includes arrows to indicate how a relatively high flow rate of gases supplied to a user may be utilised to effectively push or drive the supplied gases further or deeper into a user's airway than when the person is under normal or typical self-driven respiratory conditions, or when a patient has a diminished respiratory drive.

The respiratory therapy system 100 comprises a housing 106 that at least partially houses both the flow generator 102 and the humidifier 104 (e.g. the respiratory therapy system 100 may comprise an integrated flow generator/humidifier apparatus). In other configurations the flow generator 102 and humidifier 104 may have separate housings. A hardware controller 108 is shown to be in electronic communication with the flow generator 102 and the humidifier 104, although in some configurations the hardware controller 108 might only communicate with the flow generator 102 or the humidifier 104. The hardware controller 108 may comprise a microcontroller or some other architecture configured to direct the operation of controllable components of the respiratory therapy system 100, including but not limited to the flow generator 102 and/or the humidifier 104. An input/output module 110 is shown to be in electronic communication with the controller 108. The input/output module 110 may be configured to allow a user to interface with the controller 108 to facilitate the control of controllable components of the respiratory therapy system 100, including but not limited to the flow generator 102 and/or the humidifier 104, and/or view data regarding the operation of the respiratory therapy system 100 and/or its components. The input/output module 110 might comprise, for example, one or more buttons, knobs, dials, switches, levers, touch screens, speakers, displays and/or other input or output peripherals that a user might use to view data and/or input commands to control components of the respiratory therapy system 100.

As further shown in FIG. 1, a supplementary gas source 124 may be used to add one or more supplementary gases to the gases flowing through the respiratory therapy system 100. The one or more supplementary gases join the gas flow generated by the flow generator 102. The supplementary gas source 124 may be configured to deliver one or more supplementary gases including but not limited to air, oxygen ($O_2$), carbon dioxide ($CO_2$), nitrogen ($N_2$), nitrous oxide (NO), and/or hellox (a mixture of helium and oxygen). The supplementary gas source 124 may deliver the one or more supplementary gases via a first supplementary gas lumen 128 to a location upstream of the flow generator 102, and/or may deliver the one or more supplementary gases via a second supplementary gas conduit 132 to a location downstream of the flow generator 102 and/or upstream of the humidifier 104. One or more supplementary flow valves 126, 130 may be used to control the rates at which the one or more supplementary gases can flow from the supplementary gas source 124 and through the first and/or second supplementary gas conduits 128, 132. One or more of the supplementary flow valves 126, 130 may be in electronic communication with the controller 108, which may in turn control the operation and/or state of the one or more of the supplementary flow valves 126, 130. In other configurations, the supplementary gas source 124 may be configured to add one or more supplementary gases downstream of the humidifier 104.

As shown in FIG. 1, a conduit 112 extending from the humidifier 104 links the humidifier 104 to a patient interface 200. The conduit 112 may comprise a conduit heater 114 adapted to heat gases passing through the conduit 112. In other configurations the conduit heater 114 may not be present. The patient interface 200 is shown to be a nasal cannula, although it should be understood that in some configurations, other patient interfaces may be suitable. For example, in some configurations, the patient interface 200 may comprise a sealing or non-sealing interface, and may comprise a nasal mask, an oral mask, an oro-nasal mask, a full face mask, a nasal pillows mask, a nasal cannula, an endotracheal tube, tracheostomy tube, a combination of the above or some other gas conveying system. In a preferred embodiment, the patient interface 200 is a non-sealing interface such as a nasal cannula, which allows gases to be exchanged with the environment. For example, the non-sealing cannula allows carbon dioxide to be removed and/or cleared from the patient's airways while the patient receives flow therapy from the system 100. Further, in the preferred embodiment, the patient interface 200 is in the form of a nasal interface, such that the system does not interfere with other oral airway equipment and/or devices, for example, a tracheal tube in an intubation procedure. Accordingly, the patient may continue to receive flow therapy throughout the intubation procedure.

As shown, in some configurations the patient interface 200 may also comprise a gas sensing module 120 adapted to measure a characteristic of gases passing through the patient interface 200. In other configurations the gas sensing module 120 could be positioned and adapted to measure the characteristics of gases at or near other parts of the respiratory therapy system 100. The gas sensing module 120 may comprise one or more sensors adapted to measure various characteristics of gases, including but not limited to pressure, flow rate, temperature, absolute humidity, relative humidity, enthalpy, gas composition, oxygen concentration, carbon dioxide concentration, and/or nitrogen concentration. Gas properties determined by the gas sensing module 120 may be utilized in a number of ways, including but not limited to closed loop control of parameters of the gases. For example, in some configurations flow rate data taken by a gas sensing module 120 may be used to determine the instantaneous flow, which in turn may be used to determine the respiratory cycle of the patient to facilitate the delivery of flow in synchronicity with portions of the respiratory cycle. The gas sensing module 120 may communicate with the controller 108 over a first transmission line 122. In some configurations, the first transmission line 122 may comprise a data communication connection adapted to transmit a data signal. The data communication connection could comprise a wired data communication connection such as but not limited to a data cable, or a wireless data communication connection such as but not limited to Wi-Fi or Bluetooth. In some configurations, both power and data may be communicated over the same first transmission line 122. For example, the gas sensing module 120 may comprise a modulator that may allow a data signal to be 'overlaid' on top of a power signal. The data signal may be superimposed over the power signal and the combined signal may be demodulated before use by the controller 108. In other configurations the first transmission line 122 may comprise a pneumatic communication connection adapted to transmit a gas flow for analysis at a portion of the respiratory therapy system 100.

Additionally as shown a physiological sensor module 121 may be present. The physiological sensor module 121 may be configured to detect various characteristics of the patient or of the health of the patient, including but not limited to heart rate, EEG signal, EKG/ECG signal, inertial sensors attached to the patient (e.g.: chest) to detect movement, blood oxygen concentration (via, for example, a pulse oximeter), blood $CO_2$ concentration, transcutaneous $CO_2$ (TcCO2) and/or blood glucose. Similarly, the physiological sensor module 121 may communicate with the controller 108 over a second transmission line 123. The second transmission line 123 may comprise wired or wireless data communication connections similarly to the first transmission line 122, and power and data may be communicated similarly. The physiological sensor module 121 may be used, for example, to determine the blood oxygen saturation of the patient.

Figure 2:
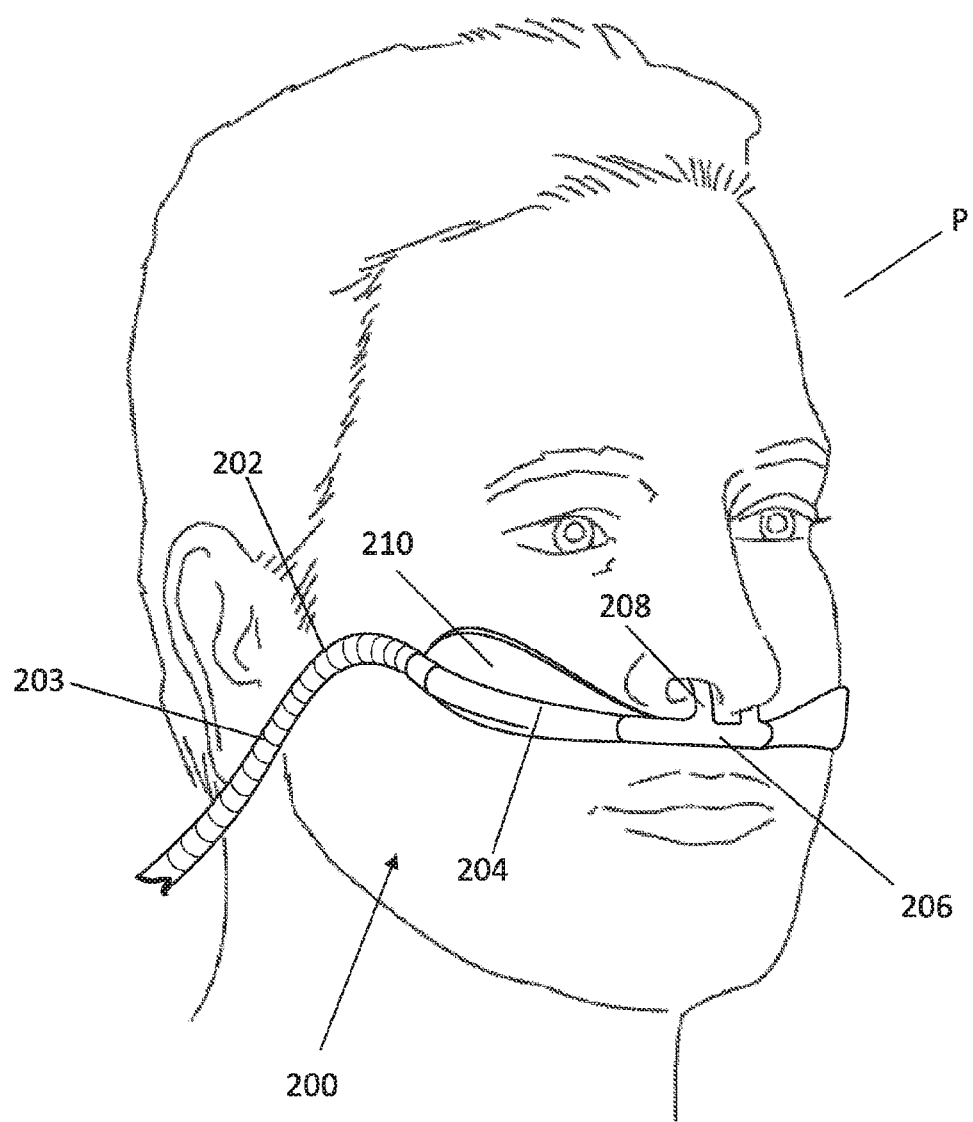
FIG. 2 shows a patient wearing a patient interface.

FIG. 2 shows a patient P wearing a patient interface 200, for example the patient interface 200 of the respiratory system of FIG. 1. In the illustrated non-limiting configuration, the patient interface 200 is a nasal cannula. The patient interface 200 comprises a first gas lumen 202 defined by a tubular wall. The first gas lumen 202 is adapted to receive gases from the respiratory therapy system 100 (for example, via the conduit 112 shown in FIG. 1) and channel the gases to the patient P. The illustrated first gas lumen 202 is defined at least in part by a wall within which gases can be channeled. The first gas lumen 202 may comprise a reinforcement element 203 adapted to strengthen and/or add rigidity to the first gas lumen to prevent deformation or collapse of the first gas lumen 202 arising due to the application of forces against the first gas lumen 202. The reinforcement element 203 may include a number of structures, including but not limited to plastic or metallic reinforcing beads that lie in or on the wall of the first gas lumen 202.

The first gas lumen 202 is in pneumatic communication with a flow manifold 206. The flow manifold 206 receives gases from the first gas lumen 202 and passes them to one or more nasal delivery elements 208 (e.g. prongs). The one or more nasal delivery elements 208 extend outwardly from the flow manifold 206. The one or more nasal delivery elements 208 are adapted to be non-sealingly positioned in one or more nares of the patient P. As shown, the patient interface 200 comprises two nasal delivery elements 208 adapted to be positioned one in each of the patient's nares. Each nasal delivery element 208 may be shaped or angled such that it extends inwardly towards a septum of the patient's nose. Alternatively the first patient interface 200 may be a sealing nasal interface.

Additionally, each nasal delivery element may be shaped or angled such that a tip of each nasal delivery element points, in use, towards a back of the head of the patient P. In the embodiment shown in FIG. 2, the flow manifold 206 receives flow from one lateral side of the flow manifold 206 (e.g. with respect to an imaginary vertical plane bisecting the face of the patient P) and channels flow to each of the nasal delivery elements 208. In other configurations, the patient interface 200 may comprise greater (for example, three or four) or fewer (for example, one) nasal delivery element 208.

In other configurations, each nasal delivery elements 208 can have different properties. For example, one of a pair of nasal delivery elements 208 can be relatively long and the other nasal delivery element 208 can be relatively short. In some configurations, the flow manifold 206 may be configured to receive flow from two lateral sides of the flow manifold 206 (e.g. from a 'left' and 'right' of the flow manifold 206 instead of just the 'left' of the flow manifold 206 as seen in FIG. 2). In some such configurations, multiple gas lumens may be used to provide for pneumatic communication between the flow manifold 206 and the respiratory therapy system 100. In some configurations, the flow manifold 206 may be configured to receive flow from a non-lateral side of the flow manifold 206 (e.g. from a 'bottom' or 'top' of the flow manifold 206).

The patient interface may further comprise mounts and/or supports, e.g., cheek supports 210, for attaching and/or supporting the gas lumen 202 on the patient's face. Alternatively, the patient interface may be held in place via one or more headstraps or headgear.

Further, first gas lumen 202 may comprise a first portion 204 configured to transition from a first configuration in which a first level of gases is able to pass through the first portion 204 to a second configuration in which a second level of gases is able to pass through the first portion 204. This feature will be described in more detail below.

Figure 3:
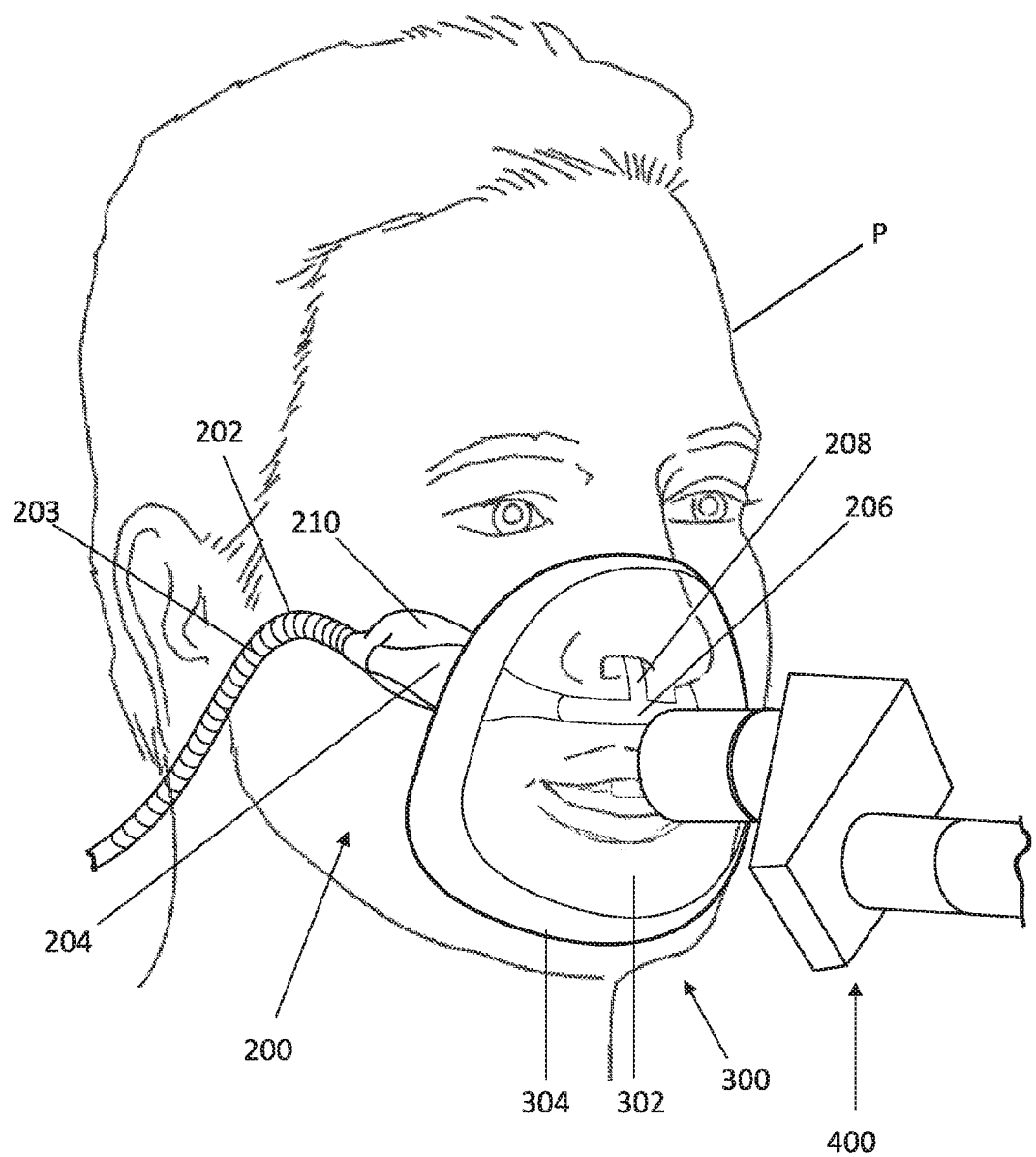
FIG. 3 shows a patient wearing a patient interface (a first patient interface) and a face mask (a second patient interface).

FIG. 3 shows a non-limiting exemplary embodiment of a patient P wearing the patient interface 200 as shown in FIG. 2 (a first patient interface) underneath a face mask 300 assembly (a second patient interface). FIG. 3 schematically shows the face mask as a transparent structure in order to illustrate the patient interface 200 under it.

A system may find benefit in the selective delivery of separate therapies to a patient using different patient interfaces. The system and devices as described find particular application in emergency resuscitation, around intubation of a patient receiving high flow therapy, ear, nose, and throat (ENT) surgery, in assisting with conditioning of a patient in a pre-operative state prior to administration of anaesthetics, and during post-extubation and recovery.

Face mask assembly 300 may be used as or with a second respiratory support subsystem and/or to deliver one or more substances other than a substance delivered by the cannula 200, for example anesthetic agents or oxygen, to the patient, or the same substance but at different flow and/or pressure levels. Accordingly, the embodiment shown in FIG. 3 allows for the delivery of gas from multiple sources via two respiratory support subsystems. Additionally, this configuration may allow the patient interface 200 to be left on the patient throughout the surgical procedure and/or into recovery (whether or not the patient continues to receive flow therapy through the patient interface 200 throughout the procedure).

In the embodiment shown, face mask assembly 300 comprises a full face mask 302 configured to cover both the patient's nose and mouth. In other configurations, the face mask 300 may be a nasal mask or oral mask which is placed over the patient interface 200 to cover only the patient's nasal region or only the patient's mouth.

As shown, the face mask 302 comprises a seal region 304 adapted to seal against the patient's face. The face mask assembly 300 is connected to a second gas source, for example via a filter element 400, which supplies the one or more other gases to the patient via the face mask. That is, the second gas source is preferably different from the source supplying gas (for example, supplementary gas source 124/flow generator 102) to the patient interface 200.

In a preferred embodiment, the face mask assembly 300 is connected to a separate gas source or a separate respiratory support device. For example, the respiratory support can be a ventilator or a CPAP or a high flow therapy device or a manual resuscitator (for example a hand held face mask with bag).

Alternatively the mask assembly 300 could be connected to an anesthetic device and anesthetic gas, or air, or oxygen, or a combination of gases, can be delivered via the mask 302.

The embodiment shown in FIG. 3 allows for the delivery of gas from multiple sources via at least two different respiratory support modes, and further allows a doctor, clinician or medical professional to quickly and easily change the type of respiratory support mode.

In one particular application, a patient preparing for anaesthesia can be pre-oxygenated by delivering a high flow of oxygen via a nasal cannula. In some circumstances, anaesthesiologists managing the sedation of a patient may want to switch between delivery of gas flow from one patient interface (for example a nasal cannula) and delivery of gas flow from another patient interface, such as via a face mask. Delivery of gas from a nasal cannula together with gas from a mask, or even delivery of gas from a cannula while a mask is sealed over the cannula, may cause an increase in pressure, which could damage the patient's lungs. Anaesthesiologists also use a mask with a bag to oxygenate a patient, and in some instances find it more comfortable to use a bag mask if a patient's vital signs being to drop. In such a situation, as described earlier, flow through the cannula as well as pulsing gases flow from a bag mask can cause over pressure in the lungs and potential lung damage. In some situations a medical professional may wish to switch between different respiratory systems or support modes. In first mode respiratory support may be provided by first respiratory support system (for example via the patient interface 200) and in a second mode respiratory support may be provided by a second respiratory support system (for example via the patient interface 300), with the support from the first system switched off. For example, the additional flow from the high flow may also modify the expected behaviour of the anaesthetic circuit, and therefore it may be advantageous to be able to turn the additional flow from the first respiratory system off.

In some configurations, the switching between two respiratory support modes or subsystems may be facilitated by a structure of the first gas lumen (first conduit 202), which has a first portion 204 configured to transition from a first configuration in which a first level of gases is able to pass through the first portion 204 to a second configuration in which a second level of gases is able to pass through the first portion 204.

Preferably, the first portion 204 is configured to be more collapsible or otherwise better adapted at changing the flow of gas through the first portion 204 (therefore reducing the flow of gas through the lumen and to the patient) than other portions of the lumen 202.

Figure 4:
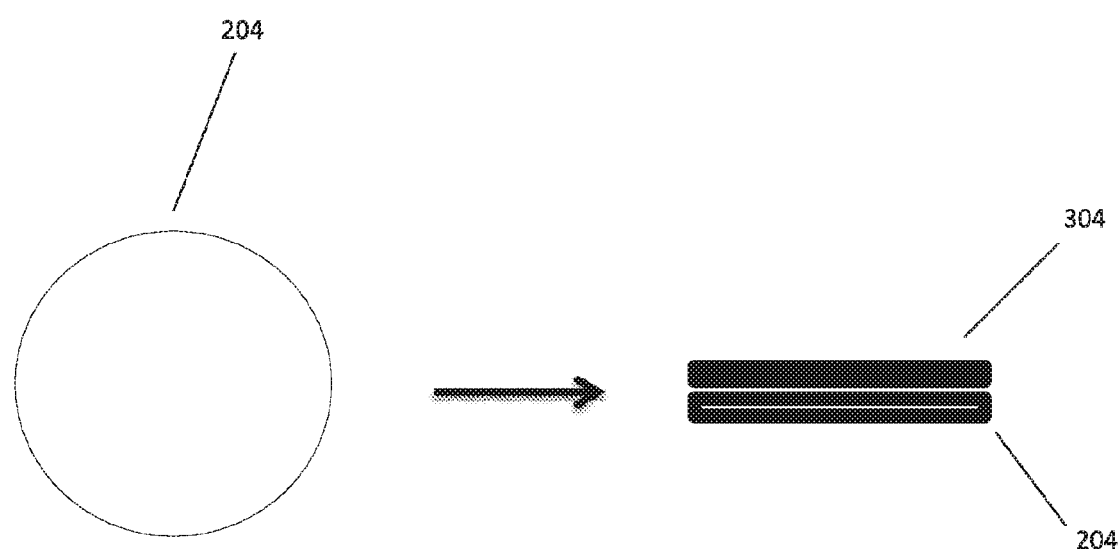
FIG. 4 shows a cross-section of a portion of a patient interface or conduit.

In other embodiments, the first configuration or first condition is a substantially open configuration and the second configuration or second condition is a substantially closed configuration. That is, the lumen 202 is configured to be more collapsible, deformable or otherwise adapted to fully close off the flow at the first portion 204 than at other portions of the lumen 202. FIG. 4 shows one example of this configuration, in which the lumen (for example the lumen 202 of FIG. 3) at first portion 204 is substantially closed by the seal 304 of face mask 302. In such an embodiment, the first portion (i.e. the more collapsible or deformable section) of the first gas lumen should be of a length that is greater than a width of a section of a seal of the face mask that bears over the first portion of the first gas lumen. This ensures the seal of the face mask does not bear over a non-collapsible section of the first gas lumen. For example, the first portion may extend from a distance of 35 mm or less from the centre of a user's nose to at least 50 mm from the centre of a user's nose, the first portion having a length of at least 15 mm. In some embodiments the length of the first portion may be at least 15 mm, 20 mm, 25 mm, 30 mm, 35 mm, 40 mm, 45 mm, 50 mm or greater.

The first portion 204 may progress between the first and second configurations based on a relative level of force applied to an external wall, or experienced by an internal wall, of the first portion 204. For example, as shown in FIG. 3, the force may be applied by the seal 304 of face mask 302. In this example, first portion 204 is configured to be positioned under the seal 304 of the face mask 302. Alternatively, the force may be applied to first portion 204 by other means, e.g., clamps (not shown). In some embodiments, the seal of the face mask acting on the first portion of the gas lumen causes the first portion to form a seal or at least a partial seal between the first patient interface and the flow generator. Additionally, the seal of the face mask forms a seal or at least a partial seal over the first portion of the gas lumen. Switching between respiratory support therapies is therefore achieved simply by applying a mask to the patient's face so that the seal of the mask collapses (partially or completely) the first portion of the gas lumen to 'turn off' or reduce the therapy supplied by the first interface and also provides a seal between the face mask and the external surface of the first portion such that therapy can be provided exclusively or at least predominantly by the mask. In some embodiments the removal of the mask from the patient's face allows the therapy supplied by the first interface to recommence.

According to FIGS. 12A-15B, the following disclosure relates to a conduit, whether as a part of a conduit or the entirety of a conduit, or a conduit provided as an interconnection between other conduits or components associated with a patient interface, such as a nasal cannula or mask. These figures illustrate further exemplifications of a collapsible type conduit, capable of being in a first configuration or first condition such that a lumen or gas flow path of the conduit is kept open or maintained in a gas flow capability, yet deformed or distorted or buckled under application of a force or load into a second configuration or second condition in which the lumen or gas flow path is substantially closed or occluded or obstructing of the flow of gas therethrough. Further, in the second configuration or condition the collapsible type conduit provides a collapsed form that may aid in ensuring the seal of the mask is able to form a seal or at least a partial seal over the conduit together with the patient's face.

The form or array of forms of FIGS. 12A to 15B may be independent of the conduit wall or an internal wall surface. That is, the form or forms may not be attached or connected to the conduit wall or an internal surface thereof. Alternatively, the form or array of forms of FIGS. 12A to 15B may be attached along the wall of the conduit in a portion of the inner circumference (lateral perimeter) of the conduit only. This can allow the form or forms to independently move of the conduit wall, or move relative to the conduit wall, allowing for their distortion or buckling or other change in shape or orientation to allow for the re-configuration from a first condition toward a second condition.

FIG. 12A to 15B provide sectional side views (or views with the conduit wall transparent) of a conduit 400, or at least a part length of a conduit 400, for use as a part of a respiratory therapy delivery system (such as, but not limited to the system of FIG. 1). The conduit or part length of the conduit 400 comprises at least one form or an array of forms 401 that is/are supportive, or form a part, of a conduit wall 402. An internal surface 403 of said conduit wall 402 forms a lumen or gas flow path 404 of the conduit 400.

The at least one form or the array of forms 401 is/are biased so as to preferentially maintain the lumen or gas flow path in a first condition (for example that shown by FIGS. 12A, 13A, 13B, 14A, 15A). The first condition being a substantially open or a substantially non-collapsed conduit wall condition, which allows for a flow of gas unimpeded to a further component associated with a respiratory therapy delivery system, such as a patient interface or to a further section of conduit.

The conduit or part length of the conduit 400 comprising the at least one form or the array of forms 401 is/are configured to be distortable or buckle from the first condition to a second condition (for example that shown by FIGS. 12B, 14B, 15B) in response to a force or load 405 applied to an outside surface 406 of the conduit wall 402 comprising the at least one form or the array of forms 401.

The second condition being a configuration or condition in which there is a substantially closed or substantially collapsed conduit wall condition or where the lumen or gas flow path 404 are substantially closed, blocked, occluded or otherwise obstructed as to a gas flow therethrough, or there may be intermediate positions of these, such as partially closed or collapsed or partially closed or blocked or occluded or otherwise partially obstructed as to the gas flow therethrough for restrictions of gas flow. It will be appreciated where reference is made to a second condition and the gas flow path may alternatively be put into partial stages of these, as noted above. Such partial stages can be applied across the various embodiments and configurations disclosed herein, except where a complete closure is required for additional reasons.

According to some configurations, the at least one form or array of forms 401 can be substantially unrestrictively distortable or buckling in response to application of the force or load 405.

In terms of the form being "unrestricted" or substantially "unrestrictively" allowing for the distortion or buckling or other change in shape of the form, this means that the "form" does not actively prevent the form from being changed in shape/configuration when the force/load is applied.

The force or load applied to the outside surface 406 of the conduit wall 402 may be applied, for example, by a part of a patient interface such as the seal of a full face mask, being placed into contact with the conduit 400. For example, where a nasal cannula may be in operative position as a first patient interface upon a patient, and a second patient interface, such as a mask, is additionally provided to deliver a respiratory therapy to the patient, the second patient interface can provide the force or load upon the conduit 400.

The load or force can be manually applied by a user, such as by a medical professional. This may be achieved by pressing on the conduit.

The relative distortion or buckling of the at least one form or array of forms 401 from the first condition to the second condition is to a pre-determined distorted or buckled orientation or arrangement or configuration of the least one form or the array of forms.

The force or load 405 applied to the outside surface of the conduit, in use, must be sufficient so as to overcome the bias exerted by the form 401 in supporting or maintaining the conduit 400 in the first configuration or condition (i.e. the "open" lumen condition). As such, the force or load 405 which must be applied to the outside surface 406 of the conduit 400 must be sufficient so as to induce distortion or buckling of the at least one form or array of forms 401 and alter the conduit from the first condition toward the second condition against a gases pressure within conduit. Further the force must be sufficient to hold the conduit in the second condition against the internal pressure of the conduit.

The second condition can be a preferentially pre-determined re-configuration (or re-arrangement or re-orientation) of the at least one form or the array of forms 401. For example, the form 401 can be designed or configured so that in transitioning from the first condition to the second condition, the ultimate second condition is accounted for in the ability for the form 401 to distort or buckle or otherwise be reconfigured.

In the second condition, the internal surfaces 403 of the conduit wall 402 can be effectively brought together upon themselves, whether as a complete bringing together of these internally or partially so. For example, see in particular FIGS. 14B and 15B in which the conduit 400 is in a "closed" configuration. The internal surfaces 403 can be brought together, whether to be in contact with, or to be substantially adjacent with, each other, or to provide for the substantially closed or substantially collapsed conduit wall 402 condition or where the lumen or gas flow path 404 are substantially occluded or provide an obstruction as to a gas flow therethrough. Partial configurations can also be achieved of these substantially "closed" conditions, for example to achieve a constriction or restriction of the gas flow, rather than a total obstruction or closure of the gas flow path.

The form 401 is configured so as to be supportive of the conduit wall 402, and biased so as to maintain the conduit toward or in the first condition.

The form of the array of forms 401 is/are capable of being distorted or buckled (or re-arranged or re-configured) from the first condition toward the second condition upon application of the force or load 405, yet a reduction or removal of the force or load 405 allows the form or array of forms 401 to return or recover the conduit 400 to or toward the first condition.

The conduit could be made of a single material that has the appropriate resilience to hold the first condition or configuration, while being able to be depressed to the second condition or configuration. Alternatively, the conduit could be made of two materials, and the second material provides the structure to allow the conduit to hold or maintain the first condition and then move to the second condition under a force or load. In such an embodiment, there may be a polymeric conduit comprising a series of structures or forms inside, embedded within, or surrounding the conduit wall. In another embodiment, for example where the conduit is made of a single material, the structures or forms would not be required because the material would have the necessary properties to maintain the first condition.

The form 401 can be a spiraled or helically wound or coiled member being of a pitch angle of greater than about 20° to about 70°, or about 25° to about 65°, or about 35° to about 55°, or about 45° from a horizontal longitudinal axis extending along the conduit or the at least part of the conduit comprising the form or array of forms, or being an angle relative to the conduit wall, the pitch angle being the angle between each wind or coil of the member.

The form 401 can be a spiraled or helically wound or coiled member having a pitch of greater than about ¼ the internal diameter of the conduit to about 10 times the internal diameter of the conduit, or about ½ to about 8 times the internal diameter of the conduit, or about ⅔ to about 6 times the internal diameter of the conduit, or about 1 times to about 4 times the internal diameter of the conduit, or the pitch being substantially the same length as the internal diameter of the conduit, pitch being the distance from a centre to a centre of adjacent spirals or helical windings or coils of the member.

The form 401 can be a spiraled or helically wound or coiled member being of a pitch angle or a pitch (or both), such that application of the load or force 405 to an outside surface 406 of the conduit 400 allows the form 401 to fold over upon itself or to be re-oriented so that the form 401 lies in a substantially flat orientation when in the second condition.

Figure 13A:
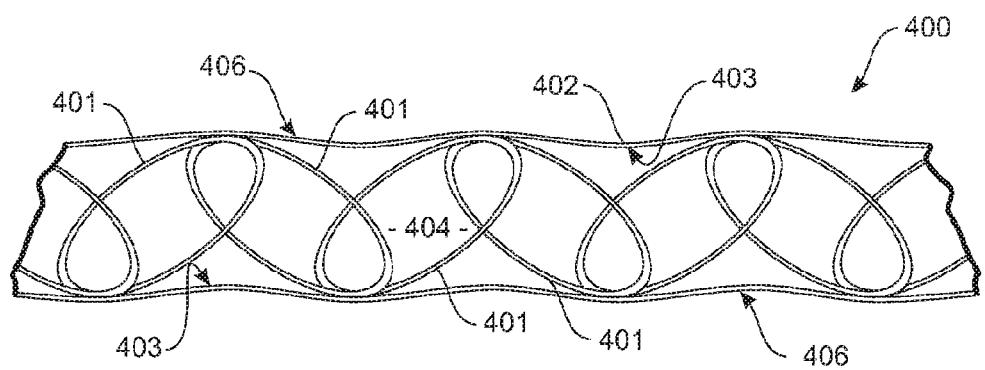
FIG. 13A shows a cross section of a portion of another embodiment of a collapsible conduit, shown in a generally first "open" lumen or gas flow path condition.
Figure 13B:
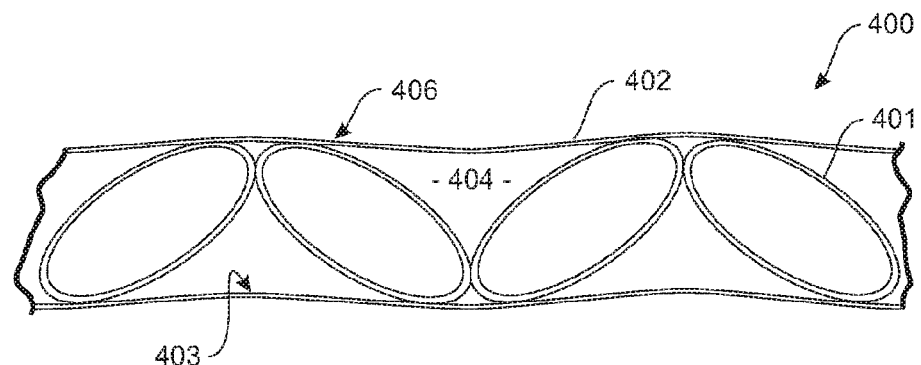
FIG. 13B shows a cross section of a portion of another embodiment of a collapsible conduit, shown in a generally first "open" lumen or gas flow path condition.

The form 401 can be a series of rings or ring members, such as that shown in FIGS. 13A, B. Each ring of the series including a hinged inter-connection to at least one other ring. The hinged inter-connection can facilitate the distortion or buckling (such as a hinged distortion from the first condition shape) of the form 401.

The form can be a series of hingedly connected components, arranged so as to provide for at least a substantially continuous support of the conduit wall 402 at least in the part length of the conduit 400 comprising the form 401.

Spirally or helically wound or coiled members, or ring members, may be formed from a relatively rigid material that is able to deform elastically between the first and second configurations of the conduit. Suitable materials may include plastics materials known by persons skilled in the art, or metal materials, for example steel or stainless steel, or high tensile metals, also known by those persons skilled in the art.

In further configurations, the conduit wall 402 can comprise of at least one form or an array of forms 401 extending substantially longitudinally along a conduit wall 402, or at least substantially longitudinally along the part length of the conduit wall 402 comprising the form 401. As such, at least one form or the array of forms 401 can be a flap or hinge formed as a part of or provided at or within a conduit wall 402. For example, see FIGS. 14A-15B which illustrate a conduit cross section adapted to collapse by application of an external force.

The flap or hinge can allow for the conduit wall 402 to effectively be folded over upon itself. In such an arrangement, the form or array of forms 401 may be a concertina-type arrangement (e.g. see FIG. 14A, B) or a bellows-type arrangement (e.g. see FIGS. 15A, B). Such an arrangement allowing for the conduit 400 to be distorted or buckled from the first condition to the second condition under application of the force or load 405. In such configurations, where for example the form 401 is a hinge, such a hinge or other articulation may be formed as a part of or provided at or within a conduit wall 402. It will be appreciated the configurations noted above may be utilised by employing a plurality of such hinges formed as part of a conduit wall 402, with these forms extending substantially longitudinally along a conduit wall, or at least substantially longitudinally along the part length of the conduit wall comprising such forms. In such embodiments, the conduit could be made of a single material that has the appropriate resilience to hold the first condition or configuration, while being able to be depressed to the second condition or configuration. Alternatively, the conduit could be made of two materials, and the second material provides the structure to allow the conduit to hold or maintain the first condition and then move to the second condition under a force or load. In such an embodiment, there may be a polymeric conduit comprising a series of structures or forms inside, embedded within, or surrounding the conduit wall. In another embodiment, for example where the conduit is made of a single material, the structures or forms may not be required where the material has the necessary properties to maintain the first condition, yet is able to collapse to the second condition. In some configurations a thickness of the wall section may vary to achieve a variation in collapsibility between a collapsible portion of the tube and a remainder or non-collapsible portion of the tube, as described in a further embodiment below.

Again with reference to FIGS. 14A to 15B, in some embodiments, the cross section of a collapsible portion of a conduit 400 comprises a single folding portion on a side of the collapsible portion. The folding portion extends between an outer side 406a of the conduit and an inner side 406b of the conduit. In use the inner side of the conduit is in contact with a patient's face. The folding portion comprises a pair of side portions 407. The side portions diverge from a folding point 407a to present an externally facing acute or obtuse angle 407b when in the first condition. In the second condition, the cross section deforms at the folding point 407b so that the pair of side portions 407 come together to collapse the collapsible portion to the second condition.

Figures 14A, 14B:
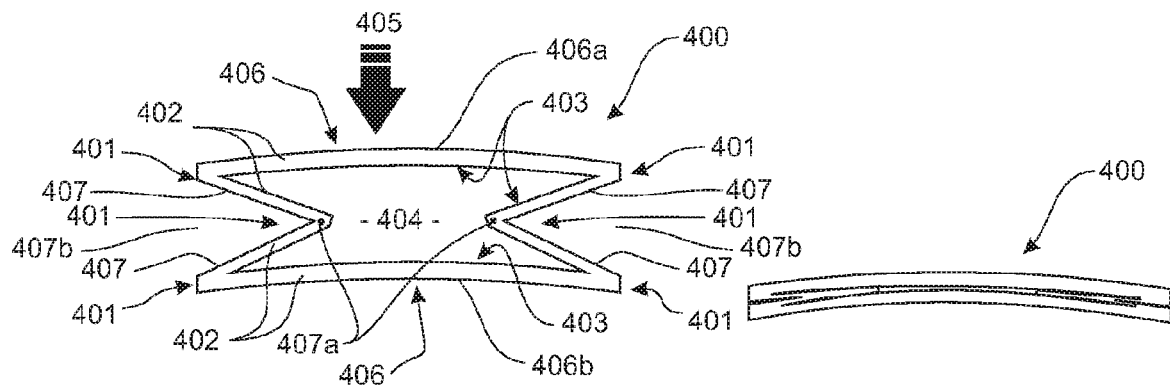
FIG. 14A, B show cross sections of a portion of another embodiment of a collapsible conduit.
FIG. 14B shows the same conduit in a more "closed" lumen or gas flow path or second condition.

In FIG. 14A, the cross section comprises a first said single folding portion on a first side of the collapsible portion, and a second said single folding portion on a second side of the collapsible portion, the second side opposite to the first side.

The first and second folding portions extend between the outer side 406*a* of the conduit and the inner side 406*b* of the conduit.

Figures 15A, 15B:
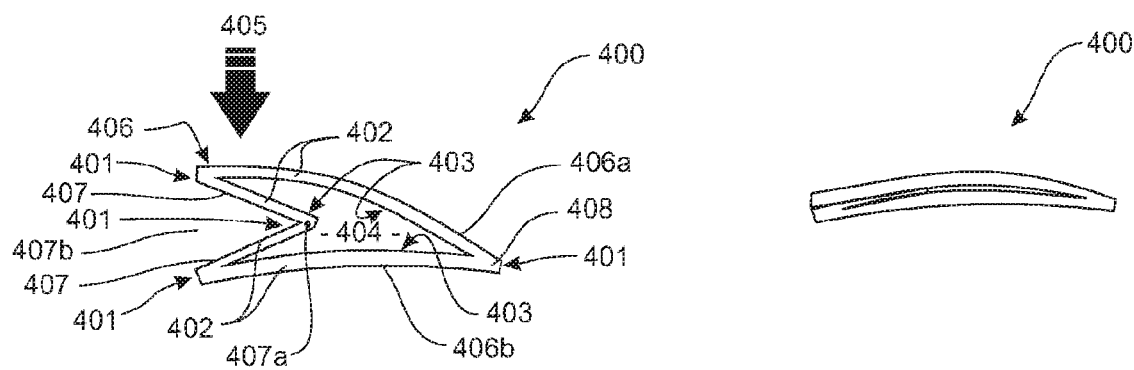
FIG. 15A, B show cross sections of a portion of another embodiment of a collapsible conduit.
FIG. 15B shows the same conduit in a more "closed" lumen or gas flow path or second condition.

In FIG. 15A, the cross section comprises the single folding portion (comprising the side portions 407) on a first side of the collapsible portion and a second folding point 408 at a second side of the collapsible portion, the second side opposite to the first side. The outer side 406*a* of the conduit and the inner side 406*b* of the conduit diverge from the second folding point 408. The inner and outer sides of the conduit fold together at the second folding point when transitioning from the first configuration to the second configuration.

In some embodiments, the angle 407*b* between the side portions 407 is an acute angle. For example the angle may be less than 60 degrees, or 55 degrees, or 50 degrees, or 45 degrees, or 40 degrees, or 35 degrees.

In the second condition, as shown in FIGS. 14B and 15B, the collapsible portion collapses so that external surfaces of the side portions 407 are in contact, and internal surfaces of the side portions 407 contact internal surfaces of the inner side 406*a* and the outer side 406*b* of the conduit.

Figure 16A:
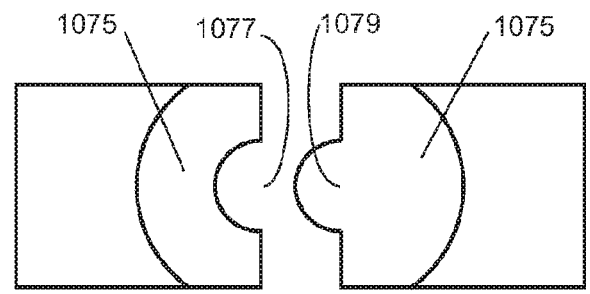
FIG. 16A shows an embodiment of a collapsible conduit comprising a gate to close the lumen of the tube.

With reference to FIGS. 16A to 16C in some embodiments, a valve may be provided in the conduit. The valve may be operable by an external force provided by the mask or a user pressing against the conduit or a mechanism of the valve. For example with reference to FIG. 16A, a further alternative embodiment is a gate within the conduit. The gate may comprise a pair of doors or bulkheads 1075 that move towards each other and preferably close when the conduit is pressed or squeezed. In some embodiments the doors may overlap, and/or each door is complementarily shaped to fit together without overlapping. The doors could be positioned within the conduit, and may be attached to or integrally formed with the conduit, so that as the conduit is squeezed the doors move together to close the lumen of the conduit. Alternatively, the doors could protrude through the walls of the conduit and move (slide) relative to the conduit. The gate may have a recess 1077 on one of the doors and a complementary protrusion 1079 on the other of the doors. There may be one or more gates provided. In an alternative embodiment, the gate may be a single door or bulkhead that slides across the conduit, or is attached to one side of the conduit and with a gap between the door and an opposite side of the conduit, so that as the conduit is squeezed the door closes against the opposite side of the conduit. The door may have an opening, to provide a minimum flow level past the gate when in a closed position. The door or doors of the gate are movable in a transverse direction across the conduit from a first position in which substantially a first level of gases from said gas source pass through said conduit to a second position in which a second level of gases pass through the conduit. For example, the door or doors may be perpendicular to a longitudinal axis of the conduit/flowpath, or may be at an angle (e.g. 45 degrees) to the flow path. The first position may be a substantially open configuration and the second position may be a substantially closed configuration. The first level of gases may be greater than the second level of gases. The direction of the gate sealing may be transverse, or may be approximately transverse, to the direction of gas flow, which may help to reduce the required force to close the gate and close the lumen, as the force of the flow is not directly opposing the direction of the gate closure. In some embodiments, a contact area where the pair of doors meet, or where the one door closes against a side of the conduit, may be relatively small so that a low actuation force is required to create a seal. For example, the width of a contact area where the doors meet or where the door contacts the conduit side wall may be 10-20% of the diameter of the conduit In one position, the gate will allow gas to pass through the conduit. In another position, the gate will restrict the gas from passing through the conduit. Such gates may completely close the conduit or may provide for a partial closing or a constriction of the gas flow path.

In FIG. 16B, a valve 549 may comprise a depressible valve member 550. A user/medical professional, or the mask 300, may press against a valve member 550 extending through a side wall of the conduit 553, to move the valve member 550 into the conduit 553. A diaphragm or other resilient member 551 may be acted on by the valve member 550 to press the resilient member 551 across a lumen of the conduit 553 to block flow through the conduit 553. In some embodiments the resilient member 551 is stretched to block flow, and biases the valve member 550 to an open position. In other embodiments the valve member 550 is biased to the open state by the internal pressure of the gases flow in the conduit 553. FIG. 16B(i) shows the valve 549 in an open configuration with the valve member 550 and resilient member 551 extending from the side wall of the conduit 553. FIG. 16B(ii) shows the valve member 550 depressed to extend into the conduit 553 and block flow. FIGS. 16C(i) and 16C(ii) show a similar arrangement. The valve 548 also comprises a valve seat 552 that is biased against the valve member 554, to bias the valve member 554 away from the closed position.

In other embodiments, the system may comprise other valve arrangements for stopping flow to the patient interface. For example, a butterfly valve with a valve element that is manually turned (for example through 90 degrees) by a user between an open position and a closed position may be provided.

Accordingly, in some embodiments as described above, a device comprising a collapsing portion of a conduit or patient interface 200, or a valve located in the conduit or patient interface, provides a device for switching respiratory therapy between two modes, wherein the patient interface 200 provides the first respiratory therapy mode and the mask assembly 300 provides a second respiratory mode. The modes may be switched when the first portion 204 of the lumen 202 transitions from the first configuration to the second configuration.

In one embodiment, this transitioning is provided by the face mask 302. That is, when the face mask is placed onto the patient, the seal 304 of the face mask may apply a force onto the first portion 204, transitioning the first portion 204 from its first configuration to its second configuration, and preferably reducing or stopping the delivery of the first therapy mode, and preferably additionally form a seal with the seal of the mask, so that the mask seals with the first portion of the tube and the patient's face. Accordingly, the structure of the patient interface 200 or a conduit providing a flow of gases to the patient interface 200 allows a medical professional to quickly change the type of respiratory support being delivered to the patient without having to remove the interface providing the first respiratory mode.

In some embodiments where the first respiratory support mode is high flow therapy, the structure of the patient interface 200 allows the medical professional to stop or minimise the flow rate, and start the second respiratory therapy (e.g., via a ventilator or a CPAP or a high flow therapy device or an anaesthetic device) easily and simultaneously. Further, this allows for the anaesthesiologist or medical professional managing the sedation of a patient to have precise knowledge of the flow delivered to the patient, as the gas delivered by the second patient interface is not being diluted by the gas provided by the first patient interface.

In some embodiments, the first portion 204 may progress between the first and second configurations based on a level of pressure of gases passing through the first portion of the gases lumen. That is, the first portion of the first gases lumen may be in the first configuration when the flow pressure is above a first predetermined pressure level, and in the second configuration when the flow pressure falls below or increases above the first predetermined pressure level.

In another embodiment, the first portion 204 may be self-collapsing. That is, it may be partially or fully collapsed (second configuration) when there is no gas or a low/reduced flow of gas flowing through it, and expands (first configuration) when there is some level of gas flowing through it.

Figure 6:
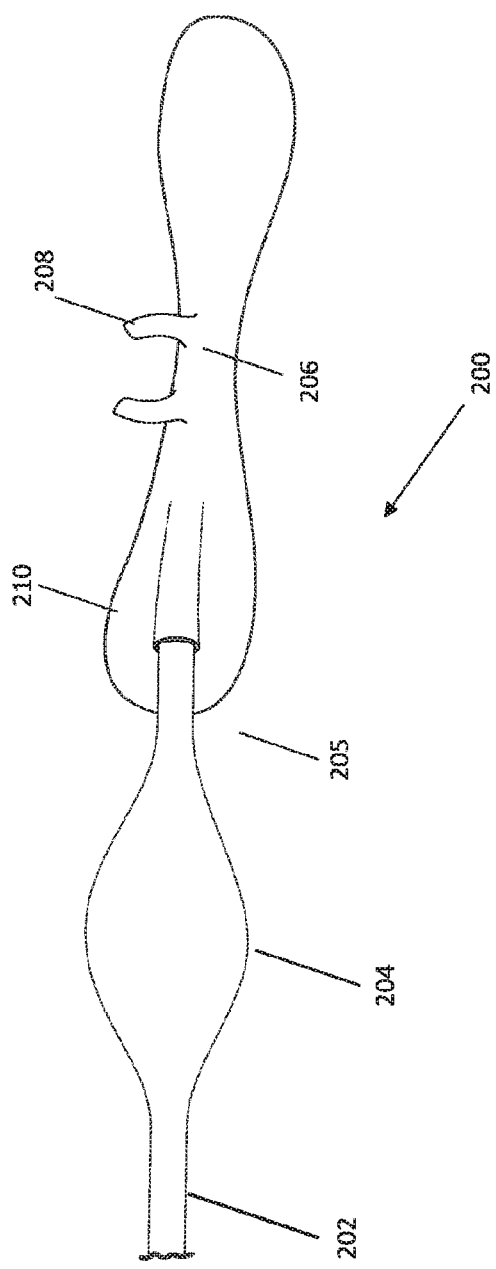
FIG. 6 shows a patient interface.
Figure 7:
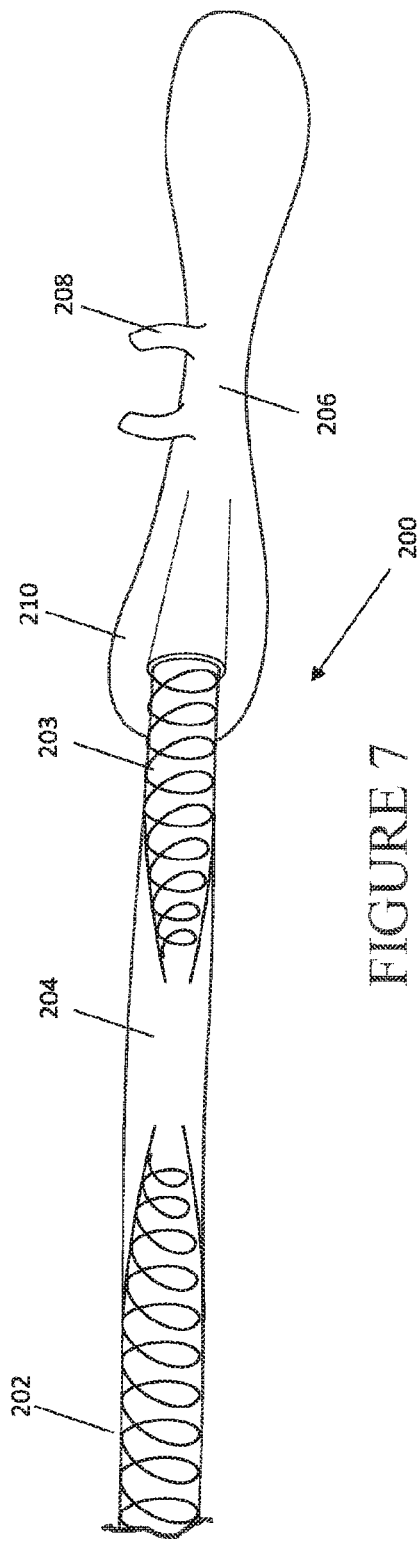
FIG. 7 shows a patient interface.
Figure 8:
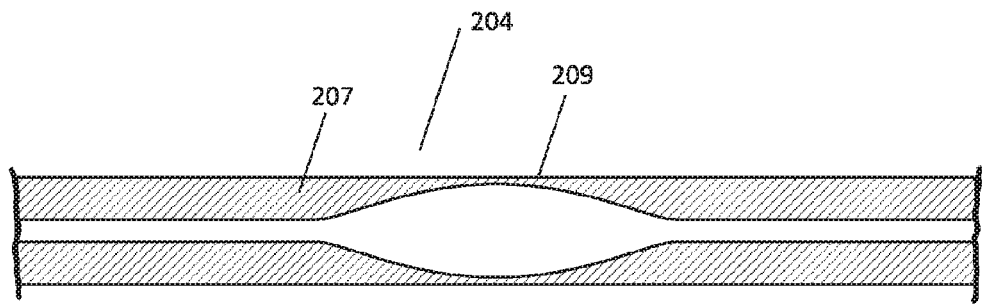
FIG. 8 shows a portion of a patient interface or conduit.

FIGS. 6 to 8 show various alternative examples for providing first portion 204 to lumen 202, via one or more variations in geometry, material property, structure and/or composition of the lumen across the first portion 204.

In one example, as shown in FIG. 8, the first portion 204 comprises a wall 209 that is thinner than one or more walls 207 of other portions of the first gases lumen. 8. Preferably, there is a substantially smooth, or substantially linear, transition in thickness between the wall 209 of the first portion 204 and the one or more walls 207 of other portions of the first gases lumen 202. A smooth transition may assist to prevent or reduce turbulent flow, improve hygiene, and/or reduce the likelihood of the gases conduit kinking.

Additionally or alternatively, the first portion 204 comprises a wall that is more flexible than walls of other portions of the first gases lumen 202. In one embodiment, the variation in flexibility is due to the material of the wall. In another embodiment, the variation in flexibility may additionally or alternatively be due to reinforcement element 203 provided along substantially the entire length of the lumen except at first portion 204 (as shown in FIG. 7). Preferably, there is a substantially smooth, or substantially linear, transition in flexibility between the wall 209 of the first portion 204 and the one or more walls 207 of other portions of the first gases lumen 202, for example, by providing a tapering of the reinforcement element towards the first portion 204.

In an alternative configuration shown in FIG. 6, the first portion 204 may comprise a wider section (i.e., larger cross-sectional area) compared to other portions of the lumen 202. This may reduce the amount of force and/or internal pressure required to deform and/or collapse this portion.

According to the configuration of FIGS. 6-8, a further alternative could be to provide a conduit that is devoid of structure or reinforcements or other forms to support the wall of the conduit. Such a configuration would allow the conduit to be squashed or collapsed with relative ease. That is, the conduit is devoid of any spiral or helical bead or other reinforcements. The tube can be maintained in an "open" or first condition or configuration by the pressure of the gas provided with the conduit itself. Application of a fore or load upon the conduit wall can squash, crush or otherwise collapse the conduit at that portion where the force or load is being applied. Such a conduit may form a part of a more general gas supply conduit (for example the first portion 204 of the first gas conduit 202), or may be provided as a relatively short length of conduit to be provided as an inter-connection between other components within a respiratory therapy delivery system. For example, the collapsible conduit may be provided as a short section of conduit connecting two other sections conduit, or to a patient interface. Such a conduit may be provided in such a system or breathing circuit close to the patient's face so that subsequent application of another interface to the patient (e.g. where the conduit is supplying gas to a nasal cannula and a full-face mask is applied over the top thereof), a part of this other interface may be used to provide for the force or load upon such an unstructured or non-supported conduit, as described above with reference to FIG. 3.

In an alternative configuration, the entire tube defining the first gas lumen 202 may be configured to collapse or otherwise be altered to change the level of gases passing through the lumen. Accordingly, in one example, force may be applied to any portion of the first gas lumen in order to reduce the gas flow through the lumen. However, it will be appreciated that this configuration may lead to unintentional collapse of the lumen due to kinks or other external forces on the lumen. Accordingly, it is preferable to provide only a portion of the lumen (i.e., first portion 204) which has this property.

While only one first portion 204 has been described, it should be understood that more than one similar portions may be provided. For example, where the flow manifold 206 is configured to receive flow from two sides of the flow manifold 206 via two gas lumens, two first portions 204 may be provided, one on each gas lumen, which may be configured to be collapsed (partially or fully) by the seal 304 of face mask 302.

Figure 5:
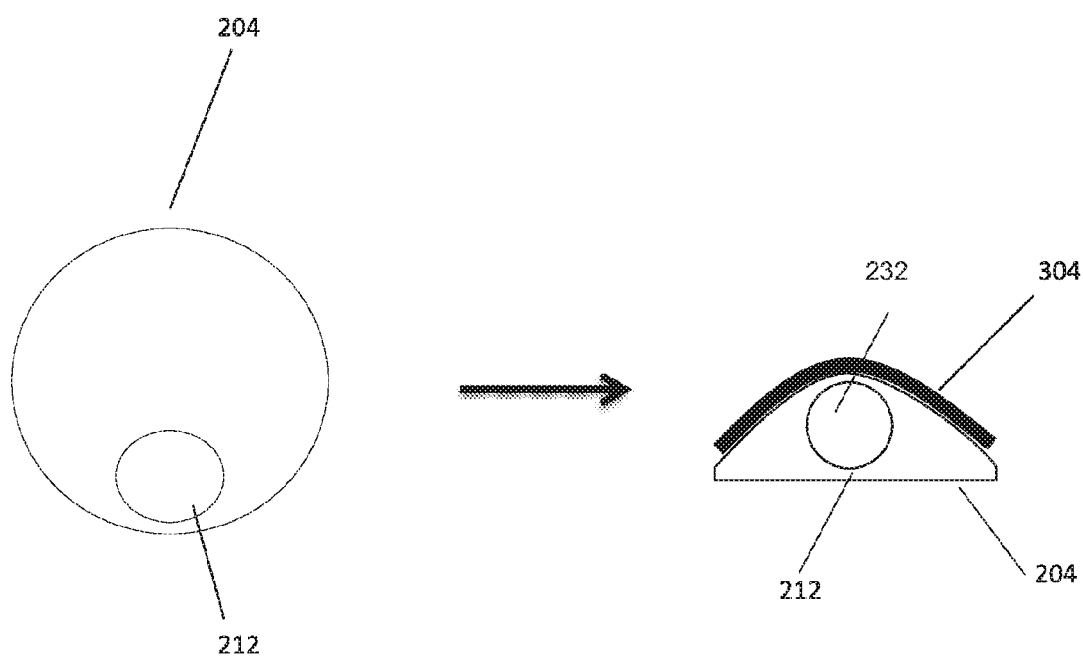
FIG. 5 shows a cross-section of a portion of a patient interface or conduit.
Figure 9:
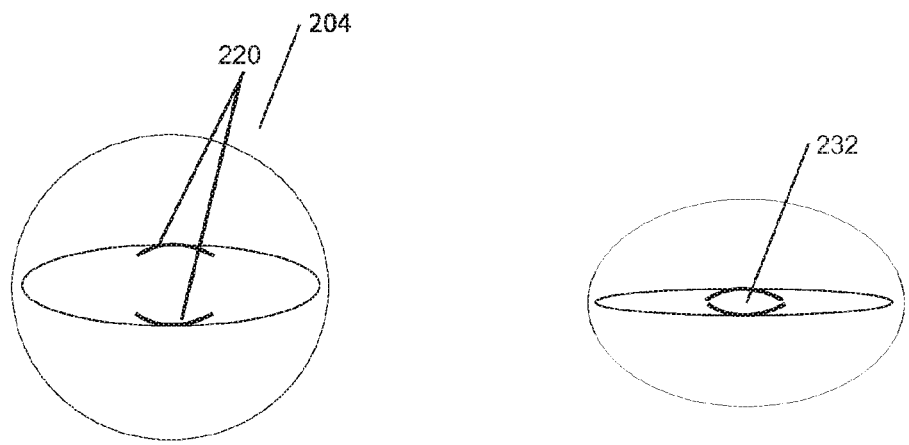
FIG. 9 shows a cross-section of a portion of a patient interface or conduit.
Figure 10:
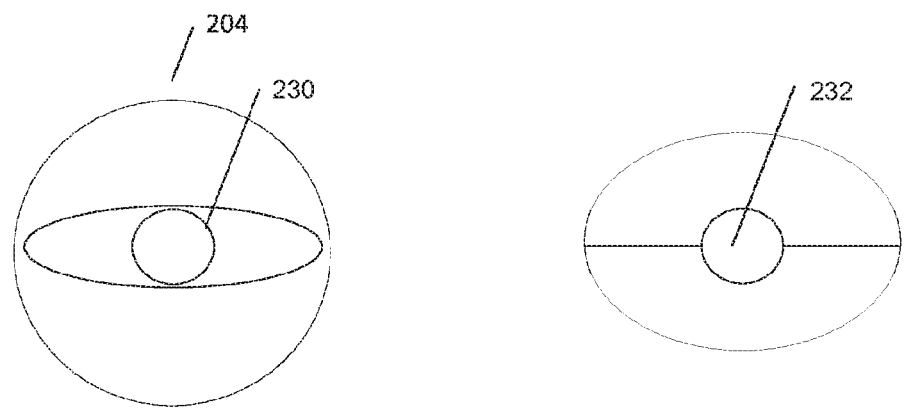
FIG. 10 shows a cross-section of a portion of a patient interface or conduit.

FIGS. 5, 9 and 10 show alternative configurations, where the first portion 204 is provided with an element about, within or under its wall in order to limit compression of the first portion 204. Preferably, the element is configured to allow the passage of a minimum level of flow through the lumen regardless of the configuration of the first portion 204. For example, in the non-collapsed condition a flow greater than a minimum level may flow through the lumen (the first portion of the lumen). In the collapsed state, the element defines the minimum flow level that can be delivered by the lumen at a pressure delivered by the flow generator. Alternatively, a minimum level of flow may be a level controlled by, e.g., controller 108 according to one or more physiological characteristics measured from the patient.

In FIG. 9, the element is a reinforcing element 220 which maintains a small opening or a second gases lumen 232 within first portion 204, to maintain a minimum level of flow even when the first portion 204 is maximally compressed or collapsed. As shown, the reinforcing element is substantially less compressible than the wall of the first portion 204, to maintain a smaller opening in the portion under said external force and/or said lower flow pressure through the tube. In the configuration shown, the reinforcing element 220 comprises substantially rigid portions on the opposing inner surface of the wall of the first portion 204. The rigid portions 220 are not continuous in this example, to enable the surrounding wall to collapse and seal around the rigid portions, forming a smaller opening. The rigid element may be integrally formed with the wall of 204, overmolded or otherwise attached to the wall. In this configuration, the second lumen 232 is formed when the elements 220 are brought together e.g., during compression of the first portion by face mask seal 304.

In FIG. 10, the element is an inner tube 230 defining a second gases lumen 232 through, at or near the inner region of the first portion 204. As shown, the tube 230 is substantially more rigid than the wall of first portion 204, to maintain a minimum level of flow through the lumen even when the first portion 204 is maximally compressed or collapsed. The inner tube 230 may be substantially coaxial with the first gas lumen 202, and may be connected to the same gas supply as the first gases lumen 202, or may be supplied by a different gas supply.

FIG. 5 shows another embodiment, in which the element 212 is provided on one internal section of the wall of the first portion 204. Element 212 holds the walls apart to form maintain a small opening or second gases lumen 232 within first portion 204, to maintain a minimum level of flow even when the first portion 204 is maximally compressed or collapsed. The element 212 may comprise a hollow cross-sectional area (as shown in FIG. 5), in which case, gas may also flow through the element 212. Alternatively, the element 212 may have a solid cross-sectional area, and holds the surrounding walls of first portion 204 apart, such that some gas may flow around the element 212.

Figure 18:
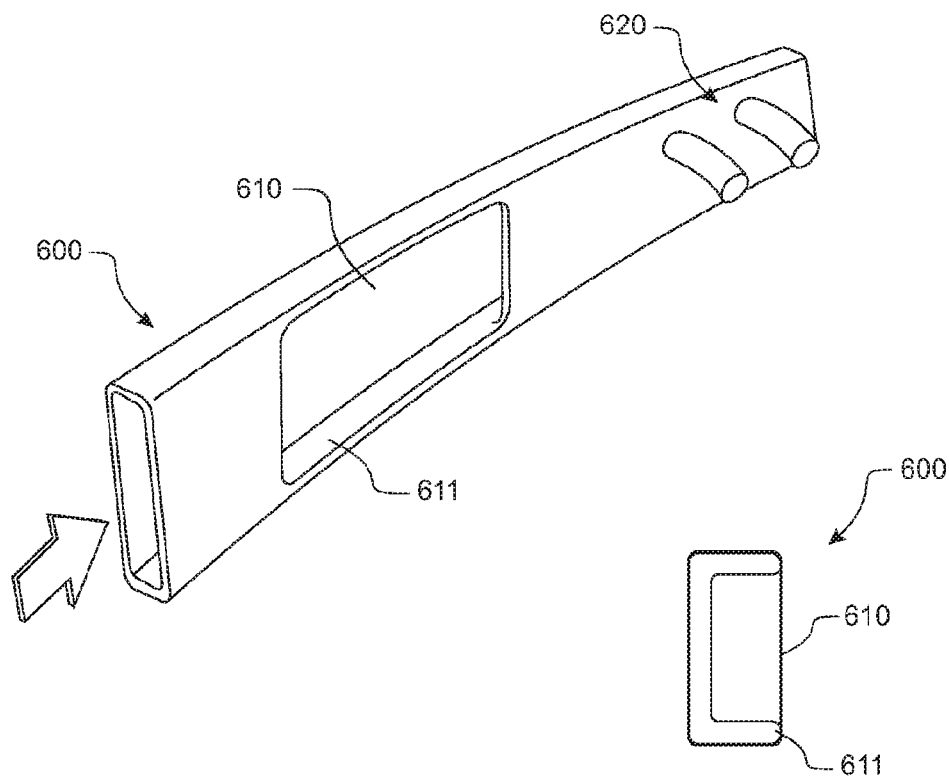
FIG. 18 shows a tube comprising a window in a wall of the tube and with a perimeter portion around the window configured to seal against the face of a user.

In some embodiments a gases conduit or tube comprises a window portion that is open onto the face of a user during use. An exemplary embodiment is illustrated in FIG. 18. In use, the window portion 610 of the tube 600 is located on the face of the user so that a perimeter 611 of the window portion of the tube seals against the user's face. The tube may comprise a seal around the perimeter of the window to seal against the user's face, for example the tube may comprise a lip or other seal arrangement located around the window to seal against the user's face. During use, the perimeter 611 of the window 600 seals against the user's face, such that the user's face essentially forms a wall of the tube blocking the window to provide a sealed lumen for the flow of gases to the user's airway via a patient interface 620. In use, the patient interface 620 may be used with a face mask, with a seal of the face mask extending over the tube 600 in a position that corresponds with the window 610 of the tube. Like in other embodiments described herein, a force provided by the seal of the face mask against a user's face can occlude the tube to prevent a flow of gases to the user via the patient interface. By providing a window in a side of the tube the tube has less material to be compressed by the force of the face mask against the user's face. Thus the window portion of the tube reduces the amount of force required to compress the tube and close the lumen provided by the tube. A lateral cross section of the tube 600 is provided in FIG. 18. As illustrated, in some embodiments the tube comprises a relatively flat cross section, so that the distance the tube must be flattened to occlude the tube is reduced, compared to a conventional circular cross section. In some embodiments the tube may comprise a membrane covering the window. The membrane is thinner than the thickness of the wall of the tube. As the membrane is thin, the amount of material in the tube wall to be compressed to occlude the tube lumen is reduced, reducing the collapse pressure of the tube.

Figure 19:
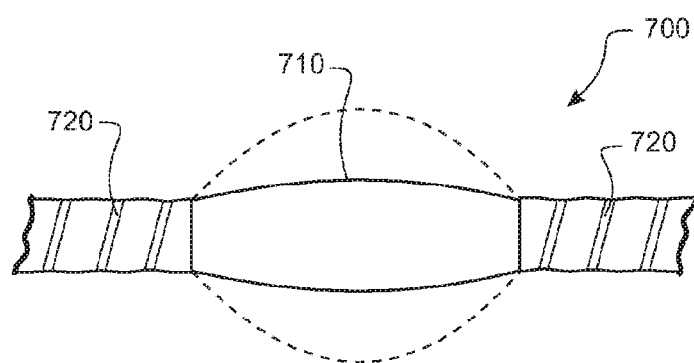
FIG. 19 shows a tube for providing a flow of respiratory gases to a user comprising a bladder to accumulate a gases volume to reduce pressure increases in the lumen of the tube.

In some embodiments a respiratory gases tube or conduit may comprise a balloon or accumulator or bladder (herein a bladder). The bladder may form or provide a portion of the lumen of the tube, for example as illustrated in FIG. 19. The bladder 710 is a section of the tube 700 that has a reduced wall thickness and/or is formed of a more resilient material than a remainder 720 of the tube. In some embodiments the bladder may be integrally formed with portions of the tube extending from each end of the bladder. In some embodiments, the bladder may be releasably attachable to a tube. For example, each end of the bladder may be attached to a tube so that the tube comprises a first length of tube attached to one end of the bladder, the bladder, and a second length of tube attached to the other end of the bladder.

The tube 700 comprising a bladder 710 may be used to provide a flow of gases to a user via a patient interface. The bladder 710 may act as a gases accumulator, such that the bladder inflates with an increase in gases pressure in the tube. An un-inflated configuration is illustrated in FIG. 19, with an inflated configuration indicated by the dashed lines in FIG. 19. The bladder may act to reduce pressure fluctuations seen at the patient interface, since pressure spikes in the lumen of the tube are smoothed out by the bladder expanding for increases in pressure. Further, where the patient interface, such as a nasal cannula, is used together with a face mask to provide more than one flow of respiratory gases to user, there may be a risk of increased pressure of gases provided to the user, as the pressure of gas flow provided to the user from each interface may combine to result in an increased gases pressure at the user's airways. The bladder may reduce the occurrence of an increased pressure at the patient, by expanding under an increasing pressure which in turn may reduce the pressure increase at the patient. The bladder may be used to accumulate a flow of gases if used together with a collapsible conduit described above. In some embodiments, the bladder provides a visual indication or indicator of an increased pressure in the lumen of the tube, signalling to the user or another person such as a care giver that the flow or pressure provided to the user may need to be reduced.

In some embodiments the tube 700 may comprise a venting arrangement, such that once an increased pressure is reached the venting arrangement operates to vent respiratory gases from the lumen of the tube into a bladder. For example, the bladder may be configured to be in communication with the lumen via the vent when in an open or venting configuration. The vent may open once a pressure reaches a threshold to vent gases into the bladder. The bladder therefore acts as an accumulator to prevent respiratory gases being vented to atmosphere. The bladder also may act as a visual indicator or indication of an increased lumen pressure which may correspond with an increased pressure at the patient's airways or at a patient interface.

In some embodiments the bladder may be configured to accommodate a particular volume and pressure of gases amounting to a particular flow rate and pressure. A further pressure relief valve or vent may be used so that the bladder vents to atmosphere once the bladder reaches a particular vent pressure.

When the flow of gas to the nasal cannula is reduced or stopped using one or more of the devices or arrangements described above, the pressure of the gas within the conduit (e.g. conduit 202) may increase. Accordingly, it may be advantageous to provide one or more pressure relief devices to relieve the pressure within the conduit. As described in more detail below, the pressure relief devices may be devices that only relieve pressure and may be used together with separate devices that block or inhibit flow. Alternatively, the devices may relieve pressure and also restrict or block flow.

Patient interface 200 or conduit providing a flow of gases to the patient interface 200 may comprise a pressure relief valve device or arrangement that is adapted to reduce or alleviate the pressure of gases in the first gases lumen if the flow through the lumen 202 is reduced or stopped due to the collapse or partial collapse of the first portion 204.

Figure 20:
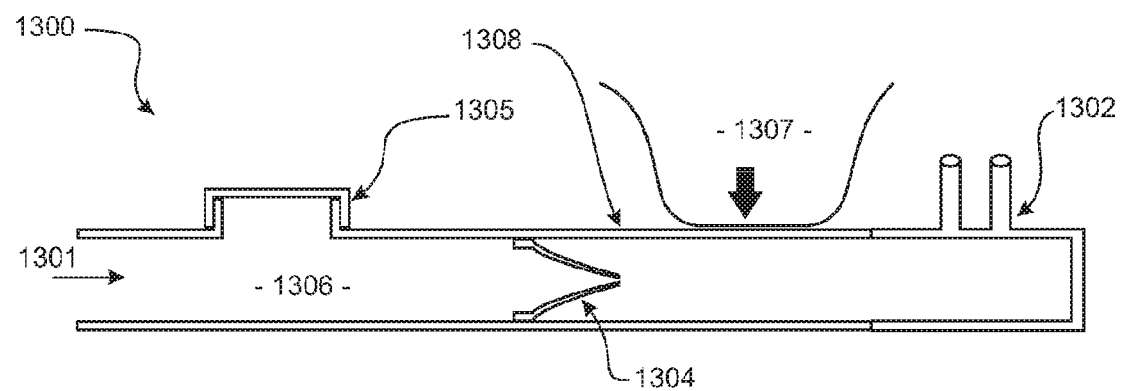
FIG. 20 shows a cross section of a tube comprising of a one-way valve (or flow direction regulator) In combination with a pressure relief device or pressure vent).

For example, as shown by FIG. 20, there may be provided a conduit 1300 for supplying or delivering a gas (of a gas flow 1301) to a patient interface 1302. The conduit may comprise a collapsible portion to be collapsed (for example by a mask seal 1307) to a closed configuration. The conduit includes a one-way valve 1304 and, relative to a direction of the flow of gas 1301 being delivered to the interface 1302, upstream of the one-way valve 1304 is a vent or pressure relief valve 1305 for venting or relieving of pressure build-up within the lumen 1306 of the conduit. The pressure relief valve can vent pressure in the conduit, for example once the collapsed portion is in the closed configuration. The one-way valve 1304 can prevent the gas being administered to the patient from a second patient interface from flowing back out the vent or pressure relief device 1305 as a back-flow of the patient interface 1302. Furthermore, the pressure relief valve or device may provide a further mechanism for ensuring that pressure delivered by the a second patient interface does not flow back through the interface 1302 due to a collapsible portion of the tube that does not completely seal the interface 1302 from the vent valve 1305. In an alternative arrangement the conduit may comprise a valve to close the conduit 1308, rather than a collapsible portion.

A one way valve 1304 may be implemented in any system described herein. For example, where a second patient interface is combined with a first patient interface, and a dual therapy is to be delivered to the patient, a one way valve may allow the medical professional to administer gas via the second patient interface, without back flow through the gas supply conduit that leads to the first patient interface (i.e. nasal cannula). Without the one way valve 1304 it may not be possible to create the desired pressure with second patient interface upon the patient due to back flow out the pressure relief valve 1305.

In some embodiments, where more than one respiratory support devices (patient interfaces) are used together, for example a nasal cannula and a full face mask, to provide more than one flow of respiratory gases to the user, one or more of the respiratory support devices may comprise one or more vents to relieve the pressure provided by the support device. Where more than one device is used to provide more than one flow of respiratory gases, there may be a risk of increased pressure of gases provided to the user, as the pressure of each gas flow provided to the user may combine to result in an increased gases pressure at the user's airways. A vent at one or more of the respiratory support devices may be provided to mitigate or reduce the risk of over pressurising a user's airways. Alternatively or additionally a controller (e.g. controller 108) may be adapted to stop or reduce a flow of gases to the patient interface when an elevated pressure in the system is measured.

Figure 17:
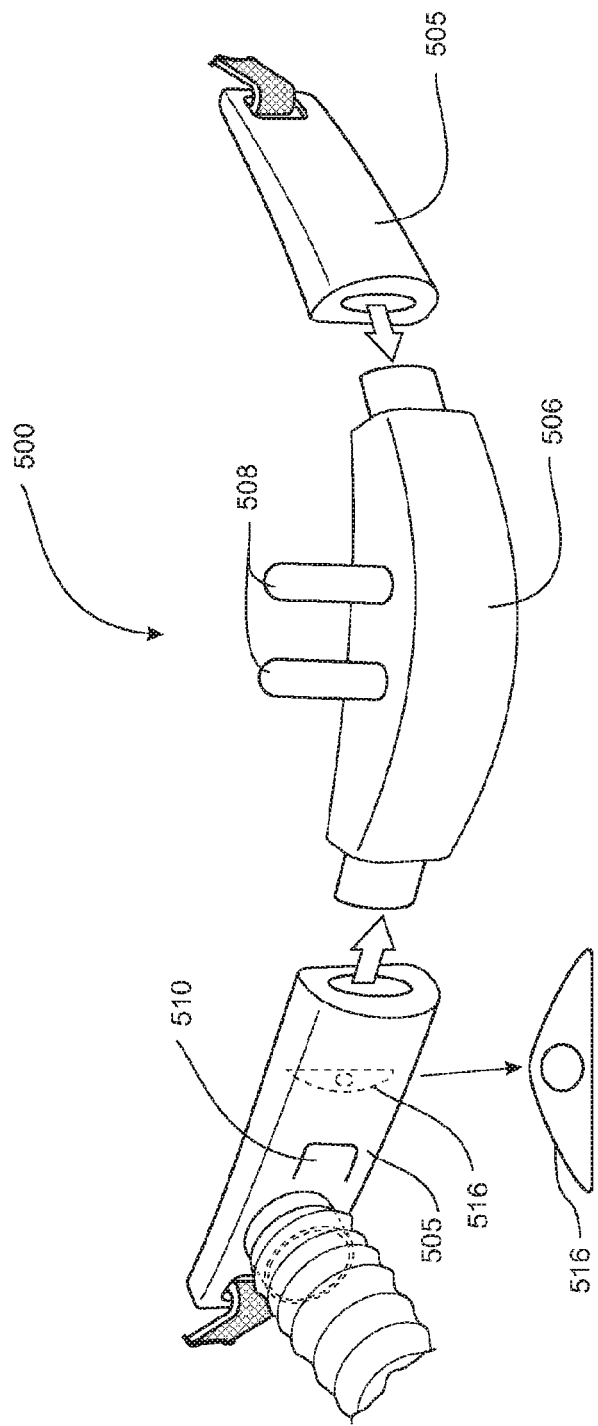
FIG. 17 is an exploded view of a cannula comprising a side arm providing a lumen for supplying a flow of gases to a user and with a vent in the side arm.

For example, a nasal cannula may comprise a vent to operate to limit the pressure provided by the cannula. In some embodiments, a cannula comprising a side arm or arms may comprise a venting arrangement in one or both side arms. An exemplary embodiment is illustrated in FIG. 17. The side arm 505 of cannula 500 may comprise a portion 516 (sealing portion) over which a seal of a face mask seals against, together with sealing against the face of the user. The side arm 505 comprises or provides a lumen for the flow of gases to a manifold 506 of the cannula and to the user via one or more outlets, for example nasal prongs 508. The portion 516 of the side arm may include a profile allowing the seal of the face mask to seal against the portion together with the face of the user, for example a possible cross section of which is provided in FIG. 17. The side arm 505 may include a vent 510 in the side arm at a position that is located outside of the sealing portion 516 of the side arm. In other words, the vent is located on the side arm to be outside of a sealing area of the face mask on the user's face. Where the pressure inside the face mask reaches a maximum desired pressure level, the pressure of the gases in the lumen of the side arm of the cannula increases to a corresponding level at which the vent in the side arm operates to relieve the pressure or limit the pressure at the user's airway to the desired maximum pressure. When the vent 510 operates to an open or venting position, the vent diverts gases flow to outside of the cannula and the face mask, and in a closed or non-venting position the gases flow is provided to the cannula.

In some embodiments, the seal 304 of the face mask bridging over the side arm applies a force to the side arm that causes the side arm to collapse or compress, closing the lumen of the side arm. For example, in some embodiments, the face mask seal pressing against portion 516 causes the lumen of the side arm to be occluded. The portion 516 of the side arm is inboard (downstream) of the vent 510, so that an increased pressure in the respiratory tube providing a flow of gases to the side arm resulting from the occluded or pinched side arm lumen is vented via vent 510. For example the side arm of the cannula may comprise a collapsible conduit portion as described herein. The collapsible portion of the cannula may comprise a cross section with hinging points as shown in FIG. 14A to 15B, or any other collapsible configuration described herein.

In some embodiments, a patient interface may comprise or be used together with an item over which the seal of a face mask seals. A number of embodiments for an item over which the seal of a face mask seals are shown in FIGS. 47 to 54C and 63A to 63C. The item may be a block or mount 96 in contact with, or to be placed in contact with, the patient's face. The block or mount may comprise at least one lumen therethrough for allowing a gas supply conduit to pass, or for connecting the gas supply conduit to the patient interface.

Figure 54A:
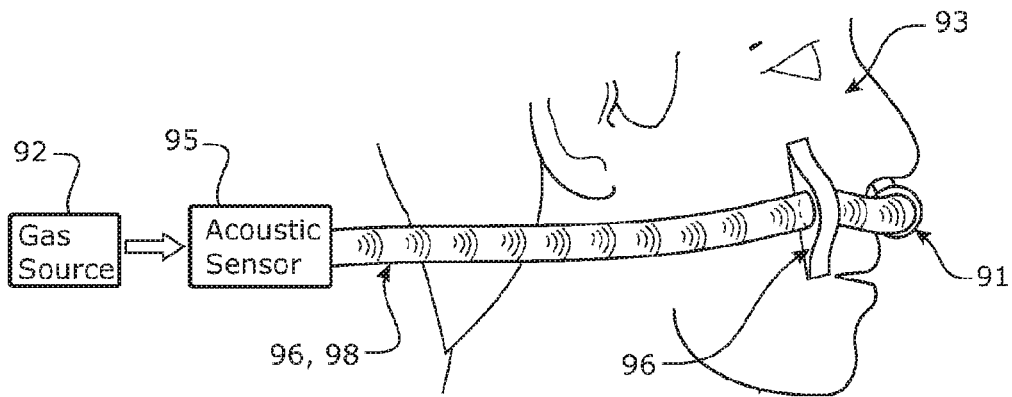
FIGS. 54A-C show how a parameter or characteristics of a gas supply conduit may change or alter, for example a deformation or change in shape of such a conduit as a result of a change in flow or pressure within the conduit, for example due to a closing of the conduit by a pressure or force exerted upon the item through which the gas is to pass. More particularly.
Figure 54B:
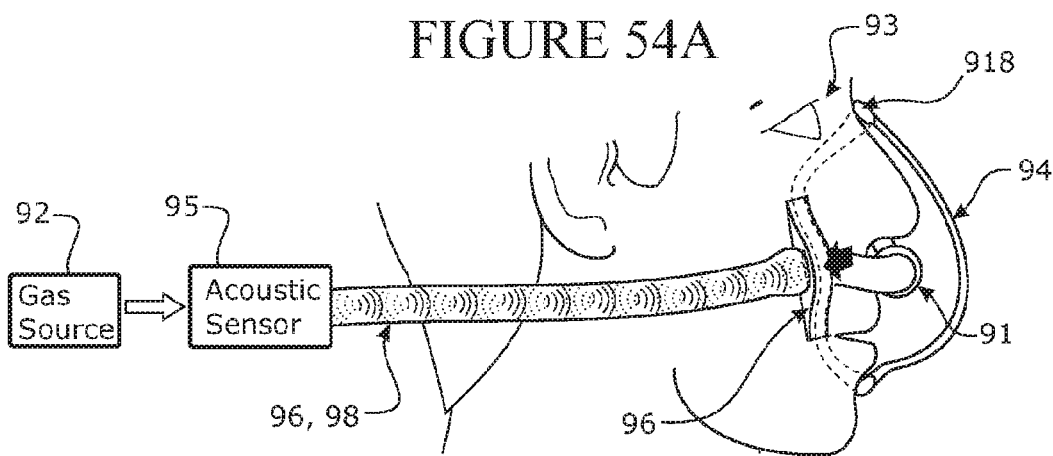
Figure 54C:
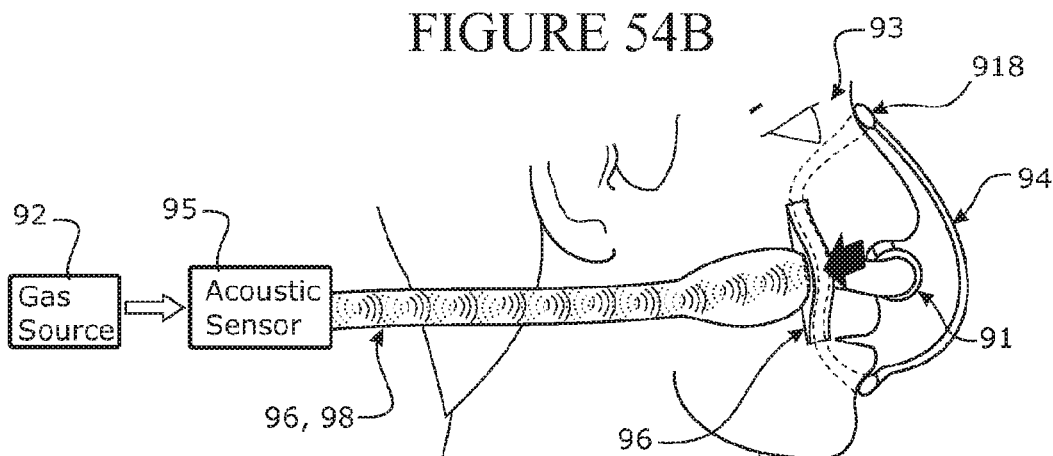

The item 96 may receive a gas supply conduit and/or may form a part of a fluid passageway for delivery of gas to the patient interface. In some embodiments, the item comprises a compressible portion or a portion that is capable of being squashed or deformed under an exerted force or pressure, e.g. from the face mask seal (FIGS. 54A to 54C). In some embodiments, one or more of the at least one lumen is located within the compressible portion or portion that is capable of being squashed or deformed. The compressible portion may be made of any suitable material, such as a polymer or silicone. A lumen and/or conduit located within the compressible portion or portion is capable of being squashed or deformed and may be compressed or deformed so as to block or obstruct (or prevent), or partially obstruct, the flow of gas from being supplied to the patient interface 91. In some embodiments, the item 96 is an integral part of a side arm of the patient interface, or may be removeably attachable to a supply conduit to the patient interface, or is removeably attachable to a side arm of the patient interface. In some embodiments, the item is a discreet component separately positionable or locatable upon a patient, more particularly upon a patient's face. The item may be a patch or pad or wearable device that is attachable or locatable upon the patient for sensing the in-situ combination of the patient interface and the face mask upon the patient during delivery of gas to the patient, wherein such a sensed combination generates a signal or output.

The item may include a venting device such that when in a collapsed configuration to prevent or reduce a flow of gases to a user, the venting device vents pressure that increases in the tube providing a flow of gases to the patient interface via the item.

In some embodiments the item resists an external force such that it does not compress or collapse in use. In such an embodiment the item may comprise a venting device to prevent or reduce the pressure at the user's airways increasing above a maximum desired pressure or prevent or reduce the flow delivered to the patient's airway. The venting device or vent of the item or patient interface may be any one or more of the vents or venting devices described herein.

In some embodiments, the patient interface and or an item associated with or used with the patient interface comprises a filter device to prevent contamination of a breathing circuit providing a flow of gases to the item or interface, and the filter device comprises a said vent or venting device.

Further description of an item 96 with reference to FIGS. 47 to 54C and 63A to 63C is provided below.

Figure 21A:
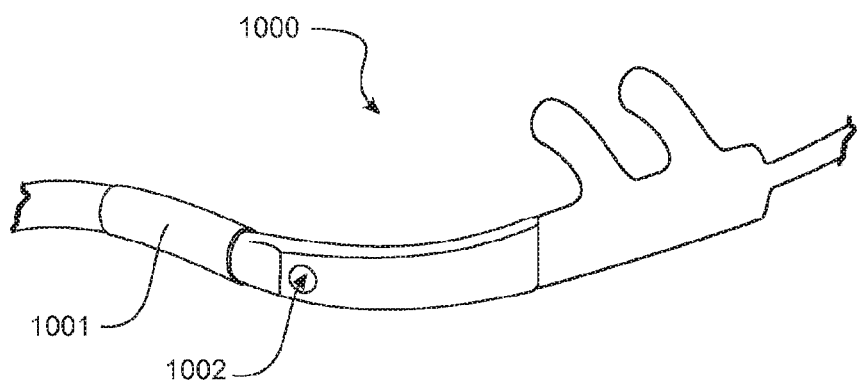
FIG. 21A to 21C shows an embodiment of a pressure relief device.

FIG. 21A shows one embodiment of a device 1000 that relieves pressure and also restricts flow of gas through the conduit 1001. The flow restriction may completely block the flow of gas, substantially block the flow of gas, or partially block the flow of gas. In a venting or open configuration the device 1000 vents or diverts gases flow from the conduit. In a non-venting or closed configuration the device allows the flow of gases to a patient interface, e.g. cannula 200 of FIG. 2. This embodiment of the pressure relief device 1000 is in the form of a collapsible conduit with a poppet valve 1002. In particular, the poppet valve 1002 has a valve stem 1003 and a valve disc 1004. The valve stem 1003 and the valve disc 1004 are relatively rigid and will not collapse or deform when the surrounding parts or components move, collapse, or deform.

A portion 1005 of the conduit 1001 may be configured to collapse or deform and restrict the flow. Part of the collapsible portion may be a first wall in the form of a relatively rigid component 1006. The relatively rigid component 1006 may have an aperture (not visible) through which the valve stem 1003 extends.

The conduit also has a generally opposing second wall 1007. During normal use the rigid component 1006 is substantially flush with an adjacent wall 1008 of the conduit such that substantially all of the gases from said gas source pass through said conduit. When a force is applied to the rigid component 1006, the rigid component moves towards the second wall 1007 to provide a passage 1009 through which gas may flow from within the conduit to exit to atmosphere. In this embodiment, the passage is provided by the aperture. In some embodiments the portion 1005 of the conduit may not comprise an aperture or vent, to operate to occlude the lumen of the conduit without venting. A separate vent or pressure relieve valve may be separately located upstream of the portion 1005.

Figure 21B:
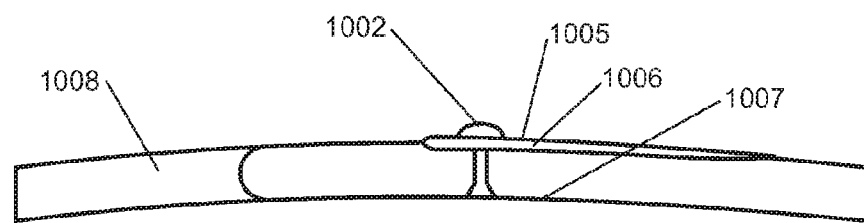
Figure 21C:
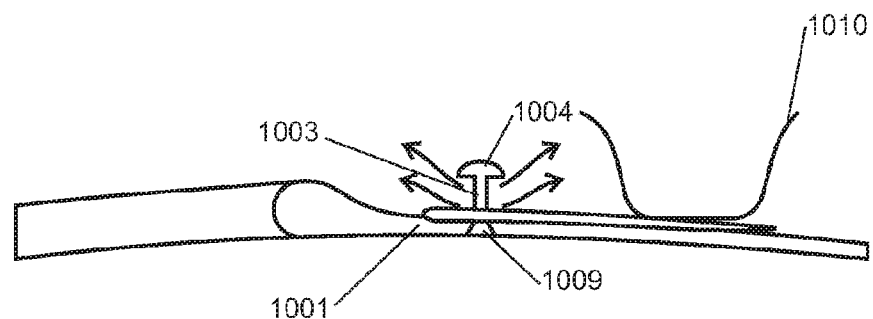

In one embodiment, the conduit can be collapsed by pressing a mask seal 1010 against the rigid component 1006. Alternatively, the conduit can be collapsed by another suitable mechanism, such as a clamp or clip, or in another alternative the conduit could be collapsed by a medical professional pressing or squeezing the conduit. When the conduit is collapsed, the rigid portion collapses and moves towards the position shown in FIG. 21C. Gas is then free to flow out of the aperture, relieving the pressure in the conduit. It will be appreciated that the flow of gas may be completely restricted, substantially restricted, or partially restricted by pressing a mask or other device against the conduit. In any of those situations, the poppet valve 1002 will open and allow gas to flow out of the aperture. The amount of gas that flows out of the aperture will depend on the pressure of the gas in the conduit and whether the flow of gas is completely restricted, substantially restricted, or partially restricted.

In an alternative embodiment, the pressure relief device may not have a poppet valve. The pressure relief device may have another type of valve, such as one of those described in relation to the other embodiments of this specification.

Figure 21D:
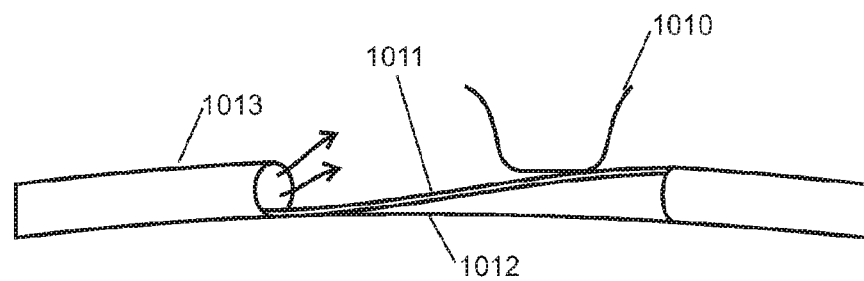
FIG. 21D shows an embodiment of a pressure relief device.
Figure 21E:
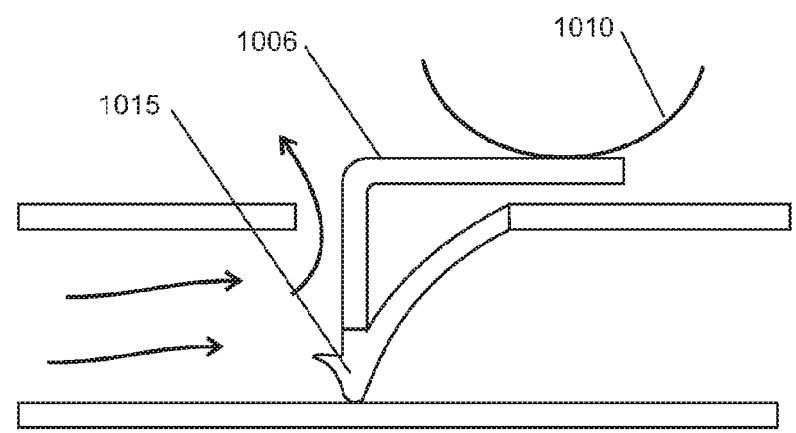
FIG. 21E shows a cross section of an embodiment of a pressure relief device.

For example the embodiments shown in FIGS. 21D and 21E do not have a poppet valve. The features and operation of this embodiment are the same as those of the embodiment shown in FIGS. 21B and 21C, except it does not have a poppet valve.

The embodiment of FIG. 21D has a first wall 1011 and a generally opposing second wall 1012. During normal use the first wall is substantially flush with an adjacent wall 1013 of the conduit such that substantially all of the gases from said gas source pass through said conduit. When a force is applied to the first wall, the first wall moves towards or away from the second wall to provide a passage through which gas may flow from within the conduit to exit to atmosphere.

The features and operation of the embodiment of FIG. 21E is similar to the embodiment of FIG. 21D, with the addition of a lip 1015 that seals against the adjacent wall during normal use. The lip 1015 may formed from a resilient material, attached to a relatively rigid component 1006 against which the mask seal 1010 acts to move the lip away from a side wall of the conduit to open the vent. The rigid component may be L shaped, with a first portion of the L shaped component lateral to the longitudinal axis of the conduit and a second portion of the L shaped component that the mask seal acts against arranged longitudinally relative to the conduit.

Figure 22A:
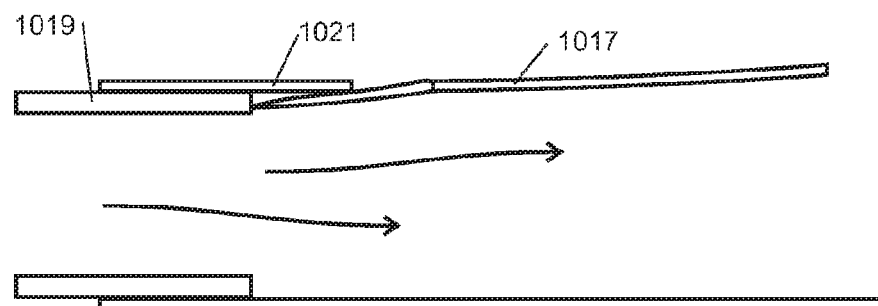
FIGS. 22A and 22B show cross sections of an embodiment of a pressure relief device.
Figure 22B:
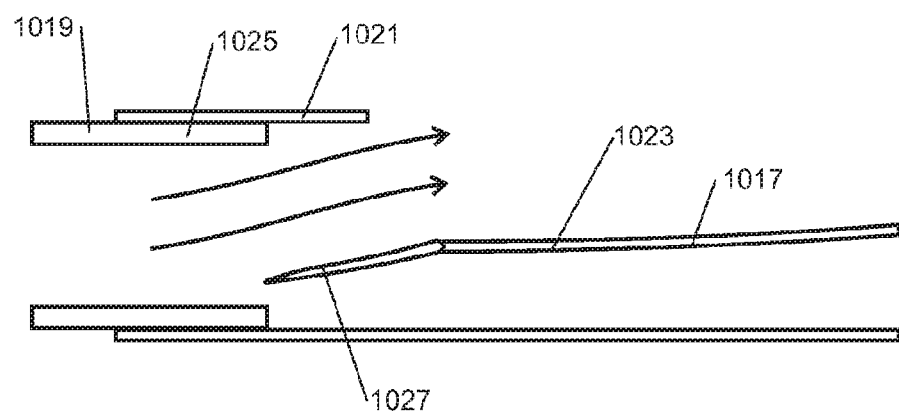

FIGS. 22A and 22B show one embodiment of a device that relieves pressure and blocks or inhibits flow. This embodiment is in the form of a conduit having a collapsible portion 1017 and a non-collapsible portion 1019.

The collapsible portion 1017 comprises a relatively flexible or soft material that collapses under applied pressure, or the portion 1017 may have a rigid portion connected to an adjacent non-collapsible portion of the conduit by a pivot that allows it to open and close. The collapsible portion 1017 preferably includes a relatively rigid portion 1023 that prevents the collapsible portion from collapsing until an intentional external force is applied, such as pressing the mask against the collapsible portion. The flexible or soft portion 1027 is located at an end of the collapsible portion to provide a seal against the non-collapsible portion 1021. The non-collapsible portion may optionally comprise a rigid portion 1025. In alternative embodiments, the rigid portion may be omitted such that a tongue 1027 of the collapsible portion seals against the wall of the conduit. The collapsible portion has an extended tongue 1027 that secures the collapsible portion below the wall of the conduit to prevent the collapsible portion from opening outwards under pressure from the gas flow. During normal use the collapsible portion is substantially flush with the adjacent wall of the conduit such that substantially all of the gases from said gas source pass through said conduit. The collapsing portion may act as a flap to move between a closed position illustrated in FIG. 22A and an open or venting position illustrated in FIG. 22B.

The collapsible portion is arranged such that when an external force is applied, such as the mask being placed on the patient's face, the collapsible portion will collapse. The non-collapsible portion is relatively rigid and will not collapse or deform when the collapsible portion moves, collapse, or deform.

When the collapsible portion of the conduit is collapsed, the rigid portion 1023 moves towards the position shown in FIG. 22B providing a passage through which gas may flow from within the conduit to exit to atmosphere. Gas is then free to flow out of an aperture created between the tongue 1027 and the non-collapsible portion 1019, relieving the pressure in the conduit. It will be appreciated that the flow of gas may be completely restricted, substantially restricted, or partially restricted by adding a mask or other device on the conduit. In any of those situations, the collapsible portion collapse or deform and allow gas to flow out of the aperture. The amount of gas that flows out of the passage will depend on the pressure of the gas in the conduit and whether the flow of gas is completely restricted, substantially restricted, or partially restricted. The amount the collapsible portion collapses into the conduit (and therefore the amount of venting achieved) may be controlled by a user by altering a sealing force provided by the face mask 300 over the collapsible portion.

FIGS. 23A to 23C shows another pressure relief device. In this embodiment, the pressure relief device comprises a flexible portion or valve member 1031 that extends over and closes an aperture 1033 in the conduit. When viewed from above, the flexible portion has an elliptical shape. When viewed from the side, the flexible portion is curved to fit the shape of the conduit. The flexible portion is also curved when viewed from the end and matches the curve of the conduit. Alternatively, the flexible portion may have a curvature that does not substantially match the curvature of the conduit or may be substantially planar. In these alternative embodiments, the flexible portion will have a natural or non-deformed position and will be biased towards that natural position to close the aperture. A relief pressure at which the flexible portion lifts away from the aperture can be determined by properties of the material used for the flexible portion and/or by the size and shape of the flexible portion.

FIG. 23b shows the valve without the flexible portion 1031. The flexible portion has a stem 1032 that fits into a hole in a member extending across the aperture. A retention mechanism (e.g. an enlarged diameter portion) 1032*a* on the stem 1032 holds the flexible portion in place.

The flexible portion 1031 is or comprises a flexible or resilient material, for instance, silicone. Under the standard operating gas pressure, the flexible portion will cover the aperture and prevent or at least substantially inhibit gas from flowing out of the conduit through the aperture, as shown in FIG. 23*c*. When the pressure of the gas in the conduit reaches a threshold pressure, the edges of the flexible portion will move away from the conduit and the flexible portion will have the shape shown in FIG. 23*d*.

The aperture 1033 may have a shape that is similar to the shape of the flexible member, that is, the shape may be elliptical when viewed from above. In further alternative embodiment, there may be two or more apertures that are closed by the flexible member. In another alternative embodiment, there may be two or more apertures, with each aperture being closed by a flexible member. As shown in FIG. 23*a*, an advantage of more than one flexible member is that there should always be at least one flexible member that is not resting on a surface or occluded and is free to move and open.

Figure 23E:
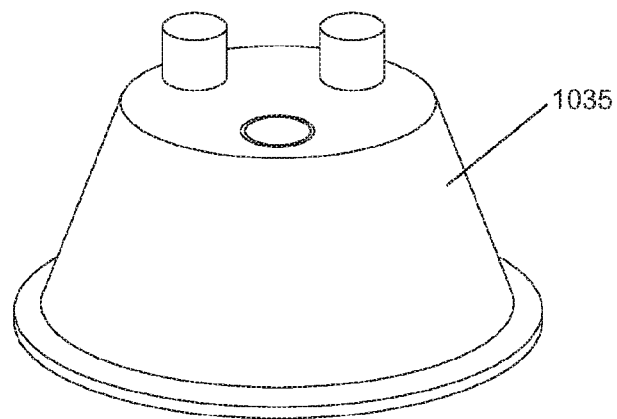
FIG. 23E to 23G show an embodiment of a pressure relief device.
Figure 23F:
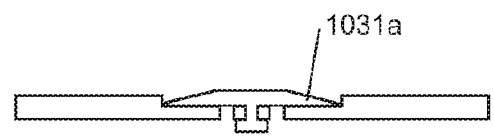
Figure 23G:
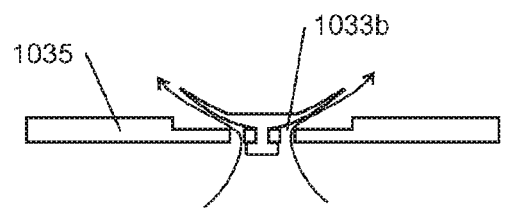

FIGS. 23E to 23G, show a pressure relief device similar to that shown in FIGS. 23A to 23D except that the pressure relief device is located within a chamber 1035. Positioning the pressure relief device at the chamber may be advantageous as the pressure relief device is not venting gases near the patient. The pressure relief device is protected as it is not on the flexible conduit but is located on a separate chamber to which the conduit is in fluid communication. In addition, the pressure relief device may be remote from bedding and other items that might be near the patient and which could block or interfere with the vent.

Figure 24A:
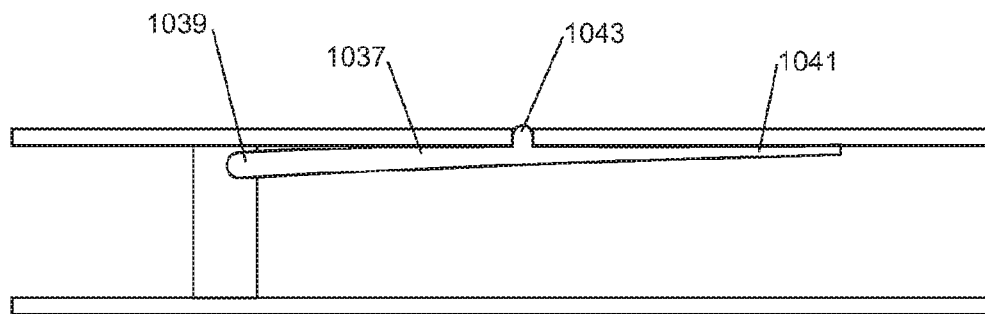
FIGS. 24A and 24B show cross sections of an embodiment of a pressure relief device.
Figure 24B:
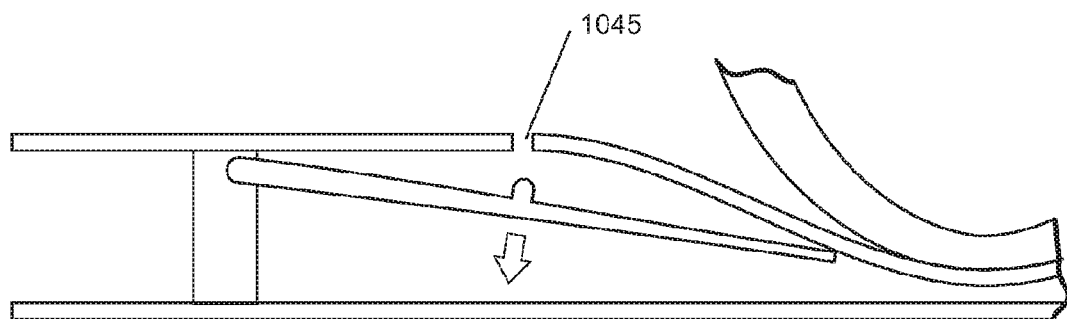

FIGS. 24A and 24B show one embodiment of a device that relieves pressure and blocks or inhibits flow. In this embodiment, the pressure relief device has a lever 1037 mounted within the conduit, the lever including a pivot 1039, an operating portion 1041, and a sealing portion 1043 that substantially seals an aperture 1045 in the conduit such that substantially all of the gases from said gas source pass through said conduit. In this configuration, the operating portion 1041 is on one side of the pivot 1039 and the sealing portion 1043 is on the same side of the pivot. In this embodiment, the lever 1037 is a leaf spring positioned inside the conduit. The conduit may have dimensions and be formed from one or more materials that are soft or flexible so the conduit does not retain its shape without the support of other components. The leaf spring 1037 would prevent or at least substantially inhibit the conduit from collapsing, deforming or closing unless an external force is applied.

The sealing portion 1043 is in the form of a boss or protuberance that engages the aperture 1045 in the conduit. When the boss or protuberance engages the aperture, gas is prevented or at least substantially inhibited from flowing out of the conduit.

When the operating portion 1041 is moved, for example by a mask pressing on the conduit directly above the operating portion, the lever 1037 is caused to pivot about the pivot 1039 and the sealing portion 1043 moves away from the aperture 1045 to provide a passage through which gas may flow from within the conduit to exit to atmosphere.

Figure 25A:
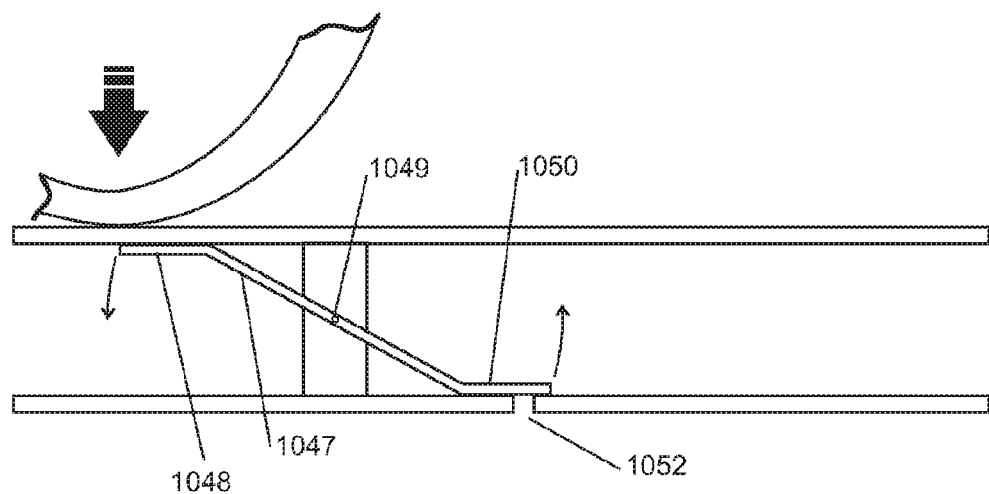
FIGS. 25A and 25B show cross sections of an embodiment of a pressure relief device.
Figure 25B:
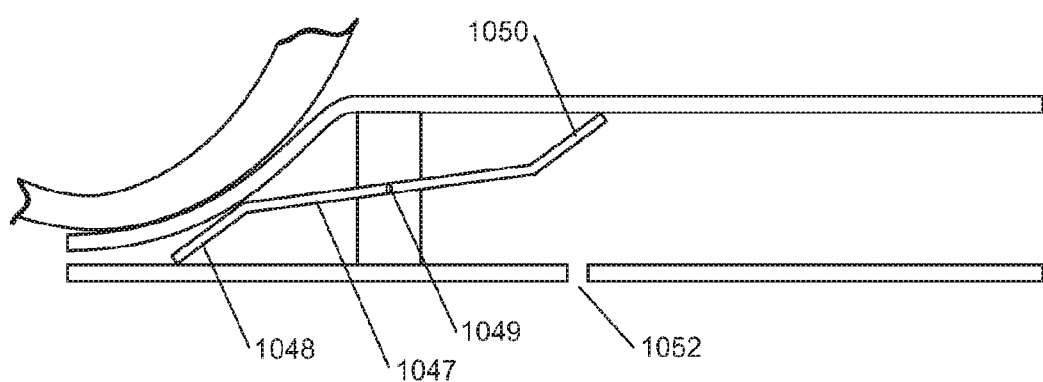

FIGS. 25A and 25B show another embodiment of a device that relieves pressure. This embodiment is for use with a conduit that is collapsible or has a collapsible portion.

In this embodiment, the pressure relief device has a lever 1047 mounted within the conduit, the lever including a pivot 1049, an operating portion 1048, and a sealing portion 1050 that substantially seals the aperture 1052 in the conduit such that substantially all of the gases from said gas source pass through said conduit. In this embodiment the lever 1047 is a rigid component positioned inside the conduit. In this configuration, an operating portion 1048 is on one side of a pivot 1049 and the sealing portion 1050 is on the other (opposite) side of the pivot 1049. The mask seal acts against a side of the conduit to act against the operating portion to cause the lever to pivot on the pivot point. The pivoting of the lever moves the sealing portion out of engagement with the aperture on an opposite side of the conduit. The sealing portion 1050 may have a boss or protuberance that engages the aperture 1052.

When the collapsible portion of the conduit is collapsed, the lever 1047 moves towards the position shown in FIG. 25B. Gas is then free to flow out of the aperture 1052, relieving the pressure in the conduit. It will be appreciated that the flow of gas may be completely restricted, substantially restricted, or partially restricted by adding a mask or other device on the conduit. In any of those situations, the lever 1047 moves and allows gas to flow out of the aperture 1052. The amount of gas that flows out of the aperture will depend on the pressure of the gas in the conduit and whether the flow of gas is completely restricted, substantially restricted, or partially restricted. In some embodiments the lever 1047 is biased towards a closed position in which the aperture is closed. In order to open the aperture a force is required (e.g. by application of a face mask seal) to move the lever against the bias. One benefit of the arrangement illustrated in FIGS. 25A and 25B is that the flow is vented on a side of the tube that faces away from the person applying the mask to the patient. In some embodiments it is preferred to vent or direct the flow of gases in a direction away from the patient and/or caregivers.

In an alternative embodiment, another component or portion of the patient interface may be provided with a lever. For example, the cannula may have a lever.

Figure 26A:
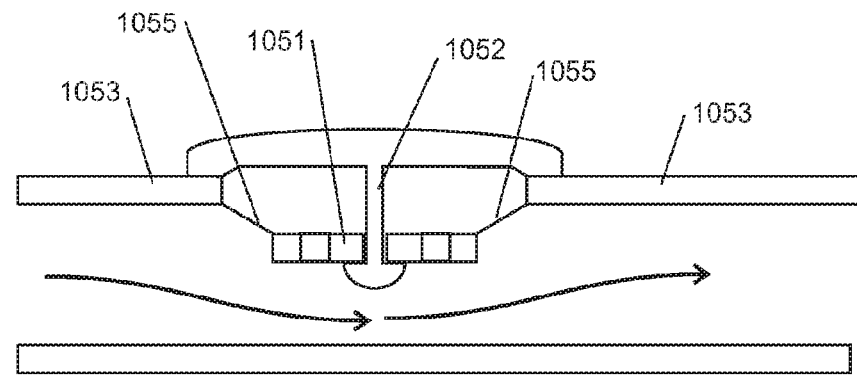
FIGS. 26A and 26B show cross sections of an embodiment of a pressure relief device.
Figure 26B:
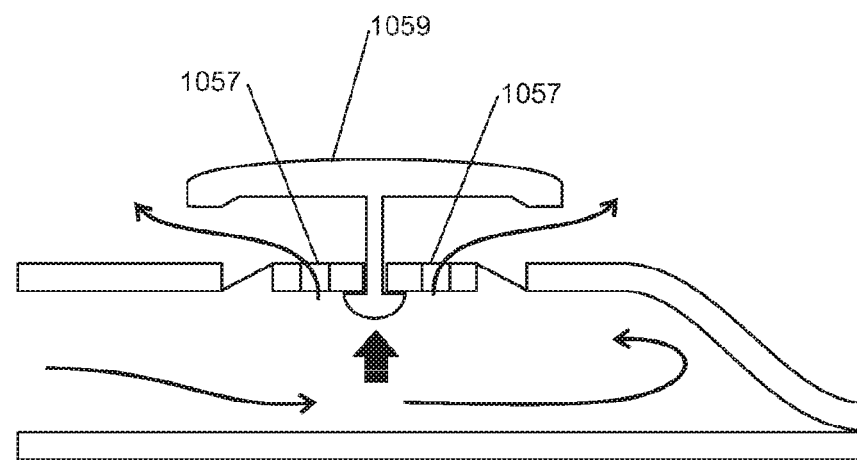

FIGS. 26A and 26B show another pressure relief device. In this embodiment, the conduit has a movable portion 1051 that is positioned connected to adjacent portions 1053 of the conduit by thin joining portions or a web 1055. The movable portion has one or more apertures 1057. A disc or valve member 1059 extends over and seals or at least substantially seals the conduit. As show in FIG. 26A, the disc 1059 seals against portions of the conduit adjacent the movable portion. The disc 1059 has a stem 1052 for connecting the disc to the movable portion 1051 of the conduit.

The thin joining portion or web 1055 is created such that the pressure relief device stays in the closed position until the pressure within the conduit reaches a threshold pressure. When the pressure of the gas in the conduit reaches the threshold pressure, the movable portion 1051 pops into a second configuration where the joining portion is deflected upwards allowing flow to vent out of the apertures 1057.

FIGS. 27A to 27D show another pressure relief device. In this embodiment, the pressure relief device comprises a valve member that is a flexible arm 1061, and a body portion 1062 that partially or fully wraps around the conduit. The flexible arm and body portion are preferably integrally formed as a unitary member. When the pressure of the gas in the conduit reaches a threshold pressure, the pressure would force the flexible arm 1061 to bend into an upwardly curved position shown in broken lines in FIG. 27A. Gas is then free to flow out of an aperture 1063, relieving the pressure in the conduit. In some embodiments the arm could be rotated/repositioned on the conduit by a user so that the vent aperture 1063 remains uncovered if venting was desired all the time or for an extended time period. The arm could be made of, for instance, a piece of silicone, spring steel, other suitable plastic material or metallic material.

Figure 27A:
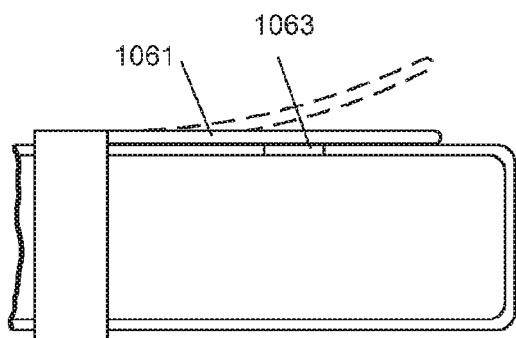
FIG. 27A to 27D show an embodiment of a pressure relief device.
Figure 27B:
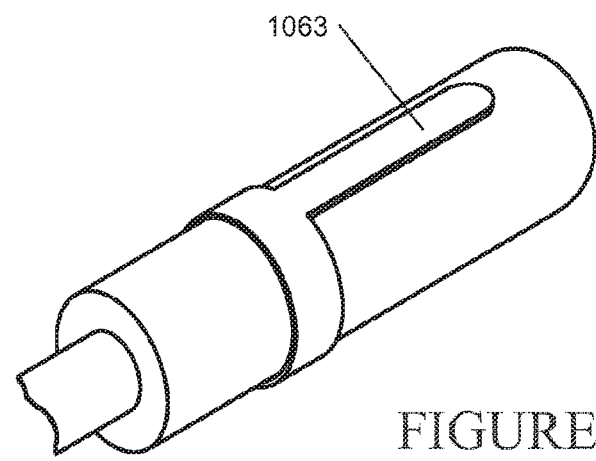
Figure 27C:
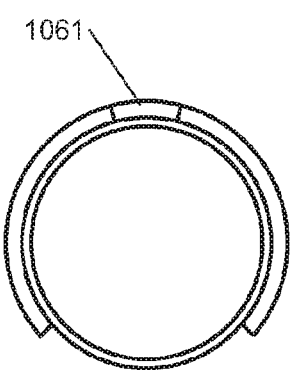
Figure 27D:
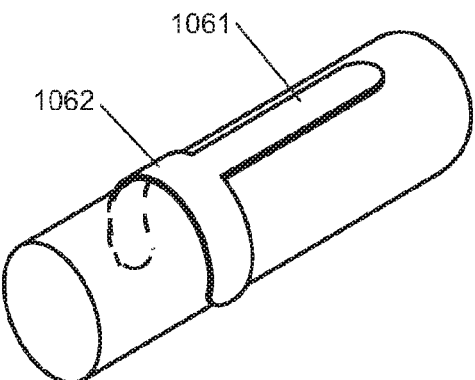
Figure 27E:
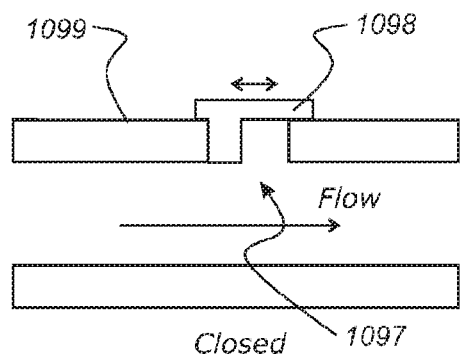
FIG. 27E to 27F show cross sections of an embodiment of a pressure relief device.
Figure 27F:
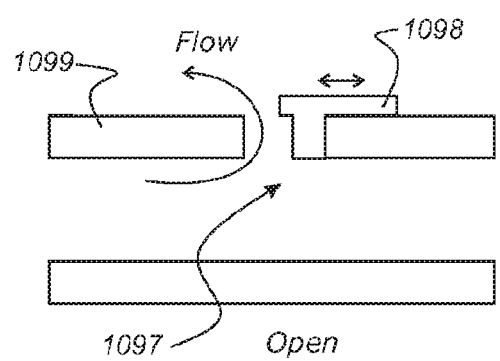

FIGS. 27E and 27F show another pressure relief device. In this embodiment the pressure relief device comprise a sliding member 1098 provided in a wall of a conduit 1099. The member 1098 is slidable between an open position to uncover an aperture 1097 in a wall of the conduit, as shown in FIG. 27F, and a closed position to cover the aperture 1097, as shown in FIG. 27E. A user may slide the member 1098 to the open position when the user wishes to use a mask together with the first patient interface, to vent pressure from the conduit that may be collapsed by the mask.

Figure 27G:
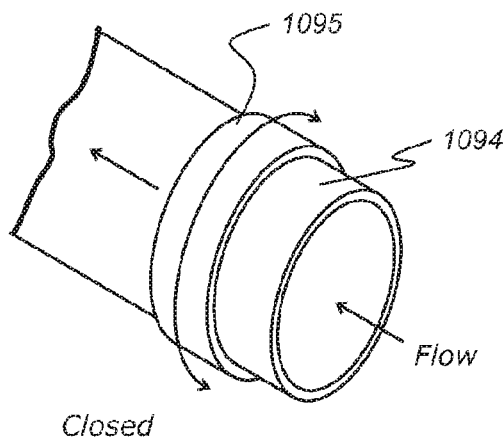
FIG. 27G to 27H show an embodiment of a pressure relief device.
Figure 27H:
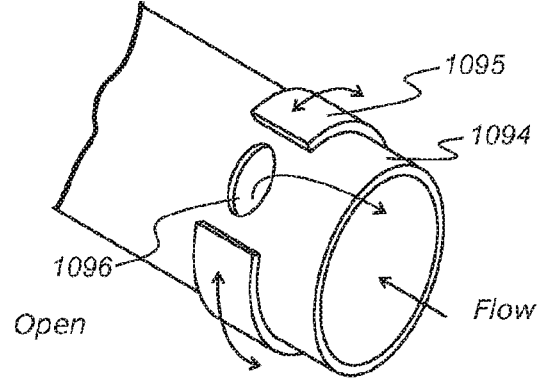

FIGS. 27G and H show another pressure relief device. In this embodiment the pressure relief device comprises a sleeve or ring element 1095 is provided over a wall of the conduit. The member 1095 may be rotatable between an open position to uncover an aperture in a wall of the conduit 1094, as shown in FIG. 27H, and a closed position to cover the aperture 1096, as shown in FIG. 27E. Alternatively the sleeve 1095 may be slidable to cover and uncover the aperture 1096. The sleeve or ring element 1095 may have an aperture to be aligned with the aperture 1096 in the wall of the conduit 1094, or may extend partway around the conduit 1094 so that the sleeve 1095 may be positioned with the aperture 1096 of the conduit 1094 positioned between circumferential ends of the sleeve 1095, as shown in FIG. 27H.

Figure 27I:
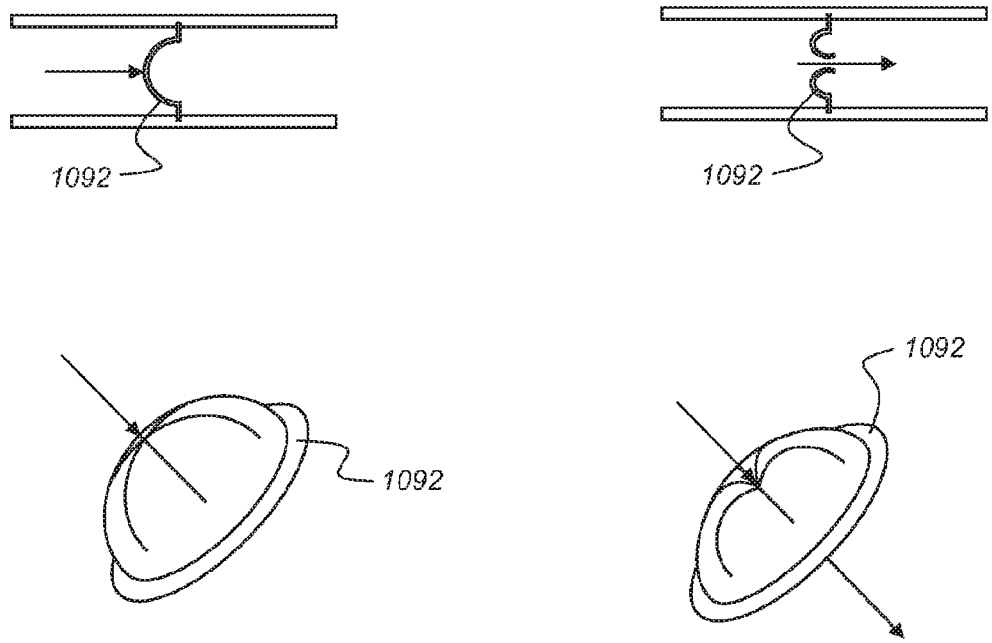
FIGS. 27I and 27J show an embodiment of a pressure relief device.
Figure 27J:

FIGS. 27I and J show another pressure relief device. The pressure relief device comprises a silicone valve member 1092. Excessive pressure in the system may cause a slit in the silicone member 1092 to open, to relieve pressure in the system. The silicone member may be a diaphragm comprising the slit.

Figure 28:
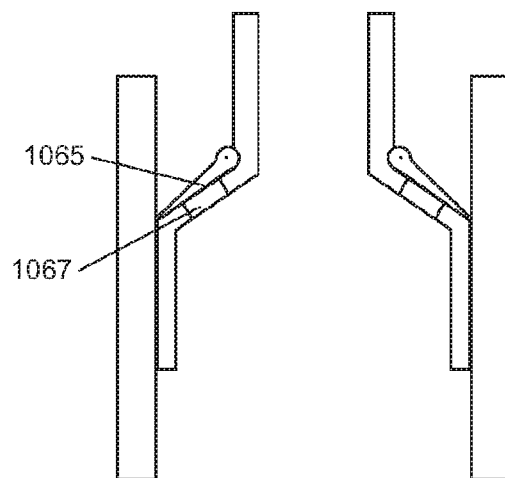
FIG. 28 shows a cross section of an embodiment of a pressure relief device.

FIG. 28 shows a cross section of another pressure relief device. This embodiment may be positioned in a relatively rigid component, such as in a filter.

In this embodiment, the pressure relief device comprises a flexible portion or valve member 1065 that extends over and closes an aperture 1067 in the conduit. The flexible portion is or comprises a flexible or resilient material, for instance, silicone. The flexible portions have a natural position shown in FIG. 28 and will be biased towards that natural position. In an alternative embodiment, the flexible portion could be replaced with a relatively rigid portion that is biased, for example with a spring, to return to the position shown in FIG. 28.

Under the standard operating gas pressure, the flexible portion 1065 will cover the aperture and prevent or at least substantially inhibit gas from flowing out of the conduit through the aperture. When the pressure of the gas in the conduit reaches a threshold pressure, the flexible portions will move away from the apertures, allowing gas to flow through the apertures, relieving the pressure in the conduit.

FIG. 28 shows two apertures 1067 that are closed by the flexible member. In another alternative embodiment, there may be one or more apertures, with each such aperture being closed by a corresponding flexible member. One flexible member may close two or more apertures. The aperture may be formed as a slot extending circumferentially.

Figure 29:
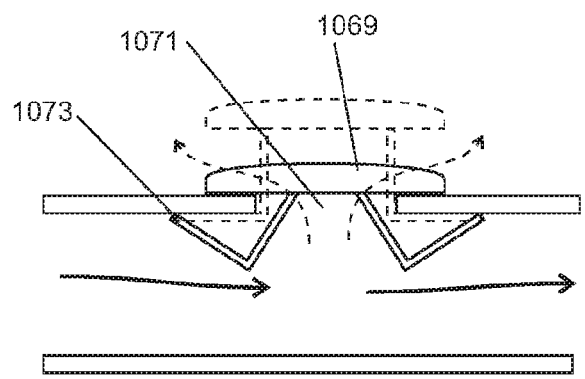
FIG. 29 shows a cross section of an embodiment of a pressure relief device.

FIG. 29 shows another pressure relief device. This embodiment is shown positioned in a conduit. This embodiment has a valve member 1069 that closes an aperture 1071 to prevent or at least substantially inhibit gas flowing through the aperture. The pressure relief device has a pair of legs 1073 between the conduit and the valve member 1069. The legs are biased into the position shown in solid lines. The shape and composition of the legs will be chosen and design such that they hold the valve member in the closed position until the pressure reaches a threshold point, at which the valve opens (position shown in broken lines). When the pressure drops, and the force on the valve member is reduced, the valve member will return to the closed position shown in solid lines. Alternatively, a user could manually press the valve into the closed position when the mask is removed.

Figure 30A:
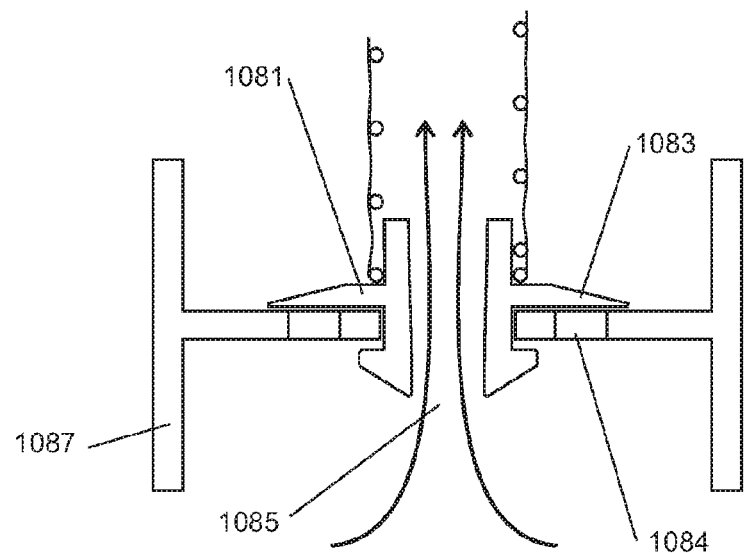
FIGS. 30A and 30B show cross sections of an embodiment of a pressure relief device.
Figure 30B:
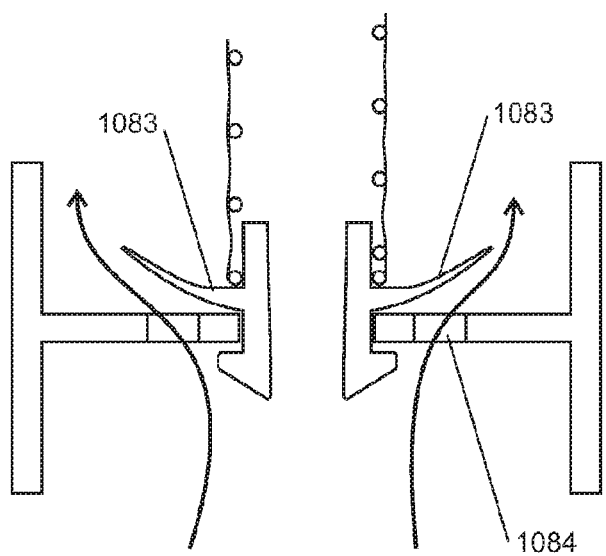

FIGS. 30A, 30B show another pressure relief device. This embodiment may be positioned in a relatively rigid component, such as in a filter.

This embodiment of the pressure relief device has a valve member 1081 with outwardly extending flaps 1083. The flaps close apertures 1084 in a rigid component. The centre of the valve has an aperture 1085 through which gas may flow into a conduit. When the pressure of the gas in the conduit reaches a threshold pressure, the flaps lift. The flaps are preferably flexible and resilient.

Figure 31:
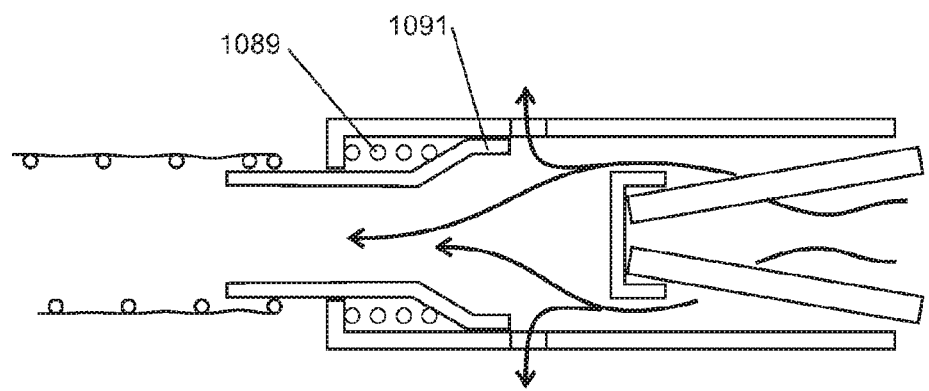
FIG. 31 shows a cross section of an embodiment of a pressure relief device.

This embodiment of the pressure relief device could be positioned, for instance, in a filter 1087. However, it will be appreciated that this embodiment of the pressure relief device could be located anywhere in the gas flow path within a rigid portion. FIG. 31 shows a pressure relief device located at the end of a filter, but this is not necessary. It could be positioned anywhere in the system.

This embodiment of the pressure relief device is for use with a component of a respiratory support system that delivers pressurised gas from a gas source to a patient. The component of the respiratory support system has an aperture. The pressure relief device comprises a valve body 1091 engageable with a conduit that delivers pressurised gas from a gas source to a patient. The valve body is located within the component of the respiratory support system and has a portion that is sealingly engageable with the aperture. During normal use the valve body is biased towards sealing the aperture in the component of the respiratory support system such that substantially all of the gases from a gas source pass through the conduit. When the pressure of the gas within the conduit reaches a threshold pressure the valve body clears the aperture in the component of the respiratory support system to provide a passage through which gas may flow from within the component of the respiratory support system to exit to atmosphere. In this embodiment a spring 1089 holds the valve body 1091 in the normal use position (closed) position until the pressure of the gas in the conduit reaches a threshold pressure.

A number of the above described pressure relief devices are incorporated with or comprise or provide a collapsible portion of a conduit, and are actuated between a closed or non-venting configuration and an open or venting configuration by that portion of the conduit collapsing under the influence of an external force. The external force may be provided by the seal of a face mask placed over the collapsible portion of the conduit, or by a user or medical profession pressing the collapsible portion. For example embodiments described with reference to FIGS. 21B to 22B and 24A to 25B are pressure relief devices that are actuated by an external force provided to the collapsible portion. In such embodiments, the venting devices may be operated between venting and non-venting positions by a second interface pressing against a component of the device, for example lever 1050 in the embodiment of FIG. 25A. Alternatively a user or medical professional may operate the device by pressing a component of the device.

A number of the above described pressure relief devices are actuated between a closed or non-venting configuration and a venting or open configuration by a system pressure, for example embodiments of FIGS. 23A to 23G and 26A to 30. These embodiments operate once the system pressure increases above a threshold. The devices may sense the pressure directly, for example the pressure acting on a valve member of the pressure relief device. Alternatively these devices may be operated by a controller that receives a pressure indication from a sensor located within the system, so that once the sensed pressure reaches a threshold the controller energises an actuator (e.g. solenoid) to actuate the valve member between the non-venting and venting configurations. Alternatively a mechanical switch or actuator may be provided that a user or medical professional can manipulate to actuate the valve member between the non-venting and venting configurations.

Figure 32:
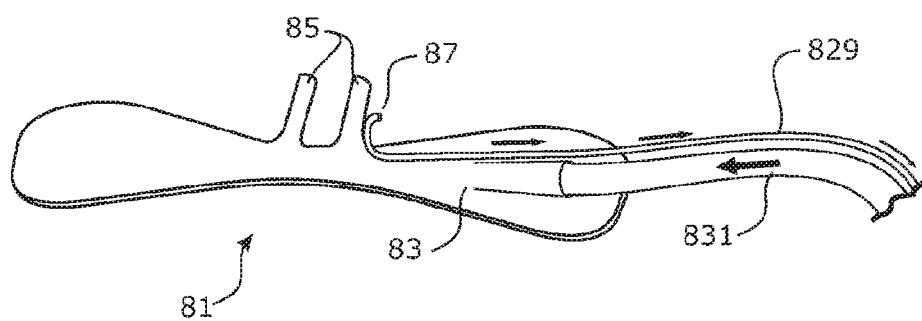
FIG. 32 is a schematic perspective view of a nasal cannula and associated conduits.
Figure 33:
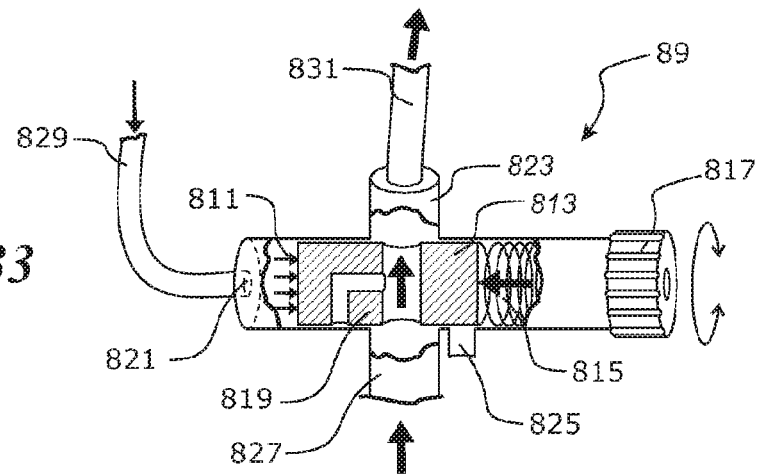
FIG. 33 is a cross section of a mechanical valve or pressure relief device in a position allowing a flow of gas to be delivered to a patient or user.
Figure 34:
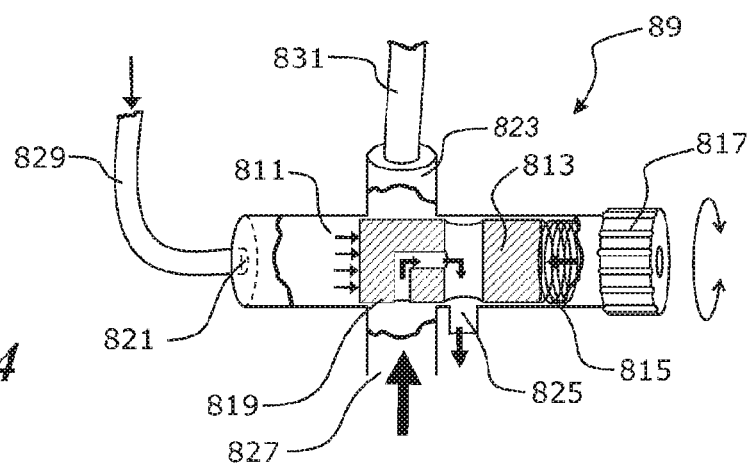
FIG. 34 is a cross section of the mechanical valve of FIG. 33 in a position preventing a flow of gas from being delivered to a patient or user.

Another pressure relief device is described with reference to FIGS. 32 and 34. The pressure relief device 89 is shown in FIGS. 33 and 34, and a nasal cannula 81 adapted for use together with the pressure relief device is shown in FIG. 32. The cannula 81 and pressure relief device may be used together in a respiratory support system, for example system 100 of FIG. 1. The pressure relief device 89 is adapted to sense a system pressure, for example a pressure delivered to a patient via the cannula 81. The nasal cannula 81 has a body portion 83 locatable upon a face of a patient in an operational position. The nasal cannula 81 also has at least one nasal prong 85 extending from the body portion 83, the nasal prong 85 is adapted to direct a flow of gas into a nare of the patient's nose when the body portion is in the operational position. In the embodiment shown, the nasal cannula has two prongs 85.

The system also has a pressure sensing or sampling line or conduit 829. In the illustrated embodiment the sensing line 829 has an opening or inlet 87 at or near the nare of the patient's or user's nose to sample/sense the pressure at that location, however, the pressure sensing line could be used to sense the system pressure at another location within the system. The pressure relief device 89 is a mechanical valve. In the illustrated embodiment the pressure relief device comprises a shuttle or piston 813. The pressure relief device 89 selectively controls the flow of gas into the nare of the patient's nose from the nasal prong 85. An outlet end 821 of the pressure sensing line is open to the piston 813 so that the piston 813 senses or is acted on by the pressure sensed by the pressure sensing line, described in more detail below. In the illustrated embodiment, the piston 813 senses the pressure at the nares via the pressure line 829. In such an embodiment, the pressure relief device may be used as a safety pressure limiting device to ensure a maximum allowable pressure at the patient is not exceeded. In an alternative embodiment, a pressure may be measured to provide an indication that a second support system has been applied to the patient. For example, a face mask may be applied to the patient, wherein the face mask may occlude a portion of the conduit 831. With the face mask applied or the conduit occluded, a system pressure within the conduit may increase. A pressure sensor may sense the pressure to provide an indication that the mask has been applied. The increased pressure can operate the device 89, to vent the pressure in the conduit 831. The nasal cannula 81 is configured such that a second respiratory support system may be used simultaneously. For example, a face mask (indicated by broken lines and the reference number 8100 in FIG. 35) may be placed over the patient's mouth, nose and the cannula 81, as described previously with reference to FIG. 3.

In the illustrated example of FIGS. 32 to 34, the pressure line 829 and valve 89 are arranged such that when the pressure in or near the nare of the patient's nose is above a predetermined value, pressure acting on the piston causes the valve 89 to move to a closed configuration or partially closed configuration to restrict the flow of gas into the nare of the patient's nose from the nasal prong 85. When the pressure in or near the nare of the patient's nose is below the predetermined value, the valve 89 will be in an open configuration to allow the flow of gas into the nare of the patient's nose from the nasal prong 85.

The flow rate could be controlled so that the system pressure does not exceed the predetermined value. The predetermined value may be:
  a default value
  A 'safe' value set by user,
  a pressure maintained by the cannula flow before an face mask is placed over the cannula, or
  related to the flow rate ie Allowable pressure=A×Flow Rate^B+C×Flow Rate^B−1 . . . , where A, B, C etc are constants.

The predetermined value may be a fixed value or an adjustable value. If the value is adjustable, it may be adjusted by either the user, controller or both With reference to FIGS. 33 and 34, the valve 89 has a housing 811, a valve member or piston 813, a compression spring 815, and a rotatable knob 817. The rotation of the knob is indicated with arrows in FIGS. 33 and 34.

The housing 811 has a flow source inlet 819, a measured pressure inlet 821 a flow source outlet 823 and an excess flow outlet 825. The flow source inlet receives a flow from the flow source (e.g. a high flow from flow generator 102 of FIG. 1) via a flow source conduit 827. The measured pressure inlet 821 receives pressure dependent on a pressure sensed at the sensing end 87 of the pressure conduit 829. The flow source outlet 823 delivers gas to the patient via a cannula conduit 831. In the illustrated embodiment, the cannula conduit 831 and measured pressure conduit 829 extend between the cannula 81 and the pressure relief device 89. In the embodiment shown, the two conduits 829, 831 are aligned together.

The spring 815 biases the valve member 813 towards the position shown in FIG. 33, and the force of the pressure in or near the nare of the patient's nose relative to the spring force controls whether the flow from the flow source is delivered to the patient or not. With reference to FIG. 33, if the pressure in or near the nare of the patient's nose is less than the opposing pressure provided by the spring 815, the valve member 813 is urged towards the open position by the spring, and flow of gas is delivered from the flow source to the patient. With reference to FIG. 34, if the pressure in or near the nare of the patient's nose is greater than the opposing pressure by the spring force 815 (and friction within the device), the valve member 813 is urged to a closed position by the flow pressure sensed by the pressure line 829, and the flow of gas is not delivered to patient. In the embodiment shown, the flow from the flow source is vented via the excess flow outlet 825.

The tension of the spring 815 may be a fixed spring tension or may be an adjustable spring tension, as shown in FIG. 33. An example of adjustable spring tension is an adjustable Positive End Expiratory Pressure (PEEP) valve. By rotating the knob 817, it is possible to control the opposing force of the spring 815, by adjusting the preload, relative to the force of the measured patient pressure. Adjustment could be achieved through other methods such as a linear actuator.

The system may operate in an on/off manner. That is, the valve 89 may have an open position in which gas flows unimpeded through the valve and a closed position in which gas is prevented from flowing through the valve. In an alternative embodiment, the system may have a valve member with one or more intermediate positions in which flow is partially restricted. The one or more intermediate positions provide variable control of the flow. There could be an audible noise generated when flow is vented to signal venting to the user eg: through a restricted orifice at the vent.

In an alternative embodiment, the system may have a valve member with one or more intermediate positions in which flow is partially vented. The one or more intermediate positions provide variable control of the flow.

In an alternative embodiment, pressure relief may also be controlled by electronic switching where an electrical signal controls a valve that controls the flow of gas to the patient.

Figure 35:
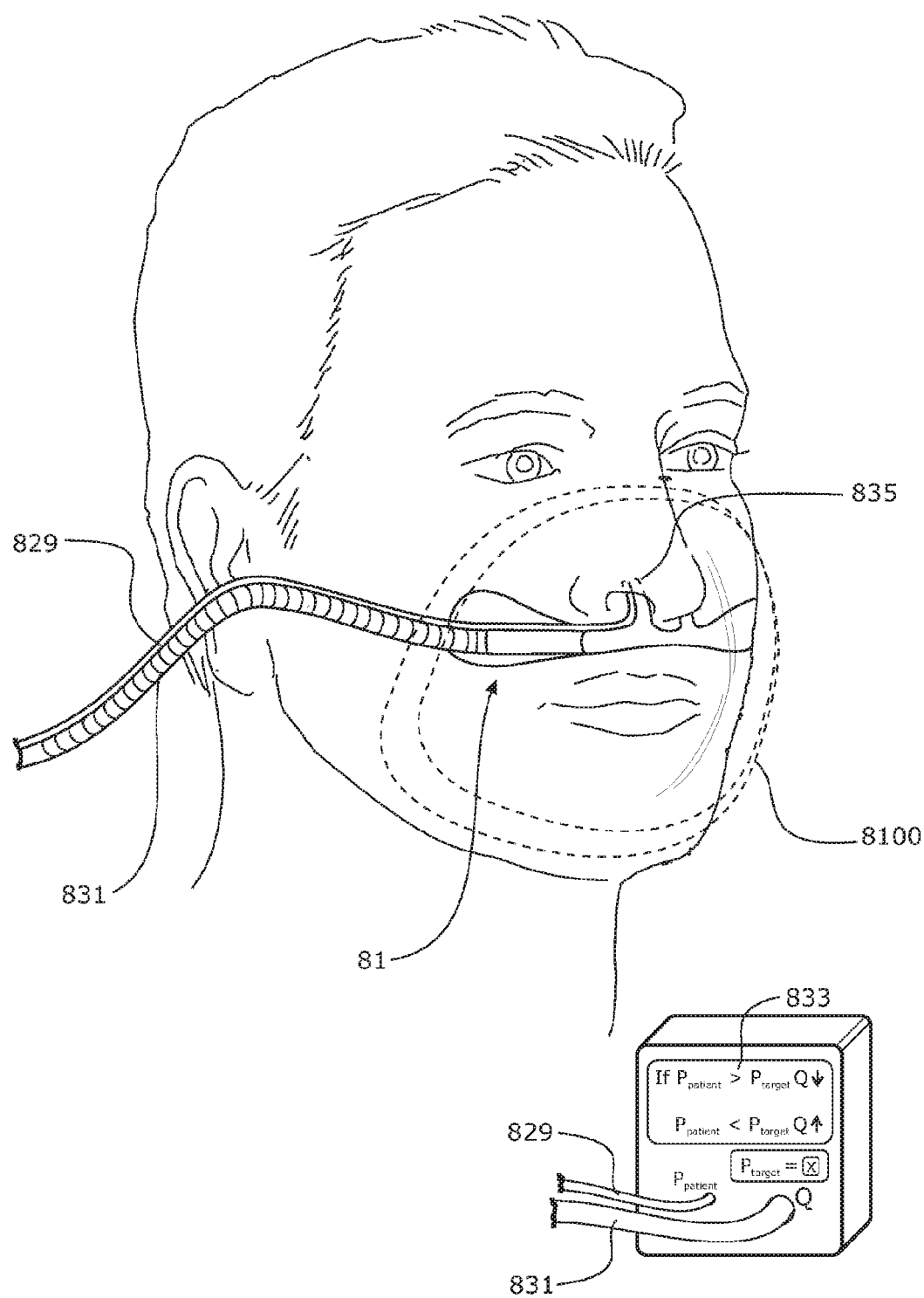
FIG. 35 is a perspective view showing a patient interface (similar to that of FIG. 2 or 3) in an operational position on a user together with a graphic user interface.

With reference to FIG. 35, pressure relief could be controlled by a processor having software. Unless described below, the features and operation of the second embodiment shown in FIG. 35 are the same as those described in relation to FIGS. 32 to 34. In this embodiment, the system further comprises at least one processor and a user interface 833. The predetermined value is set by and/or displayed to the user via the user interface 833. For example a maximum pressure (Ptarget) is set by the user. Additionally or alternatively, the system may have a default value. A typical default value may be 20-40 cm H2O, or in some configurations about 0 cm H2O.

A pressure sensor 835 detects the pressure in or near the nare of the patient's nose, or at some point in the system, and data indicating the pressure is transmitted to the controller. The data indicating the measured pressure is compared to data indicating the predetermined value by the controller, for example maximum pressure (Ptarget). The flow (Q) delivered to the patient via the nasal cannula is adjusted accordingly to ensure the Ptarget is not exceeded. In particular, the processor is adapted to control a valve (e.g. pressure relieve valve 89) or flow generator to restrict the flow of gas into the nare of the patient's nose from the nasal prong when the pressure in or near the nare of the patient's nose is above the predetermined value, and allow the flow of gas into the nare of the patient's nose from the nasal prong when the pressure in or near the nare of the patient's nose is below the predetermined value.

In an alternative embodiment, the controller may have two pressure sensors with a known obstruction in between (ie an orifice plate). The differential pressure between the two pressure sensors can be used to determine the flow rate. Using this flow rate the system can control to achieve this flow rate as long as the pressure does not exceed the allowable Pmax for the given flow rate. This could be described by a mathematical equation, a stepwise function or a lookup table in the software.

When the valve 89 is closed and the controller knows there is no flow, a calibration can occur to account for pressure sensor drift and adjust a flow sensor offset accordingly. Such a calibration routine may be carried out for any electrically controlled pressure relief device described herein. Where valve 89 is controlled by a controller the valve member 813 may not be a piston that senses the sampled system pressure. The position of the valve member is actuated by an actuator (e.g. a solenoid) controlled by the controller in response to the pressure measured by the sensor 835.

The pressure sensor 835 may be located in a variety of different positions. For example, the pressure sensor 835 may be located at or near the nasal cannula, or inside an area that may be covered by a face mask. In some configurations, the pressure sensor 835 is located at or near the at least one nasal prong 85. For example on a nasal prong, inside patient nares, as shown in FIG. 35 or on the patient interface. In some configurations, the pressure sensor is located on a conduit adapted to deliver gas to the nasal cannula. In some configurations, the pressure sensor is located at or near the flow generator or the pressure relief device. In some configurations the pressure sensor is located on the humidification chamber, a dryline (conduit from the flow generator to the humidifier) or gas tube. In some configurations the pressure sensor 835 or pressure line 829 is mounted remotely and the pressure is connected via a conduit from any of these positions.

The systems described may comprise a face mask 8100 (e.g. an anaesthetic mask) that is placed over the nasal cannula 81, the patient's nose, and/or the patient's mouth. The mask 8100 delivers gas flow or pressurised gas in addition to the flow (e.g. high flow therapy) being received by the user through the nasal cannula 81. Accordingly, the pressure delivered to the patient's airways can exceed an allowable pressure. This can occur when a sealed mask is being used. Therefore a pressure relief feature or a reduction in flow may be used to prevent the exceeding of an allowable pressure.

The pressure relief device could be a flow controller positioned within the system to limit the flow/pressure delivered to the patient. The flow controller can be operable based on the inputs from the pressure sensor or a pressure within the system provided/sensed via the pressure sampling line. In some configurations, the flow controller controls the flow of the high flow therapy device. Alternatively, the flow controller controls a second gas source or flow generator. For example, the flow controller can control the flow of gas for the face mask. In a further alternative, the flow controller controls the flow of gas for the high flow therapy device and the second gas source or flow generator.

The mask flow source (not shown) may be controlled by its own adjustable pressure relief valve (not shown). An independent pressure relief on the cannula that can be set by the user means the user has more control over the pressure delivery from each flow source.

The specific pressure relief device embodiments described herein aim to limit the amount of pressure delivered to the patient. In particular, the specific embodiments described can be used in situations involving multiple respiratory support systems being used simultaneously, such as a nasal cannula and an anaesthetic mask.

The specific embodiments described herein may also be used without other respiratory support systems, that is, the nasal cannula may be the only respiratory support systems used on a patient. The embodiments described could limit the amount of delivered pressure from a high flow source.

A method of providing respiratory support to a patient will now be described. The nasal cannula 81 is placed upon a face of a patient in an operational position, as shown in FIG. 35. A flow of gas is directed into a nare of the patient's nose via the nasal prongs 85. The pressure is measured or sensed at some point in the system, for example by a sensor in or near the nare of the patient's nose or by a valve member of the pressure relief valve (for example via pressure line 829). If the pressure is above a predetermined value, the flow of gas into the nare of the patient's nose from the nasal prong is restricted. The flow rate may be reduced, or may be prevented from flowing.

The flow may be restricted when a change (increase) in pressure is sensed. Alternatively, the flow may be restricted when the measured pressure exceeds zero if a sensor is positioned on the outside of cannula such that it is covered by a face mask 8100 when the mask is placed on the patient but is not inside the patient's nares. Alternatively, the flow may be restricted when the pressure exceeds a predetermined threshold pressure determined for a certain flow rate if sensor/pressure line is used to sense pressure inside the system, wherein the system pressure may be influenced by application of the mask over the cannula, the mask causing a back pressure in the system. In the last two alternatives described, it is assumed a mask 8100 has been applied.

If the pressure is below the predetermined value, the flow of gas into the nare of the patient's nose from the nasal prong is allowed.

Controlling/restricting the flow of gas into the nare of the patient's nose will result in an excess/undesired flow of gas from the gas source. That excess/undesired flow of gas could be dealt with in a variety of ways. For example, it may be vented outside the mask/nasal cannula area. Alternatively, the excess/undesired high flow gas could be redirected back at the flow source. In other embodiments, the excess/undesired high flow gas may not require venting if the flow source can be shutoff by blocking the flow or in the case of a source from a flow generator such as a blower the source could be turned off. In an alternative embodiment, the total flow to the patient may be controlled/restricted by the pressure relief device. A sensor may measure the flow, and venting occurs dependent on a flow limit.

Figure 36:
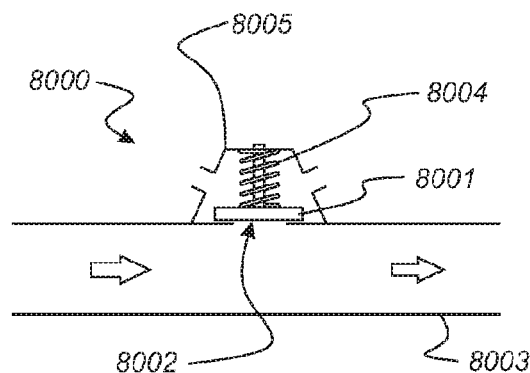
FIG. 36 shows an embodiment of a pressure relief device in a closed configuration.
Figure 37:
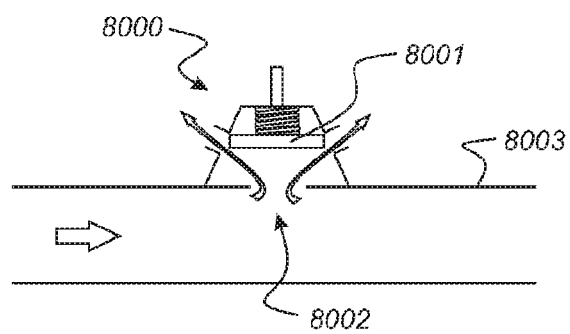
FIG. 37 shows the same device in a venting or open configuration.

FIG. 36 shows another embodiment of a pressure relief device 8000 in a closed state. FIG. 37 shows the same pressure relief device 8000 in an open state. The device comprises a valve member 8001. The valve member 8001 seals over an aperture 8002 in a side wall of the conduit 8003. When a pressure in the breathing conduit 8003 exceeds a predetermined pressure, the valve member 8001 moves away from the aperture 8002 to allow venting via the aperture 8002 as shown in FIG. 37. The pressure relieve device 8000 may also comprise a biasing member 8004 (for example a spring) to bias the valve member 8001 to the closed position sealing the aperture 8002. When the pressure in the breathing conduit exceeds the predetermined pressure, the valve member 8001 moves away from the aperture 8002 against the biasing member 8004. The pressure relieve device 8000 preferably comprises a cap or housing 8005, to house the valve member 8001 on an outer side of the conduit 8003. The cap or housing 8005 may help the valve from becoming inadvertently blocked.

Figure 38A:
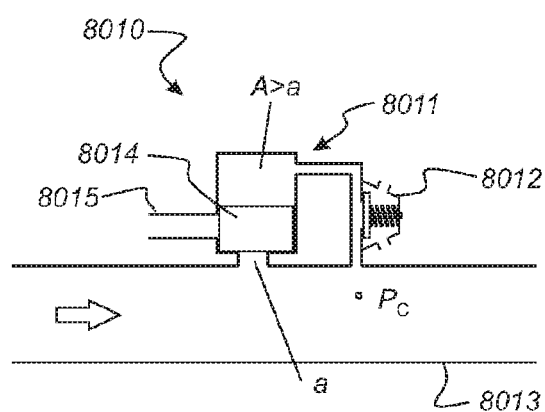
FIG. 38A shows an embodiment of a pressure relief device in a closed configuration.
Figure 38B:
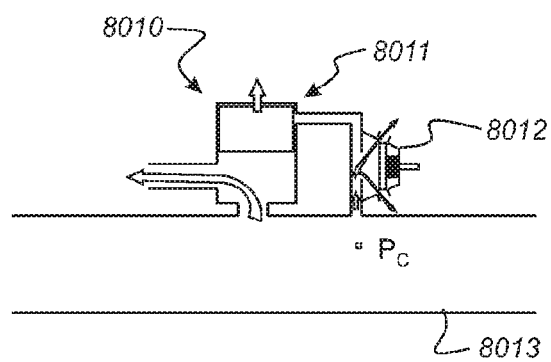
FIG. 38B shows the same device in a venting or open configuration.

FIGS. 38A and 38B show a pressure relief device 8010 that comprises a main valve 8011 and a pilot valve 8012 to control operation of the main valve 8011. When the pressure in the conduit 8013 (Pc) is less than a predetermined value the pilot valve 8012 is shut. With the pilot valve 8012 shut, Pc is applied to both sides of a piston 8014 of the main valve 8011. The piston 8014 has a first side having a first area (A) and a second side having a second area (a) that is smaller than the first area (A). The pressure Pc acts directly on the first side of the position 8014, and the pressure PC acts on the second side of the piston 8014 via the pilot valve 8012 when the pilot valve 8012 is shut. The larger area of the first side of the piston 8014 results in a greater force applied to that side of the piston 8014 holds the piston 8014 in a closed position. When the pressure Pc is greater than a predetermined value the pilot valve 8012 is opened, venting flow from the conduit 8013 as shown in FIG. 38B. This causes the pressure on the second side of the piston 8014 to be less than the pressure on the first side of the piston 8014, in which case the piston moves from the closed position to an open position. This allows gas from the conduit 8013 to vent via the main exhaust port 8015 of the main valve 8011 of the pressure relief device 8010.

Figure 39:
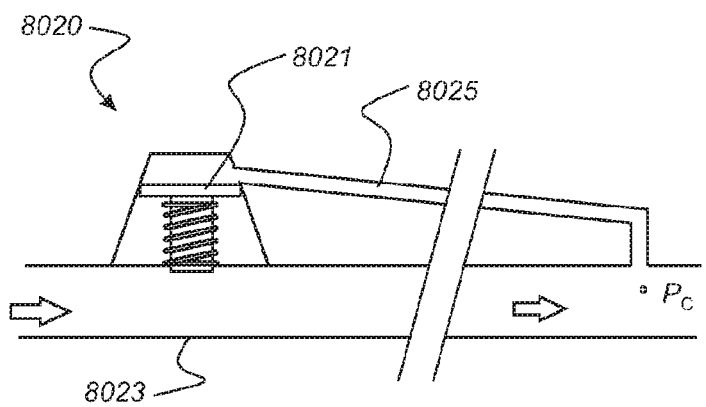
FIG. 39 shows an embodiment of a valve for closing a conduit, the valve shown in an open configuration.
Figure 40:
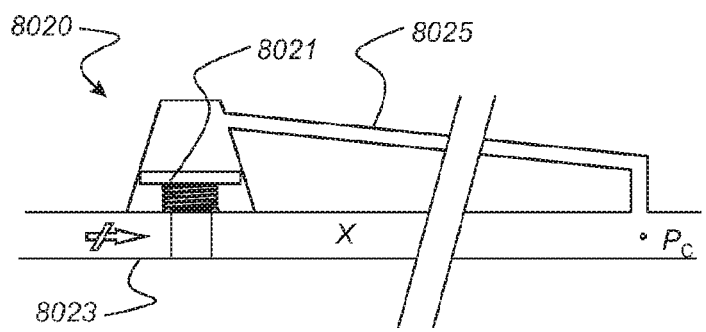
FIG. 40 shows the same valve in a closed position.

FIG. 39 shows a valve 8020 which shuts off flow if the pressure, Pc, is above a predetermined value. The pressure may be local to the valve 8020 or may be sensed by the valve 8020 at another location within the system via a pressure line 8025, or like pressure line 829 described with reference to FIG. 32. When a force provided by the pressure is below the spring reaction force the plug 8021 sits in a retracted position and gas may flow down the conduit. FIG. 40 shows the plug 8021 extended and blocking the conduit 8023. This occurs when the force provided by the pressure, Pc is above the spring reaction force. The plug 8021 prevents flow through the system, until the pressure reduces, in which case the plug 8021 retracts and gas begins flowing again. When the flow is blocked it may be vented further upstream by any one of the pressure relief devices described herein, or a controller may stop the flow.

Figure 41A:
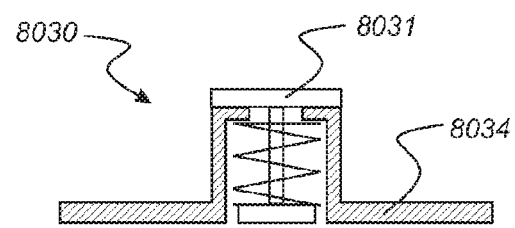
FIGS. 41A and 41B show an embodiment of a pressure relief valve.
Figure 41B:
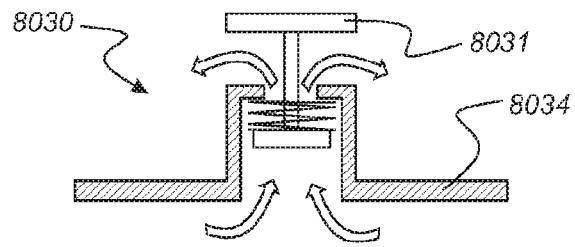

FIGS. 41A and 41B show another embodiment of a pressure relief valve 8030. FIG. 41A shows the device in its closed state. FIG. 41B shows the same device in its open state. When the pressure in the breathing conduit 8034 exceeds a predetermined pressure, the plunger 8031 moves upwards against the reaction force provided by the spring and provides a path for the gas traveling down the breathing conduit 8034 to vent.

In any embodiment the spring may not necessarily take the form of a coil spring as illustrated. Instead the spring may be but is not limited to a leaf spring, a diaphragm spring, or a compliant material.

Any of the above described pressure relief devices may be located anywhere in the system, between the flow source and the cannula. Preferably the pressure relief device is located downstream of a humidification chamber so that the humidifier controller does not need to deal with large changes of flow within the humidification chamber. Examples of suitable locations of a pressure relief device include, a filter, at the humidification chamber outlet, in a circuit connector, or as an attachment to the flow source. The pressure relief device may be in the cannula, or may be near the cannula. In some embodiments it may be preferable to have a pressure relief device at or near to the patient interface. Having the pressure relief device at or near to the patient interface has the benefit that the pressure delivered to a patient may be more accurately estimated, than a system having a pressure relief device further upstream and within the system.

In some embodiments, venting the conduit via the pressure relieve device before applying the mask over a collapsible portion of the conduit may make the conduit easier to collapse when applying the mask.

A pressurised conduit providing a flow of gases to a patient may comprises a level of hysteresis. The hysteresis in the conduit may cause a pressure relief device to open at a higher pressure than the pressure at which the pressure relief device closes. This feature would prevent or at least substantially inhibit the pressure relief device from moving in a constant fluctuation between open and closed configurations.

As described earlier, for example as described with reference to FIG. 3, a respiratory system may be provided that allows for the delivery of gas from multiple sources via at least two different respiratory support modes, and further allows a doctor, clinician or medical professional to quickly and easily change the type of respiratory support mode. A further summary of various system functionalities and embodiments is provided below, and benefits of such embodiments are outlined.

The following embodiments may be used in the respiratory therapy system described above or in any other suitable respiratory therapy system, to allow operation of high flow while easily allowing switching between respiratory support modes and/or other functionality or benefits. The embodiments may be configured to deliver gas to a patient at a high flow rate as described herein.

Functionality 1—Switching Between Therapy Modes

The following switching configurations allow operation of high flow via a first patient interface, with the ability to do one or more of the following:
- deliver accurate concentrations of volatile agent through an anaesthetic machine, using the minimum amount of agent possible, using a second patient interface
- deliver manual breaths to a patient via a bag when required via a second patient interface
- quickly and easily switch between respiratory supports, provided by a first patient interface and a second patient interface.
- check airway patency with bag and mask (a second patient interface)
- Enables clinician to take back control of manual ventilation using the bag when desired.

Currently there is no easy way to integrate the use of high flow into anesthetic practise. Although it may be possible to run high flow off a totally separate system/flow source, it would be desirable to have a configuration that allows easy interchange between respiratory support via high flow, and respiratory support via the anaesthetic machine. It would also be desirable to allow high flow to be quickly and easily turned off or reduced.

In current practice users may run high flow off a separate flow meter attached to a wall gas supply. There is no integration with the anaesthesia machine and no specialised design around the use of high flow in anaesthetic practice.

In some embodiments, a switching configuration (Switching Configuration 1) comprises a user interface device to enable a user to control gas flow in a respiratory therapy system for delivering high flow gas to a patient, the user interface device comprising:
  at least one user actuable controller or device for controlling the flow rate and/or concentration of at least one gas through a patient interface, and for substantially blocking or reducing the flow rate or turning off the flow of the at least one gas through the patient interface.

The gases may be a high flow gas. Another of said gases may be an anaesthetic gas or a supplementary gas or any other suitable gas.

The patient interface may be a nasal cannula. The user actuated controller may comprise a switch. In some embodiments the switch is positioned on the patient interface. Alternatively the patient interface may be another unsealed patient interface. In further alternative configurations combinations of multiple patient interfaces can be used for example an unsealed interface in combination with a sealed interface, or two sealed interfaces.

Figure 42A:
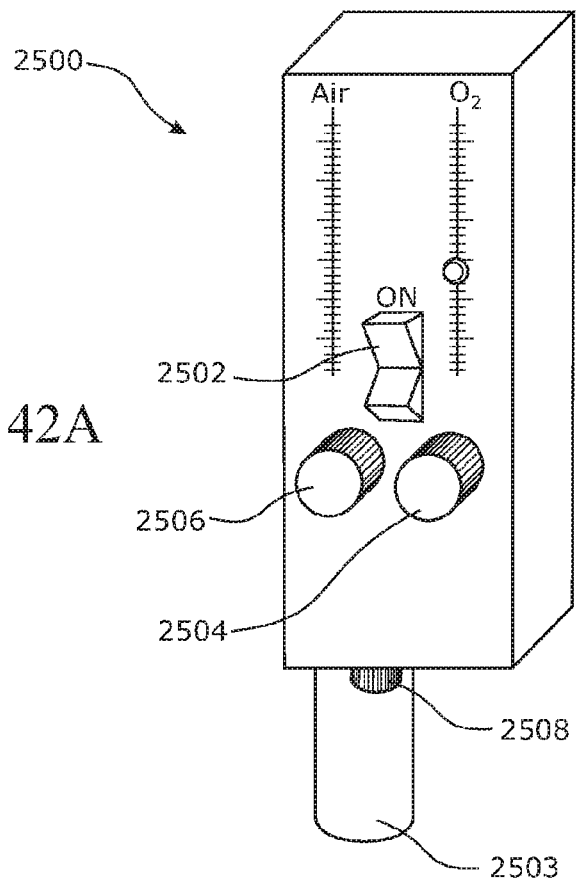
FIG. 42A shows a user interface device for use in a respiratory therapy system, for example the system shown in FIGS. 1 to 3.

In some configurations, the user interface device is a separate device remote from the patient interface. This configuration is shown in FIG. 42A. Gas flow rate is preset by the user, via the user interface device 2500. Before putting the patient interfaces (for example 200, 300 of FIG. 3) on a patient, the user sets a desired oxygen and/or air flow rate using a first user actuable controller, which may be coupled to a rotameter (eg: set to 40 LPM or 70 LPM). A second user actuable controller comprises a user actuable switch 2502 which controls a valve to the flow source(s) 2102. The switch is shown as a toggle switch, but may be in any suitable form. In a preferred embodiment the switch comprises two states and could be a 'one touch' switch, or other on/off button or lever. The switch provides a fast way to turn the flow on/off, or to rapidly increase the flow rate to the preset value, rather than a prior art approach of winding a flow up or down which can be time consuming.

Turning on the switch 2502 opens the valve allowing gas (preferably oxygen) to be delivered to patient at the preset flow rate, via the cannula 2200 for example. The user interface device 2500 has a gas connection 2503 for fluid connection to the patient interface that will be used to deliver the gas to a patient. Turning off the switch 2502 closes the valve to block flow to the patient, or at least reduces the flow rate to the patient. In one alternative, the flow to only one patient interface (e.g. a high flow interface) may be blocked or reduced. In another alternative, flow to more than one patient interface may be blocked or reduced. The valve may be turned off when the user decides to start providing a patient's respiratory support from an anaesthetic machine. The user actuable controllers 2504, 2506 enable the user to blend gases, e.g. air and oxygen, and/or to enable the flows of the two gases to be set independently. Alternatively there may be provided only one type of gas, e.g.: oxygen. The user interface device may comprise more user actuable controllers to enable three or more gases to be blended in desired ratios.

Alternatively, the functionality of two or more of user actuated controllers 2502, 2504, 2506 could be combined.

For example, a single user interface such as a touch screen may be provided to enable a user to blend the gases and block or reduce flow to the patient.

The on/off switch 2502 may also control power to the humidity generator 2104. For example, if humidity is generated via electrical energy in a tube, an electrical connection 2508 may be used to power the tube. When the switch 2502 is turned off this may also cut power to the electrical connection and thereby to the tube. In this way the humidity and flow may be turned on/off simultaneously.

Instead of completely 'off', the flow could instead be reduced, to say 5 LPM, when the switch is switched to 'off' mode. This may be beneficial as a minimum 'back-up' flow. For example, if the clinician forgets to turn the high flow back on immediately after extubating the patient, a low flow rate will at least provide some oxygenation of the patient. The minimum flow may be preset at a value that is likely to meet a patient's inspiratory demand (eg: 30 LPM). Maximum flow may be 70 LPM or greater, for example 100 LPM or 150 LPM. There may be multiple pre-set values, e.g. more than 2 preset values, for example 0, 30 and 70 lpm. These could be actuated with a switch or mechanism with 3 or more positions that correspond to the different preset values.

Figure 43A:
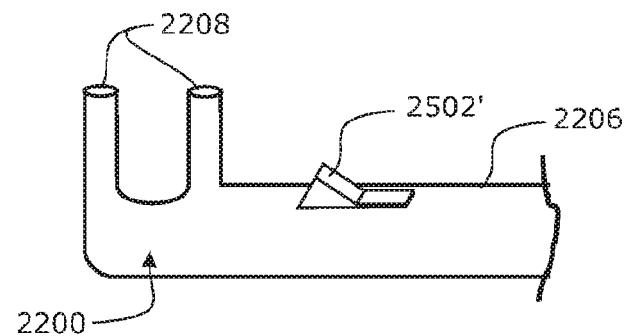
FIGS. 43A-43C show an alternative switch configuration for a user interface device.
Figure 43B:
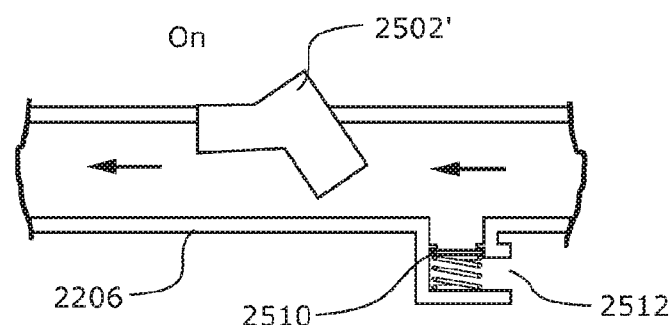
Figure 43C:
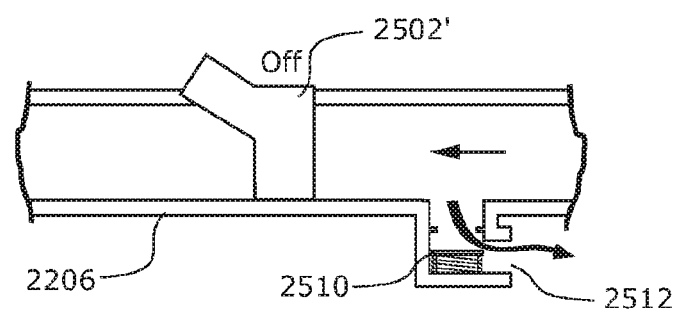

Alternatively, the switch 2502' could be on the cannula 2200 for ease of access, as shown in FIGS. 43A-43C. In this case the switch 2502' could be a mechanism that either allows the flow to pass through to the interface when in an on/open configuration (FIG. 43B) or blocks the flow to the cannula when in an off/closed configuration (FIG. 43C). In other words, the switch 2502' is a valve; the terms switch and valve may be used interchangeably to refer to a valve, unless the context suggests otherwise. Various valve arrangements have been described above, for example with reference to FIGS. 21A to 22B. When blocked, the delivered flow may vent via a pressure relief valve 2510 along the gas conduit 2510 as shown in FIG. 43C or vent back at the gas supply, or the valve may have a venting arrangement.

This configuration may be provided as a mechanical-type switch or valve 2502' that when activated allows for the restriction, occlusion or complete obstruction (i.e. closure or blockage) of the flow path through the gas conduit or a gas flow through a patient interface, such as a nasal cannula.

Activation of the switch 2502' can be manually performed by a user, or alternatively the switch may be activated by placement of the second patient interface onto the switch (i.e. as a patient interface, such as a mask, is placed onto a patient, or when the patient interface being placed onto the patient comes into contact with the switch 2502' which may be provided as part of a first patient interface, such as a nasal cannula or a conduit, as described earlier with reference to FIGS. 21A to 22B).

The switch 2502' may partially or completely block off the gas flow path to partially or wholly prevent the flow of gas through the conduit or a gas flow path through the patient interface (such as a nasal cannula). As such, the flow of gas to the terminal end of the conduit or outlet of the first patient interface can be stopped. The switch 2502' may be provided as a part or component of a conduit, or a patient interface.

In some configurations, the conduit or the patient interface comprising the switch may include a vent or pressure relief device to relieve pressure build-up due to activation of the switch and the flow of gas to the outlet from the conduit or to the outlet or outlets of the patient interface being partially or completely stopped or prevented.

In some configurations, when activated, the switch is partially blocking of the gas flow path through the conduit or the patient interface or may be completely blocking of the flow path. The switch may be located or positioned at various useful locations, for example at a foot pedal for operation by a user's foot, or a remote switch which can be attached to a bed, anaesthesia face mask, pole, anaesthetist's clothing etc.

The switch 2502' may be particularly provided for use in conjunction with a self-supporting tube (i.e. the tube is not a self-collapsing or a collapsible tube).

Alternatively, the configuration of a switch 2502' may be used in conjunction with a collapsing tube 2202 (FIG. 42B, or in accordance with any other collapsing conduit embodiment described herein) to supply high flow gas to the cannula. The tube is configured to collapse and allow the mask to seal over the tube. In one example, the tube can be collapsed by adding a mask on the tube, as described earlier. Alternatively, the tube can be collapsed by any suitable mechanism, for example a physical structure, or by varying or controlling the flow and/or pressure delivered via the tube. In such an embodiment, the collapsed tube may not completely occlude the tube, the switch or valve 2502' occluding the tube.

Advantages of Switching Configuration 1 in combination with a collapsible tube include one or more of:

- Does not require removal of cannula—allows mask to seal on face over cannula for bagging patient.
- Flow is already stopped so inhibiting flow through cannula is not reliant on pressure of mask seal against a collapsible tube. Also mask does not have to push against force of gas flow built up in tube.
- Clinician can use existing bag/mask consumables.
- High flow may be stopped or reduced by switch at the gas supply source (rather than vented) which will help to conserve oxygen supplies In one embodiment, at least one section of the cannula tube 2202 is only patent (open and unobstructed) when gas flow is delivered. If the high flow gas source (for example source 124 of FIG. 1) is turned off, or the flow significantly reduced, the tube will be easier to collapse. High flow may be turned off/reduced because the user wants to use mask ventilation. In some embodiments, having the tube collapse may allow the mask to seal more effectively on the face.

Figure 42B:
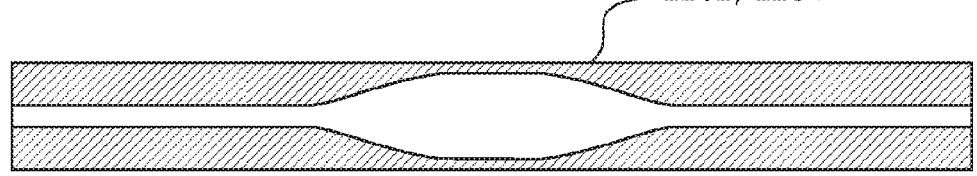
FIG. 42B shows a portion of a collapsible tube for delivering high flow gas to a patient interface, for example a cannula.

The wall thickness of the tube 2202 could be reduced at the collapsible portion shown in FIG. 42B and described earlier to reduce structural rigidity and allow collapse, or other features may be utilised to allow for the tube or lumen to be reduced, closed or blocked.

In some embodiments, a switching configuration (Switching configuration 2) comprises a respiratory therapy system comprising:

a cannula for delivering a high flow gas to a patient;
a mask for delivering a gas to the patient;
and a pressure sensor associated with the cannula;
wherein the system is configured to adjust flow of the high flow gas through the cannula in response to at least one type of pressure change sensed by the sensor.

The pressure sensor may be provided on an external surface of the cannula or on an external surface of a tube in fluid communication with the cannula.

The system may be configured to reduce or substantially stop flow of the high flow gas when the pressure sensor detects a pressure increase. The pressure sensor may be configured to detect a pressure increase in response to the mask being placed on the patient, the patient exhaling, or actuation of an anaesthetic bag.

The system may further comprise a valve to partially or substantially block flow of the high flow rate gas through the cannula in response to the detected pressure increase.

Figure 44A:
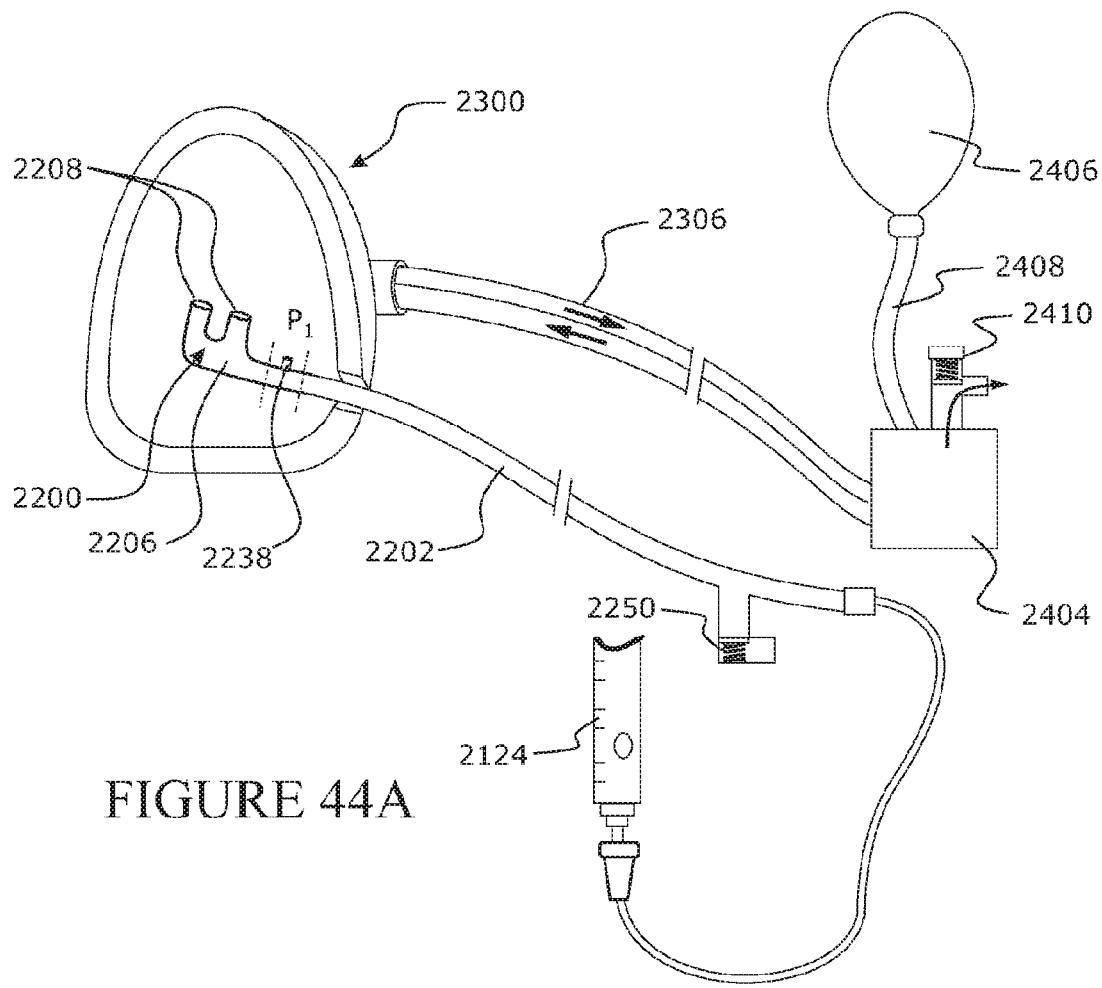
FIG. 44A shows a pressure-actuated changeover configuration for use in the respiratory therapy system.

As shown in FIG. 44A, high flow gas is supplied through the cannula 2200 from an auxiliary gas supply; e.g. via a flowmeter 2124. Ventilation to the mask 2300 is supplied by an anaesthetic machine 2404 and bag 2406 via suitable lumens or tubes 2306. A pressure sensor 2238 is provided on an external surface of tube 2200/cannula 2200 interface to measure a pressure P1 of the system. During high flow delivery, the pressure sensor 2238 will normally read P1=0, where P1=0 is ambient pressure. When a mask 2300 is applied over top of the cannula 2200 (such as when the clinician wants to bag-mask ventilate the patient) the pressure P1 will increase slightly, above ambient pressure. This pressure change may be pneumatically or electrically communicated back to the high flow gas source. High flow is then adjusted by the processor, for example turned off or reduced, in response.

Figure 44B:
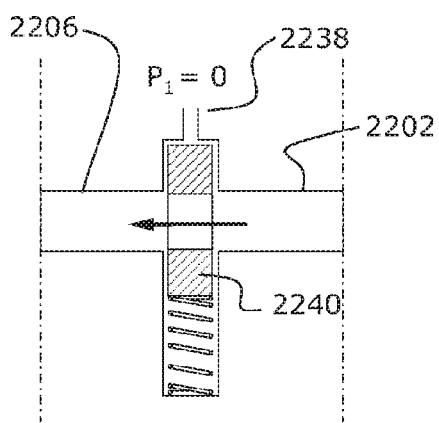
FIG. 44B shows a valve of the pressure-actuated changeover configuration in an open position.
Figure 44C:
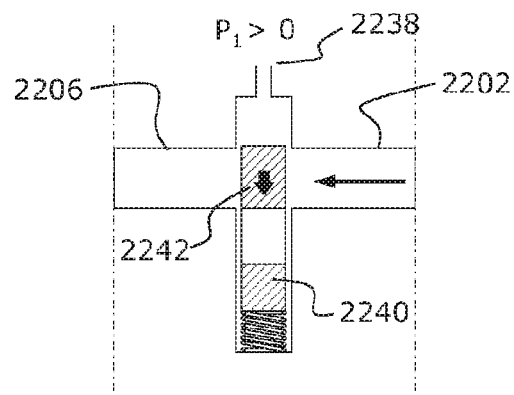
FIG. 44C shows the valve of the pressure-actuated changeover configuration in a closed position.

If the pressure is pneumatically communicated, the pressure change may activate a valve 2240, blocking the flow source as shown in FIG. 44C. When the P1=0 the valve 2240 is open as shown in FIG. 44B, allowing high flow gas to the cannula 2200. When the pressure P1 is increased >0 this depresses a plunger 2242 in the flow path, blocking or partially blocking the high flow gas. Blocking the flow may open a vent 2250 in the high flow gas conduit 2202 to allow the excess flow to escape, or may turn off the flow source providing the flow of gas. The pressure P1 will be further elevated when the bag 2406 is squeezed and additional flow is forced into the mask 2300, and also during exhalation, where the bag is not squeezed but the patient's expired breath will be captured in the mask.

Figure 44D:
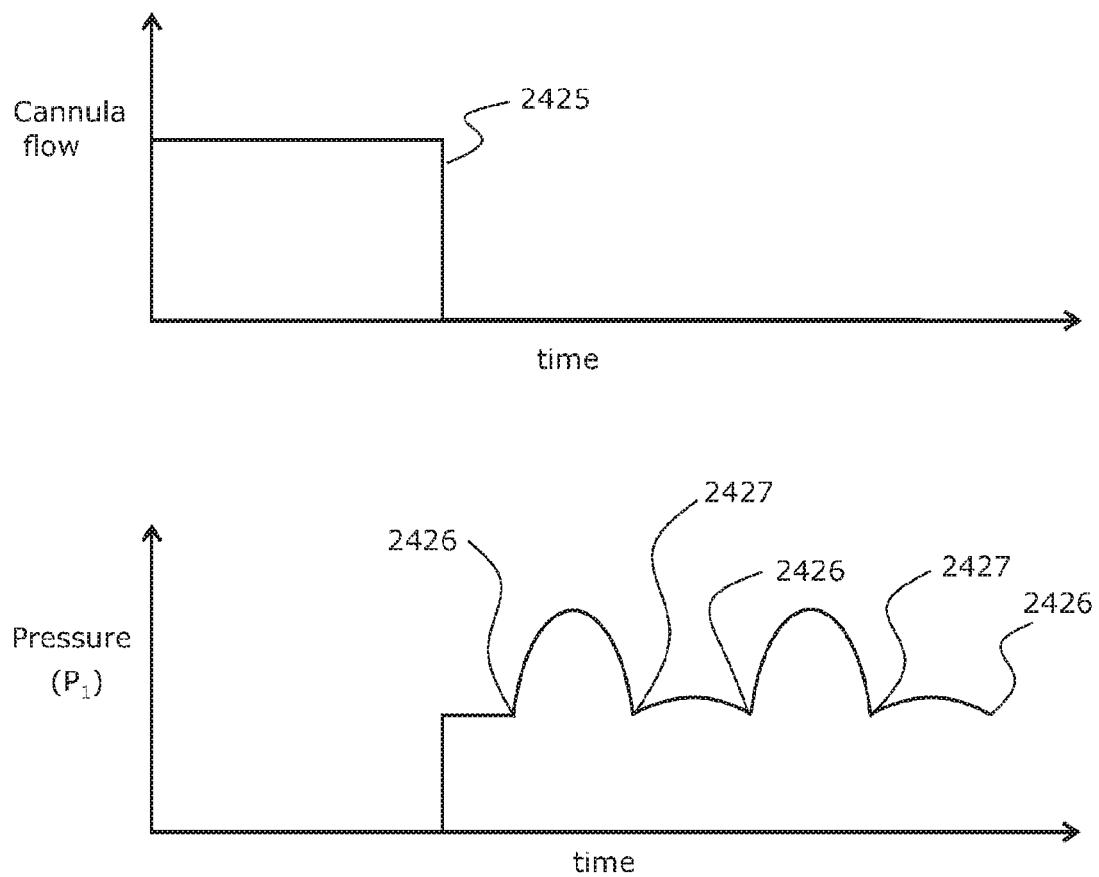
FIG. 44D shows an exemplary plot of cannula flow and pressure versus time during use of the pressure-actuated changeover configuration.

FIG. 44D shows a potential flow pattern resulting from the configuration of 44A. High flow/cannula flow 2426 is initially delivered, and pressure at P1=0. The mask 2300 is applied ('mask on'), pressure at P1 increases and the cannula 2200 flow is stopped (at 2425 in FIG. 44D). The user starts squeezing the anaesthetic bag 2406 (at 2426 in FIG. 44D) causing a further increase in P1 during inspiration. If the pressure increase in the mask 2300 exceeds the APL (adjustable pressure limiting) valve setting this may cause an APL valve on an anaesthetic machine 2410 to vent and a plateau in pressure. When the user stops squeezing the bag 2406, P1 firstly increases as the patient begins to passively expire (at 2427 in FIG. 44D and then reduces as the patient reaches the end of expiration.

Alternatively, high/cannula flow may be reduced at 'mask on' and this reduction may vary depending on the pressure measured at P1. For example, a higher pressure measured at P1 may result in a large reduction in the delivered flow whereas a lower pressure measured at P1 may result in a small reduction in the delivered flow.

If the pressure change is instead electrically communicated back to the high flow gas supply 2102 this may block or reduce the flow rate by actuating a valve, flow restrictor or opening a vent that enables the flow to divert though an orifice of comparatively low resistance. Alternatively the pressure may be communicated pneumatically, e.g. via a pressure line terminating at pressure sensor 2238, but the actuation of flow reduction/blocking is performed in software by the controller 2108 or another processor.

To ensure only partial flow restriction of the high flow gas, the spring force in the flow restrictor valve 2240 may be designed to not compress when subjected up to 40 cmH$_2$O pressure. It is likely that the APL valve will be set at less than 40 cmH$_2$O. Thus, the APL valve 2410 will vent any additional pressure measured in the mask 2300 above 40 cmH$_2$O and the spring will never be subjected to >40 cmH$_2$O. This ensures the high flow gas supply valve stays open, always permitting some high flow through to the patient. Alternatively a relatively light spring may be used in the valve 2240 such that only a small pressure is required to fully block the high flow gas (eg: 1-2 cmH$_2$O which may be applied only by the action of having the mask 2300 over top of the cannula).

Advantages of Switching Configuration 2 include one or more of:

Clinician can use existing bag/mask consumables.
Does not require removal of cannula—allows mask to seal on face over cannula for bagging patient.
High flow is automatically stopped by the system—does not require user to manually turn high flow on/off.
High flow may be stopped or reduced by the system (rather than vented), which will help to conserve oxygen supplies.
Allows user to set a 'minimum' level of high flow delivery or pressure at all times.
Mask does not have to completely seal conduit to cannula to block/reduce high flow. May be easier than fully collapsing tube.
If high flow is blocked completely, mask flow does not have to overcome the back pressure from the high flow gas source.
Pressure measurement can be quite sensitive—not reliant on user creating good seal with mask In some embodiments, a switching configuration (Switching configuration 3) comprises a respiratory therapy system comprising:

a cannula circuit for delivering a high flow gas to a patient through a cannula;
a bag circuit to enable a user to manually deliver gas to a patient by actuating a bag;
and a connector that connects the bag circuit to the cannula circuit, the connector comprising a separation to substantially prevent high flow gas from travelling into the bag circuit.

The connector may be configured to enable both high flow gas and gas from the bag circuit to be delivered to a patient through the cannula. Alternatively, the connector may be configured to substantially prevent delivery of high flow gas to the cannula when the bag circuit is connected to the cannula circuit.

The separation may comprise one or more walls or valves in the connector.

The cannula may be a nasal cannula with at least one prong for receipt in a patient's nares, the cannula comprising inflatable cuff(s) associated with the prong(s) to assist with creating a seal in the patient's naris or nares.

The system may be configured to inflate the cuff(s) in response to actuation of the bag.

This configuration additionally or alternatively comprises a nasal cannula for delivering gas to a patient, the cannula comprising at least one prong for receipt in a patient's naris, the cannula comprising inflatable cuff(s) associated with the prong(s) to assist with creating a seal in the patient's naris or nares.

Figure 45A:
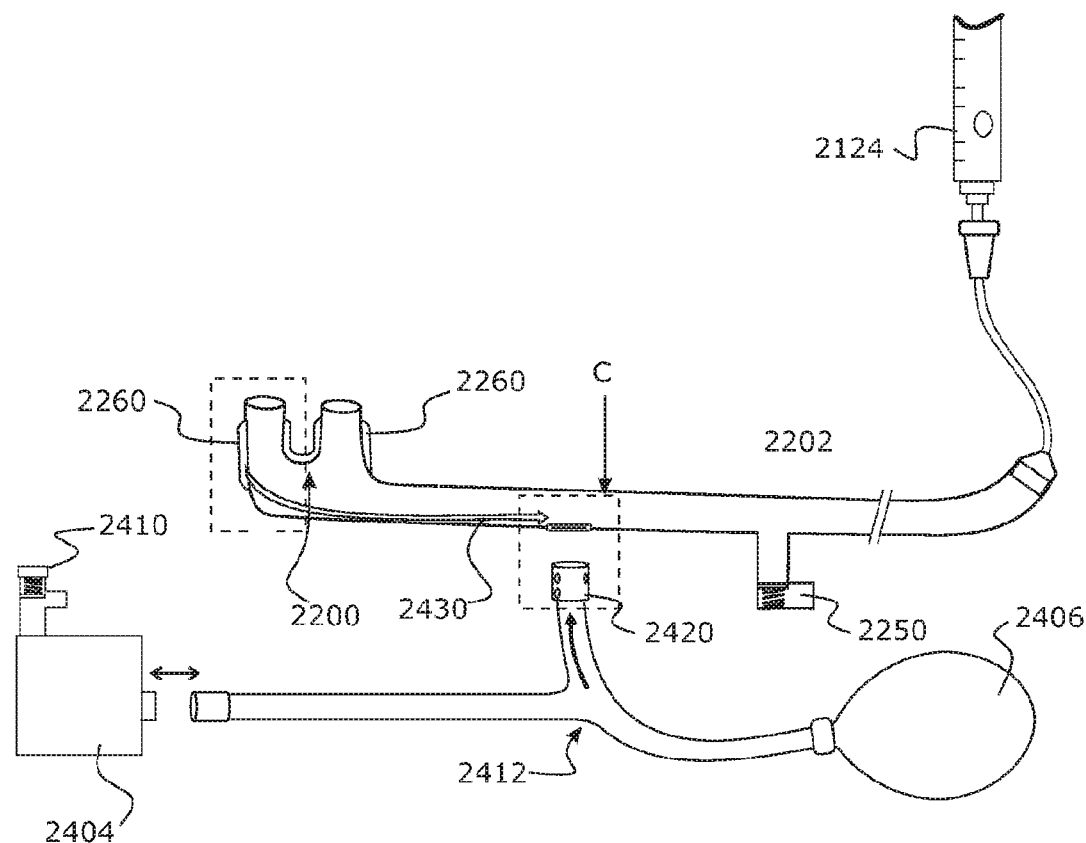
FIG. 45A shows a connection-actuated changeover configuration for use in the respiratory therapy system.

See FIG. 45A. High flow is delivered from auxiliary gas supply/flow meter 2124, through a cannula circuit comprising a cannula 2200, for example during a pre-oxygenation phase. When the user wants to manually deliver gas to a patient, i.e. provide manual breaths to patient, (eg: if the patient has become apnoeic and the user wants to keep the patient's lungs recruited), the bag circuit 2412 is attached into the high flow gas supply tube of the cannula circuit (at coupling region C). The high flow gas supply tube has a valve to prevent leakage when the bag circuit is not attached.

The bag circuit 2412 comprises a connector 2420 (shown in FIGS. 45C-i and 45C-ii). The upstream side has a restricted opening 2422 that limits the amount of high flow gas that can pass through the connector along the tube 2202 to the patient (any excess gas may be vented further upstream via vent 2250). The connector 2422 has a valve 2424 to separate the high flow gas HFG from the gas coming from the bag BF. This allows gas delivery to the patient to be from the high flow gas (HFG) or the bag flow source (BF) and stops the high flow gas HFG travelling back against the bag flow BF and inflating the bag 2406. This means the clinician has control over the bag inflation with only the fresh gas supply from the anaesthetic machine 2404.

The user may wish to have complete control over the patient's inspiratory gas flow, via the bag 2406, and only allow high flow delivery during expiration. When gas is delivered from the bag 2406 when it is squeezed, the elevated pressure, caused by the forced gas flow from the bag, may shut a valve in the high flow gas supply tube, completely blocking, or restricting, the high flow gas during inspiration. This valve may be allowed to open when no bag flow exists, allowing high flow gas to be delivered on expiration.

Referring now to FIG. 45A when the bag 2406 is inflated by fresh gas from the anaesthetic machine 2404, then actuated by squeezing the bag, the bag gas BF will flow up through the connector 2420 and out to the patient. Squeezing the bag 2406 causes the valve to block, or at least reduce, the high flow gas and prevent HFG from being delivered to the patient. The HFG may be vented further upstream. The valve is designed so as to require a low force from the BF flow pressure to overcome the HFG pressure. Eg: in FIGS. 45C-i and 45C-ii there is a large surface area that the BF flow acts on, and the direction of blocking the HFG flow is perpendicular (rather than in line with) the HFG flow. This means the valve does not have to close against an opposing HFG flow. The valve could be simply held open (in the down position as illustrated) by its own weight or could also have a spring above to increase the level of force required to close. Squeezing the bag 2406 may also deliver a sidestream of gas (SG) to inflatable cuffs 2260 on the cannula prongs 2208 (the cuffs may be in fluid communication to inflate together), via a conduit 2430 as shown in FIG. 45A. The gas SG to the prongs inflates the cuffs 2260 on the prongs creating a seal in the nares. As clinicians want to have control over the patient's breath, a seal is required to achieve this effectively (normal practice uses a sealing mask).

When the bag 2406 is released the valve is opened and HFG can flow to the patient (see FIG. 45C-i). Flow is no longer supplied to the cuffs 2260, and the cuffs deflate. That releases the interface seal and the patient is able to passively expire, with gas flow exhaling around the prongs 2208. Releasing the seal is important if a minimal level of high flow gas is being still delivered continuously (through the restricted orifice). If the seal is not released, continuous gas delivery could cause hyper-inflation of the patient. Also, releasing the interface seal means that the additional high flow gas will not be forced back down the prongs during expiration, which may inflate the bag more than the clinician was expecting. In this way the prongs are always inflated when flow from the bag is delivered and always deflated when the bag is not squeezed and high flow is delivered.

The cuffs 2260 could be designed to inflate at a very low pressure, so would remain inflated throughout the whole inspiration even when bag flow BF is low at either end of the inspiratory phase, or may inflate at a higher level. This second case could produce increasing levels of inflation as the bag 2406 is squeezed harder/more flow is supplied. This may help the clinician modulate the pressure delivered to the patient, as greater inflation causes more seal and thus greater pressure delivery.

Figure 45B:
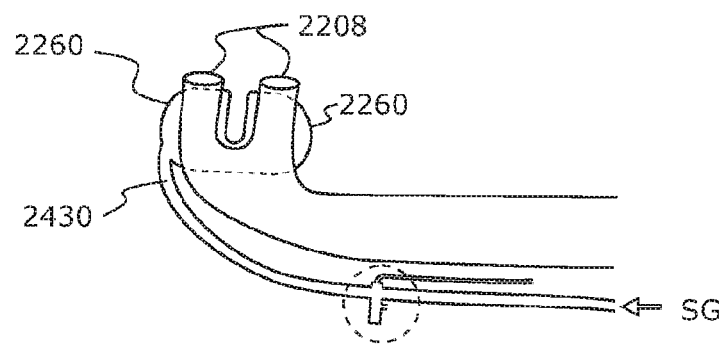
FIG. 45B shows a portion of the connection-actuated changeover configuration of FIG. 45A.

Alternatively, the conduit 2430 to the cuffs 2260 could be fitted with a non-return valve to maintain constant inflation throughout the use of the bag and prevent deflation unless high flow is initiated. For example, with reference to FIGS. 45B, 45B-i and 45B-i, when the bag is squeezed and SG flows, a non-return valve 2261 (shown as ball check valve) is open allowing the cuffs 2260 to inflate. A pressure tap (line) 2501 which measures the pressure in the HFG stream ($P_{HFG}$) could be used to block or unblock the flow of SG to the cuffs via valve 2340. When there is no HFG delivery PHFG is approximately 0. This allows SG to flow to the cuffs (FIG. 45B-i) through valve 2340. When the bag stops being squeezed, the check valve 261 closes, preventing the prongs deflating back into the bag. Stopping the flow from the bag opens the valve 2240 shown in FIG. 45C to allow HFG to flow. The HFG flow causes PHFG to increase, and via the pressure line 2501 the valve 2340 is operated to unblock a vent device 2262 and allowing the cuffs to deflate via this vent, as shown in FIG. 45B-ii.

FIG. 45D-i shows the flow patterns. Prong (cannula) 2200 flow is delivered to the patient. Initially high flow is delivered. Then the connector 2420 is inserted, and the bag 2406 is squeezed creating positive bag flow, and reducing the high flow. The prong flow is the total flow delivered to the patient as a combination of the high flow and bag flow. The prongs inflate until fully inflated then remain at a constant level of inflation (deflation prevented by the non-return valve). When bag flow is stopped high flow delivery increases again. The prongs deflate when the bag flow is stopped and high flow is delivered.

As an addition, an inflatable mouth insert could be coupled to the nasal prongs 2208. This could be useful for mouth breathers, to prevent loss of pressure during respiratory support if they have their mouth open.

Having a minimal high flow gas supply maintained even when bagging the patient ensures delivery of PEEP (positive end-expiratory pressure). In this way it can be ensured that the patient always receives some level of positive pressure which can help to prevent atelectasis. FIG. 45D-ii shows the waveforms for when at least a low level of HFG is maintained at all times (valve in FIG. 45C only partially blocks HFG).

Figure 45E:
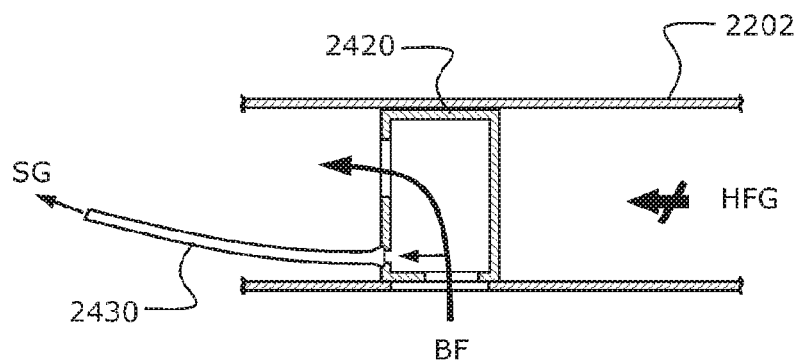

If the user wants to administer volatile agents to the patient, delivery of high flow will affect the concentration, diluting it and requiring additional agent to be added to get the correct concentration. This can be costly. In an alternative embodiment the high flow gas supply may be completely blocked when the bag circuit connector 2420 is inserted. In this case there would be no orifice on the right hand side of the connector as shown in FIG. 45E. This would mean that when connected, ventilation is only supplied from the bag 2406 controlled by the clinician. This may be more intuitive for the clinician, who would know that when the bag is connected that is the sole source of ventilation, and no high flow will be provided.

If the prongs 2208 are not sealed throughout the whole breath cycle, volatile agent may still be lost to the atmosphere, which may be undesirable. When a mask is used in prior art systems, the volatiles can be recycled through the closed (sealed) system.

FIGS. 45B-iii and 45B-iv shows a possible embodiment where the cuff gas supply contains a non-return valve 2261 that is not opened by the high flow starting. Here, once gas flows into the cuffs 2260 it cannot escape again. This maintains the cuff inflation after the bag 2406 has been first squeezed. This is safe when high flow is blocked, i.e. when the connector 2420 embodiment in FIG. 45E is used, as the patient can expire back into the bag 2406/anesthetic machine 2404. The clinician can control this and there is limited risk of hyper-inflation. Returning expired gas back to the machine 2404 helps save agents, saving money, and preventing drugs being administered into the room which may be dangerous for attending caregivers. With a non-return valve 2261, the cuffs 2260 will remain inflated unless actively deflated, e.g. via a user actuable release valve 2262 shown on the left hand side of the non-return valve 2261. This could be actuated by a user pressing on a portion of the valve 2262 to vent the pressure inflating the cuffs. Alternatively, this release valve 2262 could be connected to the bag tube connector 2420 so that the valve is released when the bag tube is disconnected from the system. Maintaining the cuff seal also means the clinician has complete control of the patient's breath over the whole cycle.

Figure 45F:
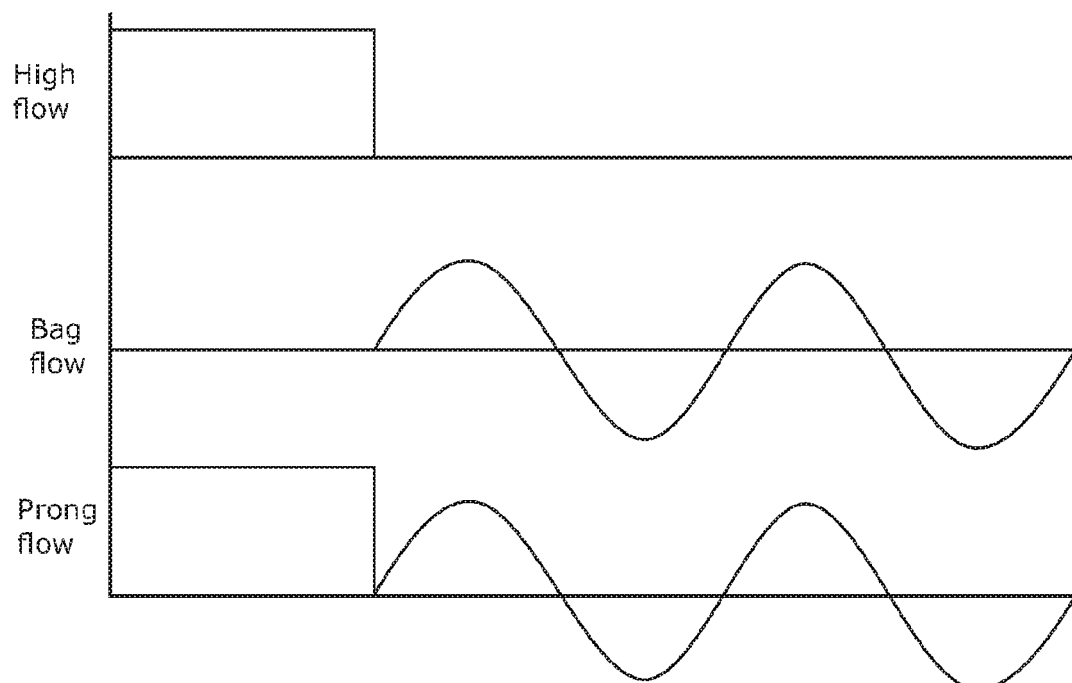

FIG. 45F shows the flow patterns for this. High flow falls to zero once the connection 2420 is inserted and the HFG is blocked. Prong flow is what is ultimately delivered to the patient.

An APL valve can still be set by the user to control the pressure relief when the bag 2406 is connected. If the prongs are inflated/sealing, excess pressure delivery will be vented via the APL. If the prongs are deflated because the bag 2406 is not connected there is limited risk of barotrauma. If the prongs are deflated when the bag is connected but during a non-sealing expiration, minimal pressure will be communicated to the anaesthetic machine, but as the prongs are deflated there is again limited risk of barotrauma.

Advantages of Switching Configuration 3 include one or more of:
No mask—only cannula interface:
Do not have to change interface on patient
Do not have difficulty of getting good mask seal
Cannula more comfortable—Increased patient tolerance
High flow is automatically vented by system when bag in use—does not require user to manually turn high flow on/off
Prongs can be held sealed throughout whole breath cycle when bag is used. Volatile agents will be returned to the anaesthetic machine, saving agents and preventing them from escaping into the room
Improves visibility, access to patient's airway and user does not have to hold mask on patient In some embodiments, a switching configuration (Switching configuration 4) comprises a respiratory therapy system comprising:
a cannula circuit for delivering a high flow gas to a patient through a cannula;
a bag circuit to enable a user to manually deliver gas to a patient by actuating a bag, the bag circuit in fluid communication with the cannula circuit; and
a valve arranged to allow the delivery of high flow gas to the cannula when the bag is not actuated, and to allow the delivery of gas from the bag circuit to the cannula when the bag is actuated.

This configuration additionally or alternatively comprises a nasal cannula for delivering gas to a patient, the cannula comprising at least one prong for receipt in a patient's naris, the cannula comprising inflatable cuff(s) associated with the prong(s) to assist with creating a seal in the patient's naris or nares.

Figure 46A:
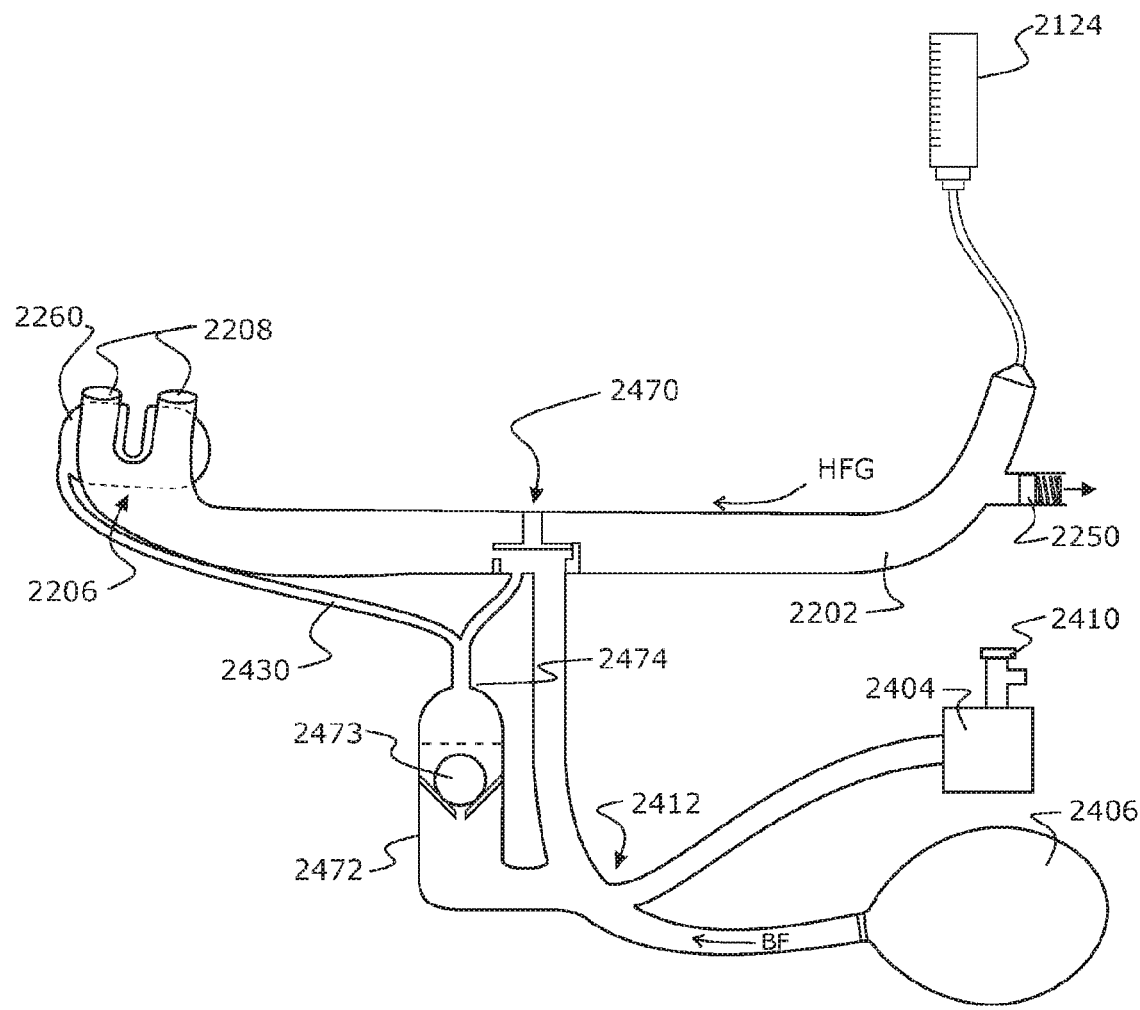
FIG. 46A shows a bag-actuated changeover configuration for use in the respiratory therapy system.

See FIG. 46A. The bag circuit 2412 comprising the bag 2406 is permanently connected into the high flow cannula circuit 2202. A valve system 2470 controls whether flow is delivered from high flow source 2124 or bag 2406/anaesthetic machine 2404. Change between supports is actuated by flow from the bag 2406 when it is actuated by squeezing. The bag acts as the master controller. If the bag is actuated, bag ventilation is the primary respiratory support. If the bag is left unused, high flow will be delivered to the cannula 2200. Much of the above description in the previous configuration also applies to this configuration.

Figure 46B:
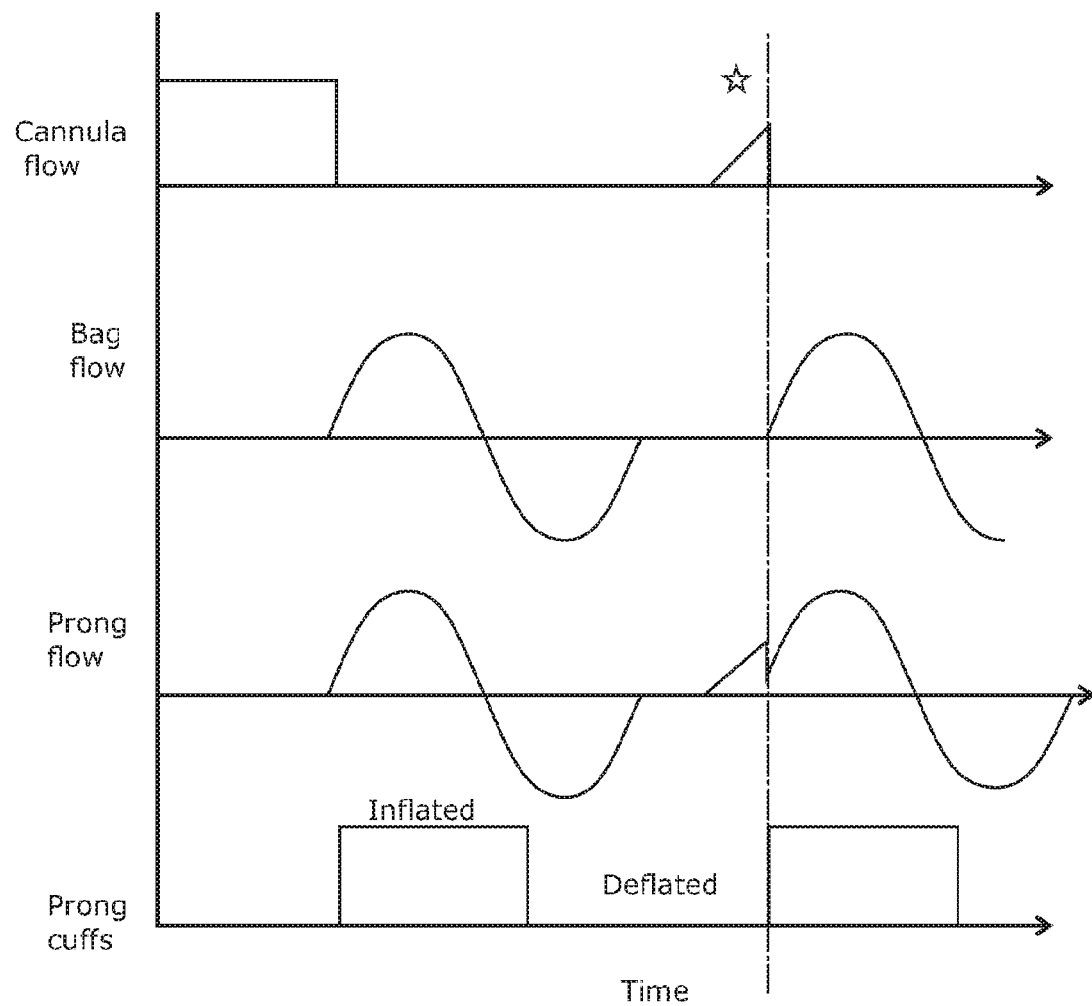
FIG. 46B shows an exemplary plot of high flow, bag flow, cannula flow, and prong cuff status versus time during use of the bag-actuated changeover configuration.

Referring to FIG. 46B, high flow is normally delivered to a patient (when the bag 406 is not squeezed). When bag is squeezed this closes a valve 2470, which may be of the type shown in FIG. 45C-i or 45C-ii. This blocks, or at least reduces, the high flow gas supply to the patient. This allows gas to be delivered to the patient from the bag only 2406 (bag gas may also inflate prong cuffs as above). Squeezing the bag also delivers gas to a gas reservoir 2472 shown below the valve in FIG. 46A.

The reservoir 2472 has a non-return valve 2473 so that it is filled from the bottom by the bag flow BF but flow can only exit from the top orifice 2474. The reservoir may be a rigid or alternatively an expandable material that increases to accommodate more air when BF flows. The orifice has a restricted opening to control the rate of gas leak. When the bag 2406 is released/not squeezed, no more flow is delivered from the bag, and the patient will be able to passively expire. During this time, the flow reservoir 2472 will begin to discharge and the flow from the reservoir 2472 will continue to hold closed the valve 2470 blocking the high flow gas source. The orifice 2474 may be sized so that when the reservoir 2472 is full, it takes approximately the time for one exhalation to empty (eg: 3 seconds). Thus the valve 2470 will be held closed throughout expiration as well. Alternatively a valve 2470 may be energised by a controller to hold the valve for a period, for example exhalation time. The reservoir 2472 may also be connected to the prong cuffs 2260, to provide flow to the cuffs during expiration as well and hold them inflated throughout the whole breath cycle. This means patient expiratory flow will be back into the tube to the bag/anaesthetic machine.

If the bag 2402 is not squeezed after this time, this would indicate the clinician has finished bagging the patient. The reservoir 2472 will empty, allowing the high flow gas valve 2470 to open and the prong cuffs to deflate and high flow gas will then begin to flow again (see ★ on FIG. 46B). If bagging is recommenced the high flow will again be blocked.

This system blocks high flow during the whole breath when the patient is being bagged, and also maintains the interface seal. Therefore the clinician has control over the gas delivered to the patient during this time, and also enables accurate control of volatile agent delivery. If the prongs are held sealed throughout expiration, all expiratory flow will be returned to the anaesthetic machine. This means volatile agents will be returned to the anaesthetic machine, saving agents and preventing them from escaping into the room.

Again, the APL valve 2410 can still be set by the user to control the master pressure relief when the bag 2406 is used. If the bag is not being used the prongs will be deflated so there is limited risk of barotrauma.

Advantages of Switching Configuration 4 include:
Integrated design—faster, no user input to change between systems (doesn't require insertion of tube).
Automatic switching between therapies when bag squeezed.
High flow is automatically vented by system when bag in use
does not require user to manually turn high flow on/off
Prongs can be held sealed throughout whole breath cycle when bag is used.
Volatile agents will be returned to the anaesthetic machine, saving agents and preventing them from escaping into the room.
Prong cuffs automatically released at end of expiration No mask—only cannula interface.

Advantages of one or more of the switching configurations include one or more of:
allow high flow to be easily turned on/off
when turned on, flow rate immediately increases to a preset value, preventing delays in therapy (for example in emergency)
a switch mechanism allows a rapid drop in high flow flow/pressure when closed.
turning flow and humidity off when not required, saves gas and power
allow cannula/interface to be left in place
only partially blocking the high flow gas supply means that a minimum flow rate may still be delivered to the patient. This may be useful to ensure PEEP (positive end-expiratory pressure) is provided right to the end-of expiration. The current manual bag-mask ventilation strategy from an anaesthetic machine does not provide PEEP at the very endpoint.
easy switching between respiratory systems (high flow and bag-mask ventilation)
allow user to have control over ventilation and drug delivery with a sealed interface as they are accustomed to in current practice
sealing of interface controlled to allow expiration when high flow delivered
No mask—only cannula interface:
Simpler/easier, do not have to change interface on patient
Do not have difficulty of getting good mask seal
cannula more comfortable than mask—increased patient tolerance.

Functionality 2—Conscious/Apnoeic Therapy Setting
clinicians have to manually change respiratory support settings as patient's condition changes.
existing interfaces do not allow use throughout intubation so typically no support is given during apnoeic period during intubation attempts
minimal ventilation support may be given post-extubation.

Current respiratory support systems do not automatically change the type of support when spontaneous breathing or apnoea is detected. This is because the clinician usually changes or removes the interface at this point anyway.

It would be desirable to provide different therapy settings during patient consciousness, and then once patient becomes apnoeic.

A respiratory therapy system that is suitable for conscious/apnoeic therapy setting, comprises:
a patient interface for delivering gas to a patient; and
a processor configured to control flow of gas through the patient interface to deliver gas to a patient at a first flow rate and/or pressure when the patient is spontaneously breathing, and configured to deliver gas to a patient at a second flow rate and/or pressure when the patient is not spontaneously breathing.

The system may be configured to detect the presence of apnoea and configured to deliver gas at the second flow rate and/or pressure in response to the detection of apnoea. The system may be configured to detect the presence of apnoea based on the reduction of activation of brain signals, diaphragm signal, airway pressure, or $CO_2$ measurements.

The first flow rate and/or pressure may comprise a relatively low flow rate and/or pressure, and the second flow rate and/or pressure may comprise a relatively high flow rate and/or pressure.

The processor may be the controller 108 or may be any other suitable type of processor. The processor may be a remote processor.

Figure 65A:
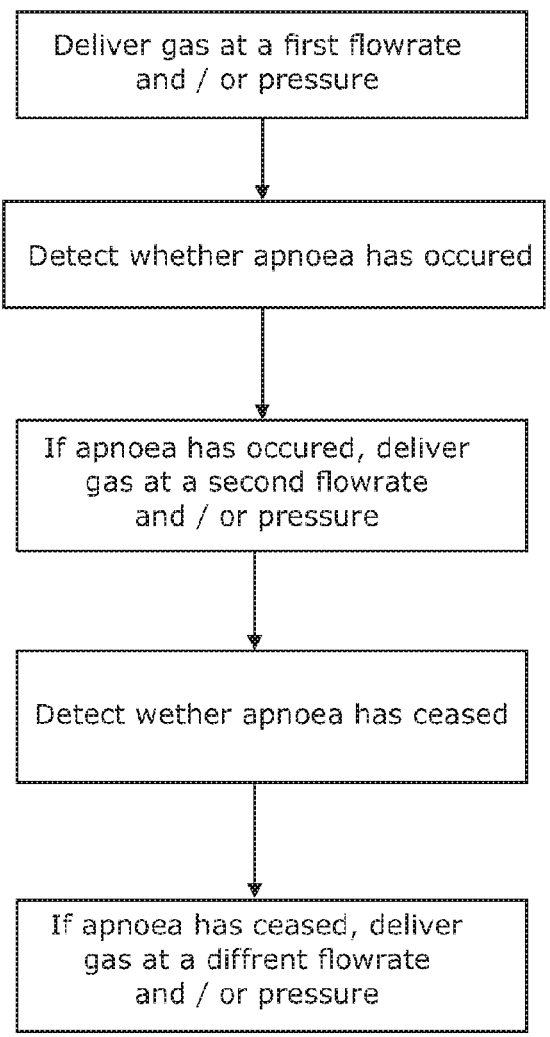
FIG. 65a shows a flow chart of exemplary steps that may be performed by a conscious/apnoeic therapy setting configuration and method in the respiratory therapy system.

FIG. 65*a* shows example steps that may be performed using the method and system of this configuration.

Figure 65B:
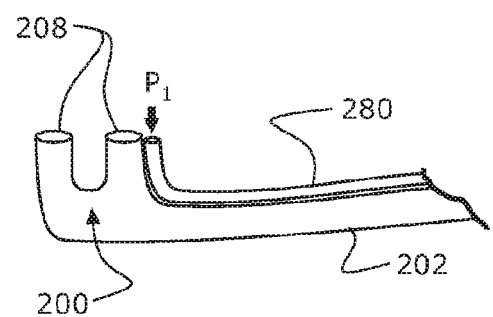
FIG. 65b shows the incorporation of a pressure sampling line into a cannula for use in the conscious/apnoeic therapy setting configuration and method.
Figure 65C:
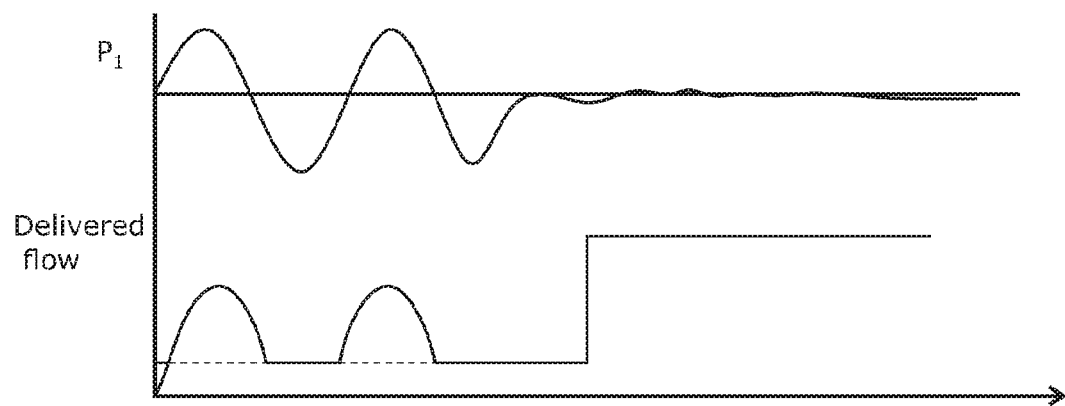
FIG. 65c shows an exemplary plot of pressure and gas flow versus time for the conscious/apnoeic therapy configuration and method.

This method and configuration may have one or more of the following features:
The therapy could be changed between a low flow/low pressure setting when patient is awake and high flow/pressure when patient is asleep. For example deliver 30-40 LPM when spontaneously breathing (or a flow likely to meet inspiratory demand), increased to 70 LPM for apnoeic oxygenation.
Presence of apnoea could be based on the reduction of activation of brain signals (EEG), diaphragm signal (EMG), airway pressure or $CO_2$ measurements:
EEG: The medulla oblongata of the brainstem contains an inspiratory center composed of neurons that send signals to the diaphragm and external intercostal muscles. EEG sensors on the scalp may monitor activity of the medulla oblongata to detect when inspiratory signals are being sent, or cease to be sent. Alternatively frequency analysis could be used to detect changes in certain EEG frequencies. For example delta waves have 0.5-4 Hz frequency band with 20-400 ρV amplitudes and are encountered in the situations of very low activity of brain, such as during general anesthesia. An increase in the amplitude or presence of the delta frequency band may indicate anaesthesia has taken effect and hence when apnoea has commenced.
EMG: Respiratory muscle EMG signal. (eg: via Edi probe down airway, or EMG sensors placed on diaphragm or intercostal muscles). Spontaneous inspiration generates a positive electrical signal as the respiratory muscles move to create a negative lung pressure for inspiration. Regular EMG fluctuations may indicate breathing. Reduction of EMG fluctuation may indicate when anaesthesia has taken effect and apnoea has commenced.
Airway Pressure measurements: for example through the patient interface 200. FIG. 65*b* shows one example of how a pressure line 280 may be incorporated on a cannula 200. Regular pressure fluctuations indicate breathing. FIG. 65*c* shows a possible flow pattern. The delivered flow during spontaneous breathing may fluctuate to meet the patient's inspiratory demand and just deliver a base level flow during expiration to provide PEEP, or other desired flow characteristics, or may deliver a constant flow during spontaneous breathing, for example, 30 L/min. As anaesthesia takes effect a reduction in fluctuations indicates apnoea. At this point the flow is increased.

CO₂ measurement: eg: via end-tidal monitoring. Similar to airway pressure method, fluctuations indicate breathing, relative stability in the recording indicates apnoea.

There may be a suitable 'wait period' or delay (eg: 5 seconds) after reduction of breathing is detected before the therapy changes as shown in FIG. 65*c*.

Alternatively for patients that are at risk of aspiration the therapy may instead reduce the delivered pressure at onset of apnoea to mitigate the risk of regurgitation (eg: during rapid sequence induction). In this case at apnoea the flow may be reduced or left at a low level and the oxygen concentration maximised instead.

Similarly when the return of spontaneous breathing is detected at the end of anaesthesia there may also be a change in therapy, such as an increase or reduction of flow rate or pressure for example. Once apnoea has ceased and spontaneous breathing is detected, the flow rate and/or pressure may be adjusted back to the first flow rate and/or pressure, or to a different flow rate and/or pressure that differs from that during apnoea, for example to take into account the following:

- it is known that in many patients, respiratory function post-operatively can be challenging. For example, obese patients can exhibit a rapid deterioration of gas exchange following extubation for the same reasons apparent in the pre-operative period. Reduction of aerated lung volume due to atelectasis, narrowing of small airways and difficulty in mobilizing airway secretions may lead to the so-called postoperative pulmonary restrictive syndrome, resulting in hypoxaemia.

Further, after a period of mechanical ventilation the threshold at which the PaCO₂ stimulates the return of spontaneous ventilation is increased, thus delaying the return of spontaneous ventilation. Also, the ventilatory response to acidosis is blunted, reducing a patient's ability to compensate. Anaesthetic drugs also reduce the normal protective response to hypoxia, even at low volatile drug concentrations. So as low concentrations of volatile drug may last several hours into the postoperative period a patient may continue to be at risk of hypoxemia.

Once the return of spontaneous breathing has been established, delivering a high flow rate and/or oxygen concentration post-anaesthesia may help to reduce the inspiratory work of breathing, increase arterial oxygenation and compensate for a reduced respiratory drive that may persist post-anaesthesia. See FIG. 65*d*.

Figure 65D:
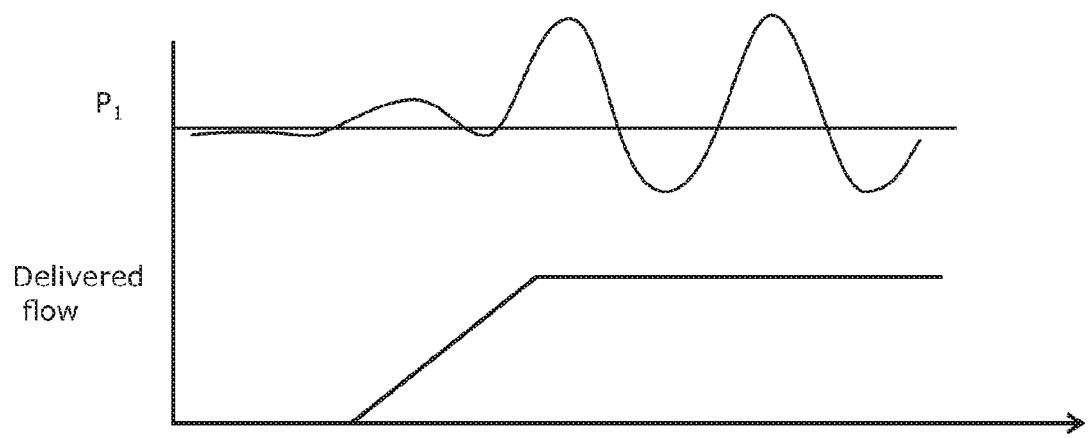
FIG. 65d shows an exemplary plot of pressure and gas flow versus time post-anaesthesia for the conscious/apnoeic therapy configuration and method.

Any changes in flow/pressure may follow a ramp increase, rather than a step-wise increase, as shown in FIG. 65*d*.

Advantages of the conscious/apnoeic therapy setting functionality include one or more of:

Improved patient comfort during consciousness, improves patient tolerance and therefore improves therapy efficacy as therapy is able to be delivered continuously. Additional pressure support is likely not required, as the patient's respiratory drive will be functioning normally Additional therapy support provided once patient is unconscious, useful as patient's respiratory drive is weakened during apnoea. Also helps to increase oxygenation prior to intubation attempts.

Increased oxygenation at apnoea is commenced automatically, as soon as possible, rather than waiting for user to initiate. Maximises period of oxygenation before intubation Functionality 3—Compensation for Effect of Suction Clinicians often suction inside the patient's airway immediately prior to intubation to remove secretions, to improve view and reduce the risk of aspiration. If the patient has just undergone a period of pre-oxygenation this suctioning can act to remove the oxygenated gas from the patient's airway, reducing their oxygen reserves. Current respiratory support systems do not automatically compensate for the effect of suctioning.

A respiratory therapy system that is suitable for compensating for the effect of suction, comprises:

a patient interface for delivering gas to a patient;

a sensor arranged to sense fluctuations in pressure in the patient interface or in a conduit in fluid communication with the patient interface; and a processor configured to adjust flow of gas to the patient interface to deliver gas at an increased flow rate to the patient interface if a reduction in airway pressure is sensed.

The processor may be configured to adjust flow of gas to the patient interface to deliver gas at an increased flow rate to the patient interface if the reduction in airway pressure is determined to be occurring during and/or after apnoea, or at any other time where the patient's breath pattern is deemed not to be a natural breath pattern.

The processor may be the controller 108 or may be any other suitable type of processor. The processor may be a remote processor.

Figure 66A:
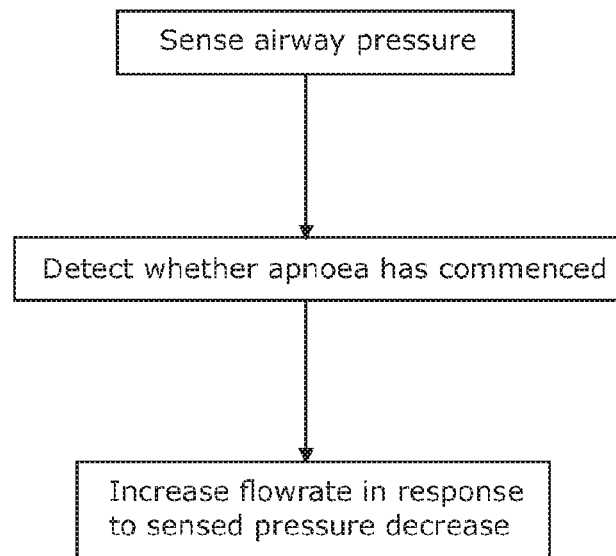
FIG. 66a shows a flow chart of exemplary steps that may be performed by a suction compensation configuration and method in the respiratory therapy system.

FIG. 66*a* shows example steps that may be performed using the method and system of this configuration.

Figure 66B:
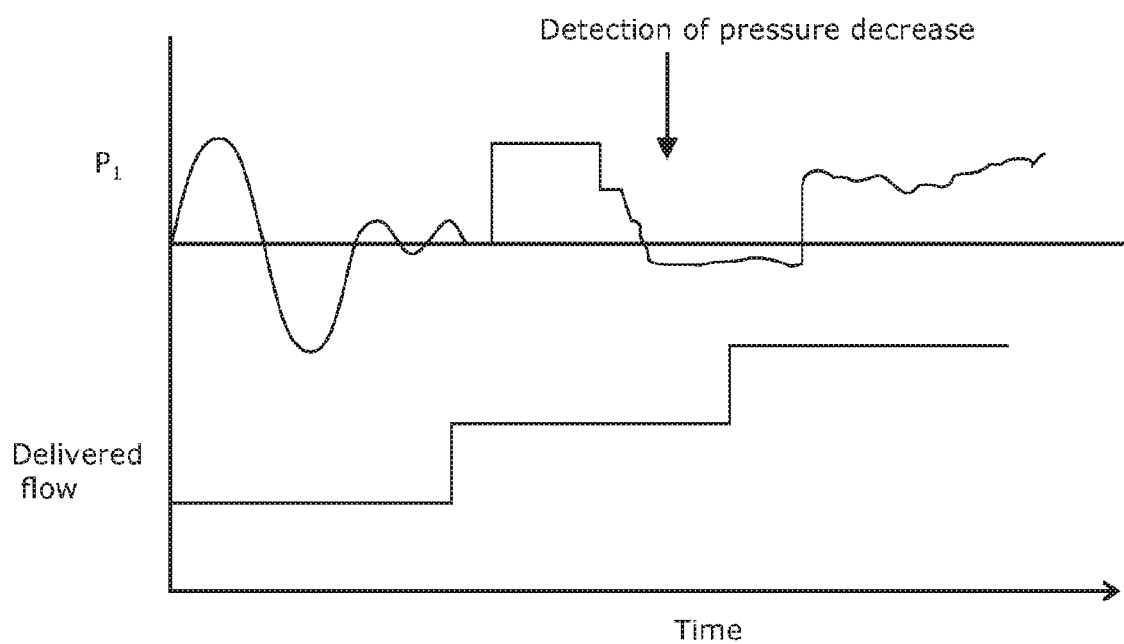
FIG. 66b shows an exemplary plot of pressure and gas flow versus time for the suction compensation configuration and method.

This method and configuration may have one or more of the following features:

A patient interface such as a cannula 200 has a pressure sensor 280 thereon, the pressure sensor arranged to sense or detect fluctuations in airway pressure in the patient interface or in a conduit in fluid communication with the patient interface. The pressure sensor 280 could instead be positioned on the conduit rather than the cannula itself. Once it has been detected that apnoea has commenced (using one of the methods described in the section above) a reduction in the airway pressure would indicate either a spontaneous breath inhalation, or a pressure reduction due to suctioning. If this is detected immediately after apnoea it is likely to be due to suctioning. At this point the delivered flow rate and/or oxygen concentration could be relatively increased (eg: to 70 LPM 100% oxygen) to compensate for the oxygen gas that will be removed by suctioning. FIG. 66*b* shows a patient first breathing spontaneously at a set delivered flow. Once breathing is suppressed (onset of apnoea) the delivered flow increases. The pressure sensor 280 records this increase as indicated by P1. After a short period the pressure begins to decrease. Despite the increased flow rate the pressure may go negative if a lot of suction pressure is used. This is a strong sign that suctioning is being used. The flow then increases again to compensate and P1 returns to a higher level. Alternatively, the delivered flow may be increased proportionally to the airway pressure reduction (i.e. more suctioning initiates greater compensation). Alternatively a signal from the suction device may be used such that when suctioning is initiated the flow rate of the high flow rate is increased Advantages of a suction compensation configuration includes:
- minimising effect of suction on patient's oxygen reserves.
- Increased oxygenation is commenced automatically, as soon as suctioning detected, rather than waiting for user to initiate. Maximises oxygenation before intubation Functionality 4—Connection to Facilitate Continued Therapy During Transport Minimal ventilation support may be given during transport as current high flow systems are not easily transportable. Instead a low flow oxygen cannula will typically be used, attached to a barb on an oxygen bottle. As described above post-anaesthetic patients are at risk of respiratory distress and low flow oxygen may provide insufficient support.

Current high flow systems cannot connect directly to a flow meter such as that on an oxygen bottle. They may be able to connect via another tube and a humidifier but this may be perceived as cumbersome and require the humidifier to be transported with the patient.

After transport to the recovery ward, low flow may continue to be used again as the caregiver may not wish to change the interface again, and this can usually be connected via a barb connection to a flow meter on the wall. This again may provide insufficient respiratory support.

A configuration that is suitable for facilitating continued therapy during transport comprises a patient interface for use in a respiratory therapy system, the patient interface comprising:
- a cannula for delivering gas to a patient;
- a connector portion in fluid communication with the cannula and configured for removably connecting the cannula to a complementary connector portion on a main gas conduit for delivering high flow gas to the cannula;
- and a secondary conduit in fluid communication with the cannula, the secondary conduit configured to provide fluid communication between the cannula and an alternative gas source.

The connector portion in fluid communication with the cannula may be configured to seal when the connector portion is disconnected from the complementary connector portion on the main gas conduit.

This configuration advantageously provides direct connection of high flow interface to a barb on flow meter. No humidifier will be used as transport is likely to be short and therefore loss of humidity will have negligible effect on patient condition.

Figure 67A:
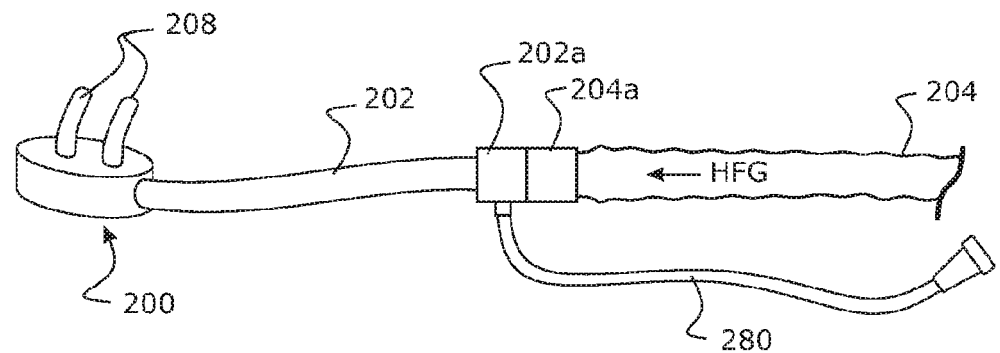
FIG. 67a shows a patient interface configuration to facilitate therapy during transport.
Figure 67B:
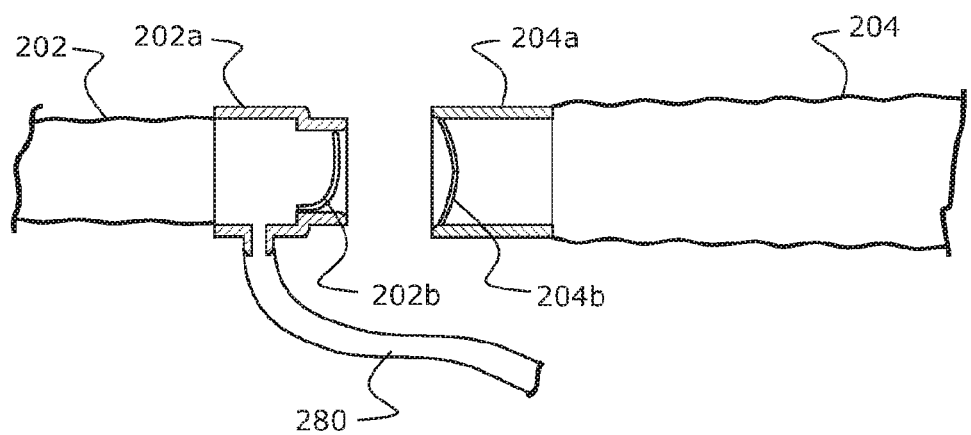
FIG. 67b shows cross-sectional details of a connector of the patient interface when connected.
Figure 67C:
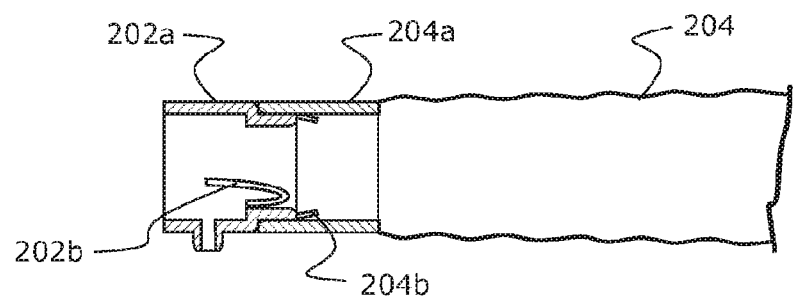
FIG. 67c shows cross-sectional details of the connector when disconnected.

See FIG. 67a. High flow gas HFG is normally delivered via a main gas conduit 204. When patient is to be transported, the cannula tube 202 is disconnected from the main gas conduit 204 and the secondary conduit 280 is connected to the transport gas supply. The secondary conduit may be a tube for example. FIG. 67b shows connection of the cannula 202 to the main gas conduit 204. The main gas conduit 204 and a conduit 202 coupled to the cannula have complementary connector portions 202a, 204a. When disconnected, both connector portions 202a, 204a seal. The gas supply may be vented back at the high flow gas source or there may be some control to turn the high flow off on disconnection. When the connector portions 202a, 204a are engaged, the cannula connection 202a forces open the gas conduit valve 204b and the flow of gas through the gas conduit 204 opens the valve 202b on the cannula connection.

Figure 67D:
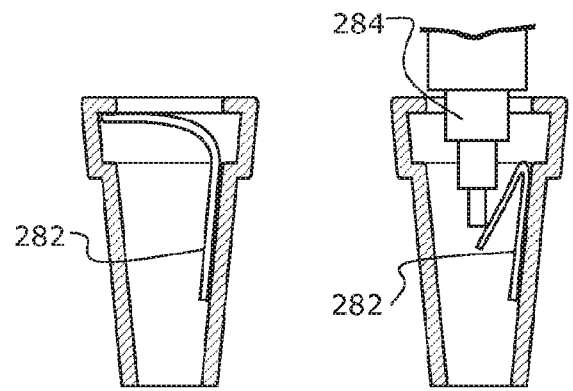
FIG. 67d shows cross-sectional details of a connector or coupling on the secondary conduit of the patient interface configuration.
Figure 67E:
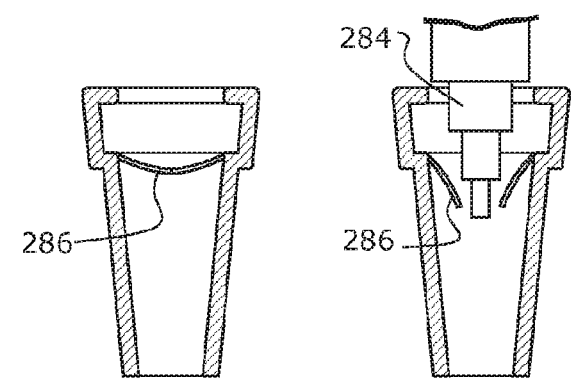
FIG. 67e shows cross-sectional details of an alternative connector or coupling on the secondary conduit of the patient interface configuration.

FIGS. 67d and 67e show the valves for the end of the secondary gas tube 280. In FIG. 67d, a one-sided valve 282 is forced open by the gas supply barb 284 entering the connection. FIG. 67e shows a duckbill-type valve 286. Both are naturally held closed by the gas supply when the main gas conduit is connected.

Figure 67F:
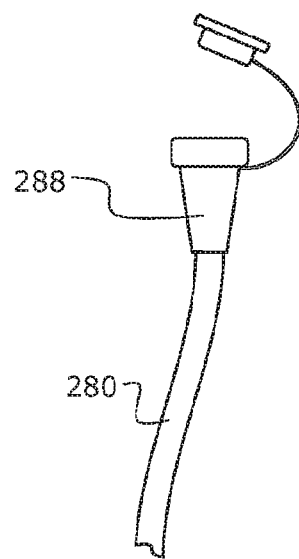
FIG. 67f shows a closure that may be used on the secondary tube instead of one of the valves of FIG. 67d or 67e.

Alternatively, FIG. 67f shows a cap 288 that may be used which will seal the end of the secondary tube and would be removed when the user wishes to connect it to the supply gas.

While a collapsing conduit or other switching methods described above may be useful options for stopping or preventing the flow of gas to a patient interface (e.g. using an item such as a collapsible block or pad in contact with, or to be placed in contact with, or which may be attachable or mountable to a patient), if the gas continues to flow into the collapsed conduit that is going into the nasal cannula, the pressure may build up in the conduit and eventually the conduit could burst or the gas could force its way through the collapsed portion of the conduit and into the nasal cannula. This could cause unwanted pressure in the patient's lungs or airway.

As described above, the system may be provided with a pressure relief device to avoid these issues. However, in addition or alternatively to the above described embodiments, mask detection arrangements may be particularly useful. For example, where a patient interface is used to deliver a flow of gas to the patient's airways, caution may be required when both routes to the patient's airway are being utilised. For example, where a nasal cannula is being used to deliver a flow of gas to the nasal passages and where a mask is being used to deliver a flow of gas to the patient's airways via the patient's mouth and/or nose (and may optionally be providing the flow of gas in a manner where the mask is a sealed-type interface, such as by creating a seal between the mask and the patient), the potential for an over-pressure situation to arise may be heightened. A system for recognising the dual application of operating or operational interfaces may allow for a warning to be issued of such a situation or there may be activation or controlling of a part of the respiratory system to prevent both patient interfaces from delivering their respective sources of gas simultaneously. Such a signalled or controlled system may assist in minimising or reducing the likelihood of accidental over-pressurisation of the patient's airway. Alternatively mask detection arrangements may be used to switch between respiratory modes. For example, a first patient interface may provide a first flow of gases to a patient, and once a second patient interface is applied to the patient, detection of the second interface facilitates the switching off of the first flow of gases, to allow a second flow of gases to be provided by the second patient interface.

In some embodiments, a sensor arrangement may be provided, the sensor arrangement comprising one or more sensors. One or more sensors may be located upon, embedded within or provided on parts of one or more of the patient interfaces, or an item associated with such interfaces, used for delivering a flow of gas to a patient.

In some embodiments, a respiratory system may comprise a controller configured to sense the presence of a second patient interface (such as a mask) and alert the user and/or adjust the high flow therapy accordingly, without the placement of any sensors on the first or second patient interfaces. For instance, the controller may sense a change in pressure, change in flow, or change in a fan motor speed of a flow generator as a result of the placement of a mask on the patient. The controller may reduce or cease the administration of high flow therapy in response to the change in pressure, change in flow, or change in motor speed. The controller may additionally or alternatively alert the user via an alarm (such as a visual or audible alarm) in response to the change in pressure, change in flow, or change in motor speed. In an embodiment, the respiratory system comprises a humidifier and a chamber with a chamber inlet and a chamber outlet and the pressure sensor system is positioned at the chamber outlet. In another embodiment, the system comprises a flow sensor at the chamber inlet and/or chamber outlet. The flow sensor may be a heated bead sensor. Alternatively, the flow sensor may be an ultrasonic flow sensor integrated with the controller. Any other flow sensor known to those skilled in the art could be substituted According to the various forms of the disclosure herein, and referring to FIG. 47, in at least one particular form there is a respiratory therapy system comprising a first patient interface 91 for delivery of a flow of gas (from a gas source 92) to a patient 93, and a second patient interface 94 for delivery of a flow of gas to the patient. The second patient interface 94 may be connected to the same gas source as the first patient interface 91, or alternatively, may be connected to a second gas source such as an anaesthetic machine (not shown). Preferably the gas source to the second patient interface 94 is different from the gas source to the first patient interface 91. As shown, the gas supply to the second patient interface 94 may be supplied via connection port 919. A sensor or sensors 95 is/are then provided to be associated with one or more of:

the first patient interface 91,
the second patient interface 94,
both the first and second patient interfaces 91, 94,
an item 96 associated with the first patient interface 91,
an item 96 associated with the second patient interface 94,
an item 96 associated both the first and second patient interfaces 91, 94,
an item 96 to be associated with the patient 93.

The sensor or sensors 95 sense an in-situ combination of the first patient interface 91 and the second patient interface 94 upon the patient during delivery of gas to the patient 93; such a sensed combination of interfaces generating a signal or output 97.

The signal or output 97 can be used to directly or indirectly control or activate a further system or device which determines a flow of gases being provided to one or both of the first and second patient interfaces 91, 94, or more particularly to a first patient interface 91, such as but not limited to, a nasal cannula. The signal or output may be provided in the form of a wired connection or a wireless connection.

The signal or output 97 may alternatively be fed to, or activate or control (or activate and control) one or more of the following system outcomes:

a visual alarm or warning
an audible alarm or warning, including but not limited to a whistle,
a haptic or tactile feedback fed or directed to a wearable electronic device, including but not limited to: watches, phones, head mounted displays or other articles of clothing incorporating such an electronic device,
a flow controller, including a flow valve or flow generator, preferably for controlling the flow of gas being directed to the first patient interface 91; optionally in addition or separately, including controlling the flow of gas being directed to the second patient interface 94,
a pressure regulator or pressure throttling device, preferably for controlling the pressure of gas being directed to the first patient interface 91; optionally in addition or separately, including controlling the pressure of gas being directed to the second patient interface 94,
a diverter to divert the flow of gas otherwise to be controlled to a vent,
a micro-processor associated with the flow controller or the pressure regulator (or both) or flow diverter or vent,
a graphical user interface (GUI).

Advantageously, the signal or output 97 of the sensed in-situ combination provides for control of the flow (or pressure) of the gas being directed to the first patient interface 91.

The one or more sensors 95 utilised in such configurations may be one or a combination of any one of the following in sensing the in-situ combination:

optical sensors (including infra-red, IR)
acoustic (including audible or ultrasonic) sensors
pressure or flow sensors of the pressure or flow, or both pressure and flow, of gas in a supply conduit 98 supplying a gas to the first patient interface 91, or (a separate gas supply conduit feeding a gas to) the second patient interface 94, or both the first and second patient interfaces 91,94, or of the pressure or flow (or both) of the gas delivered to the patient's respiratory system or a part of the patient respiratory system,
electrical conductivity or resistance electrodes embedded within, or placed on a part of, one or more of:
the first patient interface 91,
the second patient interface 94,
both the first and second interfaces 91,94,
an item 96 associated with the first or the second or both the first and second patient interfaces 91,94,
an item 96 to be associated with the patient,
radio-frequency or proximity sensing sensors to sense the in-situ combination,
mechanically activated or triggered sensors, comprising but not limited to: a mechanical switch activated or triggered by being depressed or being placed into contact with another surface, pressure relief valves or pressure sensitive valves, solenoid valves, mechanical valves with a pre-determined spring constant, optionally a pressure relief valve comprising of a whistle activated by the release of gas from the valve when moving to the open position from the closed position.

Figure 47:
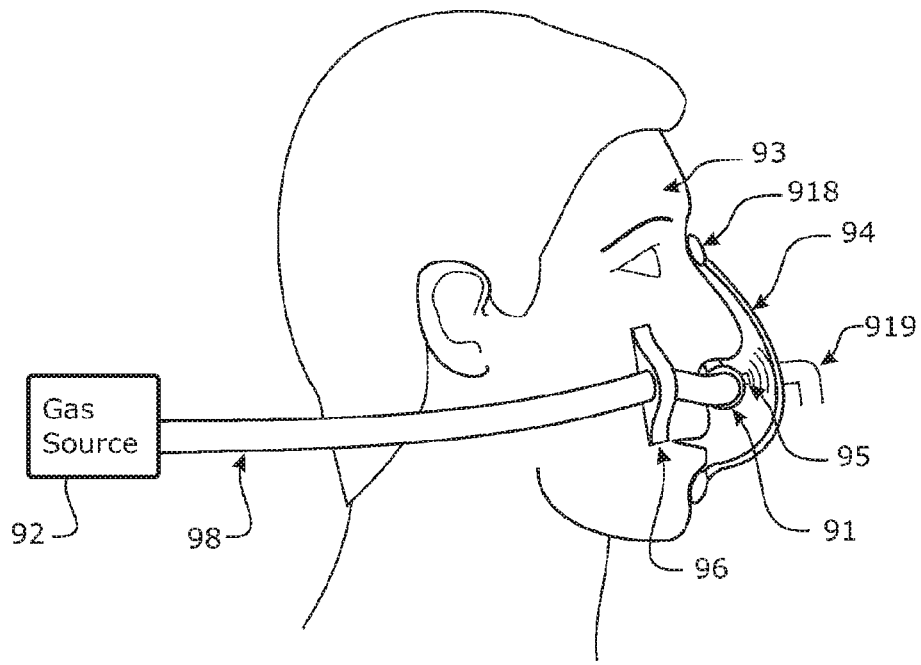
FIG. 47 is a side view showing a combination nasal cannula in operational position on a user, in combination with a full face mask.
Figure 48:
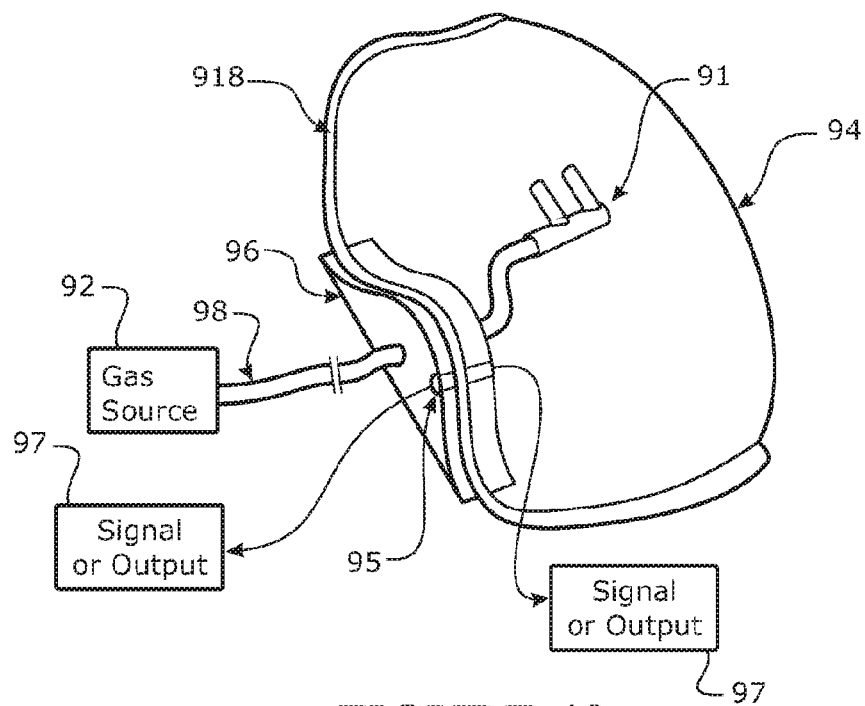
FIG. 48 shows a closer view of the combination of a nasal cannula patient interface and a full face mask, with a sensing system incorporated into at least an item and the mask which is placed into proximity or contact with the item.

FIGS. 47 and 48 illustrate a first patient interface 91 in combination with a second patient interface 94, the second patient interface 94 being placed substantially in contact with an item 96 that is in the form of a block or pad in contact with, or to be placed in contact with, or which may be mountable or attachable to the patient 93. A seal part 918 is shown in substantial contact with the item 96 in FIG. 48. In FIG. 47, the sensor 95 is positioned on the first patient interface 91, and this sensor 95 detects the placement of the second patient interface 94 on the patient. The sensor 95 may be, for example, an optical sensor (including infra-red, IR) or an acoustic (including audible or ultrasonic) sensor, or a pressure sensor. In FIG. 47, the block or pad 96 allows the second patient interface 94 to be placed over the supply conduit 98 without collapsing the conduit 98. The block or pad 96 also allows the second patient interface 94 to substantially seal over supply conduit 98.

In various configurations, the one or more sensors 95 may be located upon, embedded within or placed or positioned in a respiratory system at a position other than on a patient interface or an item 96 associated with a patient interface. Such sensors 95 may be utilised as stand-alone sensors or where a plurality of sensors need to each sense the in-situ combination of a first and second patient interface 91, 94 upon a patient 93, such that a positive signal or output 97 is provided to the provide for an activation or controlling of a device or the system (or a warning). In this way, false positive sensed signals may be avoided or minimised.

It may also be contemplated that at least one secondary sensor (not shown) may need to sense the placement of the first patient interface on the patient to determine when the first patient interface is in-situ or another sensed situation in order for the signals or outputs 97 from other sensors 95 to then be utilised in an overall system for providing a signal or output 97 of a sensed in-situ combination. For example, a secondary sensor may be provided on a first patient interface 91, such as a nasal cannula to sense when such an interface is actually provided in an operational position or in-use configuration with the patient 93. This would prevent other sensors from operating when the first patient interface 91 is not in place or operational position on the patient. Preferably, the default system would be such that the sensor 95 did not operate when the secondary sensor indicated that the first patient interface 91 was not in use, but this would not cause cessation of the gas flow.

One example of such a secondary sensor may be a temperature sensor to sense the patient's temperature or skin temperature which may be used as indicative of the first patient interface 91 being placed in position upon the patient's face. The use of such a temperature sensor, or other secondary sensors (such as a proximity sensor, or optical sensors or acoustic sensors) can be used to determine when the first patient interface 91 is in operation and/or in place on the patient 93.

In this variation, once such secondary sensors sense and determine the first patient interface 91 is in place on the patient 93, then any other sensors associated with other patient interfaces or items 96 associated with such interfaces may have their signals or outputs 97 used (i.e. there could be a master or primary signal or output needed in order to allow subsequent sensors to the have their subsequent or secondary signals or outputs used)—however variations of such configuration are contemplated and this is only exemplification of one form.

In a further configuration, one or more sensors 95 may be provided as a part of an item 96 which may be mounted or attached to the patient 93 (e.g. their face). Such an item 96 can be configured to allow for a gas supply conduit 98 to pass through the item, in which case the item 96 can be configured or provide for a lumen 99 so that a gas supply may be fluidly connected from one side of the item to another side from which a further gas supply conduit extends to provide for fluid connection to a first patient interface (e.g. a nasal cannula). Such an item 6 may be a block or pad, for example such as that shown in FIGS. 47-51, 53-54C. Such an item 96 may comprise of one or more sensors 95 for sensing when a first patient interface 91 is in operation and/or when a second patient interface 94 (e.g. a mask) comes into engagement with at least a part of the item 96 (e.g. a seal of a second patient interface 94 becomes engaged or contacts a part of the item). In any of these situations, a signal or output 97 can be generated and can be used to control the system or provide for feedback (e.g. warnings or other such 'system outcomes' as described above).

In a further configuration, one or more sensors 95 may be provided as a part of or together with a conduit 98 providing a flow of gases to the first patient interface or the second patient interface. The conduit with sensor may sense when a first patient interface 91 is in operation and/or when a second patient interface 94 (e.g. a mask) comes into engagement with at least a part of the conduit 98 (e.g. a seal of a second patient interface 94 becomes engaged or contacts a part of the conduit). In any of these situations, a signal or output 97 can be generated and can be used to control the system or provide for feedback (e.g. warnings or other such 'system outcomes' as described above). In some embodiments the conduit may be integrally formed as part of the first patient interface. For example, the first patient interface 91 may be a nasal cannula that comprises a conduit portion for providing a flow of gases to a nasal prong or prongs of the cannula.

In one configuration, at least one of the sensors 95 provided as a part of the item 96 or conduit 98 may be optical sensors (including infra-Red, IR), radio-frequency tags (RF tags), mechanically activated switch type sensors, acoustic type sensors, electrical resistance devices (e.g. strain gauges), or may use pairs of electrodes to sense changes.

For example, based on a known dielectric constant between a pair of electrodes or based on a change in the known capacitance of a material due to a change in the dielectric, for example such as a result of a second patient interface 94 being placed into contact with the item 96, or at or near to the sensor, a sensed signal or output 97 can be generated.

Figure 49:
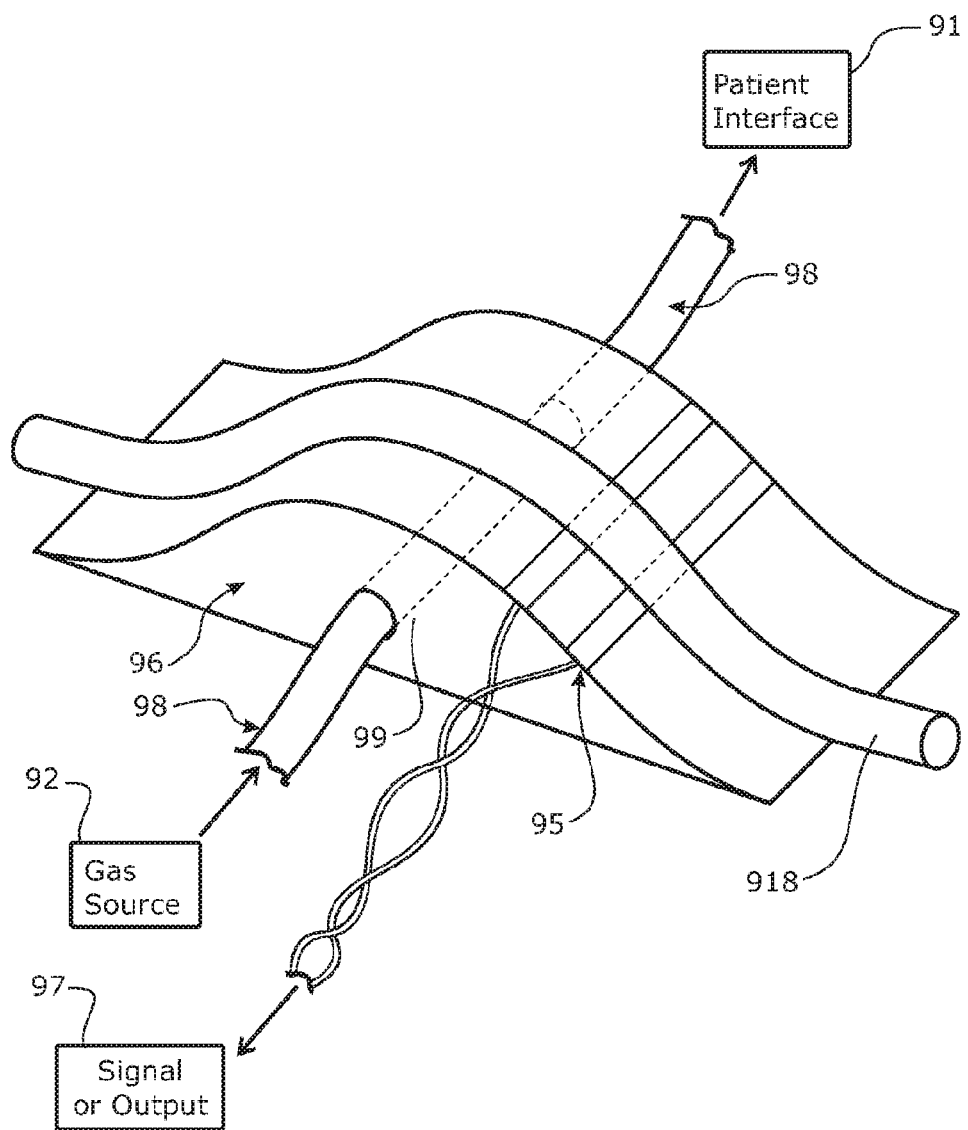
FIG. 49 shows an item in the form of a block or pad which can be mounted or located on, or placed in contact with, a user (e.g. their face), and through which a gas supply conduit passes to provide a flow of gas to a patient interface (e.g. a first patient interface in the form of a nasal cannula) and where the item comprises at least one sensing system.

On one configuration for example as shown in FIG. 49, a sensor 95 may be a pair of electrodes such as that described above, provided as part of an item 96 which is to be mounted or attached to the patient, for example a pad or block. The item 96 allows for a gas supply conduit 98 to be fed through the item 96 (or the conduit 98 is connected to the item 96 at each end of the lumen 99 through the item 96). When a part of an interface, such as a seal portion 918 of a second patient interface (remainder of this interface not shown for simplicity) comes into contact with the item 96, the sensor 95 in this configuration senses a change in capacitance or dielectric and generates a signal or output 97.

In another configuration, a sensor 95 may be an optical sensor provided as a part of the item 96. In such a version, see for example FIG. 53, the item 96 may comprise of an optically transmissive portion 910 or may comprise of an optically clear or transparent window. When an object, such as a second patient interface 94 is placed or comes into contact with the window or blocks the window either wholly or partially, optical characteristics within the optical sensor may be modified or varied. For example, there may be total internal reflection of a light from a light source 911 within such an optical sensor portion 912 of the item prior to the window being blocked or covered. When a second patient interface 94 is placed in contact with the window, there is a modification of the optical characteristics of the sensor system, for example the light may then become a frustrated internal reflection and such a change sensed. A signal or output 97 can then be generated.

Figure 51:
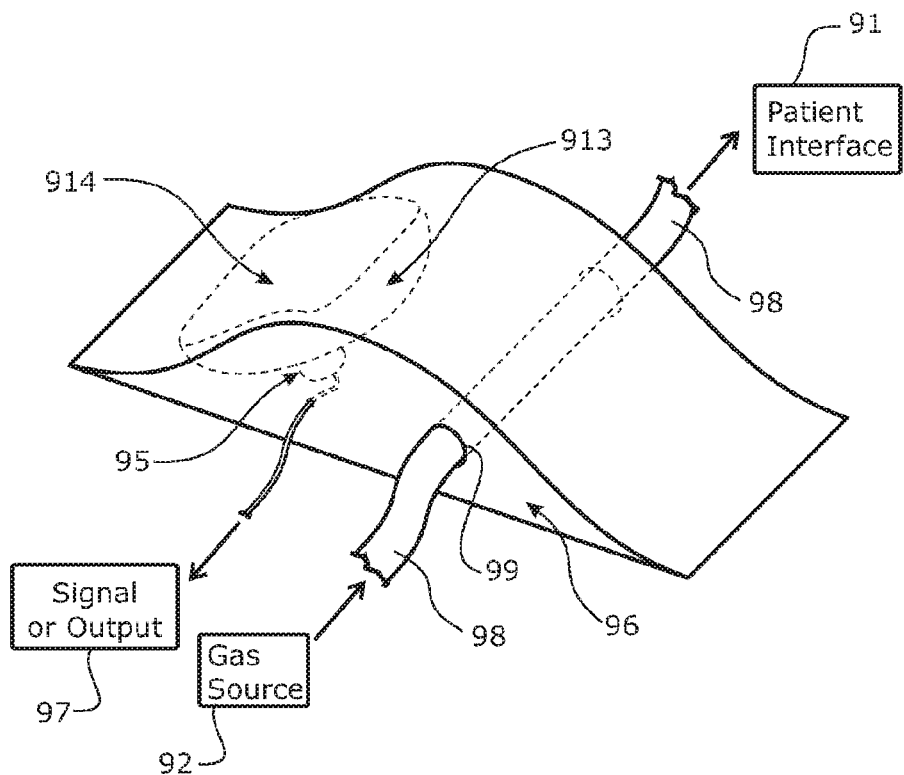
FIG. 51 shows another embodiment of an item in the form of a block or pad in which a region of the item comprises a sensing system, for example a pressure sensitive sensing system.
Figure 52:
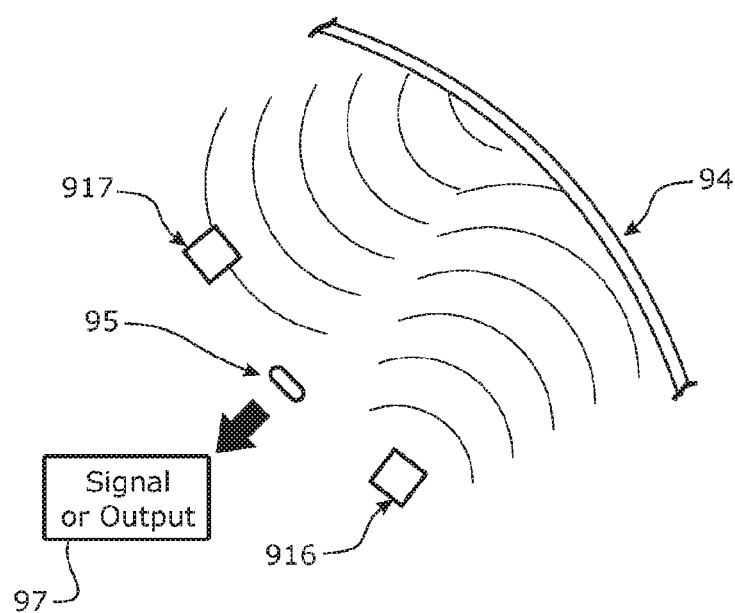
FIG. 52 illustrates application of an acoustic or optical sensing system utilising at least one transmitter and at least one receiver and a sensor associated with these, such a sensing system which may be utilised in combination with a patient interface to determine the location of the interface upon a patient, or in proximity or placement with another patient interface.
Figure 53:
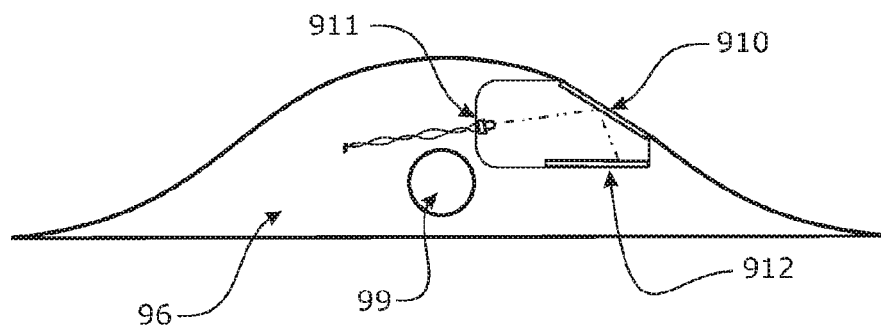
FIG. 53 is a generalized cross-section through an item in the form of a block or pad mountable to, or to be placed in contact with, a patient, in which a sensing system embedded within the item is provided, for example in the form of an optical sensing system, such an optical sensing system being utilised to determine the placement of a patient interface upon the item (e.g. a second patient interface being put into operative position on a patient).

Referring now to FIG. 51, in another configuration, any one or more of the first patient interface 91 or the second patient interface 94 or the item 96 (such as a block or pad to be placed in contact with, or which may be mountable or attachable to the patient) may comprise of a pressure sensitive sensing system. For example, the item 96 in the form of a block or pad may comprise a pressure sensor in the form of a fluid-filled chamber 913 (e.g. could be a gas) with a pressure flexible membrane 914 placed over the top and providing for a barrier layer from the chamber to an external surface of the item 96. The chamber has a known pressure. When an object, such as a patient interface (e.g. a mask) is placed in contact with the flexible membrane 914, there will be a change in pressure in the chamber 913. Such a change can be sensed and a signal or output 97 generated. It will be appreciated such a configuration may be applied to parts or portions of patient interfaces too which otherwise come into contact with the patient 93 (to sense the interface is in place on a patient) or into contact with another part of another patient interface (to sense such a combined set of patient interfaces).

Figure 50:
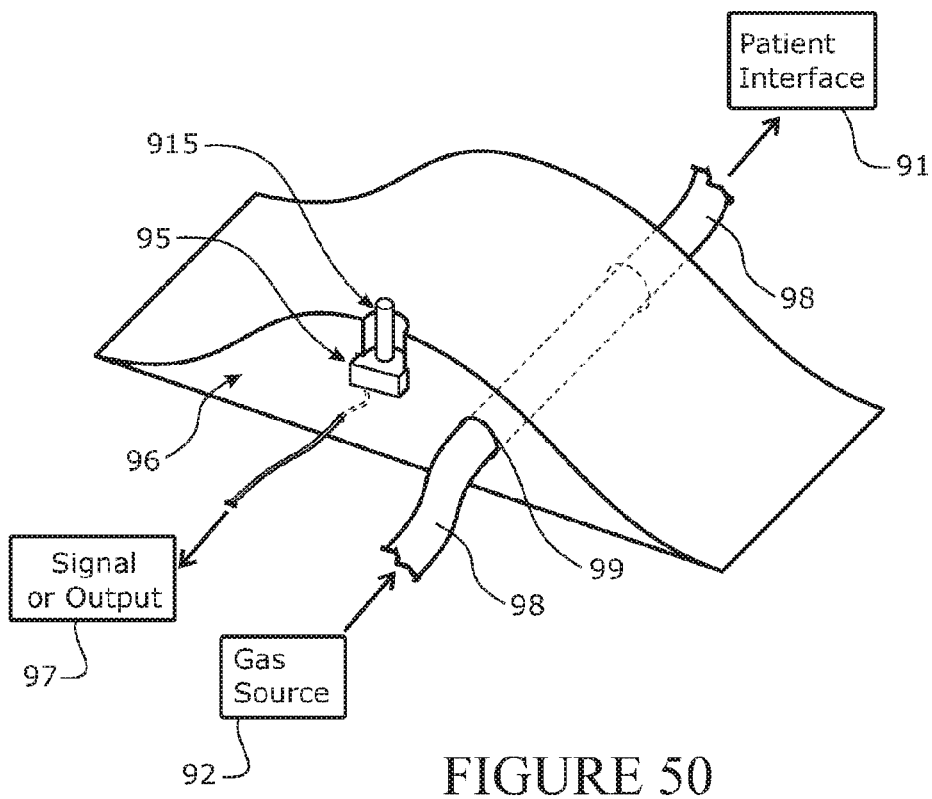
FIG. 50 shows another embodiment of an item in the form of a block or pad in which a mechanically activated or triggered switch or sensing system is provided, such a switch or sensing system to be activated or triggered when the projection is physically engaged or contacted by a further patient interface, such as a second patient interface in the form of a mask (not shown).

With reference to FIG. 50, in another configuration, the item 96 may be in the form of a block or pad to be placed in contact with, or which may be mountable or attachable to the patient 93, or one or both of the first and second patient interfaces 91, 94 may comprise of a sensor 95 in the form of a mechanical type sensor. For example, a mechanical sensor may comprise of a switch that is activated or triggered by a physical contact. For example a mechanical sensor may comprise of a projection 915 which can be depressed or moved when contact is made. Such a sensor may be incorporated into the item 96 so that application of pressure, for example from a seal region (or another part) of a second patient interface 94 can then generates a signal or output 97. Alternatively, such a mechanical sensor may be incorporated into one or both of the first and second patient interfaces 91, 94 and located at a part or region of such interfaces which will come into contact with the item 96 or the other patient interface during operational use on the patient.

In another configuration, a sensor 95 such as an acoustic sensor may be utilised in combination with an item 96 associated with a patient interface. Such a sensor may have application in a gas supply conduit 98 associated with the first patient interface 1. An acoustic wave may be sent down the conduit 98 to sense a closing or other change in parameter or characteristics of the conduit (such as a change in shape of the conduit, e.g. a section of the conduit may collapse, at least partially). An advantage of this arrangement is that existing patient interfaces may be utilised without the need for additional customisation of those interfaces to incorporate sensor systems. Acoustic waves may be sent at any suitable sampling rate, and the sensor 95 can sense either a reflected signal (due to a closure or bulging in shape of the supply conduit) or can sense a change in resonance, i.e. change in the standing wave formed in the conduit due to the conduit being closed, for example the item 96 in the form of a block or pad may collapse to close the conduit 98 between the gas source 92 and the interface 91. See for example FIGS. 54A-C.

In another configuration, a sensor 95 in the form of an optical sensor may be utilised in combination with an item 96 to be mounted or attached to the patient, or either or both of the first and second patient interfaces 91, 94. An optical sensor system may utilise a transmitter 916 and a receiver 917, the transmitter transmitting a pre-determined code (e.g. a specific binary code) and the receiver receiving and detecting the code. The sensor 95 can be used to analyse or determine and generate a signal or output 97. See FIG. 52. In such an arrangement, the optical sensor is used to effectively determine the proximity or placement of an item 96 upon the patient, or an interface upon a patient (e.g. a first patient interface) or an interface upon an item (e.g. a second patient interface 94 upon an item 96), or a second patient interface 94 in close proximity to a first patient interface 91, or to both an item 96 and a first patient interface 91, or other combinations of these.

FIG. 54A shows the interface 91 during operational use. FIG. 54B shows a second patient interface 94 now provided in co-operation or combination with the first interface 91 providing for dual therapy to the patient, yet the second patient interface 94 applying a pressure or force to the pad or block item 96, which in turn crushes, squeezes or collapses (either completely or partially) the conduit 98 (or at least the lumen 99 through which the gas feeding the first interface 91 passes therethough). Shown is the conduit 98 with a change in shape due to an increase in the pressure (i.e. due to a resistance to flow created by the squeeze, crush or collapse of the lumen 99). FIG. 54C illustrates a further embodiment of FIG. 54B in which the conduit bulges or balloons more greatly, for example due to even greater pressure build-up in the conduit or even greater resistance to flow, such as due to a complete closure of the conduit 98 or lumen 99 preventing the flow of gas to the interface 91. The acoustic sensor 95 in these embodiments is used to sense such a partially or wholly closed conduit 98 or lumen 99 and provide for a signal or output 97. Although FIGS. 54A-C illustrate one particular configuration, it will be appreciated that the item 96 may be an optional component and is not necessarily required when a sensor is to be used to sense a condition (e.g. a physical condition such as a closed conduit or lumen, or a condition of the gas flow in the conduit or lumen). The sensor 95 could be directly mounted upon or associated with the patient or an interface. Of course, the sensor arrangement described may be implemented in a system without the item 96, wherein the conduit may alternatively comprise a collapsible portion to allow the mask to seal over the conduit and with the patient's face.

In another configuration, a sensor 95 in the form of a pressure sensitive valve may be utilised to divert a flow of gas being supplied to a patient interface. For example, such a valve may be a pressure relief valve operational once a pre-determined pressure is sensed. Solenoid or mechanical valves may be used having a relatively high spring reaction force when in a closed valve position, and a relatively low spring reaction force when in an open valve position (i.e. pressure of flow venting position). Advantageously, in some configurations the valve can remain open until the pressure within the conduit drops below a threshold value, and then the valve would automatically close. Optionally, in combination with such a sensor, a whistle or audible signal may be provided, using the released flow of gas to operate the whistle. In this way, a sensed pressure opens a valve. The whistle issues as a further signal or output in addition to the controlled venting. Optionally, a supply conduit associated with a patient interface may desirably be provided with sufficient hysteresis so as to maintain the pressure within the tube so that a pressure relief valve remains open, yet without too much pressure that may otherwise force the conduit which is partially or wholly collapsed or squashed to be forced open.

In another example, one or more sensors 95 may be provided as part of the first patient interface 91 (such as a nasal cannula). For example, the first patient interface may comprise any of the sensor arrangements provided with item 96 as described above. For example, item 96 as shown in FIGS. 47 to 54C may be a portion of a nasal cannula, e.g. a portion of a side arm of a nasal cannula. As described above, such sensors 95 can be used to determine when an additional i.e. a second patient interface 94 is placed in combination with the first patient interface 91 upon a patient. Alternatively or in combination, such sensors 95 may be used to determine whether either of the first and/or second patient interfaces 91, 94 are receiving a flow of gas for delivery to the patient upon which each of the first and second patient interfaces are provided, i.e. whether the patient is receiving dual delivery of gas flows from dual patient interfaces.

Unless the context suggests otherwise, where a pressure sensor is described as being at a particular location, for example at the patient interface, this should be interpreted to mean the system is configured so that the sensor senses pressure at that location. For example, in some embodiments the sensor may be located at the particular location, or may be remote from the particular location but configured to sense pressure at the particular location via a pressure sensing or sampling line, for example like sampling line 829 of FIG. 32. A pressure sampling line may be beside or within a gas conduit providing flow of gases to a patient interface, or may be formed within a wall of such a conduit.

Figure 55A:
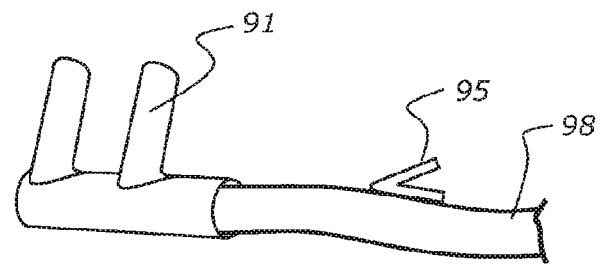
FIG. 55A to 55B show a sensor arrangement comprising a contact sensor.
Figure 55B:
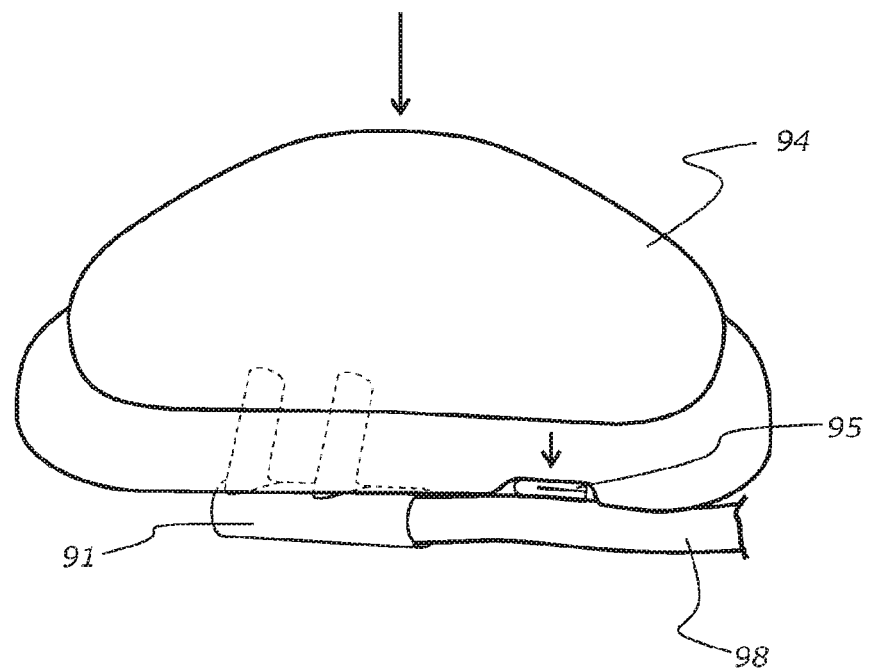
Figure 56A:
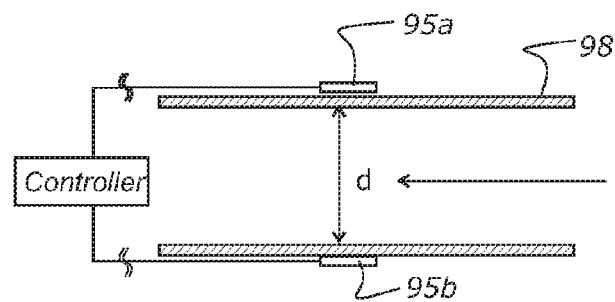
FIG. 56A to 56B show a sensor arrangement comprising a capacitive sensor.
Figure 56B:
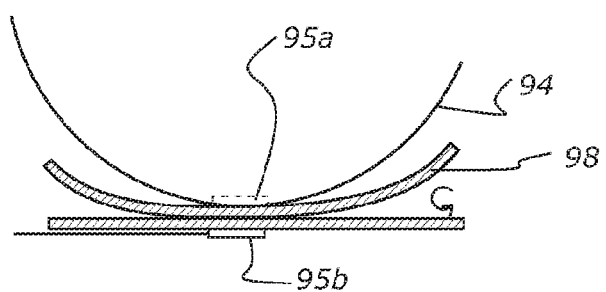

A further sensor arrangement is illustrated in FIGS. 55A and 55B. The presence of a mask could be detected by a contact sensor 95 on the first patient interface 91, item 96 or conduit 98. The contact sensor would be activated when the mask is placed over of the sensor, as shown in FIG. 55B. An electrical contact is positioned on the interface, item, or conduit in a location where the mask seal would be positioned in use. When the mask is applied the electrical contact is closed, completing an electrical circuit. The electrical contact may also be closed manually, for example by a medical professional pressing the contact. The contact may be a switch comprising electrical contacts, the switch closed to make an electrical connection between the electrical contacts by application of the mask over the switch, or by a person pressing the switch. Alternatively there may be two complementary electrical contacts, a first contact mounted on the patient interface, item or conduit, and a second contact mounted on the mask seal. With both the first and second interfaces in-situ on the user's face, the first and second contacts would be brought into contact to complete an electrical circuit. As described above, the sensor 95 may comprise a pair of electrodes, or may comprise a pair of sensor elements. As a further examples, with reference to FIGS. 56A to 58B, in some embodiments, the sensor 95 may comprise a pair of sensor elements 95a and 95b, a first one 95a of the pair of elements located on a side of a gas conduit (e.g. conduit 98) and a second one 95b of the pair of elements located on another side (e.g. opposite side) of the gas conduit 98, or on a second patient interface 94. The sensor is adapted to sense when a collapsible portion of the conduit closes. When the collapsed state of the conduit is sensed a controller may determine that a flow provided through the conduit is to be reduced or stopped. The sensor arrangement senses the relative position between the elements, to sense the configuration of the collapsible conduit. A change in distance between the two elements is sensed by a controller, to determine the open or closed state of the conduit. As shown in FIG. 56A, in one configuration the conduit is open, and with elements 95a and 95b in a spaced apart or distal configuration. In a second configuration (not shown), the conduit is collapsed, and with the elements 95a and 95b brought together. The collapsed conduit may prevent or restrict the flow and/or may communicate to the controller to stop or reduce the flow. In the alternative configuration of FIG. 56B, one of the elements 95a is located on a second patient interface 94, and one of the elements 95b is located on the conduit. The second patient interface 94 is pressed against the conduit to collapse the conduit and bring the first and second elements 95a together. As shown in FIG. 56B, in some embodiment's one element 95b is positioned on a side of the conduit opposite to a side of the conduit that the second interface contacts.

Figure 57:
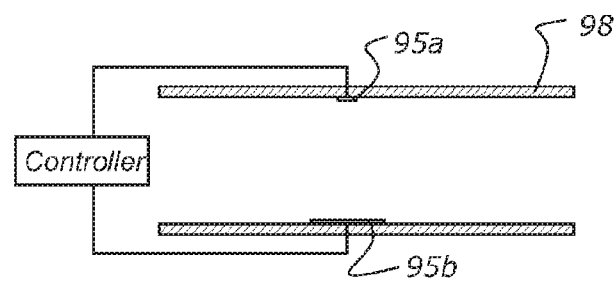
FIG. 57 shows a sensor arrangement comprising a contact sensor located within a lumen of a conduit.

The arrangement in FIGS. 56A and 56B may be a capacitive arrangement, wherein a controller is provided to sense the change in capacitance between the first and second elements caused by a change in distance between the elements. Alternatively, as shown in FIG. 57, the elements may be contact elements located within a lumen of the conduit, so that when the conduit is collapsed the elements make contact to complete an electrical circuit that a controller may detect.

Figure 58A:
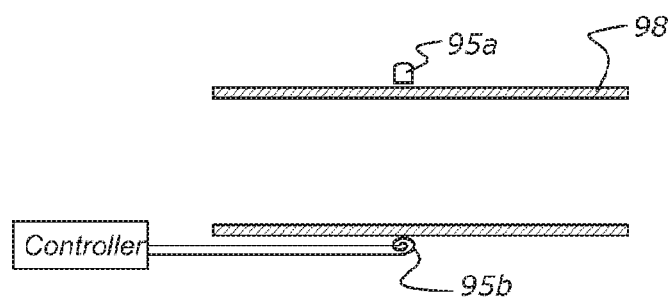
FIG. 58A to 58B show a sensor arrangement comprising an inductive sensor.
Figure 58B:
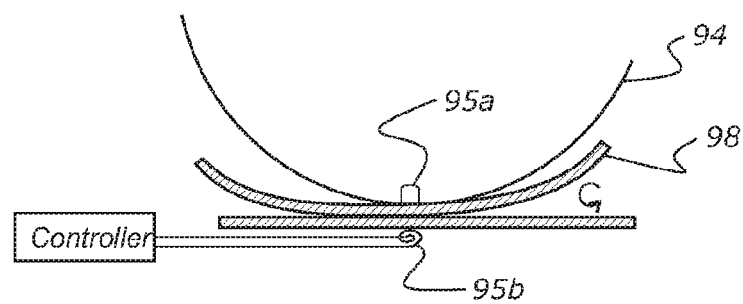

In another embodiment, the first and second elements may form an inductive arrangement. For example, as shown in FIGS. 58A and 58B, one of the pair of elements may comprise a coiled conductive member and the other one of the pair of elements may comprise a magnet material, for example ferrite. The magnetic material causes a current to flow in the conductive member that is dependent on the distance between magnetic material and the coil.

Figure 59:
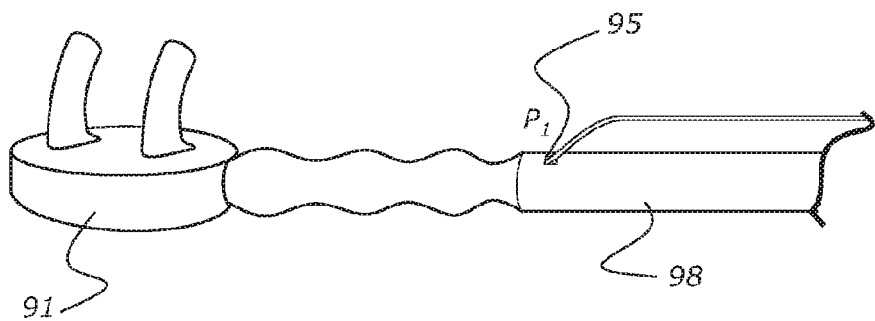
FIG. 59 shows a sensor arrangement comprising a pressure sensor.

In some embodiments, the sensor may comprise a pressure sensor located within the conduit 98 or a conduit of the first patient interface 91. The conduit may comprise a collapsible portion, as described previously. In some embodiments the sensor 95 may be located downstream of the collapsible portion, for example near a nasal prong of the first patient interface 91. In some embodiments the pressure sensor may be located upstream of the collapsible portion, for example as shown in FIG. 59. The presence of a second interface 94 may be detected by a change in pressure, sensed by the pressure sensor 95. In some embodiments, when a portion of the collapsible portion of the conduit is collapsed a pressure change is caused upstream of the collapsible portion (there may be an increase in pressure). In some embodiments, rather than there being a collapsible conduit the system may comprise a valve to close and open the conduit, wherein the valve is operated by the placement of the mask over the first patient interface. When a pressure change is detected a controller may cause a flow or pressure in the conduit to be reduced or stopped. In some embodiments, the system may maintain a small/reduced pressure/flow level within the conduit so that removal of the mask may be detected. For example, if flow was reduced to zero, removal of the mask would not cause any further pressure change and mask removal would not be detected. Once the mask is removed, flow to the first patient interface may resume, for example automatically by a controller.

Figure 60:
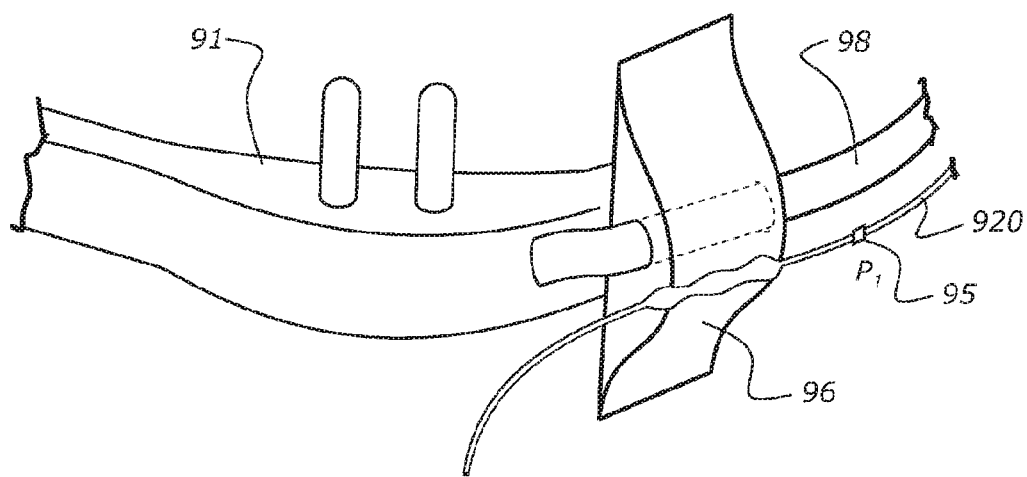
FIG. 60 shows a sensor arrangement comprising a pressure sensor.

With reference to FIG. 60, in some embodiments a gas conduit delivering flow to a patient via the first patient interface is not collapsed by application of a second patient interface. For example a spacer component 96 (as described with reference to FIG. 47) may be provided for the mask 94 to seal over and prevent the conduit 98 from collapsing. A sensing tube 920 for pressure sensing may be provided to be located between the spacer component 96 and the mask 94. A small amount of flow may be delivered along the sensing tube. The sensing tube may exit away from patient. When the mask 94 is applied, the sensing tube is collapsed between the spacer 96 and the mask 94, and a pressure in the sensing tube upstream of spacer component 96 increases which may be sensed by a pressure sensor, indicating the presence of the mask. A controller may then reduce or stop flow to the first patient interface via the gas conduit. When mask is removed, the sensing tube is no longer collapsed, and the pressure upstream of the spacer will be allowed to decrease to indicate the mask 94 has been removed. Alternatively the spacer component may comprise a collapsible lumen connected to a sensing tube.

Figure 61:
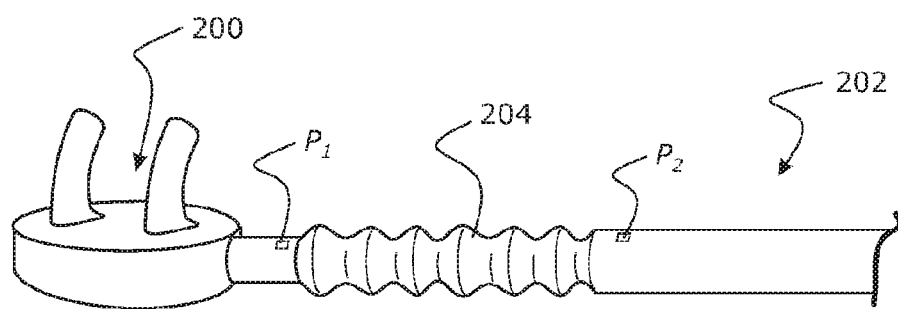
FIG. 61 shows a sensor arrangement comprising at least two pressure sensors.

With reference to FIG. 61, in some embodiments, a sensing arrangement comprises two pressure sensors, to measure pressure either side of a closable section of a gas conduit 202 providing a flow of gases to a patient, for example via a nasal interface 200. The closable section may be a collapsible section or portion 204 of the conduit, or may comprise a valve, as described previously. A first pressure sensor P1 senses pressure downstream of the closable section 204, and a second pressure sensor P2 measures pressure upstream of the closable section 204. The first pressure sensor may provide a safe pressure limit. If a delivered pressure exceeds an allowable threshold at the interface as measured by P1, the first pressure sensor P1 senses the threshold (for example a P1 threshold) has been exceeded and a controller stops flow in response. The first and second pressure sensors may additionally or alternatively be used to detect the closable section of the conduit is closed or partially closed by detecting a differential pressure across the closable section 204. By detecting the conduit has been closed or partially closed, the first and second pressure sensors may be used to detect the presence of a mask, for example in a configuration where the mask presses against the collapsible section, as described previously. When the closable portion is at least partially closed, P2 will be increased relative to P1, indicating an occlusion upstream of P2 but downstream of P1 is present. A controller may determine a differential pressure between P1 and P2 exceeds a threshold and turn off the flow to the conduit 202 in response. The P1 threshold may be different, for example may be greater than the differential pressure threshold. If P1 increases but P2 remains the same this indicates an occlusion upstream of P1 only. This may be caused by prong obstruction or sealing in the nares. In this case it may be desirable to maintain the delivered flow. Having two pressure measurements allows the system to distinguish between a prong obstruction or sealing in the nares as opposed to a collapsed or closed tube. A small amount of flow and/or pressure may need to be maintained (as described above) to detect when the mask is removed, or the method of FIG. 60 may be employed.

In various embodiments described that comprise a sensor to determine a change in flow or pressure indicative of a second interface being present, a controller in response to there being a second interface present may cause a flow or pressure in the conduit to the first patient interface to be reduced or stopped. In some embodiments, in response to there being a second interface present, it may be desirable to maintain a reduced pressure/flow within the conduit to the first patient interface, rather than zero pressure/flow, so that when the second patient interface is removed from the user's face the controller via the sensor is able to sense a change in pressure/flow as a result of the second interface being removed. In response to the second interface being removed a controller may re-establish an operational flow (for example a high flow) to the first interface.

The various configurations described herein allow for provision of an automated or controlled respiratory therapy system based on signals or outputs from one or more sensors provided with patient interfaces of items associated with those interfaces. For example, it would be useful to sense the presence of a mask when placed in combination with a nasal cannula on the same patient and to allow for an automated control of the flow of gas to one or both of those interfaces (preferably controlling the flow to the nasal cannula).

Automated control of the system may allow for controlling of valves to reduce or stop flows of gas, or for the regulation or throttling of pressure of gases being supplied to the patient, or yet other alarms or warnings to be issued so as to make aware the presence of an operational first patient interface and an operational second patient interface.

In addition, deactivation or activation, of a signal or output 97, can allow for the high flow therapy to commence or be recommenced.

Further, embodiments described above may be useful together with a single patient interface. For example, a high flow nasal cannula may be utilised together with the item 96 described herein, and/or may comprise the described sensor arrangements, and without a mask present. A change in flow provided by the flow generator may be activated manually by a user depressing item 96 or a collapsible portion of the conduit 98 or patient interface 91 with a finger, or placing a finger over a sensor 95. This may be useful in applications such as endoscopy where a user administering a flow to a patient via a cannula may wish to stop the flow.

Improvements to try and prevent or minimise the likelihood of a Barotrauma being experienced by a patient provide for a highly desirable outcome.

Various embodiments have been described for respiratory therapy systems comprising dual delivery devices, for example a nasal cannula and a face mask as described with reference to FIG. 3. In these system a device may be provided to allow or facilitate a switching of the system between different respiratory modes. For example the device may be a pressure relieve device, or a valve to open and close a lumen of the system. In some of the described embodiments, the device comprises a collapsible portion of a conduit that is adapted to collapse under a force provided by the seal of the face mask pressing on the collapsible portion. In such embodiments, the conduit or patient interface is adapted to collapse to stop or reduce a flow of gases to the patient via the patient interface (the cannula), and also provide a surface over which the face mask may seal, to form a seal about the patient's airway.

Other embodiments may not comprise a conduit or patient interface with a collapsible portion. For example, those embodiments described above that comprise sensor arrangements for detecting the presence of a face mask may not include a collapsible conduit/interface. In such embodiments the face mask must seal over the top of the first patient interface or conduit when in a normal operating configuration (i.e. when the conduit is not collapsed). Various arrangements are now described to allow a face mask to be used together with another patient interface (e.g. cannula) without a collapsible portion.

Figure 62A:
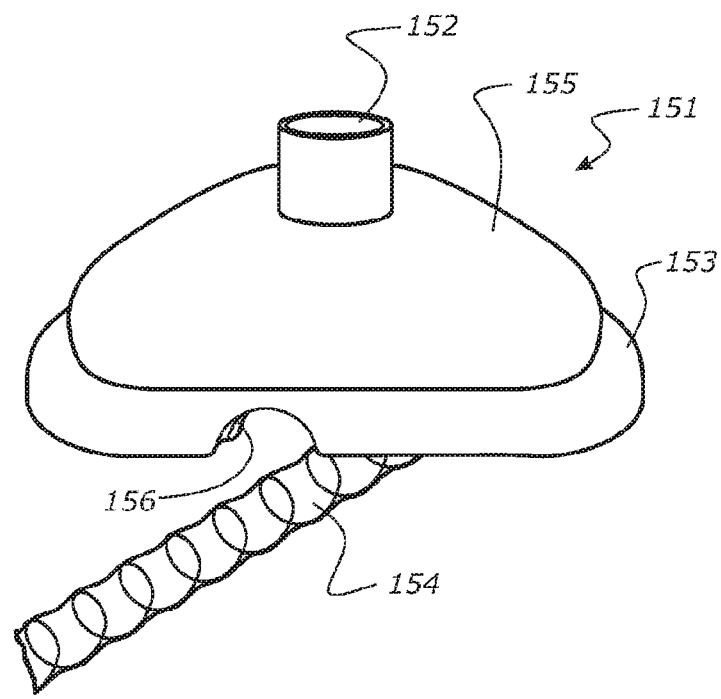
FIG. 62A shows a user interface in the form of a mask for placing over the nasal and/or oral area of a user for conveying gases to and/or from the user according to one embodiment of the disclosure, and a gas conduit which extends into a volume formed by an interior of the interface and the face of the user when the interface is worn by a user.

FIG. 62A shows a user interface 151 in the form of a mask or a mask assembly. In-use, the interface 151 is to be placed over the nasal and/or oral area, preferably both the mouth and the nose, of a user for conveying gases to and/or from the user from a gases supply system (not shown) via an aperture or a port 152 provided on the interface 151. Also shown in FIG. 62A is a gas conduit 154 which extends into an interior volume of the interface 1 also for supplying gases to and/or from the user from a gases supply system (not shown) via a second interface (not shown). In the embodiment shown, the interior volume is formed by an interior of the interface 151 and the face of the user, when the interface 151 such as the mask is worn by the user.

In some configurations, the gases supply systems which are in gases communication with the gas conduit 154 and the interface 151 via the aperture or the port 152 respectively, are separate and independent of each other. In one configuration, the gases supply system which is in gases communication with the aperture or the port 152 is a part of an anaesthesia system comprising an anaesthesia machine for delivering gas to the user, whereas the gases supply system which is in gases communication with the gas conduit 154 is a high flow humidified oxygen delivery system. A nasal interface such as a nasal cannula (not shown) may be provided at an end of the gas conduit 154 and within the interior volume of interface 151 for providing for example a high flow of oxygen or blended gases directly into the nares of the user.

Figure 62B:
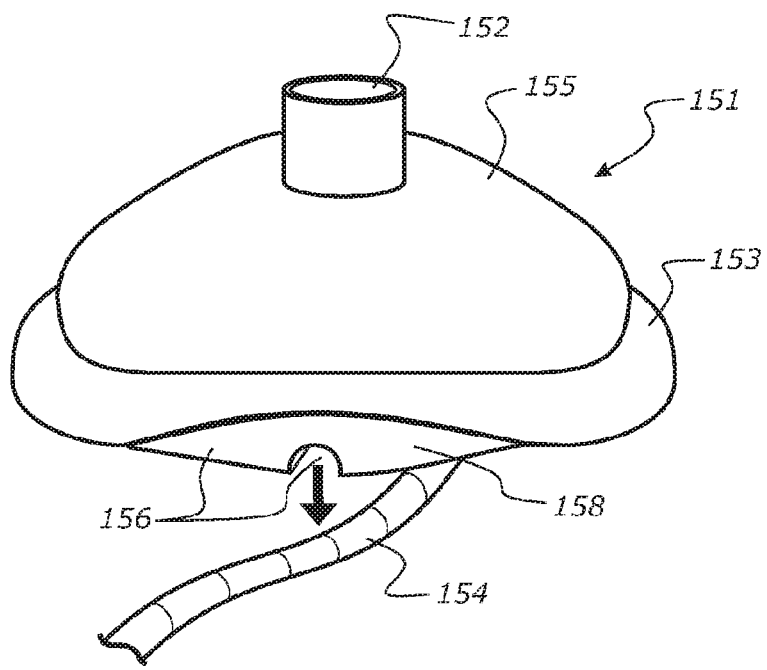
FIG. 62B shows a user interface according to another embodiment.

With reference to FIGS. 62A and 62B, the interface 151 may be provided in the form of a mask, preferably a full face mask which covers both the nose and the mouth of a user. The mask comprises a body 155, such as a shell. The shell may be made of any suitable materials such as polycarbonate, plastic and similar thereof. At or adjacent the rim of the body 155, there is provided a seal 153 which accommodates the creating or forming of the seal between the interface 151 and the user's face and/or a component so provided on said face. The seal 153 may be integrally formed with the shell 155 such as by injection moulding, or it may be formed as a separate component by any suitable process and then attached to the shell 155. The seal 153 is preferably made of a soft, flexible material to readily conform to the facial profile of a user when the interface is worn by the user to create a seal between the user's face and the interface 151. Preferably the seal is a substantially gas tight seal so the user only breathes in and/or out from the conduit 154 or the interior volume or both.

In some configurations, the interface 151 may comprise a headgear assembly for locating the interface on the face of the user in-use.

Alternatively, the interface 151 may not comprise any fixing means such as a headgear and a medical practitioner places the interface at a suitable position on a user's face and then gently pushes the interface towards the user's face to sealingly engage the interface with the user's face.

According to the disclosure, the interface 151 is configured and adapted to allow intrusion of the gas conduit 154 into the interior volume of the interface 151, while maintaining the substantially gas tight seal between the interface 151 and the user's face and/or the spacer component (e.g. in FIGS. 63A to 64) provided on the user's face.

The interface 151 comprises one or more accommodation sites or portions 156 adapted to facilitate intrusion of the gas conduit 154 into the interior volume of the body while maintaining the seal between the interface 151 and the user's face. In an exemplary embodiment as shown in FIGS. 62A and 62B, the one or more accommodation sites or portions 156 is provided on or adjacent the seal 153 and/or the body 155. In the embodiment shown, the accommodation site 156 is provided as a cut-out in the seal 153. The cut-out has a profile which is similar, or slightly smaller in dimension than the cross-section of the gas conduit 154. This is so that the gas conduit 154 can extend into or out of the interior volume of the body 155 without leaving a gap between the seal 153 and the user's face which will then compromise the seal between the seal 153 and the user's face. The geometry of the cut-out may reflect the reverse profile of the tube (e.g. corrugated) to create a better seal with the tube. The cut-out could be made of a different material to the rest of the seal, e.g. a relatively harder material, to maintain the geometry of the cut-out, or a relatively softer material to facilitate conforming around the cannula tube.

The accommodation sites or portions 156 of the interface may allow for the interface 151 to be used with a nasal cannula.

In some configurations the nasal cannula is used to deliver a relatively high flow of oxygen or a high flow of blended gases or high flow of air. The interface 151 may used for various other respiratory support or for anaesthetics delivery. As mentioned above, the interface 151 comprises a seal 153 to seal against the user's face when in-use.

The accommodation sites or portions 156 allow for the nasal cannula to be used with the interface 151 without compromising or substantially affecting or interfering with the seal between the interface 151 and the user's face. This may allow for a nasal cannula which for example delivers high flow therapy to be used in combination with the interface 151 which is used to provide other respiratory support. A medical practitioner can adjust or choose which respiratory support to be used on the user without irritating the user or medical practitioner by constantly adding or removing the user interfaces such as the mask and the nasal cannula.

In some other configurations, the accommodation sites or portions 156 allow the interface 151 to be put on a user without first removing the nasal cannula from the user's face. Various sealing structures may be utilised to facilitate a greater ease of switching between respiratory support modes without the need to change or remove one, some or any or all patient interfaces.

The accommodation site or portions 156 may be provided directly in the seal 153 and/or the body 155 of the mask such as that shown in FIG. 62A. In another embodiment, the accommodation sites or portions 156 may be provided as an extension portion 158 of the seal 153 and a cut-out is formed in the extension portion 158 instead of directly in the seal 153.

Figure 63A:
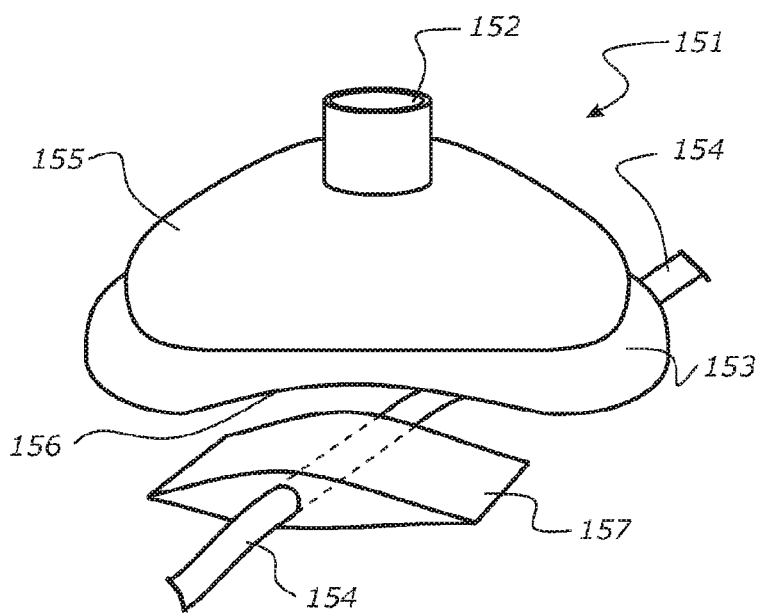
FIG. 63A shows a component provided to a portion of a conduit as a padded sleeve.
Figure 63B:
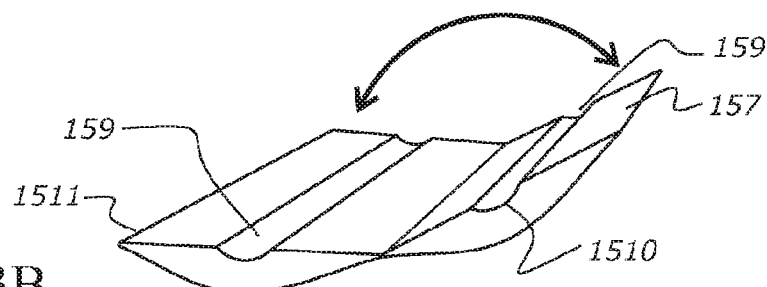
FIG. 63B shows another configuration of the component of FIG. 56a, in which the padded sleeve comprises an upper and a second portion which are pivotably or hingedly joined at one side and openable from another side to receive the conduit between the two portions.
Figure 63C:
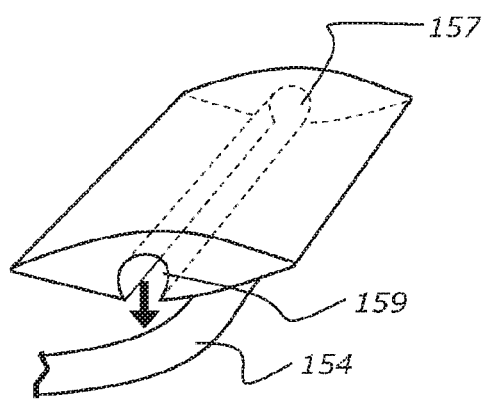
FIG. 63C shows yet another configuration of the component, in which the component is a unitary member which comprises a channel along its length to receive the conduit, the component may be snapped or dipped onto the conduit at a desirable lengthwise location.

In some configurations, a separate spacer component is provided which rests on the user's face and which assists in locating the conduit 154 on the user's face. FIGS. 63A-63C each shows a different configuration of such spacer component 157. The spacer component 157 surrounds at least a portion of the conduit 154 and preferably, the spacer component 157 is provided to the portion of the conduit 154 which engages the accommodation site or portion 156 when the interface 151 is worn by the user.

In the embodiment shown in FIG. 63A, the spacer component 157 is in the form of a padded sleeve which surrounds a length of the conduit 154. As explained above, the spacer component 157 is to allow the conduit 154 to extend across the rim of the interface 151 while maintaining the seal between the seal 153 and the user's face. In-use, the spacer component 157 is placed between the accommodation site or portions 156 and the face of the user to maintain the air tightness. The sleeve comprises a channel 159 to accommodate the conduit 154 within. In the embodiment shown, the sleeve has a greater thickness in the centre region and the thickness gradually decreases towards both lateral directions to form a leaf shaped cross section. In other configurations, the sleeve may have a different shaped cross section such as an oval or a circular cross section. In preferred embodiments the spacer component is shaped to have a flatter profile than the conduit. The flatter profile provides a surface comprising a gradual curvature over which the seal of the mask may bear to form a seal. Preferably the component 157 tapers from a thick portion through which the conduit is received to thin portions either side of the thick portion. The shape of the component 157 minimises abrupt changes in gradient, to avoid creating leaks. The spacer component comprises a channel or grove or pathway for receiving the conduit, and provide a seal or at least a partial seal with the conduit.

The spacer component 157 may be integrally formed with the portion of the conduit 154 to which it is attached, or formed as a separate component which can be removably attached to the portion of the conduit 154 such as that shown in FIG. 63B or 63C. The component may be slidable on the conduit. In some configurations, the spacer component 157 is removably attached to the portion of the conduit by for example a snap fit action such as that illustrated in FIG. 63C (or could sit over the top of the conduit without a snap fit engagement), or by inserting an end of the conduit 154 into the channel of the sleeve and then sliding the sleeve to a desirable location along the length of the conduit 154. Or alternatively, the component may comprise a first portion 1510 and a second portion 1511 and the two portions are pivotably or hingedly connected along one side of the component, and openable via another side to receive and/or clamp the conduit 154 between the two portions. Alternatively the two portions 1510 and 1511 may be permanently attached together but may fit together about the conduit. The first portion 1510 and the second portion 1511 may each have a groove or a channel 159 formed at or near the centre region of the sleeve to accommodate the conduit 154 or provide a visual indication to the user where to locate the conduit 154 between the two halves of the sleeve. The inner geometry of the channel could match that of the conduit.

In the configurations shown in FIGS. 63B-63C, the exterior for example the upper and the lower surface of the sleeve is substantially smooth to assist the creation of a gas tight seal between the interface 151 and the spacer component 157, and the spacer component 157 and the user's face.

Figure 64:
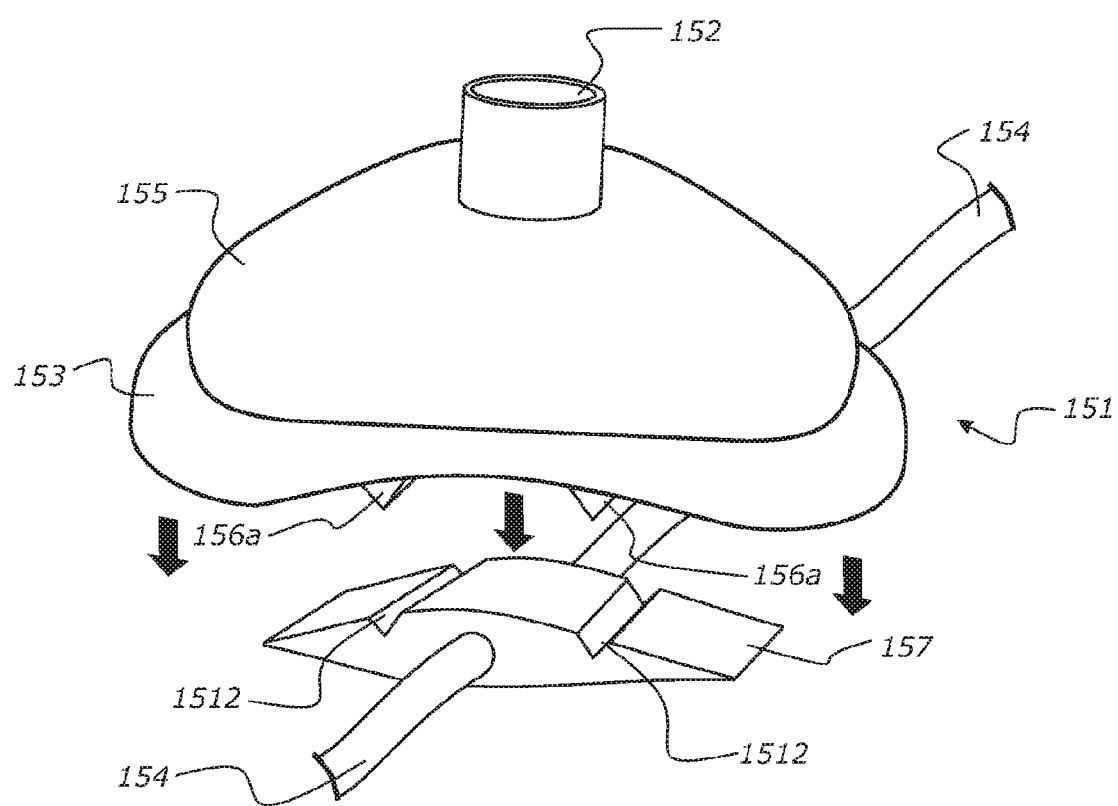
FIG. 64 shows another configuration, in which a coupling arrangement is provided to couple component to the interface.

FIG. 64 shows another configuration of the accommodation site or portions 156 and the spacer component 157. In this configuration, the interface 151 comprises a coupling arrangement for coupling to the spacer component 157 while maintaining the seal so that the spacer component 157 and the conduit 154 does not slide off or changes position when the interface 151 is put on the user's face. In one form, the coupling arrangement is provided in or near the accommodation site or portions 156 as a protrusion 156*a* extending from an underside of the seal 153, the side that directly faces the user's face when in-use. A complimentary groove 1512 is formed in the exterior of the upper surface of the spacer component 157. The groove 1512 receives the protrusion 156*a* to form the coupling arrangement and to secure the spacer component 157 in place relative to the interface 151. The protrusions could be collapsible or retract back into the mask if the mask is placed directly on the patient's face (e.g. they could have springs above them that compress and allow retraction when a force is applied that is greater than that caused by the seal with the grooves in the spacer)

In some configurations, the spacer component 157 is configured to withstand the forces exerted by the accommodation sites or portions 156 and the user's face so it does not impede the gas flow within the conduit 154 after the interface is put on the user's face. In another configuration, the spacer component 157 may be configured to resiliently deform and the portion of the conduit 154 housed therein also deforms. In this configuration, the gases communication via the conduit 154 is stopped or substantially reduced after the interface is worn by the user. Such an embodiment is described with reference to FIGS. 54A to 54C.

The spacer component 157 may be made of any deformable or resilient materials such as silicone, foam, rubber, plastic, textile and/or similar thereof.

Advantages of FIGS. 62A and 62B Configurations:
   mask seal could be designed to fit an existing cannula tube.
   Cut-out in mask can help to locate cannula tube ensuring cannula remains well positioned in nares
   Locating feature gives user confidence seal is being achieved correctly Advantage of FIG. 62B Configuration:
   extension portion 158 could be removable/fitted to existing mask and removed when not required to ensure good mask seal with face when cannula tube not in place Advantages of FIG. 63A-63C Configurations:
   can use existing mask and cannula (ie: if don't have a specific accommodation site on mask)
   Spacer can be removed when not needed
   Spacer can be purchased/used only when necessary
   Spacer not attached to mask so tube can be repositioned as desired on patent's face (if don't have a specific accommodation site on mask)

Advantage of FIG. 64 Configuration:
   specific design of both spacer and mask can ensure better sealing.
   Spacer could be designed to fit existing cannula
   Locating features give user confidence seal is being achieved correctly Where, in the foregoing description reference has been made to integers or components having known equivalents thereof, those integers are herein incorporated as if individually set forth.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

The invention claimed is:

1. A patient interface for providing respiratory support to a patient, the patient interface comprising:
   a nasal interface having an inlet and an outlet;
   a single gas conduit in communication with the inlet of the nasal interface and configured to deliver a gases flow to the outlet of the nasal interface, wherein the single gas conduit comprises a collapsible portion positioned so as to be collapsible by a seal region of a face mask or an oral mask, wherein collapsing the collapsible portion with the seal region of the face mask or the oral mask causes the patient interface to transition between a first configuration and a second configuration when the face mask or the oral mask is placed over the nasal interface by a user to cause the transition;
   wherein the first configuration allows the gases flow to pass through the nasal interface and to the patient; and
   wherein the second configuration reduces or stops the gases flow from passing through the nasal interface to the patient.

2. The patient interface of claim 1, wherein the second configuration stops the gases flow.

3. The patient interface of claim 1, wherein the second configuration reduces the gases flow.

4. The patient interface of claim 1, wherein the gases flow during the first configuration is 20-150 liters per minute.

5. The patient interface of claim 4, wherein the gases flow during the first configuration is 40-70 liters per minute.

6. The patient interface of claim 1, further comprising the face mask or the oral mask.

7. The patient interface of claim 1, wherein the patient interface is a non-sealing nasal cannula.

8. The patient interface of claim 1, wherein the gas conduit further comprises another portion that includes reinforcement elements configured to resist collapsing.

9. The patient interface of claim 1, wherein the portion has a first wall section and a second wall section, wherein a thickness of the first wall section is less than a thickness of the second wall section.

10. The patient interface of claim 1, wherein the collapsible portion comprises at least one folding portion.

11. The patient interface of claim 1, wherein the patient interface comprises a non-collapsible portion.

12. The patient interface of claim 1, wherein the collapsible portion is located at the nasal interface.

13. The patient interface of claim 1, wherein the gas conduit is integrally formed with the nasal interface as a part of the patient interface.

14. The patient interface of claim 1, wherein the collapsible portion is positioned over a cheek region of the patient.

15. The patient interface of claim 14, wherein the collapsible portion further includes a cheek support for supporting the collapsible portion relative to the cheek of the patient.

16. A patient interface for providing respiratory support to a patient, the patient interface comprising:
   a nasal interface having an inlet and an outlet;
   a single gas conduit in communication with the inlet of the nasal interface and configured to deliver a gases flow to the outlet of the nasal interface, wherein the single gas conduit comprises a collapsible portion positioned so as to be located over a cheek region of the patient, wherein collapsing the collapsible portion causes the patient interface to transition between a first configuration and a second configuration when a face mask or oral mask is placed over the nasal interface by a user such that a seal region of the face mask or the oral mask contacts the collapsible portion to cause the transition;
   wherein the first configuration allows the gases flow to pass through the nasal interface and to the patient; and
   wherein the second configuration reduces or stops the gases flow from passing through the nasal interface to the patient.

17. The patient interface of claim 16, wherein the collapsible portion of the single gas conduit is more collapsible than another portion of the single gas conduit.

18. A patient interface for providing respiratory support to a patient, the patient interface comprising:
   a nasal interface having an inlet and an outlet;
   a single gas conduit in communication with the inlet of the nasal interface and configured to deliver a gases flow to the outlet of the nasal interface, wherein the single gas conduit comprises a collapsible portion that is configured to be more collapsible than another portion of the single gas conduit, wherein collapsing the collapsible portion causes the patient interface to transition between a first configuration and a second configuration when a face mask or oral mask is placed over the nasal interface by a user such that a seal region of the face mask or the oral mask contacts the collapsible portion to cause the transition;
   wherein the first configuration allows the gases flow to pass through the nasal interface and to the patient; and
   wherein the second configuration reduces or stops the gases flow from passing through the nasal interface to the patient.

\* \* \* \* \*